(12) United States Patent
Carroll et al.

(10) Patent No.: US 7,105,499 B2
(45) Date of Patent: Sep. 12, 2006

(54) NUCLEOSIDE DERIVATIVES AS INHIBITORS OF RNA-DEPENDENT RNA VIRAL POLYMERASE

(75) Inventors: Steven S. Carroll, Yardley, PA (US); David B. Olsen, Lansdale, PA (US); Malcolm MacCoss, Freehold, NJ (US); Balkrishen Bhat, Carlsbad, CA (US); Phillip Dan Cook, Fallbrook, CA (US); Anne B. Eldrup, Encinitas, CA (US); Thazha P. Prakash, Carlsbad, CA (US)

(73) Assignees: Merck & Co., Inc., Rahway, NJ (US); Isis Pharmaceuticals, Inc., Carlsbad, CA (US)

( * ) Notice: Subject to any disclaimer, the term of this patent is extended or adjusted under 35 U.S.C. 154(b) by 335 days.

(21) Appl. No.: 10/250,873

(22) PCT Filed: Jan. 18, 2002

(86) PCT No.: PCT/US02/01531

§ 371 (c)(1), (2), (4) Date: Jan. 16, 2004

(87) PCT Pub. No.: WO02/057425

PCT Pub. Date: Jul. 25, 2002

(65) Prior Publication Data

US 2004/0110717 A1   Jun. 10, 2004

Related U.S. Application Data

(60) Provisional application No. 60/344,528, filed on Oct. 25, 2001, provisional application No. 60/299,320, filed on Jun. 19, 2001, provisional application No. 60/282,069, filed on Apr. 6, 2001, and provisional application No. 60/263,313, filed on Jan. 22, 2001.

(51) Int. Cl.
*A61K 31/7052* (2006.01)
*A61K 31/7042* (2006.01)
*A61K 31/7068* (2006.01)
*C07H 19/04* (2006.01)
*C07H 19/06* (2006.01)

(52) U.S. Cl. .......................... 514/49; 514/43; 514/45; 514/42; 514/50; 514/52; 514/46; 536/28.4; 536/28.5; 536/26.12

(58) Field of Classification Search .................. 514/49, 514/43, 45, 42, 50, 52, 46; 536/28.4, 28.5, 536/26.12, 26.13
See application file for complete search history.

(56) References Cited

U.S. PATENT DOCUMENTS

| | | | |
|---|---|---|---|
| 3,480,613 A | 11/1969 | Walton | |
| 6,348,587 B1 * | 2/2002 | Schinazi et al. | 536/25.3 |
| 6,784,161 B1 * | 8/2004 | Ismaili et al. | 514/43 |
| 2002/0019363 A1 | 2/2002 | Ismaili et al. | |
| 2002/0055483 A1 | 5/2002 | Watanabe et al. | |
| 2002/0198171 A1 | 12/2002 | Schinazi et al. | |
| 2003/0050229 A1 | 3/2003 | Sommadossi et al. | |
| 2003/0060400 A1 | 3/2003 | LaColla et al. | |

FOREIGN PATENT DOCUMENTS

| | | |
|---|---|---|
| FR | 1.581.628 | 9/1969 |
| GB | 1209 654 | 10/1970 |
| WO | WO 93/18051 | 9/1993 |
| WO | WO 99/43691 | 9/1999 |
| WO | WO 01/32153 | 5/2001 |
| WO | WO 01/60315 | 8/2001 |
| WO | WO 01/79246 | 10/2001 |
| WO | WO 01/90121 | 11/2001 |
| WO | WO 01/92282 | 12/2001 |
| WO | WO 02/18404 | 3/2002 |
| WO | WO 02/048165 A3 | 6/2002 |
| WO | WO 02/048165 A2 | 6/2002 |
| WO | WO 02/069903 A2 | 9/2002 |
| WO | WO 02/069903 A2 | 9/2002 |
| WO | WO 02/094289 A1 | 11/2002 |
| WO | WO 02/100354 A3 | 12/2002 |
| WO | WO 02/100354 A2 | 12/2002 |
| WO | WO 02/100415 A2 | 12/2002 |
| WO | WO 03/000200 A2 | 1/2003 |
| WO | WO 03/000713 A1 | 1/2003 |
| WO | WO 03/015798 A1 | 2/2003 |
| WO | WO 03/026589 A2 | 4/2003 |
| WO | WO 03/026675 A1 | 4/2003 |
| WO | WO 03/051881 | 6/2003 |
| WO | WO 03/051896 | 6/2003 |
| WO | WO 03/051897 | 6/2003 |
| WO | WO 03/051898 | 6/2003 |
| WO | WO 03/051899 | 6/2003 |
| WO | WO 03/062255 | 7/2003 |

OTHER PUBLICATIONS

Walton, E. et al., "Branched–Chain Sugar Nucleosides. V. Synthesis and Antiviral Properties of Several Branched–Chain Sugar Nucleosides", J. Med. Chem., vol. 12, pp. 306–309 (1969).

(Continued)

*Primary Examiner*—Elvis O. Price
*Assistant Examiner*—Michael C. Henry
(74) *Attorney, Agent, or Firm*—Philippe L. Durette; Melvin Winokur

(57) ABSTRACT

The present invention provides nucleoside derivatives which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and/or for the treatment of hepatitis C infection. The invention also describes pharmaceutical compositions containing such nucleoside derivatives alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the nucleoside derivatives of the present invention.

2 Claims, No Drawings

OTHER PUBLICATIONS

Matsuda, A. et al., "Radical Deoxygenation of Tert–Alcohols In 2'–Branched–Chain Sugar Pyrimidine Nucleosides: Synthesis and Antileukemic Activity of 2'–Deoxy–2'(S)–Methylcytidine", Chem. Pharm. Bull., vol. 35, pp. 3967–3970 (1987).

Matsuda, A. et al., Alkyl Addition Reaction of Pyrimidine 2'–Ketonucleosides: Synthesis of 2'–Branched–Chain Sugar Pyrimidine Nucleosides (Nucleosides and Nucleotides. LXXXI). Chem. Pharm. Bull., vol. 36, pp. 945–953 (1988).

Murai, Y. et al., "A Synthesis and an X–Ray Analysis of 2'–C–, 3'–C– and 5'–C–Methylsangivamycins", Heterocycles, vol. 33, pp. 391–404 (1992).

Limori, T. et al., "2'–C–, 3'–C– and 5'–C–Methylsangivamycins: Conformational Lock with the Methyl Group", Tetrahedron Letters, vol. 3, No. 49, pp. 7273–7276 (1991).

Wolfe, M. et al., "A Consise Synthesis of 2'–C–Methylribonucleosides", Tetrahedron Letters, vol. 36, No. 42, pp. 7611–7614 (1995).

Harry–O'kuru, R. et al., "A Short, Flexible Route toward 2'–C–Branched Ribonucleosides", J. Org. Chem., vol. 62, pp. 1754–1759 (1997).

Gallo, M. et al., "Synthesis of 2'–Modified Nucleotides", Molecules, vol. 5, pp. 727–729 (2000).

Beigelman, L. et al., "New Synthesis of 2'–C–Methylnucleosides Starting From D–Glucose and D–Ribose", Carbohydrate Research, vol. 166, pp. 219–232 (1987).

Anzai, K. et al, "A New Antibiotic, Tubercidin", The Journal of Antibiotics., vol. X, No. 5, pp. 201–205 (1957).

Tolman, R. et al., "Pyrrolopyrimidine Nucleosides. III. The Total Synthesis of Toyocamycin, Sangivamycin, Tubercidin, and Related Derivatives", Journal of the American Chemical Society, vol. 91, No. 8, pp. 2102–2108 (1969).

Tolman, R. et al., "Pyrrolo[2,3–d]pyrimidine Nucleoside Antibiotics. Total Synthesis and Structure of Toyacamycin, Unamycin B, Vengicide, Antibiotic E–212, and Sangivamycin (BA–90212)", Journal of the American Chemical Society, vol. 90, No. 2, pp. 24–526 (1968).

Siddiqi, S. et al., "Search for New Purine– and Ribose–Modified Adenosine Analogues as Selective Agonists and Antagonists at Adenosine Receptors", J. Med. Chem., vol. 38, pp. 1174–1188 (1995).

Franchetti, P. et al., "2'–Methyl Analogues of Selective Adenosine Receptor Agonists: Synthesis and Binding Studies", J. Med. Chem., vol. 41, pp. 1708–1715 (1988).

Kalinichenko, E. et al., "Substrate Specificity of Adenosine Deminase. Role of Methyl Groups at the 2'–3'–, and 5'–Carbon Atoms of Adenosine", Bioorganicheskaya Khimiya, vol. 14, No. 9, pp. 1157–1161 (1988).

Wolf, et al., "New 2'–C–Branched–Chain Sugar Nucleoside Analogs with Potential Antiviral or Antitumor Activity", Synthesis, pp. 773–778 (Aug. 1992).

* cited by examiner

NUCLEOSIDE DERIVATIVES AS INHIBITORS OF RNA-DEPENDENT RNA VIRAL POLYMERASE

CROSS REFERENCE TO RELATED APPLICATIONS

This application is the National Stage of International Application No. PCT/US2002/01531, filed 9 Jul. 2003, which claims the benefit under 35 U.S.C. 119(e) of U.S. provisional application No. 60/344,528, filed on Oct. 25, 2001; provisional application No. 60/299,320, filed on Jun. 19, 2001; provisional application No. 60/282,069, filed on Apr. 6, 2001; and provisional application No. 60/263,313, filed on Jan. 22, 2001; the contents of each of which are hereby incorporated by reference.

FIELD OF THE INVENTION

The present invention provides nucleoside derivatives which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2–15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherap.* 11: 79–96 (2000); H. Rosen, et al., "Hepatitis C virus: current understanding and prospects for future therapies," *Molecular Medicine Today*, 5: 393–399 (1999); D. Moradpour, et al., "Current and evolving therapies for hepatitis C," *European J. Gastroenterol. Hepatol.*, 11: 1189–1202 (1999); R. Bartenschlager, "Candidate Targets for Hepatitis C Virus-Specific Antiviral Therapy," *Intervirology*, 40: 378–393 (1997); G. M. Lauer and B. D. Walker, "Hepatitis C Virus Infection," *N. Engl. J. Med.*, 345: 41–52 (2001); B. W. Dymock, "Emerging therapies for hepatitis C virus infection," *Emerging Drugs*, 6: 13–42 (2001); and C. Crabb, "Hard-Won Advances Spark Excitement about Hepatitis C," *Science*: 506–507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5SB. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29: 1227–1235 (1999) and V. Lohmann, et al., "Biochemical and Kinetic Analyses of NS5B RNA-Dependent RNA Polymerase of the Hepatitis C Virus," *Virology*, 249: 108–118 (1998)]. Inhibition of HCV NS5B polymerase prevents formation of the double-stranded HCV RNA and therefore constitutes an attractive approach to the development of HCV-specific antiviral therapies.

It has now been found that nucleoside compounds of the present invention and certain derivatives thereof are potent inhibitors of RNA-dependent RNA viral replication and in particular HCV replication. The 5'-triphosphate derivatives of the nucleoside compounds are inhibitors of RNA-dependent RNA viral polymerase and in particular HCV NS5B polymerase. The instant nucleoside compounds and derivatives thereof are useful to treat RNA-dependent RNA viral infection and in particular HCV infection.

It is therefore an object of the present invention to provide nucleoside compounds and certain derivatives thereof which are useful as inhibitors of RNA-dependent RNA viral polymerase and in particular as inhibitors of HCV NS5B polymerase.

It is another object of the present invention to provide nucleoside derivatives which are useful as inhibitors of the replication of an RNA-dependent RNA virus and in particular as inhibitors of the replication of hepatitis C virus.

It is another object of the present invention to provide nucleoside compounds and certain derivatives which are useful in the treatment of RNA-dependent RNA viral infection and in particular in the treatment of HCV infection.

It is another object of the present invention to provide pharmaceutical compositions comprising the novel compounds of the present invention in association with a pharmaceutically acceptable carrier.

It is another object of the present invention to provide pharmaceutical compositions comprising the nucleoside compounds and derivatives thereof for use as inhibitors of RNA-dependent RNA viral polymerase and in particular as inhibitors of HCV NS5B polymerase.

It is another object of the present invention to provide pharmaceutical compositions comprising the nucleoside compounds and derivatives thereof for use as inhibitors of RNA-dependent RNA viral replication and in particular as inhibitors of HCV replication.

It is another object of the present invention to provide pharmaceutical compositions comprising the nucleoside compounds and derivatives thereof for use in the treatment of RNA-dependent RNA viral infection and in particular in the treatment of HCV infection.

It is another object of the present invention to provide pharmaceutical compositions comprising the nucleoside compounds and derivatives thereof in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide nucleoside compounds and certain derivatives thereof and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the nucleoside compounds and certain derivatives thereof of the present invention and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention provides a method for inhibiting RNA-dependent RNA viral polymerase, a method for inhibiting RNA-dependent RNA viral replication, and/or a method for treating RNA-dependent viral infection in a mammal in need thereof, comprising administering to the mammal a therapeutically effective amount of a compound of structural formula I which is of the stereochemical configuration:

(I)

or a pharmaceutically acceptable salt thereof;

wherein B is selected from the group consisting of

A, G, and L are each independently CH or N;
D is N, CH, C—CN, C—NO$_2$, C—C$_{1-13}$ alkyl, C—NHCONH$_2$, C—CONR$^{11}$R$^{11}$, C—CSNR$^{11}$R$^{11}$, C—COOR$^{11}$, C—C(=NH)NH$_2$, C-hydroxy, C—C$_{1-3}$ alkoxy, C-amino, C—C$_{1-4}$ alkylamino, C-di(C$_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;
E is N or CR$^5$;
W is O or S;
Y is H, C$_{1-10}$ alkylcarbonyl, P$_3$O$_9$H$_4$, P$_2$O$_6$H$_3$, or P(O)R$^9$R$^{10}$;
R$^1$ is hydrogen, C$_{2-4}$ alkenyl, C$_{2-4}$ alkynyl, or C$_{1-4}$ alkyl optionally substituted with amino, hydroxy, or 1 to 3 fluorine atoms and one of R$^2$ and R$^3$ is hydroxy or C$_{1-4}$ alkoxy and the other of R$^2$ and R$^3$ is selected from the group consisting of
hydrogen,
hydroxy,
halogen,
C$_{1-4}$ alkyl, optionally substituted with 1 to 3 fluorine atoms,
C$_{1-10}$ alkoxy, optionally substituted with C$_{1-3}$ alkoxy or 1 to 3 fluorine atoms,
C$_{2-6}$ alkenyloxy,
C$_{1-4}$ alkylthio,
C$_{1-8}$ alkylcarbonyloxy,
aryloxycarbonyl,
azido,
amino,
C$_{1-4}$ alkylamino, and
di(C$_{1-4}$ alkyl)amino; or
R$^2$ is hydrogen, C$_{2-4}$ alkenyl, C$_{2-4}$ alkynyl, or C$_{1-4}$ alkyl optionally substituted with amino, hydroxy, or 1 to 3 fluorine atoms and one of R$^1$ and R$^3$ is hydroxy or C$_{1-4}$ alkoxy and the other of R$^1$ and R$^3$ is selected from the group consisting of hydrogen, hydroxy, halogen, $C_{1-4}$ alkyl, optionally substituted with 1 to 3 fluorine atoms, $C_{1-10}$ alkoxy, optionally substituted with hydroxy, $C_{1-3}$ alkoxy, carboxy, or 1 to 3 fluorine atoms, $C_{2-6}$ alkenyloxy, $C_{1-4}$ alkylthio, $C_{1-8}$ alkylcarbonyloxy, aryloxycarbonyl, azido, amino, $C_{1-4}$ alkylamino, and di($C_{1-4}$ alkyl)amino; or $R^1$ and $R^2$ together with the carbon atom to which they are attached form a 3- to 6-membered saturated monocyclic ring system optionally containing a heteroatom selected from O, S, and $NC_{0-4}$ alkyl;

$R^4$ and $R^6$ are each independently H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^{14}$ is H, $CF_3$, $C_{1-4}$ alkyl, amino, $C_{1-4}$ alkylamino, $C_{3-6}$ cycloalkylamino, or di($C_{1-4}$ alkyl)amino;

$R^7$ is hydrogen, amino, $C_{1-4}$ alkylamino, $C_{3-6}$ cycloalkylamino, or di($C_{1-4}$ alkyl)amino;

each $R^{11}$ is independently H or $C_{1-6}$ alkyl;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^{12}$ and $R^{13}$ are each independently hydrogen, methyl, hydroxymethyl, or fluoromethyl; and $R^9$ and $R^{10}$ are each independently hydroxy, $OCH_2CH_2SC(=O)C_{1-4}$ alkyl, $OCH_2O(C=O)OC_{1-4}$ alkyl, $NHCEMeCO_2Me$, $OCH(C_{1-4}$ alkyl)$O(C=O)C_{1-4}$ alkyl,

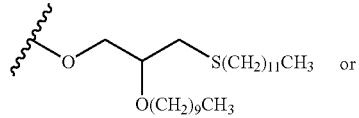

or

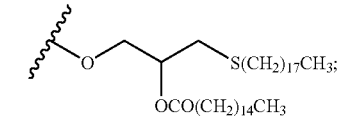

with the provisos that (a) when $R^1$ is hydrogen, one of $R^3$ and $R^4$ is hydrogen, and $R^2$ is fluoro, then the other of $R^3$ and $R^4$ is not hydrogen, halogen, azido, trifluoromethyl, $C_{1-4}$ alkyl, amino, $C_{1-4}$ alkylamino, di($C_{1-4}$ alkyl)amino, or $C_{1-10}$ alkoxy; (b) when $R^1$ is hydrogen, one of $R^3$ and $R^4$ is hydrogen, and $R^2$ is halogen, hydroxy, $C_{1-6}$ alkoxy, or $C_{2-6}$ alkenyloxy, then the other of $R^3$ and $R^4$ is not hydrogen, fluoro, or azido; and (c) when $R^1$ and $R^3$ are hydrogen and $R^2$ is hydroxy, then $R^4$ is not hydroxy.

The present invention also provides novel compounds of structural formula IV of the indicated stereochemical configuration which are useful as inhibitors of RNA-dependent RNA viral polymerase. The compounds of formula IV are also inhibitors of RNA-dependent RNA viral replication and are useful for the treatment of RNA-dependent RNA viral infection:

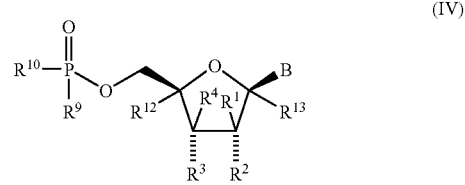

wherein B is selected from the group consisting of

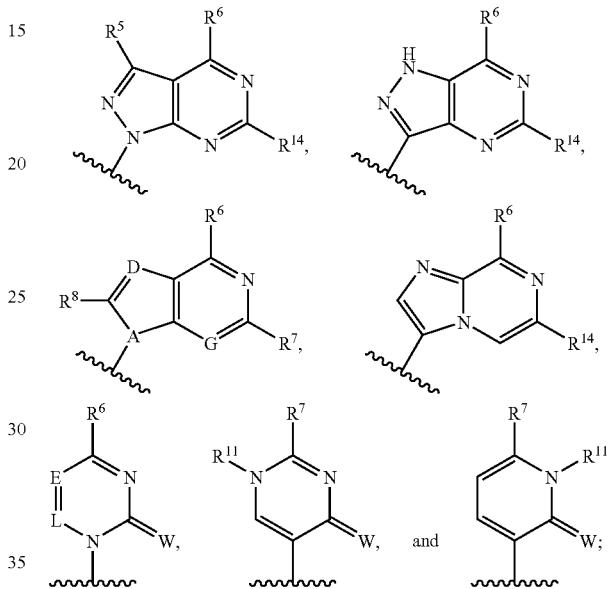

A, G, and L are each independently CH or N;

D is N, CH, C—CN, C—$NO_2$, C—$C_{1-3}$ alkyl, C—$NHCONH_2$, C—$CONR^{11}R^{11}$, C—$CSNR^{11}R^{11}$, C—$COOR^{11}$, C—C(=NH)$NH_2$, C-hydroxy, C—$C_{1-3}$ alkoxy, C-amino, C—$C_{1-4}$ alkylamino, C-di($C_{1-4}$ alkyl)amino, C-halogen, C-(1,3-oxazol-2-yl), C-(1,3-thiazol-2-yl), or C-(imidazol 2-yl); wherein alkyl is unsubstituted or substituted with one to three groups independently selected from halogen, amino, hydroxy, carboxy, and $C_{1-3}$ alkoxy;

E is N or $CR^5$;

W is O or S;

$R^1$ is hydrogen, $C_{2-4}$ alkenyl, $C_{2-4}$-alkynyl, or $C_{1-4}$ alkyl optionally substituted with amino, hydroxy, or 1 to 3 fluorine atoms and one of $R^2$ and $R^3$ is hydroxy or $C_{1-4}$ alkoxy and the other of $R^2$ and $R^3$ is selected from the group consisting of hydrogen, hydroxy, halogen, $C_{1-4}$ alkyl, optionally substituted with 1 to 3 fluorine atoms, $C_{1-10}$ alkoxy, optionally substituted with $C_{1-3}$ alkoxy or 1 to 3 fluorine atoms, $C_{2-6}$ alkenyloxy, $C_{1-4}$ alkylthio, $C_{1-8}$ alkylcarbonyloxy, aryloxycarbonyl, azido, amino,
C$_{1-4}$ alkylamino, and
di(C$_{1-4}$ alkyl)amino; or R$^2$ is hydrogen, C$_{2-4}$ alkenyl, C$_{2-4}$ alkynyl, or C$_{1-4}$ alkyl optionally substituted with amino, hydroxy, or 1 to 3 fluorine atoms and one of R$^1$ and R$^3$ is hydroxy or C$_{1-4}$ alkoxy and the other of R$^1$ and R$^3$ is selected from the group consisting of hydrogen,
hydroxy,
halogen,
C$_{1-4}$ alkyl, optionally substituted with 1 to 3 fluorine atoms,
C$_{1-10}$ alkoxy, optionally substituted with hydroxy, C$_{1-3}$ alkoxy, carboxy, or 1 to 3 fluorine atoms,
C$_{2-6}$ alkenyloxy,
C$_{1-4}$ alkylthio,
C$_{1-8}$ alkylcarbonyloxy,
aryloxycarbonyl,
azido,
amino,
C$_{1-4}$ alkylamino, and
di(C$_{1-4}$ alkyl)amino; or R$^1$ and R$^2$ together with the carbon atom to which they are attached form a 3- to 6-membered saturated monocyclic ring system optionally containing a heteroatom selected from O, S, and NC$_{0-4}$ alkyl;

each R$^4$ is independently H, OH, SH, NH$_2$, C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, or CF$_3$;

R$^4$ and R$^6$ are each independently H, OH, SH, NH$_2$, C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, or CF$_3$;

R$^5$ is H, C$_{1-6}$ alkyl, C$_{2-6}$ alkenyl, C$_{2-6}$ alkynyl, C$_{1-4}$ alkylamino, CF$_3$, or halogen;

R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino;

R$^7$ is hydrogen, amino, C$_{1-4}$ alkylamino, C$_{3-6}$ cycloalkylamino, or di(C$_{1-4}$ alkyl)amino;

each R$^{11}$ is independently H or C$_{1-6}$ alkyl;

R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;

R$^{12}$ and R$^{13}$ are each independently hydrogen, methyl, hydroxymethyl, or fluoromethyl; and R$^9$ and R$^{10}$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl,

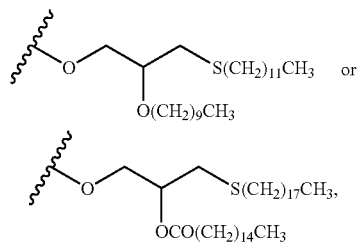

provided that at least one of R$^9$ and R$^{10}$ is not hydroxy.

The present invention further provides novel compounds of structural formula XII of the indicated stereochemical configuration which are useful as inhibitors of RNA-dependent RNA viral polymerase and in particular of HCV NS5B polymerase:

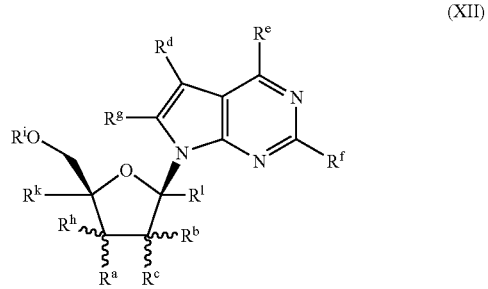

(XII)

wherein R$^a$ and R$^h$ are each independently selected from the group consisting of hydrogen, cyano, azido, halogen, hydroxy, mercapto, amino, C$_{1-4}$ alkoxy, C$_{2-4}$ alkenyl, C$_{2-4}$ alkynyl, and C$_{1-4}$ alkyl, wherein alkyl is unsubstituted or substituted with hydroxy, amino, C$_{1-4}$ alkoxy, C$_{1-4}$ alkylthio, or one to three fluorine atoms;

R$^b$ is C$_{2-4}$ alkenyl, C$_{2-4}$ alkynyl, or C$_{1-4}$ alkyl, wherein alkyl is unsubstituted or substituted with hydroxy, amino, C$_{1-4}$ alkoxy, C$_{1-4}$ alkylthio, or one to three fluorine atoms;

R$^c$ is hydrogen, fluorine, hydroxy, mercapto, C$_{1-4}$ alkoxy, or C$_{1-4}$ alkyl; or R$^b$ and R$^c$ together with the carbon atom to which they are attached form a 3- to 6-membered saturated monocyclic ring system optionally containing a heteroatom selected from O, S, and NC$_{0-4}$ alkyl;

R$^d$ is hydrogen, cyano, nitro, C$_{1-3}$ alkyl, NHCONH$_2$, CONRjRj, CSNRjRj, COORj, C(=NH)NH$_2$, hydroxy, C$_{1-3}$ alkoxy, amino, C$_{1-4}$ alkylamino, di(C$_{1-4}$ alkyl)amino, halogen, (1,3-oxazol-2-yl), (1,3-thiazol-2-yl), or (imidazol-2-yl); wherein alkyl is unsubstituted or substituted with one to three groups independently selected from halogen, amino, hydroxy, carboxy, and C$_{1-3}$ alkoxy;

R$^e$ and R$^f$ are each independently hydrogen, hydroxy, halogen, C$_{1-4}$ alkoxy, amino, C$_{1-4}$ alkylamino, di(C$_{1-4}$ alkyl)amino, C$_{3-6}$ cycloalkylamino, di(C$_{3-6}$ cycloalkyl)amino, or C$_{4-6}$ cycloheteroalkyl, unsubstituted or substituted with one to two groups independently selected from halogen, hydroxy, amino, C$_{1-4}$ alkyl, and C$_{1-4}$ alkoxy;

R$^g$ is hydrogen, C$_{1-4}$ alkyl, C$_{2-4}$ alkynyl, halogen, cyano, carboxy, C$_{1-4}$ alkyloxycarbonyl, azido, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, (C$_{1-4}$ alkyl)$_{0-2}$ aminomethyl, or C$_{4-6}$ cycloheteroalkyl, unsubstituted or substituted with one to two groups independently selected from halogen, hydroxy, amino, C$_{1-4}$ alkyl, and C$_{1-4}$ alkoxy;

R$^i$ is hydrogen, C$_{1-10}$ alkylcarbonyl, P$_3$O$_9$H$_4$, P$_2$O$_6$H$_3$, or P(O)R$^m$R$^n$;

each R$^j$ is independently hydrogen or C$_{1-6}$ alkyl;

R$^k$ and R$^l$ are each independently hydrogen, methyl, hydroxymethyl, or fluoromethyl; and R$^m$ and R$^n$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl,

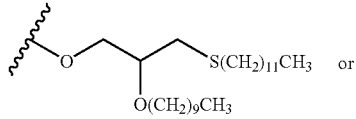

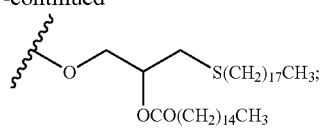

with the proviso that when $R^a$ and $R^c$ are α-hydroxy, $R^e$ is amino, $R^b$ is β-methyl and $R^h$ is hydrogen or $R^h$ is β-methyl and $R^b$ is hydrogen, and $R^f$, $R^g$, $R^i$, $R^k$, and $R^l$ are hydrogen, then $R^d$ is not cyano or $CONH_2$.

The compounds of formula XII are also inhibitors of RNA-dependent RNA viral replication and in particular of HCV replication and are useful for the treatment of RNA-dependent RNA viral infection and in particular for the treatment of HCV infection.

Also encompassed within the present invention are pharmaceutical compositions containing the compounds alone or in combination with other agents active against RNA-dependent RNA virus and in particular against HCV.

DETAILED DESCRIPTION OF THE INVENTION

The present invention provides a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I which is of the stereochemical configuration:

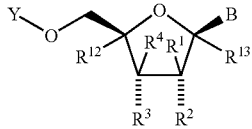

(I)

or a pharmaceutically acceptable salt thereof,
wherein B is selected from the group consisting of

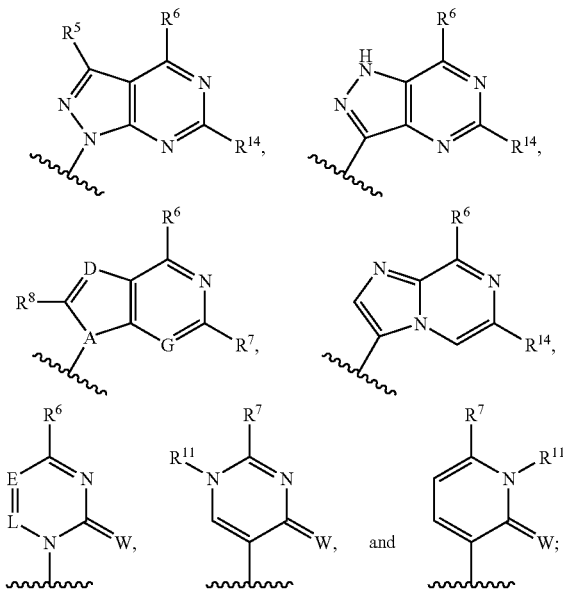

A, G, and L are each independently CH or N;
D is N, CH, C—CN, C—$NO_2$, C—$C_{1-3}$ alkyl, C—$NHCONH_2$, C—$CONR^{11}R^{11}$, C—$CSNR^{11}R^{11}$, C—$COOR^{11}$, C—C(=NH)$NH_2$, C-hydroxy, C—$C_{1-3}$ alkoxy, C-amino, C—$C_{1-4}$ alkylamino, C-di($C_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and $C_{1-3}$ alkoxy;
E is N or $CR^5$;
W is O or S;
Y is H, $C_{1-10}$ alkylcarbonyl, $P_3O_9H_4$, $P_2O_6H_3$, or P(O)$R^9R^{10}$;
$R^1$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^2$ and $R^3$ is hydroxy or $C_{1-4}$ alkoxy and the other of $R^2$ and $R^3$ is selected from the group consisting of
hydrogen,
hydroxy,
halogen,
$C_{1-4}$ alkyl, optionally substituted with 1 to 3 fluorine atoms,
$C_{1-10}$ alkoxy, optionally substituted with $C_{1-3}$ alkoxy or 1 to 3 fluorine atoms,
$C_{2-6}$ alkenyloxy,
$C_{1-4}$ alkylthio,
$C_{1-8}$ alkylcarbonyloxy,
aryloxycarbonyl,
azido,
amino,
$C_{1-4}$ alkylamino, and
di($C_{1-4}$ alkyl)amino; or
$R^2$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^1$ and $R^3$ is hydroxy or $C_{1-4}$ alkoxy and the other of $R^1$ and $R^3$ is selected from the group consisting of
hydrogen,
hydroxy,
halogen,
$C_{1-4}$ alkyl, optionally substituted with 1 to 3 fluorine atoms;
$C_{1-10}$ alkoxy, optionally substituted with hydroxy, $C_{1-3}$ alkoxy, carboxy, or 1 to 3 fluorine atoms,
$C_{2-6}$ alkenyloxy,
$C_{1-4}$ alkylthio,
$C_{1-8}$ alkylcarbonyloxy,
aryloxycarbonyl,
azido,
amino,
$C_{1-4}$ alkylamino, and
di($C_{1-4}$ alkyl)amino; or
$R^1$ and $R^2$ together with the carbon atom to which they are attached form a 3- to 6-membered saturated monocyclic ring system optionally containing a heteroatom, selected from O, S, and $NC_{0-4}$ alkyl;
$R^4$ and $R^6$ are each independently H, OH, SH, $NH_2$, $C_{1-4}$ alkylamino, di($C_{1-4}$ alkyl)amino, $C_{3-6}$ cycloalkylamino, halogen, $C_{1-4}$alkyl, $C_{1-4}$ alkoxy, or $CF_3$;
$R^5$ is H, $C_{1-6}$ alkyl, $C_{2-6}$ alkenyl, $C_{2-6}$ alkynyl, $C_{1-4}$ alkylamino, $CF_3$, or halogen;

$R^{14}$ is H, $CF_3$, $C_{1-4}$ alkyl, amino, $C_{1-4}$ alkylamino, $C_{3-6}$ cycloalkylamino, or di($C_{1-4}$ alkyl)amino;

$R^7$ is hydrogen, amino, $C_{1-4}$ alkylamino, $C_{3-6}$ cycloalkylamino, or di($C_{1-4}$ alkyl)amino;

each $R^{11}$ is independently H or $C_{1-6}$ alkyl;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^{12}$ and $R^{13}$ are each independently hydrogen, methyl, hydroxymethyl, or fluoromethyl; and $R^9$ and $R^{10}$ are each independently hydroxy, $OCH_2CH_2SC(=O)C_{1-4}$ alkyl, $OCH_2O(C=O)OC_{1-4}$ alkyl, $NHCHMeCO_2Me$, $OCH(C_{1-4}$ alkyl)$O(C=O)C_{1-4}$ alkyl,

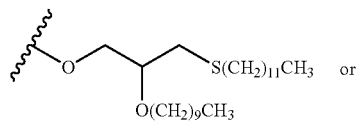 or

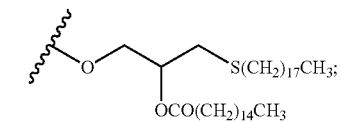

with the provisos that (a) when $R^1$ is hydrogen, one of $R^3$ and $R^4$ is hydrogen, and $R^2$ is fluoro, then the other of R3 and $R^4$ is not hydrogen, halogen, azido, trifluoromethyl, $C_{1-4}$ alkyl, amino, $C_{1-4}$ alkylamino, di($C_{1-4}$ alkyl)amino, or $C_{1-10}$ alkoxy; (b) when $R^1$ is hydrogen, one of $R^3$ and $R^4$ is hydrogen, and $R^2$ is halogen, hydroxy, $C_{1-6}$ alkoxy, or $C_{2-6}$ alkenyloxy, then the other of $R^3$ and $R^4$ is not hydrogen, fluoro, or azido; and (c) when $R^1$ and $R^3$ are hydrogen and $R^2$ is hydroxy, then $R^4$ is not hydroxy.

In one embodiment of the present invention is the method of inhibiting RNA-dependent RNA viral polymerase, inhibiting RNA-dependent viral replication, and/or treating RNA-dependent RNA viral infection with a compound of structural formula II which is of the stereochemical configuration:

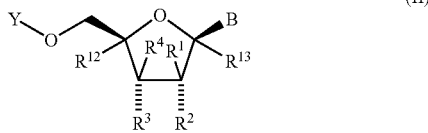 (II)

wherein B is

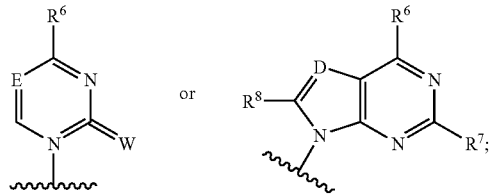

D is N, CH, C—CN, C—$NO_2$, C—$C_{1-3}$ alkyl, C—$NHCONH_2$, C—$CONR^{11}R^{11}$, C—$CSNR^{11}R^{11}$, C—$COOR^{11}$, C-hydroxy, C—$C_{1-3}$ alkoxy, C-amino, C—$C_{1-4}$ alkylamino, C-di($C_{1-4}$ alkyl)amino, C-halogen, C-(1,3-oxazol-2-yl), C-(1,3-thiazol-2-yl), or C-(imidazol-2-yl);

wherein alkyl is unsubstituted or substituted with one to three groups independently selected from halogen, amino, hydroxy, carboxy, and $C_{1-3}$ alkoxy;

E is N or C-$R^5$;

W is O or S;

Y is H, $C_{1-10}$ alkylcarbonyl, $P_3O_9H_4$, or $P(O)R^9R^{10}$;

$R^1$ is hydrogen, $CF_3$, or $C_{1-4}$ alkyl and one of $R^2$ and $R^3$ is OH or $C_{1-4}$ alkoxy and the other of $R^2$ and $R^3$ is selected from the group consisting of hydrogen, hydroxy, halogen, $C_{1-3}$ alkyl, trifluoromethyl, $C_{1-4}$ alkoxy, $C_{1-4}$ alkylthio, $C_{1-8}$ alkylcarbonyloxy, aryloxycarbonyl, azido, amino, $C_{1-4}$ alkylamino, and di($C_{1-4}$ alkyl)amino; or $R^2$ is hydrogen, $CF_3$, or $C_{1-4}$ alkyl and one of $R^1$ and $R^3$ is OH or $C_{1-4}$ alkoxy and the other of $R^1$ and $R^3$ is selected from the group consisting of hydrogen, hydroxy, fluoro, $C_{1-4}$ alkyl, trifluoromethyl, $C_{1-4}$ alkoxy, $C_{1-4}$ alkylthio, $C_{1-8}$ alkylcarbonyloxy, azido, amino, $C_{1-4}$ alkylamino, and di($C_{1-4}$ alkyl)amino; or $R^1$ and $R^2$ together with the carbon atom to which they are attached form a 3- to 6-membered saturated monocyclic ring system optionally containing a heteroatom selected from O, S, and N$C_{0-4}$ alkyl;

$R^4$ and $R^6$ are each independently H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^7$ is hydrogen, amino, $C_{1-4}$ alkylamino, $C_{3-6}$ cycloalkylamino, or di($C_{1-4}$ alkyl)amino;

each $R^{11}$ is independently H or $C_{1-6}$ alkyl;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl;

$R^{12}$ and $R^{13}$ are each independently hydrogen or methyl; and $R^9$ and $R^{10}$ are each independently hydroxy, $OCH_2CH_2SC(=O)C_{1-4}$ alkyl, or $OCH_2O(C=O)C_{1-4}$ alkyl;

with the provisos that (a) when $R^1$ is hydrogen, one of $R^3$ and $R^4$ is hydrogen, and $R^2$ is fluoro, then the other of $R^3$ and $R^4$ is not hydrogen, halogen, trifluoromethyl, $C_{1-4}$ alkyl, amino, $C_{1-4}$ alkylamino, di($C_{1-4}$ alkyl)amino, or $C_{1-4}$ alkoxy; (b) when $R^1$ is hydrogen, one of $R^3$ and $R^4$ is hydrogen, and $R^2$ is halogen, hydroxy, or $C_{1-4}$ alkoxy, then the other of $R^3$ and $R^4$ is not hydrogen, fluoro, or azido; and (c) when $R^1$ and $R^3$ are hydrogen and $R^2$ is hydroxy, then $R^4$ is not hydroxy.

In a second embodiment of the present invention is the method of inhibiting RNA-dependent RNA viral polymerase, inhibiting RNA-dependent RNA viral replication, and/or treating RNA-dependent RNA viral infection with a compound of structural formula III which is of the stereochemical configuration:

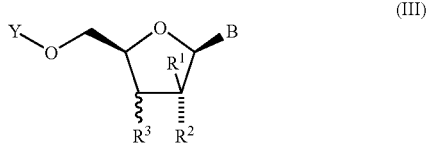

wherein B is

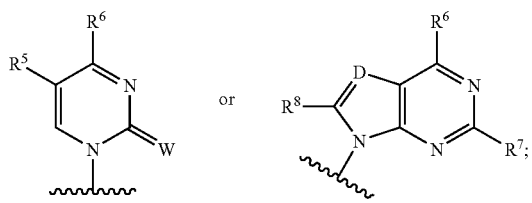

D is N, CH, C—CN, C—NO2, C—$C_{1-3}$ alkyl, C—NHCONH$_2$, C—CONR$^{11}$R$^{11}$, C—CSNR$^{11}$R$^{11}$, C—COOR$^{11}$, C-hydroxy, C—$C_{1-3}$ alkoxy, C-amino, C—$C_{1-4}$ alkylamino, C-di($C_{1-4}$ alkyl)amino, C-halogen, C-(1,3-6oxazol-2-yl), C-(1,3-thiazol-2-yl), or C-(imidazol-2-yl); wherein alkyl is unsubstituted or substituted with one to three groups independently selected from halogen, amino, hydroxy, carboxy, and $C_{1-3}$ alkoxy;

W is O or S;

Y is H, $C_{1-10}$ alkylcarbonyl, $P_3O_9H_4$, $P_2O_6H_3$, or P(O)R$^9$R$^{10}$;

R$^1$ is hydrogen, CF$_3$, or $C_{1-4}$ alkyl and one of R$^2$ and R$^3$ is OH or $C_{1-4}$ alkoxy and the other of R$^2$ and R$^3$ is selected from the group consisting of
hydrogen,
hydroxy,
fluoro,
$C_{1-3}$ alkyl,
trifluoromethyl,
$C_{1-8}$ alkylcarbonyloxy,
$C_{1-3}$ alkoxy, and
amino; or R$^2$ is hydrogen, CF$_3$, or $C_{1-4}$ alkyl and one of R$^1$ and R$^3$ is OH or $C_{1-4}$ alkoxy and the other of R$^1$ and R$^3$ is selected from the group consisting of
hydrogen,
hydroxy,
fluoro,
$C_{1-3}$ alkyl,
trifluoromethyl,
$C_{1-8}$ alkylcarbonyloxy,
$C_{1-3}$ alkoxy, and
amino; or R$^1$ and R$^2$ together with the carbon atom to which they are attached form a 3- to 6-membered saturated monocyclic ring system optionally containing a heteroatom selected from O, S, and NC$_{0-4}$ alkyl;

R$^6$ is H, OH, SH, NH$_2$, $C_{1-4}$ alkylamino, di($C_{1-4}$ alkyl) amino, $C_{3-6}$ cycloalkylamino, halogen, $C_{1-4}$ alkyl, $C_{1-4}$ alkoxy, or CF$_3$;

R$^5$ is H, $C_{1-6}$ alkyl, $C_{2-6}$ alkenyl, $C_{2-6}$ alkynyl, $C_{1-4}$ alkylamino, CF$_3$, or halogen;

R$^7$ is hydrogen, amino, $C_{1-4}$ alkylamino, $C_{3-6}$ cycloalkylamino, or di($C_{1-4}$ alkyl)amino;

each R$^{11}$ is independently H or $C_{1-6}$ alkyl;

R$^8$ is H, halogen, CN, carboxy, $C_{1-4}$ alkyloxycarbonyl, N$_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl; and R$^9$ and R$^{10}$ are each independently hydroxy, OCH$_2$CH$_2$SC(=O)t-butyl, or OCH$_2$O(C=O)iPr;

with the provisos that (a) when R$^1$ is hydrogen and R$^2$ is fluoro, then R$^3$ is not hydrogen, trifluoromethyl, fluoro, $C_{1-3}$ alkyl, amino, or $C_{1-3}$ alkoxy; (b) when R$^1$ is hydrogen and R$^2$ is fluoro, hydroxy, or $C_{1-3}$ alkoxy, then R$^3$ is not hydrogen or fluoro; and (c) when R$^1$ is hydrogen and R$^2$ is hydroxy, then R$^3$ is not β-hydroxy.

In a class of this embodiment is the method of inhibiting RNA-dependent RNA viral polymerase, inhibiting RNA-dependent RNA viral replication, and/or treating RNA-dependent RNA viral infection with a compound of structural formula III wherein B is

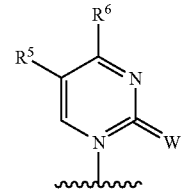

and W, Y, and the R substituents are as defined under this second embodiment.

In a second class of this embodiment is the method of inhibiting RNA-dependent RNA viral polymerase, inhibiting RNA-dependent RNA viral replication, and/or treating RNA-dependent RNA viral infection with a compound of structural formula m wherein B is

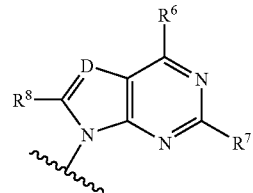

and Y, D, and the R substituents are as defined under this second embodiment.

In a third embodiment of the present-invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picornaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a fourth embodiment of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this classy the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a fifth embodiment of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Illustrative of the invention is a method for inhibiting RNA-dependent RNA viral polymerase, inhibiting RNA-dependent RNA viral replication, and/or treating RNA-dependent RNA viral infection wherein the compound is selected from:

2'-O-methyl-cytidine,
2'-C-methyl-cytidine,
3',5'-di-O-octanoyl-2'-O-methyl-cytidine,
3'-O-octanoyl-2'-O-methyl-cytidine,
2'-C-methyl-adenosine,
8-amino-2'-C-methyladenosine,
4-amino-7-(2-C-methyl-β-D-ribofuranosyl)-7H-pyrrolo[2,3-d]pyrimidine-5-carbonitrile,
4-amino-7-(2-C-methyl-β-D-ribofuranosyl)-7H-pyrrolo[2,3-d]pyrimidine-5-carboxamide,
3'-deoxy-3'-methyl-cytidine,
4-amino-7-(3-deoxy-3-methyl-β-D-ribofuranosyl)-7H-pyrrolo[2,3-d]pyrimidin-5-carboxamide,
3'-deoxy-adenosine,
4-amino-7-(3-deoxy-β-D-ribofuranosyl)-7H-pyrrolo[2,3-d]pyrimidine,
4-amino-7-(3-deoxy-β-D-ribofuranosyl)-7H-pyrrolo[2,3-d]pyrimidin-5-carboxamide,
3'-amino-3'-deoxyadenosine,
2-amino-3,4-dihydro-4-oxo-7-(β-D-ribofuranosyl)-7H-pyrrolo[2,3-d]pyrimidin-5-carboxamide,
4-amino-7-(β-D-ribofuranosyl)-7H-pyrrolo[2,3-d]pyrimidin-5-carboxamide,
2-amino-3,4-dihydro-4-oxo-7-(13-D-ribofuranosyl)-7H-pyrrolo[2,3-d]pyrimidin-5-carbonitrile,
2-amino-5-ethyl-7-(β-D-ribofuranosyl)-7H-pyrrolo[2,3-d]pyrimidin-4(3H)-one,
6-amino-1-(β-D-ribofuranosyl)-1H-imidazo[4,5-c]pyridin-4(5H)-one, 3'-deoxyguanosine,
2-amino-7-(3-deoxy-β-D-ribofuranosyl)-7H-pyrrolo[2,3-d]pyrimidin-4(3H)-one,
2'-O-methylguanosine,
2-amino-7-(2-O-methyl-β-D-ribofuranosyl)-7H-pyrrolo[2,3-d]pyrimidin-4(3H)-one,
2-amino-7-(2-O-methyl-β-D-ribofuranosyl)-5H-pyrrolo[3,2-d]pyrimidin-4(3H)-one,
7-(2-O-methyl-β-D-ribofuranosyl)-7H-pyrrolo[2,3-d]pyrimidine,
3'-deoxycytidine,
2-amino-5-methyl-7-(β-D-ribofuranosyl)-7H-pyrrolo[2,3-d]pyrimidin-4(3H)-one,
2-amino-3,4-dihydro-4-oxo-7-(2-O-methyl-β-D-ribofuranosyl)-7H-pyrrolo-[2,3-d]pyrimidin-5-carbonitrile,
2-amino-5-methyl-7-(2-O-methyl-β-D-ribofuranosyl)-7H-pyrrolo[2,3-d]pyrimidin-4(3H)-one,
8-azidoguanosine,
8-aminoguanosine,
8-bromoadenosine,
8-aminoadenosine,
8-bromoguanosine,
3'-deoxy-3'-fluorocytidine,
3'-deoxy-3'-fluoroguanosine,
4-amino-7-(3-deoxy-3-fluoro-β-D-ribofuranosyl)-7H-pyrrolo[2,3-d]pyrimidin-5-carboxamide,
2-amino-4-chloro-7-(2-O-methyl-β-D-ribofuranosyl)-7H-pyrrolo[2,3-d]pyrimidin-5-carbonitrile,
2-amino-4-chloro-5-ethyl-7-(2-O-methyl-β-D-ribofuranosyl)-7H-pyrrolo[2,3-d]pyrimidine,
2-amino-4-chloro-5-methyl-7-(2-O-methyl-β-D-ribofuranosyl)-7H-pyrrolo-[2,3-d]pyrimidine,
2-amino-7-(2-O-methyl-β-D-ribofuranosyl)-7H-pyrrolo[2,3-d]pyrimidin-4(3H)-thione,
2-amino-4-chloro-7-(2-O-methyl-β-D-ribofuranosyl)-7H-pyrrolo[2,3-d]pyrimidine,
2-amino-7-(β-D-ribofuranosyl)-7H-pyrrolo[2,3-d]pyrimidine,
2-amino-4-chloro-7-(β-D-ribofuranosyl)-7H-pyrrolo[2,3-d]pyrimidine,
2-amino-4-chloro-5-methyl-7-(β-D-ribofuranosyl)-7H-pyrrolo[2,3-]pyrimidine,
1-(β-D-ribofuranosyl)-1H-pyrazolo[3,4-d]pyrimidin-4(3H)-one,
4-amino-1-(β-D-ribofuranosyl)-1H-pyrazolo[3,4-d]pyrimidine,
2-amino-6-chloro-9-(β-D-ribofuranosyl)-9H-purine,
2-amino-4-chloro-7-(β-D-ribofuranosyl)-7H-pyrrolo[2,3-d]pyrimidin-5-carbonitrile,
6-methyl-9-(β-D-ribofuranosyl)-9H-purine,
2-amino-7-(2-deoxy-2-fluoro-β-D-arabinofuranosyl)-7H-pyrrolo[2,3-d]pyrimidin-4(3H)-one,
2-amino-4-chloro-7-(2-deoxy-2-fluoro-β-D-arabinofuranosyl)-7H-pyrrolo[2,3-d]pyrimidine,
2-amino-7-(β-D-arabinofuranosyl)-7H-pyrrolo[2,3-d]pyrimidin-4(3H)-one,
2-amino-7-(β-D-arabinofuranosyl)-3,4-dihydro-4-oxo-7H-pyrrolo[2,3-d]pyrimidin-5-carbonitrile,
2-amino-5-methyl-7-(β-D-arabinofuranosyl)-7H-pyrrolo[2,3-d]pyrimidin-4(3H)-one,
9-(β-D-arabinofuranosyl)-9H-purin-6(1H)-one,
1-(β-D-arabinofuranosyl)-1H-cytosine,
2-amino-4-chloro-5-methyl-7-(β-D-arabinofuranosyl)-7H-pyrrolo[2,3-d]pyrimidine,
3'-deoxy-3'-(fluoromethyl)-guanosine,
2'-amino-2'-deoxycytidine,
4-amino-7-(3-deoxy-β-D-ribofuranosyl)-7H-pyrrolo[2,3-d]pyrimidin-5-carbonitrile,
2'-methyladenosine,
4-amino-7-(2-O-methyl-β-D-ribofuranosyl)-7H-pyrrolo[2,3-d]pyrimidine,
3'-amino-3'-deoxy-2'-O-methyl-adenosine, 3'-deoxy-3'-methyl-uridine,
6-amino-1-(3-deoxy-β-D-ribofuranosyl)-1H-imidazo[4,5-c]pyridin-4(5H)-one,
6-amino-1-(3-deoxy-3-fluoro-β-D-ribofuranosyl)-1H-imidazo[4,5-c]pyridin-4(3H)-one,
3'-deoxy-3'-fluorouridine,
3'-deoxy-3'-fluoroadenosine,
2-amino-7-(2-deoxy-β-D-ribofuranosyl)-3,4-dihydro-4-oxo-7H-pyrrolo[2,3-d]-pyrimidin-5-carbonitrile,
3'-deoxy-5-methyl-uridine,
3'-deoxy-2'-O-(2-methoxyethyl)-3'-methyl-5-methyluridine,
2'-amino-2'-deoxy-uridine,
2-amino-9-(β-D-arabinofuranosyl)-9H-purin-6(1H)-one,
3'-deoxy-3'-methylguanosine,
2'-O-[4-(imidazolyl-1)butyl]guanosine,
2'-deoxy-2'-fluoroguanosine,
2'-deoxyguanosine,
2-amino-7-(2-deoxy-2-fluoro-β-D-ribofuranosyl)-7H-pyrrolo[2,3-d]pyrimidin-4(3H)-one,
2-amino-7-(3-deoxy-β-D-ribofuranosyl)-3,4-dihydro-4-oxo-7H-pyrrolo[2,3-d]pyrimidin-5-carbonitrile,
2-amino-5-iodo-7-(β-D-ribofuranosyl)-7H-pyrrolo[2,3-d]pyrimidin-4(3H)-one,
2-amino-7-(3-deoxy-3-methyl-β-D-ribofuranosyl)-7H-pyrrolo[2,3-d]pyrimidin-5-carbonitrile,
2-amino-7-(β-D-ribofuranosyl)-7H-pyrrolo[2,3-d]pyrimidin-4(3H)-one,
2-amino-7-(2-deoxy-β-D-ribofuranosyl)-7H-pyrrolo[2,3-d]pyrimidin-4(3H)-one,
2-amino-7-(3-deoxy-3-methyl-β-D-ribofuranosyl)-7H-pyrrolo[2,3-d]pyrimidin-4(3H)-one,
2-amino-7-(3-deoxy3-fluoro-β-D-ribofuranosyl)-7H-pyrrolo[2,3-d]pyrimidin-4(3H)-one,
6-amino-1-(2-O-methyl-β-D-ribofuranosyl)-1H-imidazo[4,5-c]pyridin-4(5H)-one,
6-amino-1-(2-deoxy-β-D-ribofuranosyl)-1H-imidazo[4,5-c]pyridin-4(5H)-one,
6-amino-1-(3-deoxy-3-methyl-β-D-ribofuranosyl)-1H-imidazo[4,5-c]pyridin-4(5H)-one,
6-amino-1-(2-deoxy-2-fluoro-β-D-ribofuranosyl)-1H-imidazo[4,5-c]pyridin-4(5H)-one,
6-amino-1-(β-D-arabinofuranosyl)-1H-imidazo[4,5-c]pyridin-4(5H)-one,
2'-O-[2-(N,N-diethylaminooxy)ethyl]-5-methyluridine,
5-ethynyl-2'-O-(2-methoxyethyl)-cytidine,
1-(2-C-methyl-β-D-arabinofuranosyl)uracil,
5-methyl-3'-deoxycytidine,
2-amino-2'-O-methyladenosine,
2'-deoxy-2'-fluoroadenosine,
3'-deoxy-3'-fluoroadenosine,
3'-deoxy-3'-methyladenosine,
2-amino-7-(2-deoxy-β-D-ribofuranosyl)-7H-pyrrolo[2,3-d]pyrimidine,
4-amino-7-(3-deoxy-3-fluoro-β-D-ribofuranosyl)-7H-pyrrolo[2,3-d]pyrimidin-5-carboxamide,
4-amino-7-(3-deoxy-β-D-ribofuranosyl)-7H-pyrrolo[2,3-d]pyrimidin-5-carboxamide,
4-amino-7-(2-O-methyl-β-D-ribofuranosyl)-7H-pyrrolo[2,3-d]pyrimidine,
4-amino-7-(β-D-arabinofuranosyl)-7H-pyrrolo[2,3-d]pyrimidine,
4-amino-1-(3-deoxy-3-fluoro-β-D-ribofuranosyl)-1H-imidazo[4,5-c]pyridine,
4-amino-7-(β-D-ribofuranosyl)-7H-pyrrolo[2,3-d]pyrimidine (tubercidin),
4,6-diamino-7-(13-D-ribofuranosyl)-7H-pyrrolo[2,3-d]pyrimidine,
2-amino-7-(3-deoxy-3-fluoro-β-D-ribofuranosyl)-7H-pyrrolo-[2,3-d]pyrimidin-5-carboxamide,
4-amino-1-(3-deoxy-β-D-ribofuranosyl)-1H-imidazo[4,5-c]pyridine,
4-amino-1-(3-deoxy-3-methyl-β-D-ribofuranosyl)-1H-imidazo[4,5-c]pyridine,
4-amino-1-(β-D-ribofuranosyl)-1H-imidazo[4,5-c]pyridine,
4-amino-1-(2-C-methyl-β-D-ribofuranosyl)-1H-pyrazolo[3,4-d]pyrimidine,
4-amino-7-(3-deoxy-3-fluoro-β-D-ribofuranosyl)-7H-pyrrolo[2,3-d]pyrimidine; and
the corresponding 5'-triphosphates, 5'-[bis(isopropyloxycarbonyloxymethyl)]monophosphates, 5'-mono-(S-$C_{1-4}$ alkanoyl-2-thioethyl)monophosphates, and 5'-bis-(S-$C_{1-4}$ alkanoyl-2-thioethyl)monophosphates thereof;
or a pharmaceutically acceptable salt thereof.

Further illustrative of the invention is a method for inhibiting RNA-dependent RNA viral polymerase, inhibiting RNA-dependent RNA viral replication, and/or treating RNA-dependent RNA viral infection wherein the compound is selected from:
2'-O-methyl-cytidine,
2'-C-methyl-cytidine,
3',5'-di-O-octanoyl-2'-O-methyl-cytidine,
3'-O-octanoyl-2'-O-methyl-cytidine,
4-amino-1-(β-D-ribofuranosyl)-1H-pyrazolo[3,4-d]pyrimidine,
4-amino-7-(2-C-methyl-β-D-ribofuranosyl)-7H-pyrrolo[2,3-d]pyrimidine-5-carbonitrile,
4-amino-7-(2-C-methyl-β-D-ribofuranosyl)-7H-pyrrolo[2,3-d]pyrimidine-5-carboxamide,
2'-C-methyladenosine,
8-amino-2'-C-methyladenosine,
3'-deoxy-3'-methyl-cytidine,
4-amino-7-(3-deoxy-3-methyl-β-D-ribofuranosyl)-7H-pyrrolo[2,3-d]pyrimidin-5-carboxamide,
3'-deoxyadenosine,
4-amino-7-(3-deoxy-β-D-ribofuranosyl)-7H-pyrrolo[2,3-d]pyrimidine,
4-amino-7-(3-deoxy-β-D-ribofuranosyl)-7H-pyrrolo[2,3-d]pyrimidin-5-carboxamide,
3'-amino-3'-deoxyadenosine,
2-amino-3,4-dihydro-4-oxo-7-(β-D-ribofuranosyl)-7H-pyrrolo[2,3-d]pyrimidin-5-carboxamide,
4-amino-7-(β-D-ribofuranosyl)-7H-pyrrolo[2,3-d]pyrimidin-5-carboxamide,
2-amino-3,4-dihydro-4-oxo-7-(β-D-ribofuranosyl)-7H-pyrrolo[2,3-d]pyrimidin-5-carbonitrile,
2-amino-5-ethyl-7-(β-D-ribofuranosyl)-7H-pyrrolo[2,3-d]pyrimidin-4(3H)-one,
6-amino-1-(β-D-ribofuranosyl)-1H-imidazo[4,5-c]pyridin-4(5H)-one,
3'-deoxyguanosine,
2-amino-7-(3-deoxy-β-D-ribofuranosyl)-7H-pyrrolo[2,3-d]pyrimidin-4(3H)-one,
2'-O-methylguanosine,
2-amino-7-(2-O-methyl-β-D-ribofuranosyl)-7H-pyrrolo[2,3-d]pyrimidin-4(3H)-one,
2-amino-7-(2-O-methyl-β-D-ribofuranosyl)-5H-pyrrolo[3,2-d]pyrimidin-4-(3H)-one,
7-(2-O-methyl-β-D-ribofuranosyl)-7H-pyrrolo[2,3-d]pyrimidine,
3'-deoxy-cytidine,
2-amino-5-methyl-7-(β-D-ribofuranosyl)-7H-pyrrolo[2,3-d]pyrimidin-4(3H)-one,
2-amino-3,4-dihydro-4-oxo-7-(2-O-methyl-β-D-ribofuranosyl)-7H-pyrrolo-[2,3-d]pyrimidine-5-carbonitrile, 2-amino-5-methyl-7-(2-O-methyl-β-D-ribofuranosyl)-7H-pyrrolo[2,3-d]pyrimidin-4(3H)-one,
8-azidoguanosine,
8-aminoguanosine,
8-bromoadenosine,
8-aminoadenosine,
8-bromoguanosine,
3'-deoxy-3'-fluorocytidine,
3'-deoxy-3'-fluoroguanosine,
4-amino-7-(3-deoxy-3-fluoro-β-D-ribofuranosyl)-7H-pyrrolo[2,3-d]-pyrimidin-5-carboxamide,
2-amino-4-chloro-7-(2-O-methyl-β-D-ribofuranosyl)-7H-pyrrolo[2,3-d]pyrimidin-5-carbonitrile,
2-amino-4-chloro-5-ethyl-7-(2-O-methyl-β-D-ribofuranosyl)-7H-pyrrolo[2,3-d]pyrimidine,
2-amino-4-chloro-5-methyl-7-(2-O-methyl-β-D-ribofuranosyl)-7H-pyrrolo-[2,3-d]pyrimidine,
2-amino-7-(β-D-ribofuranosyl)-7H-pyrrolo[2,3-d]pyrimidine,
2-amino-4-chloro-7-(β-D-ribofuranosyl)-7H-pyrrolo[2,3-d]pyrimidine,
2-amino-4-chloro-5-methyl-7-(β-D-ribofuranosyl)-7H-pyrrolo[2,3-d]pyrimidine,
2-amino-7-(2-deoxy-2-fluoro-β-D-arabinofuranosyl)-7H-pyrrolo[2,3-d]pyrimidin-4(3H)-one,
4-amino-1-(2-C-methyl-β-D-ribofuranosyl)-1H-pyrazolo[3,4-d]pyrimidine,
2-amino-7-(β-D-arabinofuranosyl)-7H-pyrrolo[2,3-d]pyrimidin-4(3H)-one, and
2-amino-7-(β-D-arabinofuranosyl)-3,4-dihydro-4-oxo-7H-pyrrolo[2,3-d]pyrimidin-5-carbonitrile; and
the corresponding 5'-triphosphates, 5'-[bis(isopropyloxycarbonyloxymethyl)]monophosphates, 5'-mono-(S-pivaloyl-2-thioethyl)monophosphates, and 5'-bis-(S-pivaloyl-2-thioethyl)monophosphates thereof;
or a pharmaceutically acceptable salt thereof.

Even further illustrative of the present invention is a method for inhibiting RNA-dependent RNA viral polymerase, inhibiting RNA-dependent RNA viral replication, and/or treating RNA-dependent RNA viral infection wherein the compound is selected from
2'-O-methyl-cytidine,
2'-C-methyl-cytidine,
3',5'-di-O-octanoyl-2'-O-methyl-cytidine,
3'-O-octanoyl-2'-O-methyl-cytidine,
4-amino-1-(β-D-ribofuranosyl)-1H-pyrazolo[3,4-d]pyrimidine,
4-amino-7-(2-C-methyl-β-D-ribofuranosyl)-7H-pyrrolo[2,3-d]pyrimidine-5-carbonitrile,
4-amino-7-(2-C-methyl-β-D-ribofuranosyl)-7H-pyrrolo[2,3-d]pyrimidine-5-carboxamide,
2'-C-methyladenosine,
8-amino-2'-C-methyladenosine,
8-bromoguanosine,
8-aminoguanosine,
8-aminoadenosine,
4-amino-7-(3-deoxy-β-D-ribofuranosyl)-7H-pyrrolo[2,3-d]pyrimidine,
2-amino-4-chloro-5-ethyl-7-(2-O-methyl-β-D-ribofuranosyl)-7H-pyrrolo[2,3-d]pyrimidine,
2-amino-3,4-dihydro-4-oxo-7-(β-D-ribofuranosyl)-7H-pyrrolo[2,3-d]pyrimidin-5-carboxamide,
4-amino-1-(2-C-methyl-β-D-ribofuranosyl)-1H-pyrazolo[3,4-d]pyrimidine,
2-amino-4-chloro-7-(2-O-methyl-β-D-ribofuranosyl)-7H-pyrrolo[2,3-d]pyrimidin-5-carbonitrile;
and the corresponding 5'-triphosphates thereof;

2'-O-methylcytidine-5'-[bis-(S-pivaloyl-2-thioethyl)phosphate],
2-amino-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate],
3'-deoxyguanosine-5'-[bis-(S-pivaloyl-2-thioethyl)phosphate], and
3'-deoxycytidine-5'-[bis-(S-pivaloyl-2-thioethyl)phosphate];
or a pharmaceutically acceptable salt thereof.

Yet further illustrative of the invention is a method for inhibiting RNA-dependent RNA viral polymerase, inhibiting RNA-dependent RNA viral replication, and/or treating RNA-dependent RNA viral infection wherein the compound is selected from:
2'-O-methylcytidine,
2'-C-methylcytidine,
3',5'-di-O-octanoyl-2'-O-methyl-cytidine,
3'-O-octanoyl-2'-O-methyl-cytidine,
4-amino-7-(2-C-methyl-β-D-ribofuranosyl)-7H-pyrrolo[2,3-d]pyrimidine-5-carbonitrile,
4-amino-7-(2-C-methyl-β-D-ribofuranosyl)-7H-pyrrolo[2,3-d]pyrimidine-5-carboxamide,
2'-C-methyladenosine,
8-amino-2'-C-methyladenosine,
2'-O-methylcytidine-5'-[bis-(S-pivaloyl-2-thioethyl)phosphate],
2-amino-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate], and
3'-deoxycytidine-5'-[bis-(S-pivaloyl-2-thioethyl)phosphate];
or a pharmaceutically acceptable salt thereof.

The present invention also provides novel compounds of structural formula IV of the indicated stereochemical configuration which are useful as inhibitors of RNA-dependent RNA viral polymerase:

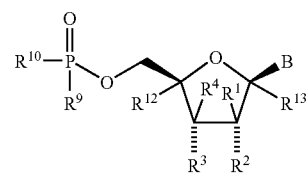

(IV)

wherein B is selected from the group consisting of

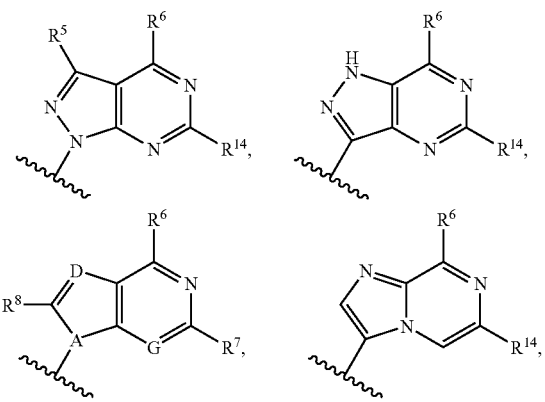

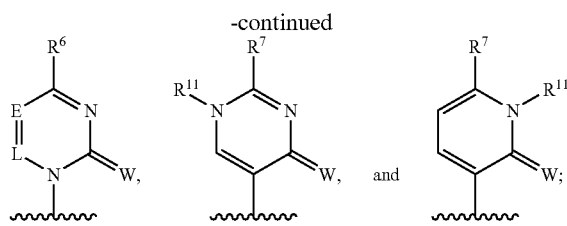

A, G, and L are each independently CH or N;

D is N, CH, C—CN, C—NO$_2$, C—C$_{1-3}$ alkyl, C—NHCONH$_2$, C—CONR$^{11}$R$^{11}$, C—CSNR$^{11}$R$^{11}$, C—COOR$^{11}$, C-hydroxy, C—C$_{1-3}$ alkoxy, C-amino, C—C$_{1-4}$ alkylamino, C-di(C$_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;

E is N or CR$^5$;

W is O or S;

R$^1$ is hydrogen, C$_{2-4}$ alkenyl, C$_{2-4}$ alkynyl, or C$_{1-4}$ alkyl optionally substituted with amino, hydroxy, or 1 to 3 fluorine atoms and one of R$^2$ and R$^3$ is hydroxy or C$_{1-4}$ alkoxy and the other of R$^2$ and R$^3$ is selected from the group consisting of hydrogen,
hydroxy,
halogen,
C$_{1-4}$ alkyl, optionally substituted with 1 to 3 fluorine atoms,
C$_{1-10}$ alkoxy, optionally substituted with C$_{1-3}$ alkoxy of 1 to 3 fluorine atoms,
C$_{2-6}$ alkenyloxy,
C$_{1-4}$ alkylthio,
C$_{1-8}$ alkylcarbonyloxy,
aryloxycarbonyl,
azido,
amino,
C$_{1-4}$ alkylamino, and
di(C$_{1-4}$ alkyl)amino; or R$^2$ is hydrogen, C$_{2-4}$ alkenyl, C$_{2-4}$ alkynyl, or C$_{1-4}$ alkyl optionally substituted with amino, hydroxy, or 1 to 3 fluorine atoms and one of R$^1$ and R$^3$ is hydroxy or C$_{1-4}$ alkoxy and the other of R$^1$ and R$^3$ is selected from the group consisting of hydrogen,
hydroxy,
halogen,
C$_{1-4}$ alkyl, optionally substituted with 1 to 3 fluorine atoms,
C$_{1-10}$ alkoxy, optionally substituted with hydroxy, C$_{1-3}$ alkoxy, carboxy, or 1 to 3 fluorine atoms,
C$_{2-6}$ alkenyloxy,
C$_{1-4}$ alkylthio,
C$_{1-8}$ alkylcarbonyloxy,
aryloxycarbonyl,
azido,
amino,
C$_{1-4}$ alkylamino, and
di(C$_{1-4}$ alkyl)amino; or R$^1$ and R$^2$ together with the carbon atom to which they are attached form a 3- to 6-membered saturated monocyclic ring system optionally containing a heteroatom selected from O, S, and NC$_{0-4}$ alkyl;

R$^4$ and R$^6$ are each independently H, OH, SH, NH$_2$, C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, or CF$_3$;

R$^5$ is H, C$_{1-6}$ alkyl, C$_{2-6}$ alkenyl, C$_{2-6}$ alkynyl, C$_{1-4}$ alkylamino, CF$_3$, or halogen;

R$^{14}$ is H, CF$_3$, C$_{1-4}$ alkyl, amino, C$_{1-4}$ alkylamino, C$_{3-6}$ cycloalkylamino, or di(C$_{1-4}$ alkyl)amino;

R$^7$ is hydrogen, amino, C$_{1-4}$ alkylamino, C$_{3-6}$ cycloalkylamino, or di(C$_{1-4}$ alkyl)amino;

each R$^{11}$ is independently H or C$_{1-6}$ alkyl;

R$^8$ is H, halogen, CN, carboxy, C$_{1-4}$ alkyloxycarbonyl, N$_3$, amino, C$_{1-4}$ alkylamino, di(C$_{1-4}$ alkyl)amino, hydroxy, C$_{1-6}$ alkoxy, C$_{1-6}$ alkylthio, C$_{1-6}$ alkylsulfonyl, or (C$_{1-4}$ alkyl)$_{0-2}$ aminomethyl;

R$^{12}$ and R$^{13}$ are each independently hydrogen or methyl; and

R$^9$ and R$^{10}$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl,

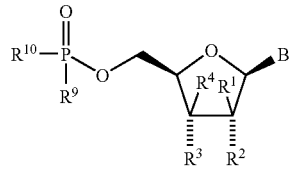

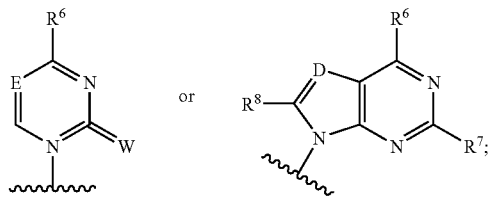

provided that at least one of R$^9$ and R$^{10}$ is not hydroxy.

The compounds of formula IV are also inhibitors of RNA-dependent RNA viral replication and are useful for the treatment of RNA-dependent RNA viral infection.

In one embodiment, there are provided novel compounds of structural formula V which are of the stereochemical configuration:

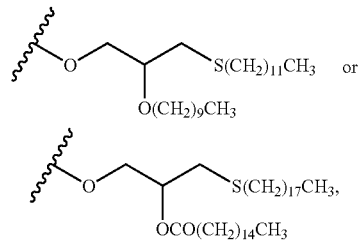

wherein B is

D is N, CH, C—CN, C—NO$_2$, C—C$_{1-3}$ alkyl, C—NHCONH$_2$, C—CONR$^{11}$R$^{11}$, C—CSNR$^{11}$R$^{11}$, C—COOR$^{11}$, C-hydroxy, C—C$_{1-3}$ alkoxy, C-amino, C—C$_{1-4}$ alkylamino, C-di(C$_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and C$_{1-3}$ alkoxy;

W is O or S;

E is N or C-$R^5$;

$R^1$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^2$ and $R^3$ is hydroxy or $C_{1-4}$ alkoxy and the other of $R^2$ and $R^3$ is selected from the group consisting of hydrogen, hydroxy, halogen, $C_{1-3}$ alkyl, trifluoromethyl, $C_{1-4}$ alkoxy, $C_{1-4}$ alkylthio, $C_{1-8}$ alkylcarbonyloxy, aryloxycarbonyl, azido, amino, $C_{1-4}$ alkylamino, and di($C_{1-4}$ alkyl)amino, or, $R^2$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^1$ and $R^3$ is hydroxy or $C_{1-4}$ alkoxy and the other of $R^1$ and $R^3$ is selected from the group consisting of hydrogen, hydroxy, fluoro, $C_{1-4}$ alkyl, trifluoromethyl, $C_{1-4}$ alkoxy, $C_{1-4}$ alkylthio, $C_{1-8}$ alkylcarbonyloxy, azido, amino, $C_{1-4}$ alkylamino, and di($C_{1-4}$ alkyl)amino; or $R^1$ and $R^2$ together with the carbon atom to which they are attached form a 3- to 6-membered saturated monocyclic ring system optionally containing a heteroatom selected from O, S, and $NC_{0-4}$ alkyl;

$R^4$ and $R^6$ are each independently H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^7$ is hydrogen, amino, $C_{1-4}$ alkylamino, $C_{3-6}$ cycloalkylamino, or di($C_{1-4}$ alkyl)amino;

each $R^{11}$ is independently H or $C_{1-6}$ alkyl;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl; and $R^9$ and $R^{10}$ are each independently hydroxy, $OCH_2CH_2SC(=O)C_{1-4}$ alkyl, or $OCH_2O(C=O)C_{1-4}$ alkyl, provided that at least one of $R^9$ and $R^{10}$ is not hydroxy.

In a second embodiment, there are provided novel compounds of structural formula VI:

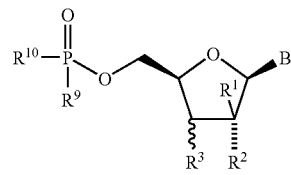

(VI)

wherein B is

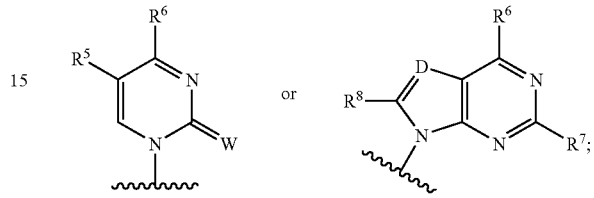

or

D is N, CH, C—CN, C—$NO_2$, C—$C_{1-3}$ alkyl, C—$NHCONH_2$, C—$CONR^{11}R^{11}$, C—$CSNR^{11}R^{11}$, C—$COOR^{11}$, C-hydroxy, C—$C_{1-3}$ alkoxy, C-amino, C—$C_{1-4}$ alkylamino, C-di($C_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and $C_{1-3}$ alkoxy;

W is O or S;

$R^1$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^2$ and $R^3$ is hydroxy or $C_{1-4}$ alkoxy and the other of $R^2$ and $R^3$ is selected from the group consisting of hydrogen, hydroxy, fluoro, $C_{1-3}$ alkyl, trifluoromethyl, $C_{1-3}$ alkoxy, $C_{1-8}$ alkylcarbonyloxy, and amino; or $R^2$ is hydrogen, $C_{2-4}$ alkenyl, $C_{2-4}$ alkynyl, or $C_{1-4}$ alkyl optionally substituted with amino, hydroxy, or 1 to 3 fluorine atoms and one of $R^1$ and $R^3$ is hydroxy or $C_{1-4}$ alkoxy and the other of $R^1$ and $R^3$ is selected from the group consisting of hydrogen, hydroxy, fluoro, $C_{1-3}$ alkyl, trifluoromethyl, $C_{1-3}$ alkoxy, $C_{1-8}$ alkylcarbonyloxy, and amino; or $R^1$ and $R^2$ together with the carbon atom to which they are attached form a 3- to 6-membered saturated monocyclic ring system optionally containing a heteroatom selected from O, S, and $NC_{0-4}$ alkyl, $R^6$ is H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$R^5$ is H, $C_{1-6}$ alkyl, $C_{2-6}$ alkenyl, $C_{2-6}$ alkynyl, $C_{1-4}$ alkylamino, $CF_3$, or halogen;

$R^7$ is hydrogen, amino, $C_{1-4}$ alkylamino, $C_{3-6}$ cycloalkylamino, or di($C_{1-4}$ alkyl)amino;

each $R^{11}$ is independently H or $C_{1-6}$ alkyl;

$R^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, or ($C_{1-4}$ alkyl)$_{0-2}$ aminomethyl; and $R^9$ and $R^{10}$ are each independently hydroxy, OCH$_2$CH$_2$SC(=O)t-butyl, or OCH$_2$O(C=O)iPr, provided that at least one of $R^9$ and $R^{10}$ is not hydroxy.

Illustrative of the novel compounds of structural formula VI of the present invention are the following:

2'-O-methylcytidine-5'-[bis-(S-pivaloyl-2-thioethyl) phosphate], 2-amino-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate], 3'-deoxyguanosine-5'-[bis-(S-pivaloyl-2-thioethyl) phosphate], 2'-O-methylguanosine-5'-[bis-(S-acetyl-2-thioethyl) phosphate], 2'-O-methylguanosine-5'-[bis-(S-pivaloyl-2-thioethyl) phosphate], 8-bromo-2'-O-methylguanosine-5'-[bis-(S-pivaloyl-2-thioethyl)phosphate], 2-amino-3,4-dihydro-7-(2-O-methyl-β-D-ribofuranosyl)4-oxo-7H-pyrrolo[2,3-d]pyrimidine-5'-[bis-(S-pivaloyl-2-thioethyl)phosphate], 2-amino-5-bromo-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate], 5-bromo-2'-O-methylcytidine-5'-[bis-(S-pivaloyl-2-thioethyl)phosphate], 3-deoxycytidine-5'-[bis-(S-pivaloyl-2-thioethyl)phosphate], and 2'-O-methylcytidine-5'-[bis(isopropyloxycarbonyloxymethyl)]phosphate.

The present invention further provides novel compounds of structural formula XII of the indicated stereochemical configuration or a pharmaceutically acceptable salt thereof which are useful as inhibitors of RNA-dependent RNA viral polymerase:

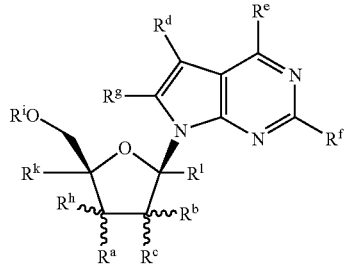

(XII)

wherein $R^a$ and $R^h$ are each independently selected from the group consisting of hydrogen, cyano, azido, halogen, hydroxy, mercapto, amino, $C_{1-4}$ alkoxy, $C_{2-4}$ alkenyl, $C_{2-4}$ alkynyl, and $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^b$ is $C_{2-4}$ alkenyl, $C_{2-4}$ alkynyl, or $C_{1-4}$ alkyl, wherein alkyl is unsubstituted or substituted with hydroxy, amino, $C_{1-4}$ alkoxy, $C_{1-4}$ alkylthio, or one to three fluorine atoms;

$R^c$ is hydrogen, fluorine, hydroxy, mercapto, $C_{1-4}$ alkoxy, or $C_{1-4}$ alkyl; or $R^b$ and $R^c$ together with the carbon atom to which they are attached form a 3- to 6-membered saturated monocyclic ring system optionally containing a heteroatom selected from O, S, and NC$_{0-4}$ alkyl;

$R^d$ is hydrogen, cyano, nitro, $C_{1-3}$ alkyl, NHCONH$_2$, CONRjRj, CSNRjRj, COORj, C(=NH)NH$_2$, hydroxy, $C_{1-3}$ alkoxy, amino, $C_{1-4}$ alkylamino, di($C_{1-4}$ alkyl)amino, halogen, (1,3-oxazol-2-yl), (1,3-thiazol-2-yl), or (imidazol-2-yl); wherein alkyl is unsubstituted or substituted with one to three groups independently selected from halogen, amino, hydroxy, carboxy, and $C_{1-3}$ alkoxy;

$R^e$ and $R^f$ are each independently hydrogen, hydroxy, halogen, $C_{1-4}$ alkoxy, amino, $C_{1-4}$ alkylamino, di($C_{1-4}$ alkyl)amino, $C_{3-6}$ cycloalkylamino, di($C_{3-6}$ cycloalkyl)amino, or $C_{4-6}$ cycloheteroalkyl, unsubstituted or substituted with one to two groups independently selected from halogen, hydroxy, amino, $C_{1-4}$ alkyl, and $C_{1-4}$ alkoxy;

$R^g$ is hydrogen, $C_{1-4}$ alkyl, $C_{2-4}$ alkynyl, halogen, cyano, carboxy, $C_{1-4}$ alkyloxycarbonyl, azido, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, ($C_{1-4}$ alkyl)$_{0-2}$ aminomethyl, or $C_{4-6}$ cycloheteroalkyl, unsubstituted or substituted with one to two groups independently selected from halogen, hydroxy, amino, $C_{1-4}$ alkyl, and $C_{1-4}$ alkoxy;

$R^i$ is hydrogen, $C_{1-10}$ alkylcarbonyl, $P_3O_9H_4$, $P_2O_6H_3$, or $P(O)R^mR^n$;

each $R^j$ is independently hydrogen or $C_{1-6}$ alkyl;

$R^k$ and $R^l$ are each independently hydrogen, methyl, hydroxymethyl, or fluoromethyl; and $R^m$ and $R^n$ are each independently hydroxy, OCH$_2$CH$_2$SC(=O)C$_{1-4}$ alkyl, OCH$_2$O(C=O)OC$_{1-4}$ alkyl, NHCHMeCO$_2$Me, OCH(C$_{1-4}$ alkyl)O(C=O)C$_{1-4}$ alkyl,

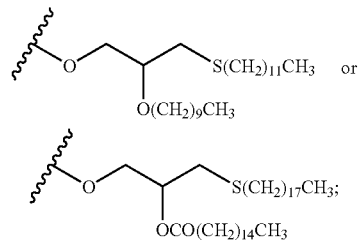

with the proviso that when $R^a$ and $R^c$ are α-hydroxy, $R^e$ is amino, $R^b$ is β-methyl and $R^h$ is hydrogen or $R^h$ is β-methyl and $R^b$ is hydrogen, and $R^f$, $R^g$, $R^i$, $R^k$, and $R^l$ are hydrogen, then $R^d$ is not cyano or CONH$_2$.

The compounds of formula XII are also inhibitors of RNA-dependent RNA viral replication and are useful for the treatment of RNA-dependent RNA viral infection.

In one embodiment of the novel compounds of structural formula XII are the compounds of structural formula XIII:

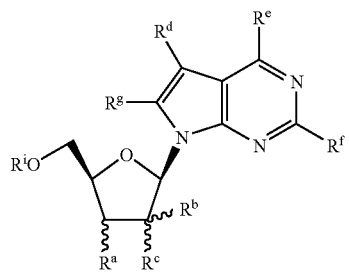

XIII wherein $R^a$ is hydrogen, halogen, hydroxy, amino, or $C_{1-3}$ alkoxy;

$R^b$ is $C_{1-3}$ alkyl, wherein alkyl is unsubstituted or substituted with hydroxy, amino, $C_{1-3}$ alkoxy, $C_{1-3}$ alkylthio, or one to three fluorine atoms;

$R^c$ is hydroxy, fluoro, or $C_{1-4}$ alkoxy;

$R^d$ is hydrogen, cyano, methyl, halogen, or $CONH_2$;

$R^g$ is hydrogen, amino, or $C_{1-4}$ alkylamino;

$R^i$ is hydrogen, $P_3O_9H_4$, $P_2O_6H_3$, or $PO_3H_2$; and $R^e$ and $R^f$ are each independently hydrogen, hydroxy, halogen, amino, $C_{1-4}$ alkylamino, di($C_{1-4}$ alkyl)amino, or $C_{3-6}$ cycloalkylamino;

with the proviso that when $R^a$ and $R^c$ are α-hydroxy, $R^e$ is amino, $R^b$ is methyl, and $R^f$, $R^g$, and $R^i$ are hydrogen, then $R^d$ is not cyano or $CONH_2$.

In a second embodiment of the compounds of structural formula XII are the compounds of structural formula XIII wherein:

$R^b$ is methyl, fluoromethyl, hydroxymethyl, difluoromethyl, trifluoromethyl, or aminomethyl;

$R^c$ is hydroxy, fluoro, or methoxy;

$R^a$ is hydrogen, fluoro, hydroxy, amino, or methoxy;

$R^i$ is hydrogen or $P_3O_9H_4$;

$R^g$ is hydrogen or amino;

$R^d$ is hydrogen, cyano, methyl, halogen, or $CONH_2$; and $R^e$ and $R^f$ are each independently hydrogen, fluoro, hydroxy, or amino;

with the proviso that when $R^b$ is β-methyl, $R^a$ and $R^c$ are α-hydroxy, $R^e$ is amino, and $R^f$, $R^g$, and $R^i$ are hydrogen, then $R^d$ is not cyano or $CONH_2$.

Illustrative of the novel compounds of the present invention of structural formula XIII which are useful as inhibitors of RNA-dependent RNA viral polymerase are the following:

4-amino-7-(2-C-methyl-β-D-arabinofuranosyl)-7H-pyrrolo[2,3-d]pyrimidine, 4-amino-7-(2-C-methyl-β-D-ribofuranosyl)-7H-pyrrolo[2,3-d]pyrimidine, 4-methylamino-7-(2-C-methyl-β-D-ribofuranosyl)-7H-pyrrolo[2,3-d]pyrimidine, 4-dimethylamino-7-(2-C-methyl-β-D-ribofuranosyl)-7H-pyrrolo[2,3-d]pyrimidine, 4-cyclopropylamino-7-(2-C-methyl-β-D-ribofuranosyl)-7H-pyrrolo[2,3-d]pyrimidine, 4-amino-7-(2-C-vinyl-β-D-ribofuranosyl)-7H-pyrrolo[2,3-d]pyrimidine, 4-amino-7-(2-C-hydroxymethyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-7-(2-C-methyl-β-D-ribofuranosyl)-7H-pyrrolo[2,3-d]pyrimidine-5-carboxylic acid, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine, 4-amino-5-fluoro-7-(2-C-methyl-β-D-ribofuranosyl)-7H-pyrrolo[2,3-d]pyrimidine, 2,4-diamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidine, 2-amino-4-cyclopropylamino-7-(2-C-methyl-β-D-ribofuranosyl)-7H-pyrrolo[2,3-d]pyrimidine, 2-amino-7-(2-C-methyl-β-D-ribofuranosyl)-7H-pyrrolo[2,3-d]pyrimidin-4(3H)-one, 4-amino-7-(2-C-ethyl-β-D-ribofuranosyl)-7H-pyrrolo[2,3-d]pyrimidine, 4-amino-7-(2-C,2-O-dimethyl-β-D-ribofuranosyl)-7H-pyrrolo[2,3-d]pyrimidine, 7-(2-C-methyl-β-D-ribofuranosyl)-7H-pyrrolo[2,3-d]pyrimidin-4(3H)-one, 2-amino-5-methyl-7-(2-C,2-O-dimethyl-β-D-ribofuranosyl)-7H-pyrrolo[2,3-d]pyrimidin-4(3H)-one, 4-amino-7-(3-deoxy-2-C-methyl-β-D-ribofuranosyl)-7H-pyrrolo[2,3-d]pyrimidine, 4-amino-7-(3-deoxy-2-C-methyl-β-D-arabinofuranosyl)-7H-pyrrolo[2,3-d]pyrimidine, 4-amino-2-fluoro-7-(2-C-methyl-β-D-ribofuranosyl)-7H-pyrrolo[2,3-d]pyrimidine, 4-amino-7-(3-C-methyl-β-D-ribofuranosyl)-7H-pyrrolo[2,3-d]pyrimidine, 4-amino-7-(3-C-methyl-β-D-ribofuranosyl)-7H-pyrrolo[2,3-d]pyrimidine, 4-amino-7-(2,4-di-C-methyl-β-D-ribofuranosyl)-7H-pyrrolo[2,3-d]pyrimidine, and 4-amino-7-(3-deoxy-3-fluoro-2-C-methyl-β-D-ribofuranosyl)-7H-pyrrolo[2,3-d]pyrimidine;

and the corresponding 5'-triphosphates;

or a pharmaceutically acceptable salt thereof.

Further illustrative of the novel compounds of the present invention of structural formula XIII which are useful as inhibitors of RNA-dependent RNA viral polymerase are the following:

4-amino-7-(2-C-methyl-β-D-arabinofuranosyl)-7H-pyrrolo[2,3-d]pyrimidine, 4-amino-7-(2-C-methyl-β-D-ribofuranosyl)-7H-pyrrolo[2,3-d]pyrimidine, 4-amino-7-(2-C-fluoromethyl-β-D-ribofuranosyl)-7H-pyrrolo[2,3-d]pyrimidine, 4-amino-5-methyl-7-(2-C-methyl-β-D-ribofuranosyl)-7H-pyrrolo[2,3-d]pyrimidine, 4-amino-5-bromo-7-(2-C-methyl-β-D-ribofuranosyl)-7H-pyrrolo[2,3-d]pyrimidine, 4-amino-5-chloro-7-(2-C-methyl-β-D-ribofuranosyl)-7H-pyrrolo[2,3-d]pyrimidine, 4-amino-5-fluoro-7-(2-C-methyl-β-D-ribofuranosyl)-7H-pyrrolo[2,3-d]pyrimidine, and 4-amino-7-(2-C,2-O-dimethyl-β-D-ribofuranosyl)-7H-pyrrolo[2,3-d]pyrimidine, and the corresponding 5'-triphosphates;

or a pharmaceutically acceptable salt thereof.

Further structurally novel nucleoside derivatives of the present invention which are useful as inhibitors of RNA-dependent RNA viral polymerase are the following:

3'-deoxy-3'-methyl-cytidine,

3',5-di-O-octanoyl-2'-O-methyl-cytidine,

3'-O-octanoyl-2'-O-methyl-cytidine, 4-amino-7-(3-deoxy-3-methyl-β-D-ribofuranosyl)-7H-pyrrolo[2,3-d]pyrimidin-5-carboxamide, 2-amino-5-ethyl-7-(β-D-ribofuranosyl)-7H-pyrrolo[2,3-d]pyrimidin-4(3H)-one, 2-amino-7-(3-deoxy-β-D-ribofuranosyl)-7H-pyrrolo[2,3-d]pyrimidin-4(3H)-one, 2-amino-7-(2-O-methyl-β-D-ribofuranosyl)-7H-pyrrolo[2,3-d]pyrimidin-4(3H)-one, -2-amino-7-(2-O-methyl-β-D-ribofuranosyl)-5H-pyrrolo[3,2-d]pyrimidin-4(3H)-one, 7-(2-O-methyl-β-D-ribofuranosyl)-7H-pyrrolo[2,3-d]pyrimidine, 2-amino-3,4-dihydro-4-oxo-7-(2-O-methyl-β-D-ribofuranosyl)-7H-pyrrolo-[2,3-d]pyrimidin-5-carbonitrile, 2-amino-5-methyl-7-(2-O-methyl-β-D-ribofuranosyl)-7H-pyrrolo[2,3-d]pyrimidin-4(3H)-one, 2-amino-4-chloro-7-(2-O-methyl-β-D-ribofuranosyl)-7H-pyrrolo[2,3-d]pyrimidin-5-carbonitrile,
2-amino-4-chloro-5-ethyl-7-(2-O-methyl-β-D-ribofuranosyl)-7H-pyrrolo[2,3-d]pyrimidine,
2-amino-4-chloro-5-methyl-7-(2-O-methyl-β-D-ribofuranosyl)-7H-pyrrolo[2,3-d]pyrimidine,
2-amino-7-(2-O-methyl-β-D-ribofuranosyl)-7H-pyrrolo[2,3-d]pyridin-4(3H)-thione,
2-amino-4-chloro-7-(2-O-methyl-β-D-ribofuranosyl)-7H-pyrrolo[2,3-d]pyrimidine,
2-amino-4-chloro-5-methyl-7-(β-D-ribofuranosyl)-7H-pyrrolo[2,3-d]pyrimidine,
2-amino-7-(2-deoxy-2-fluoro-β-D-arabinofuranosyl)-7H-pyrrolo[2,3-d]pyrimidin-4(3H)-one,
2-amino-4-chloro-7-(2-deoxy-2-fluoro-β-D-arabinofuranosyl)-7H-pyrrolo[2,3-d]pyrimidine,
2-amino-7-(β-D-arabinofuranosyl)-3,4-dihydro-4-oxo-7H-pyrrolo[2,3-d]pyrimidin-5-carbonitrile,
9-(β-D-arabinofuranosyl)-9H-purin-6(1H)-one,
3'-amino-3'-deoxy-2'-O-methyl-adenosine,
8-amino-2'-C-methyladenosine,
6-amino-1-(3-deoxy-β-D-ribofuranosyl)-1H-imidazo[4,5-c]pyridin-4(5H)-one,
6-amino-1-(3-deoxy-3-fluoro-β-D-ribofuranosyl)-1H-imidazo[4,5-c]pyridin-4(3H)-one,
3'-deoxy-2'-O-(2-methoxyethyl)-3'-methyl-5-methyluridine,
2-amino-7-(3-deoxy-β-D-ribofuranosyl)-3,4-dihydro-4oxo-7H-pyrrolo[2,3-d]pyrimidin-5-carbonitrile,
2-amino-7-(3-deoxy-3-methyl-β-D-ribofuranosyl)-7H-pyrrolo[2,3-d]pyridin-5-carbonitrile,
2-amino-7-(3-deoxy-3-methyl-β-D-ribofuranosyl)-7H-pyrrolo[2,3-d]pyridin-4(3H)-one,
2-amino-7-(3-deoxy-3-fluoro-β-D-ribofuranosyl)-7H-pyrrolo[2,3-d]pyrimidin-4(3H)-one,
6-amino-1-(2-O-methyl-β-D-ribofuranosyl)-1H-imidazo[4,5-c]pyridin-4(5H)-one,
6-amino-1-(3-deoxy-3-methyl-β-D-ribofuranosyl)-1H-imidazo[4,5-c]pyridin-4(5H)-one,
6-amino-1-(2-deoxy-2-fluoro-β-D-ribofuranosyl)-1H-imidazo[4,5-c]pyridin-4(5H)-one,
1-(2-C-methyl-β-D-arabinofuranosyl)uracil,
4-amino-1-(3-deoxy-3-fluoro-β-D-ribofuranosyl)-1H-imidazo[4,5-c]pyridine,
2-amino-7-(-3-deoxy-3-fluoro-β-D-ribofuranosyl)-7H-pyrrolo-[2,3-d]pyrimidin-5-carboxamide,
4-amino-1-(2-C-methyl-β-D-ribofuranosyl)-1H-pyrazolo[3,4-d]pyrimidine,
4-amino-1-(3-deoxy-β-D-ribofuranosyl)-1H-imidazo[4,5-c]pyridine, and
4-amino-1-(3-deoxy-3-methyl-β-D-ribofuranosyl)-1H-imidazo[4,5-c]pyridine;
and the corresponding 5'-triphosphates;
or a pharmaceutically acceptable salt thereof.

In a further embodiment the novel compounds of the present invention are useful as inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picornaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkynes of two to six total carbon atoms, or any number within this range (e.g., ethynyl, propynyl, butynyl, pentynyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "cycloheteroalkyl" is intended to include non-aromatic heterocycles containing one or two heteroatoms selected from nitrogen, oxygen and sulfur. Examples of 4–6-membered cycloheteroalkyl include azetidinyl, pyrrolidinyl, piperidinyl, morpholinyl, thiamorpholinyl, imidazolidinyl, tetrahydrofuranyl, tetrahydropyranyl, tetrahydrothiophenyl, piperazinyl, and the like.

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The term "aryl" includes both phenyl, naphthyl, and pyridyl. The aryl group is optionally substituted with one to three groups independently selected from $C_{1-4}$ alkyl, halogen, cyano, nitro, trifluoromethyl, $C_{1-4}$ alkoxy, and $C_{1-4}$ alkylthio.

The term "halogen" is intended to include the halogen atoms fluorine, chlorine, bromine and iodine.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "5'-triphosphate" refers to a triphosphoric acid ester derivative of the 5'-hydroxyl group of a nucleoside compound of the present invention having the following general structural formula VII:

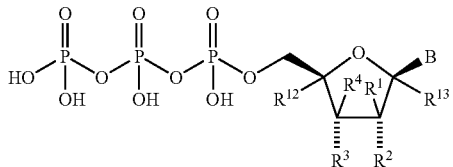

wherein B, Z, $R^1$-$R^4$, $R^{12}$, and $R^{13}$ are as defined above. The compounds of the present invention are also intended to include pharmaceutically acceptable salts of the triphosphate ester as well as pharmaceutically acceptable salts of 5'-monophosphate and 5'-diphosphate ester derivatives of the structural formulae VIII and IX, respectively,

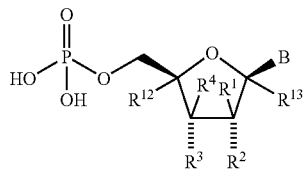

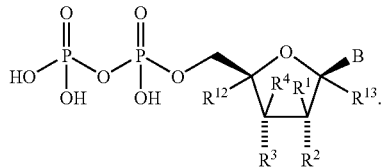

The term "5'-(S-acyl-2-thioethyl)phosphate" or "SATE" refers to a mono- or di-ester derivative of a 5'-monophosphate nucleoside of the present invention of structural formulae X and XI, respectively, as well as pharmaceutically acceptable salts of the mono-ester,

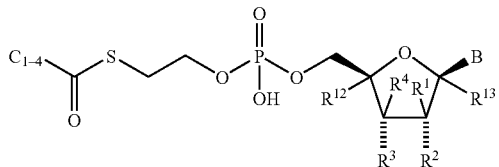

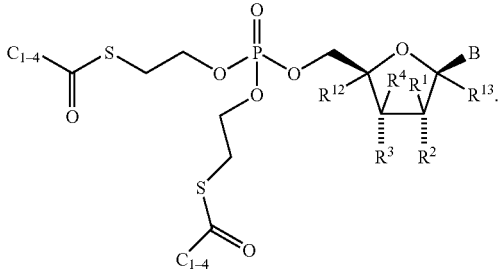

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, thymosin alpha-1, interferon-α, pegylated interferon-α peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine is an amino analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease, such as LY570310 (VX-950). HCV NS3 serine protease is an essential viral enzyme and has been described to be an excellent target for inhibition of HCV replication. Both substrate and non-substrate based inhibitors of HCV NS3 protease inhibitors are disclosed in WO 98/17679, WO 98/22496, WO 98/46630, WO 99/07733, WO 99/07734, WO 99/38888, WO 99/50230, WO 99/64442, WO 00/09543, WO 00/59929, WO 01/74768, WO 01/81325, and GB-2337262. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13–42 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IPDH, such as VX-497, which is disclosed in WO 97/41211 and WO 01/00622, (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamaitane) [for a comprehensive description of this agent, see J. Kirschbaum, *Anal. Profiles Drug Subs*. 12: 1–36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754–1759 (1997); M. S. Wolfe, et al., *Tetrahedron Lett*., 36: 7611–7614 (1995); and U.S. Pat. No. 3,480,613 (Nov. 25, 1969), the contents of which are incorporated by reference in their entirety. Such 2'-C-branched ribonucleosides include, but are not limited to, 2'-C-methyl-cytidine, 2'-C-methyl-adenosine, 2'-C-methyl-guanosine, and 9-(2-C-methyl-β-D-ribofuranosyl)-2,6-diaminopurine.

By "pharmaceutically acceptable" is meant that the carrier, diluent, or excipient must be compatible with the other ingredients of the formulation and not deleterious to the recipient thereof.

Also included within the present invention are pharmaceutical compositions comprising the novel nucleoside compounds and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of this invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics, and Therapeutic Potential," *Ann. Rep. Med. Chem.*, 35: 201–210 (2000).

Another aspect of the present invention provides for the use of nucleoside compounds and derivatives thereof and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for nucleoside compounds and derivatives thereof and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I, IV, or XII as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formulae I, IV, and XII can be combined as the active ingredient in intimate admixture with a pharmaceutical carrier according to conventional pharmaceutical compounding techniques. The carrier may take a wide variety of forms depending on the form of preparation desired for administration, e.g., oral, or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formulae I, IV, and XII may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formulae I, IV, and XII are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend nucleoside derivatives having the β-D stereochemical configuration for the five-membered furanose ring as depicted in the structural formula below, that is, nucleoside compounds in which the substituents at C-1 and C-4 of the five-membered furanose ring have the β-stereochemical configuration ("up" orientation as denoted by a bold line).

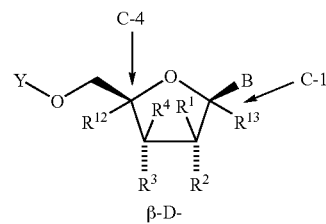

β-D-

The stereochemistry of the substituents at the C-2 and C-3 positions of the furanose ring of the compounds of the present invention is denoted either by a dashed line which signifies that the substituent, for example $R^2$ in structural formula VI, has the α (substituent "down") configuration or a squiggly line which signifies that the substituent, for example $R^3$ in structural formula VI, can have either the α (substituent "down") or β (substituent "up") configuration.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of structural formulae I, IV, and XII. An example of keto-enol tautomers which are intended to be encompassed within the compounds of the present invention is illustrated below:

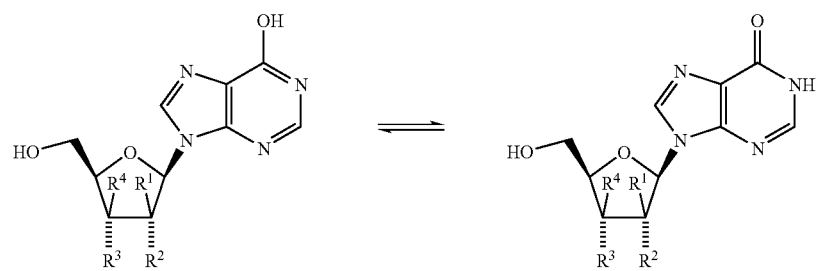

Compounds of structural formulae I, IV, and XII may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of the structural formulae I, IV, and XII may be obtained by stereospecific synthesis using optically pure starting materials or reagents of known configuration.

The stereochemistry of the substituents at the C-2 and C-3 positions of the furanose ring of the novel compounds of the present invention of structural formula XII is denoted by squiggly lines which signifies that substituents $R^a$, $R^b$, $R^c$ and $R^h$ can have either the α (substituent "down") or β (substituent "up") configuration independently of one another.

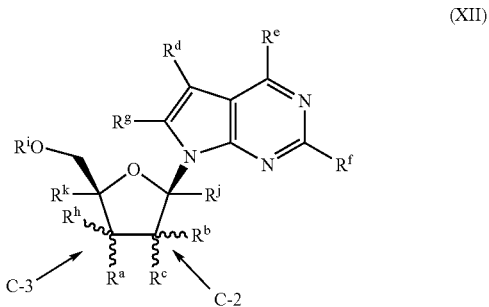

(XII)

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Preparation of the Nucleoside Compounds and Derivatives of the Invention

The nucleoside compounds and derivatives thereof of the present invention can be prepared following synthetic methodologies well-established in the practice of nucleoside and nucleotide chemistry. Reference is made to the following text for a description of synthetic methods used in the preparation of the compounds of the present invention: "Chemistry of Nucleosides and Nucleotides," L. B. Townsend, ed., Vols. 1–3, Plenum Press, 1988, which is incorporated by reference herein in its entirety.

A representative general method for the preparation of compounds of the present invention is outlined in Scheme 1 below. This scheme illustrates the synthesis of compounds of the present invention of structural formula 1-7 wherein the furanose ring has the β-D-ribo configuration. The starting material is a 3,5-bis-O-protected alkyl furanoside, such as methyl furanoside, of structural formula 1-1. The C-2 hydroxyl group is then oxidized with a suitable oxidizing agent, such as a chromium trioxide or chromate reagent or Dess-Martin periodinane, or by Swern oxidation, to afford a C-2 ketone of structural formula 1-2. Addition of a Grignard reagent, such as an alkyl, alkenyl, or alkynyl magnesium halide (for example, MeMgBr, EtMgBr, vinylMgBr, allylMgBr, and ethynylMgBr) or an alkyl, alkenyl, or alkynyl lithium, such as MeLi, across the carbonyl double bond of 1-2 in a suitable organic solvent, such as tetrahydrofuran, diethyl ether, and the like, affords the C-2 tertiary alcohol of structural formula 1-3. A good leaving group (such as Cl, Or, and I) is next introduced at the C-1 (anomeric) position of the furanose sugar derivative by treatment of the furanoside of formula 1-3 with a hydrogen halide in a suitable organic solvent, such as hydrogen bromide in acetic acid, to afford the intermediate furanosyl halide 1-4. A C-1 sulfonate, such methanesulfonate ($MeSO_2O$—), trifluoromethanesulfonate ($CF_3SO_2O$—), or p-toluenesulfonate (—OTs), may also serve as a useful leaving group in the subsequent reaction to generate the glycosidic (nucleosidic) linkage. The nucleosidic linkage is constructed by treatment of the intermediate of structural formula 1-4 with the metal salt (such as lithium, sodium, or potassium) of an appropriately substituted 1H-pyrrolo[2,3-d]pyrimidine 1-5, such as an appropriately substituted 4-halo-1H-pyrrolo[2,3-d]pyrimidine, which can be generated in situ by treatment with an alkali hydride (such as sodium hydride), an alkali hydroxide (such as potassium hydroxide), an alkali carbonate (such as potassium carbonate), or an alkali hexamethyldisilazide (such as NaHMDS) in a suitable anhydrous organic solvent, such as acetonitrile, tetrahydrofuran, 1-methyl-2-pyrrolidinone, or N,N-dimethylformamide (DMF). The displacement reaction can be catalyzed by using a phase-transfer catalyst, such as TDA-1 or triethylbenzylammonium chloride, in a two-phase system (solid-liquid or liquid-liquid). The optional protecting groups in the protected nucleoside of structural formula 1-6 are then cleaved following established deprotection methodologies, such as those described in T. W. Greene and P. G. M. Wuts, "Protective Groups in Organic Synthesis," $3^{rd}$ ed., John Wiley & Sons, 1999. Optional introduction of an amino group at the 4-position of the pyrrolo[2,3-d] pyrimidine nucleus is effected by treatment of the 4-halo intermediate 1-6 with the appropriate amine, such as alcoholic ammonia or liquid ammonia, to generate a primary amine at the C-4 position (—$NH_2$), an alkylamine to generate a secondary amine (—NHR), or a dialkylamine to generate a tertiary amine (—NRR'). A 7H-pyrrolo[2,3-d]pyrimidin-4(3H)one compound may be derived by hydrolysis of 1-6 with aqueous base, such as aqueous sodium hydroxide. Alcoholysis (such as methanolysis) of 1-6 affords a C-4 alkoxide (—OR), whereas treatment with an alkyl mercaptide affords a C-4 alkylthio (—SR) derivative. Subsequent chemical manipulations well-known to practitioners of ordinary skill in the art of organic/medicinal chemistry may be required to attain the desired compounds of the present invention.

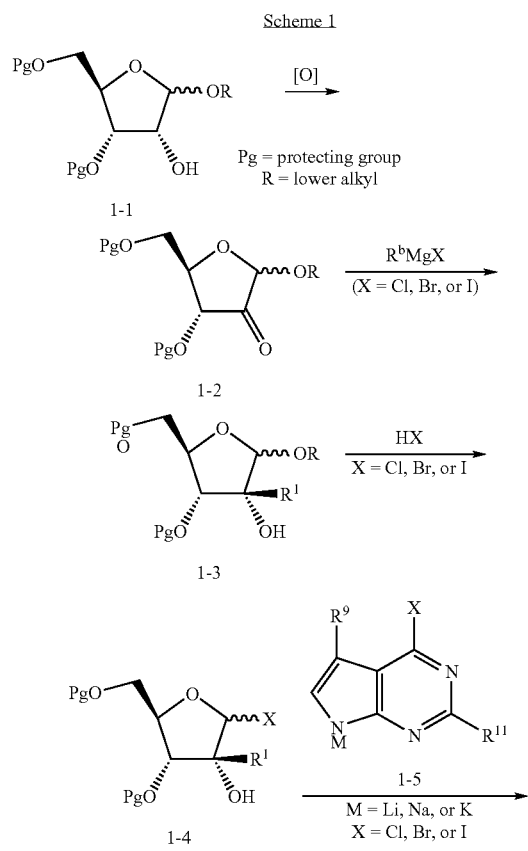

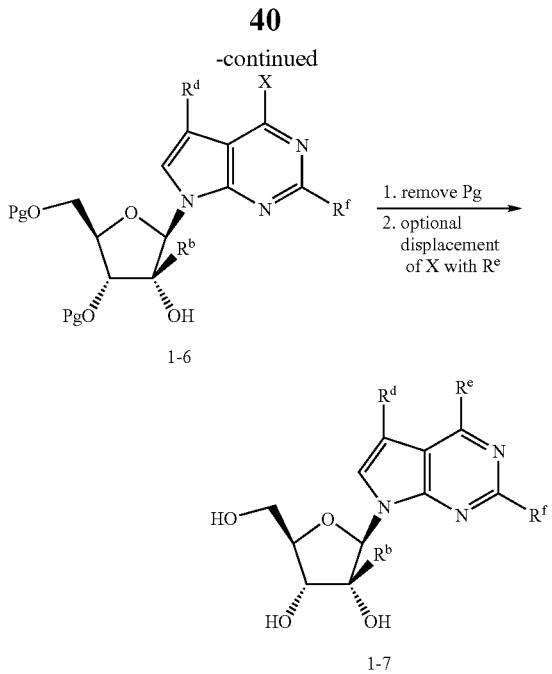

The examples below provide citations to literature publications, which contain details for the preparation of final compounds or intermediates employed in the preparation of final compounds of the present invention. The nucleoside compounds of the present invention were prepared according to procedures detailed in the following examples. The examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

EXAMPLE 1

3'-Deoxyguanosine

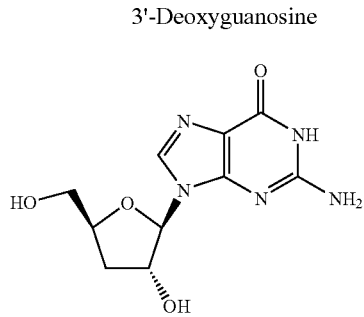

This compound was prepared following the procedures described in *Nucleosides Nucleotides*, 13: 1049 (1994).

EXAMPLE 2

3'-Deoxy-3'-fluoroguanosine

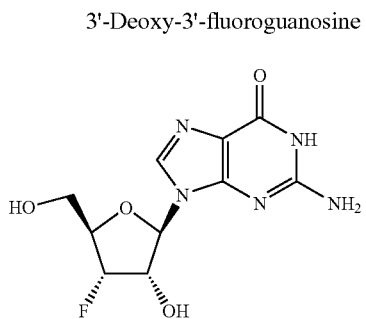

This compound was prepared following the procedures described in *J. Med. Chem.* 34: 2195 (1991).

EXAMPLE 3

8-Azidoguanosine

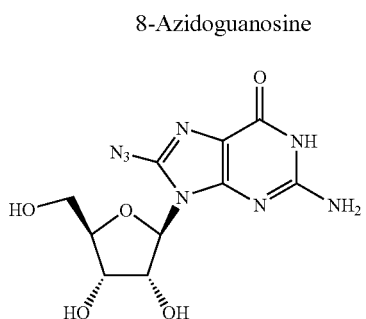

This compound was prepared following the procedures described in *Chem. Pharm. Bull.*.16: 1616 (1968).

EXAMPLE 4

8-Bromoguanosine

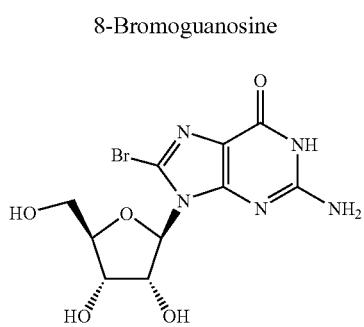

This compound was obtained from commercial sources.

EXAMPLE 5

2'-O-Methylguanosine

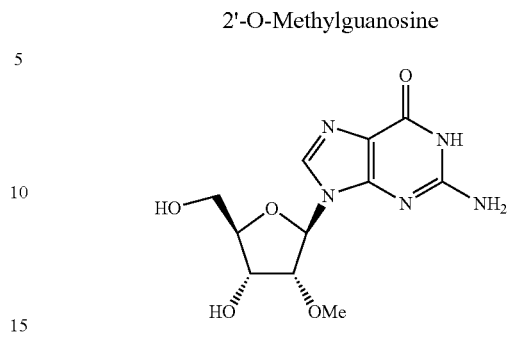

This compound was obtained from commercial sources.

EXAMPLE 6

3'-Deoxy-3'-(fluoromethyl)guanosine

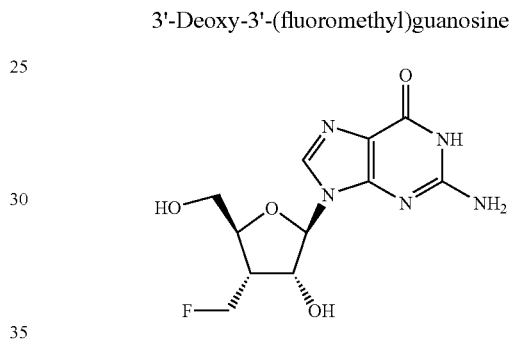

To a solution of 1,2-O-diacetyl-5-O-(p-toluoyl)-3-deoxy-3-(fluoromethyl)-D-ribofuranose (257 mg, 0.7 mmol) [prepared by a similar method as that described for the corresponding 5-O-benzyl derivative in *J Med. Chem.* 36: 353 (1993)] and $N^2$-acetyl-$O^6$-(diphenylcarbamoyl)guanine (554 mg, 1.43 mmol) in anhydrous acetonitrile (6.3 mL) was added bis(trimethylsilyl)acetamide (BSA) (1.03 g, 5 mmol). The reaction mixture was stirred at reflux for 30 minutes, and the bath was removed. The reaction mixture was cooled in an ice bath and TMS-triflate (288 mg, 1.3 mmol) was added with stirring. After addition was complete, the reaction was heated at reflux for 2 hr., the reaction mixture was poured onto ice and extracted with chloroform (5×10 mL). The combined organic layers were washed with aqueous saturated sodium bicarbonate, brine and dried over anhydrous $Na_2SO_4$. The solvent was removed under reduced pressure and the residue chromatographed over silica gel using 5% acetone/$CH_2Cl_2$ as the eluant to furnish the fully protected corresponding nucleoside derivative. This was dissolved in 1,4-dioxane (1.5 mL) to which was added 40% $MeNH_2/H_2O$ (1.3 g, 17 mmol). The reaction mixture was stirred for 1 day, evaporated and the residue crystallized with ether/MeOH to provide the title compound (58 mg). $^1H$ NMR (DMSO-$d_6$): δ 2.76–2.67 (m, 1H); 3.55–3.50 (m, 1H), 2.76–2.67 (m, 1H); 3.71–3.66 (m, 1H), 4.08–4.04 (m, 1H), 4.77–4.50 (m, 3H) 5.06 (t, 1H, J=5.3 Hz), 5.69 (d, 1H, J=3.4 Hz), 5.86 (d, 1H, J=5.1 Hz), 6.45 (bs, 2H), 7.97 (s, 1H), 10.59 (s, 1H). $^{19}F$ NMR (DMSO-$d_6$): δ –221.46 (m, F).

EXAMPLE 7

2-Amino-3,4-dihydro-4-oxo-7-(β-D-ribofuranosyl)-7H-pyrrolo[2,3-d]pyrimidin-5-carboxamide

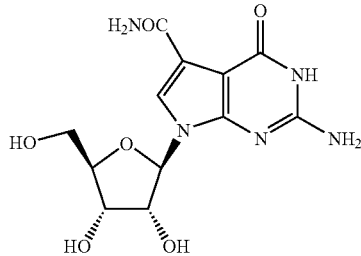

This compound was prepared following the procedures described in *Tetrahedron. Lett.* 25: 4793 (1983).

EXAMPLE 8

2-Amino-3,4-dihydro-4-oxo-7-(β-D-ribofuranosyl)-7H-pyrrolo[2,3-d]pyrimidin-5-carbonitrile

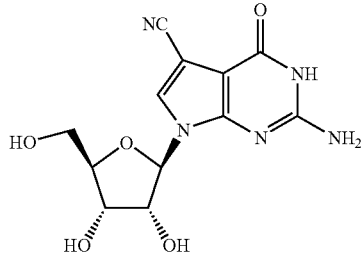

This compound was prepared following the procedures described in *J. Am. Chem. Soc.* 98: 7870 (1976).

EXAMPLE 9

2-Amino-5-ethyl-7-(β-D-ribofuranosyl)-7H-pyrrolo[2,3-d]pyrimidin-4(3H)-one

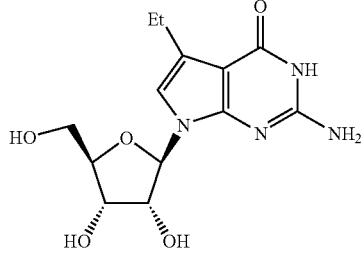

Step A: 2-Amino-7-(5-O-tert-butyldimethylsilyl-2,3-O-isopropylidene-β-D-ribofuranosyl)-4-chloro-5H-pyrrolo[2,3-d]pyrimidine To a stirred suspension of 2-amino-4-chloro-5-ethyl-1H-pyrrolo[2,3-d]pyrimidine [described in EP 866070 (1998)] (1.57 g, 8 mmol) in dry MeCN (48 mL) was added NaH (60% in mineral oil; 0.32 g, 8 mmol), and the mixture was stirred at room temperature for 1 h. A solution of 5-O-tert-butyldimethylsilyl-2,3-O-isopropylidene-α-D-ribofuranosyl chloride [generated in situ from the corresponding lactol (1.95 g, 6.4 mmol) according to Wilcox et al., *Tetrahedron Lett.*, 27: 1011 (1986)] in dry THF (9.6 mL) was added at room temperature, and the mixture was stirred overnight, then evaporated to dryness. The residue was suspended in water (100 mL) and extracted with EtOAc (200+150 mL). The combined extracts were washed with brine, dried ($Na_2SO_4$) and evaporated. The residue was purified on a silica gel column using a solvent system of hexanes/EtOAc: 7/1. Appropriate fractions were collected and evaporated to dryness to give the title compound (1.4 g) as a colorless foam.

Step B: 2-Amino-4-chloro-5-ethyl-7-(β-D-ribofuranosyl)-7H-pyrrolo[2,3-d]pyrimidine A mixture of the compound from Step A (1.19 g, 2.5 mmol) in MeOH (100 mL) and water (50 mL) was stirred with DOWEX $H^+$ (to adjust pH of the mixture to 5) at room temperature for 2.5 h. The mixture was filtered and the resin thoroughly washed with MeOH. The combined filtrate and washings were evaporated and the residue coevaporated several times with water to yield the title compound (0.53 g) as a white solid.

Step C: 2-Amino-5-ethyl-7-(β-D-ribofuranosyl)-7H-pyrollo[2,3-d]pyrimidin-4(3H)-one A mixture of the compound from Step B (104 mg, 0.32 mmol) in 2N aqueous NaOH (10 mL) was stirred at reflux temperature for 15 min. The solution was cooled in ice bath, neutralized with 2 N aqueous HCl, and evaporated to dryness. The residue was suspended in MeOH, mixed with silica gel, and evaporated. The solid residue was placed onto a silica gel column (packed in a solvent mixture of $CH_2Cl_2$/MeOH: 10/1) which was eluted with a solvent system of $CH_2Cl_2$MeOH: 10/1 and 5/1. The fractions containing the product were collected and evaporated to dryness to yield the title compound (48 mg) as a white solid.

$^1$H NMR ($CD_3OD$): δ 1.22 (t, 3H), 2.69 (q, 2H), 3.69, 3.80 (2m, 2H), 4.00 (m, 1H), 4.22 (m, 1H), 4.45 (t, 1H), 5.86 (d, 1H, J=6.0 Hz), 6.60 (d, 1H, J=1.2 Hz).

EXAMPLE 10

2-Amino-7-(3-deoxy-β-D-ribofuranosyl)-7H-pyrrolo[2,3-d]pyrimidin-4(3H)-one

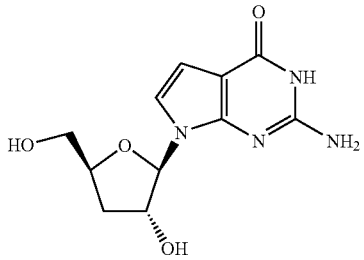

Step A: 2-Amino-7-(2,3-anhydro-β-D-ribofuranosyl)-4-methoxy-7H-pyrrolo[2,3-d]pyrimidine To a mixture of 2-amino-7-(β-D-ribofuranosyl)-4-chloro-7H-pyrrolo[2,3-d]pyrimidine (1.8 g, 6.0 mmol) in acetonitrile (80 mL) were added a solution of $H_2O/CH_3CN$ (1:9, 1.08 mL) and then a-acetoxyisobutyryl bromide (3.5 mL, 24 mmol). After 2 h stirring at room temperature, saturated aqueous $NaHCO_3$ (170 mL) was added and the mixture was extracted with EtOAc (300+200 mL). The combined organic phase was washed with brine (100 mL), dried ($Na_2SO_4$) and evaporated to a pale yellow foamy residue. This was suspended in anhydrous MeOH (80 mL) and stirred overnight with 25 mL of DOWEX OH$^-$ resin (previously washed with anhydrous MeOH). The resin was filtered, washed thoroughly with MeOH and the combined filtrate evaporated to give a pale yellow foam (1.92 g).

Step B: 2-Amino-7-(3-deoxy-β-D-ribofuranosyl)-4methoxy-7H-pyrrolo[2,3-d]pyrimidine A solution of LiEt$_3$BH/THF (1M, 75 mL, 75 mmol) was added dropwise to a cold (ice bath) deoxygenated (Ar, 15 min) solution of the compound from Step A (1.92 g) under Ar. Stirring at 0° C. was continued for 4 h. At this point the reaction mixture was acidified with 5% aqueous acetic acid (110 mL), then purged with Ar for 1 h and and finally evaporated to a solid residue. Purification on a silica gel column using MeOH/CH$_2$Cl$_2$ as eluent yielded target compound as a colourless foam (1.01 g).

Step C: 2-Amino-7-(3-deoxy-β-D-ribofuranosyl)-7H-pyrrolo[2,3-d]pyrimidine-4(3H)-one A mixture of compound from Step B (0.4 g, 1.4 mmol) in 2N aqueous NaOH (40 mL) was stirred at reflux temperature for 3 h. The solution was cooled in ice bath, neutralized with 2 N aqueous HCl and evaporated to dryness. The residue was suspended in MeOH, mixed with silica and evaporated. The residue was placed onto a silica gel column which was eluted with CH$_2$Cl$_2$/MeOH: 10/1 and 5/1 to give the title compound as white solid (0.3 g).

$^1$H NMR (DMSO-d$_6$): δ 1.85, 2.12 (2m, 2H), 3.55, 3.46 (2dd, 2H), 4.18 (m, 1H); 4.29 (m, 1H), 4.85 (7, 1H), 5.42 (d, 1H) 5.82 (d, 1H, J=2.4 Hz), 6.19 (s, 2H), 6.23 (d, 1H, J=3.6 Hz), 6.87 (d, 1H), 10.31 (s, 1H).

EXAMPLE 11

2-Amino-7-(2-O-methyl-β-D-ribofuranosyl)-7H-pyrrolo[2,3-d]pyrimidin-4(3H)-one

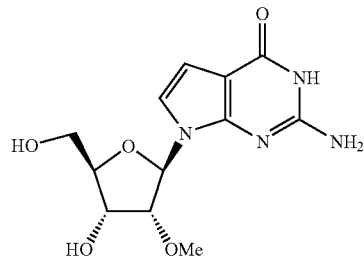

Step A: 2-Amino-4-chloro-7-(5-t-butyldimethylsilyl-2,3-O-isopropylidene-β-D-ribofuranosyl)-7H-pyrrolo[2,3-d]pyrimidine HMPT (10.65 ml, 55 mmol) was added portionwise over 30 min. to a solution of 5-O-tert-butyldimethylsilyl-2,3-O-isopropylidene-D-ribofuranose (13.3 g, 44 mmol), dry THF (135 mL), CCl$_4$ (5.62 mL, 58 mmol) under N$_2$ at −76° C. After 30 min., the temp. was raised to −20° C. In a separate flask, a suspension of 2-amino-4-chloro-1H-pyrrolo-[2,3-d]-pyrimidine (15 g, 89 mmol) in CH$_3$CN (900 mL) was treated at 15° C. with 60% NaH (3.60 g., 90 mmol.). The reaction was stirred 30 min. whereupon the previous reaction mixture was cannulated with vigorous stirring. The reaction was stirred 16 hrs. and then concentrated in vacuo. The resulting semisolid was added to ice/water/EtOAc and extracted with EtOAc (3×200 mL), dried NaSO$_4$, filtered and evaporated. The resulting oil was chromatographed on silica gel (EtOAc/Hexane 1/1) to afford the product as an oil (9.0 g).

Step B: 2-Amino-4-chloro-7-(β-D-ribofuranosyl)-7H-pyrrolo[2,3-d]pyrimidine

A solution of the compound from Step A (5.76 g, 13 mmol) in MeOH/H$_2$O (1200 mL/600 mL) and Dowex WX8-400 (4.8 g) was stirred 16 hrs. at room temperature. The resin was filtered off and the filtrate evaporated to afford the title compound as a white solid; yield 3.47 g.

$^1$H NMR (DMSO-d$_6$): δ 3.56 (m, 2H), 3.86 (m, 1H), 4.07 (m, 1H), 4.32 (m, 1H), 4.99 (t, 1H), 5.10 (d, 1H), 5.30 (d, 1H), 6.00 (d, 1H), 6.38 (d, 1H), 6.71 (s br, 2H), 7.39 (d, 1H).

Step C: 2-Amino-4-chloro-7-(2-O-methyl-β-D-ribofuranosyl)-7H-pyrrolo[2,3-d]pyrimidine A solution of the compound from Step B1(1.0 g, 3.3 mmol) in dry DMF (100 mL) at 15° C. was treated with 60% NaH (0.14 g, 3.5 mmol). After 30 min., iodomethane (47 g, 3.3 mmol) was added portionwise to the stirred solution. The reaction was stirred at room temperature for 16 hrs. and then evaporated at a temperature below 40° C. The resulting solid was chromatographed on silica gel to afford the product as a white solid; yield 0.81 g.

$^1$H NMR (DMSO-d$_6$): δ 3.25 (s, 3H), 3.54 (m, 2H), 3.87 (m, 1H), 4.07 (m, 1H), 4.22 (m, 1H), 5.01 (m, 1H), 5.16 (d, 1H), 6.07 (d, 1H), 6.37 (d, 1H), 6.70 (s br, 2H), 7.40 (s, 1H). Mass spectrum: m/z 316 (M+1)$^+$.

Step D: 2-Amino-7-(2-O-methyl-β-D-ribofuranosyl)-7H-pyrrolo[2,3-d]pyrimidin-4(3H)-one A solution of the compound from Step C (80 mg, 0.25 mmol) in NaOH/H$_2$O (1.6 g/20 ml) was heated at reflux for 7 hrs., whereupon the solution was adjusted with dilute HCl to a pH of 7 and then evaporated. Chromatography of the resulting solid on silica gel with EtOAc/MeOH 8/2 afforded the product as a white solid; yield 64 mg.

$^1$H NMR (DMSO-d$_6$): δ 3.25 (s, 3H), 3.52 (m, 2H) 3.81 (m, 1H), 4.00 (m, 1H), 4.19 (m, 1H), 5.10 (s br, 2H), 5.95 (d, 1H), 6.27 (d, 1H), 6.33 (s br, 2H), 6.95 (d, 1H), 10.55 (s br, 1H).

EXAMPLE 12

2-Amino-5-methyl-7-(β-D-ribofuranosyl)-7H-pyrrolo[2,3-d]pyrimidin-4(3H)-one

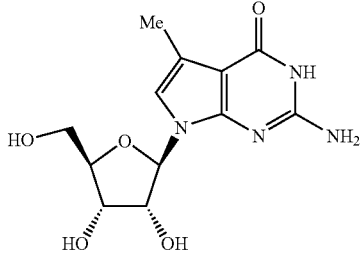

This compound is described in *Biochemistry*, 33: 2703 (1994) and was synthesized by the following procedure:

Step A: 2-Amino-7-(5-O-tert-butyldimethylsilyl-2,3-O-isopropylidene-β-D-ribofuranosyl)-4-chloro-5-methyl-7H-pyrrolo[2,3-d]pyrimidine To a stirred suspension of 2-amino-4-chloro-5-methyl-1H-pyrrolo[2,3-d]pyrimidine (*Liebigs Ann. Chem.* 1984, 4, 708) (0.91 g, 5 mmol) in dry MeCN (30 ml) was added NaH (60% in mineral oil; 0.2 g, 5 mmol) and the mixture was stirred at room temperature for 0.5 h. A solution of 5-O-tert-butyldimethylsilyl-2,3-O-isopropylidene-α-D-ribofuranosyl chloride [generated in situ from the corresponding lactol (1.22 g, 4 mmol) according to *Tetrahedron Lett.* 27: 1011 (1986)] in dry THF (6 mL) was added at room temperature, and the mixture was stirred overnight, then evaporated to dryness. The residue was suspended in water (100 mL) and extracted with EtOAc (2×100 mL). The combined organic extracts were washed with brine, dried (Na$_2$SO$_4$) and evaporated. The residue was purified on a silica gel column using a solvent system of hexanes/EtOAc:

7/1 and 5/1. Appropriate fractions were collected and evaporated to dryness to give the title compound (0.7 g) as a colorless foam.

Step B: 2-Amino-4-chloro-5-methyl-7-(β-D-ribofuranosyl)-7H-pyrrolo[2,3-d]pyrimidine A mixture of the intermediate from Step A (0.67 g, 1.4 mmol) in MeOH (70 ml) and water (35 ml) was stirred with DOWEX H+ (to adjust pH of the mixture to 5) at room temperature for 4 h. The mixture was filtered and the resin thoroughly washed with MeOH. The combined filtrate and washings were evaporated and the residue coevaporated several times with water to yield the title compound (0.37 g) as a white solid.

Step C: 2-Amino-5-methyl-7-(β-D-ribofuranosyl)-7H-pyrrolo[2,3-d]pyrimidin-4(3H)-one A mixture of intermediate from Step B (100 mg, 0.32 mmol) in 2N aqueous NaOH (20 mL) was stirred at reflux temperature for 1.5 h. The solution was cooled in ice bath, neutralized with 2 N aqueous HCl and evaporated to dryness. The residue was suspended in MeOH, mixed with silica gel and evaporated. The solid residue was placed onto a silica gel column (packed in a solvent mixture of $CH_2Cl_2$/MeOH: 10/1) which was eluted with a solvent system of $CH_2Cl_2$/MeOH: 10/1 and 5/1. The fractions containing the product were collected and evaporated to dryness to yield the title compound (90 mg) as a white solid.

$^1$H NMR (DMSO-$d_6$): δ 2.15 (d, 3H), 3.47, 3.50 (2m, 2H), 3.75 (m, 1H), 3.97 (m, 1H), 4.17 (m, 1H), 4.89 (t, 1H), 4.96 (d, 1H), 5.14 (d, 1H), 5.80 (d, 1H, J=6.4 Hz), 6.14 (s, 2H), 6.60 (q, 1H, J=1.2 Hz), 10.23 (s, 1H).

EXAMPLE 13

2-Amino-3,4-dihydro-4-oxo-7-(2-O-methyl-β-D-ribofuranosyl)-7H-pyrrolo[2,3-d]pyrimidine-5-carbonitrile

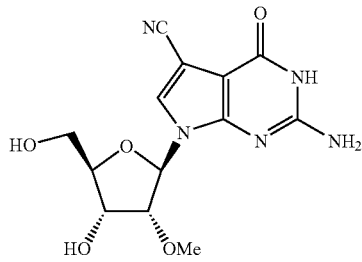

Step A: 2-Amino-4-chloro-7-β-D-ribofuranosyl-7H-pyrrolo[2,3-d]pyrimidine-5-carbonitrile This intermediate was prepared according to *J. Chem. Soc. Perkin Trans.* 1. 2375 (1989).

Step B: 2-Amino-4-chloro-7-[3,5-O-(1,1,3,3-tetraisopropyldisiloxane-1,3-diyl)-β-D-ribofuranosyl]-7H-pyrrolo[2,3-d]pyrimidine-5-carbonitrile To a solution of the compound from Step A (1.64 g, 5.00 mmol) in DMF (30 mL) was added imidazole (0.681 g, 10.0 mmol). The solution was cooled to 0° C. and 1,3-dichloro-1,1,3,3-tetraisopropyldisiloxane (1.58 g, 5.00 mmol) was added dropwise. The bath was removed and the solution stirred at room temperature for 30 minutes, evaporated in vacuo to an oil, taken up in ethyl acetate (150 mL) and washed with saturated aqueous sodium bicarbonate (50 mL) and with water (50 mL). The organic phase was dried over magnesium sulfate, filtered and evaporated in vacuo. The residue was purified on silica gel using ethyl acetate/hexane (1:2) as eluent. Fractions containing the product were pooled and evaporated in vacuo to give the desired product (2.05 g) as a colorless foam.

$^1$H NMR (DMSO-$d_6$): δ 1.03 (m, 28H), 3.92 (m, 1H), 4.01 (m, 1H), 4.12 (m, 1H), 4.24 (m, 2H), 5.67 (m, 1H), 5.89 (s, 1H), 7.17 (bs, 2H), 8.04 (s, 1H).

Step C: 2-Amino-4-chloro-7-[2-O-methyl-β-D-ribofuranosyl]-7H-pyrrolo[2,3-d]pyrimidine-5-carbonitrile To a pre-cooled solution (0° C.) of the compound from Step B (1.70 g, 3.00 mmol) in DMF (30 mL) was added methyl iodide (426 mg, 3.00 mmol) and then NaH (60% in mineral oil) (120 mg, 3.00 mmol). The mixture was stirred at rt for 30 minutes and then poured into a stirred mixture of saturated aqueous ammonium chloride (100 mL) and ethyl acetate (100 mL). The organic phase was washed with water (100 mL), dried over magnesium sulfate, filtered and evaporated in vacuo. The resulting oily residue was co-evaporated three times from acetonitrile (10 mL), taken up in THF (50 mL) and tetrabutylammonium fluoride (1.1 mmol/g on silica) (4.45 g, 6.00 mmol) was added. The mixture was stirred for 30 minutes, filtered and the filtrate evaporated in vacuo. The crude product was purified on silica using methanoldichloromethane (7:93) as eluenit. Fractions containing the product were pooled and evaporated in vacuo to give the desired product (359 mg) as a colorless solid.

$^1$H NMR (DMSO-$d_6$): δ 3.30 (s, 3H), 3.56 (m, 2H) 3.91 (m, 1H), 4.08 (m, 1H), 4.23 (m, 1H), 5.11 (m, 1H), 5.23 (m, 1H), 7.06 (m, 1H), 7.16 (bs, 2H), 8.38 (s, 1H).

Step D: 2-Amino-3,4-dihydro-4-oxo-7-[2-O-methyl-β-D-ribofuranosyl]-7H-pyrollo[2,3-d]pyrimidine-5-carbonitrile To a solution of the compound from Step D in DMF (5.0 mL) and dioxane (3.5 mL) was added syn-pyridinealdoxime (336 mg, 2.75 mmol) and then tetramethylguanidine (288 mg, 2.50 mmol). The resulting solution was stirred overnight at rt, evaporated in vacuo and and co-evaporated three times from acetonitrile (20 mL). The oily residue was purified on silica gel using methanol/dichloromethane (7:93) as eluent. Fractions containing the product were pooled and evaporated in vacuo to give the desired product (103 mg) as a colorless solid.

$^1$H NMR (DMSO-$d_6$): δ 3.30 (s, 3H), 3.57 (m, 2H), 3.86 (m, 1H), 4.00 (m, 1H), 4.21 (m, 1H), 5.07 (m, 1H), 5.17 (m, 1H), 5.94 (m, 1H), 6.56 (bs, 2H), 7.93 (s, 1H), 10.82 (bs, 1H).

EXAMPLE 14

2-Amino-5-methyl-7-(2-O-methyl-β-D-ribofuranosyl)-7H-pyrrolo[2,3-d]pyrimidin-4(3H)-one

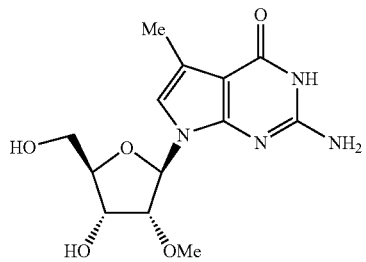

Step A: 2-Amino-4-chloro-5-methyl-7-(2-O-methyl-β-D-ribofuranosyl)-7H-pyrrolo[2,3-d]-pyrimidine Into a solution of the compound from Example 12, Step B (188 mg, 0.6 mmol) in anhydrous DMF (6 mL) was added NaH (60% in mineral oil; 26 mg, 0.66 mmol). The mixture was stirred at room temperature for 0.5 h and then cooled.

MeI (45 μL) was added at 0° C. and the reaction mixture allowed to warm to 15° C. in 5 h. Then the mixture was poured into ice-water (20 mL) and extracted with CH$_2$Cl$_2$ (100+50 mL). The combined organic extracts were washed with water (50 mL), brine (50 mL) and dried (Na$_2$SO$_4$). The evaporated residue was purified on a silica gel column with a solvent system of CH$_2$Cl$_2$/MeOH: 30/1. Appropriate fractions were pooled and evaporated to yield the title compound (50 mg) as a colorless glass.

Step B: 2-Amino-7-(2-O-methyl-β-D-ribofuranosyl)-5-methyl-7H-pyrrolo[2,3-d]pyrimidin-4(3H)-one A solution of the compound from Step A (50 mg, 0.15 mmol) in 0.5M NaOMe/MeOH (4 mL) was stirred at reflux temperature for 1.5 h. The mixture was cooled, mixed with silica gel and evaporated to dryness. The silica gel was loaded onto a silica gel column and eluted with a solvent system of CH$_2$Cl$_2$/MeOH: 30/1. The fractions containing the product were collected and evaporated to yield 2-amino-7-(2-O-methyl-β-D-ribofuranosyl)-4-methoxy-5-methyl-7H-pyrrolo[2,3-d]pyrimidine (40 mg). This was mixed with 2 N aqueous NaOH (4 mL) and stirred at reflux temperature for 10 h. The mixture was cooled in ice bath, neutralized with 2 N aqueous HCl and evaporated. The solid residue was suspended in MeOH, mixed with silica gel and evaporated. The silica gel was loaded onto a silica gel column and eluted with a solvent system of CH$_2$Cl$_2$/MeOH: 5/1. Appropriate fractions were pooled and evaporated to give the title compound (40 mg) as a white solid.

$^1$H NMR (DMSO-d$_6$): δ 2.18 (s, 3H), 3.26 (s, 3H), 3.45, 3.52 (2m, 2H), 3.82 (m, 1H), 3.97 (dd, 1H), 4.20 (m, 1H), 4.99 ((t, 1H), 5.10 (d, 1H), 5.94 (d, 1H, J=7.0 Hz), 6.19 (bs, 2H), 6.68 (s, 1H), 10.60 (br, 1H).

EXAMPLE 15

2-Amino-7-(2-deoxy-2-fluoro-β-D-arabinofuranosyl)-7H-pyrrolo[2,3-d]pyrimidin-4(3H)-one

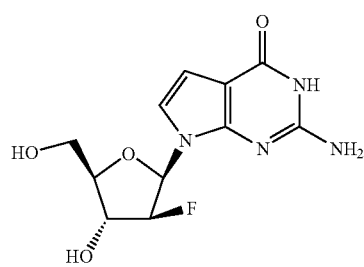

This compound was prepared following the procedures described in *J. Med. Chem.* 38: 3957 (1995).

EXAMPLE 16

2-Amino-7-(β-D-arabinofuranosyl)-7H-pyrrolo[2,3-d]pyrimidin-4(3H)-one

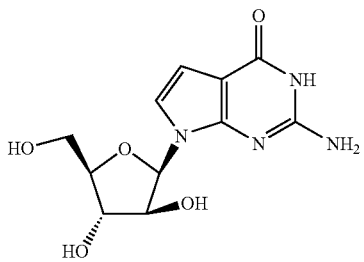

This compound was prepared following the procedures described in *J. Org. Chem.* 47: 226 (1982).

EXAMPLE 17

2-Amino-7-(β-D-arabinofuranosyl)-3,4-dihydro-4-oxo-7H-pyrrolo[2,3-d]pyrimidine-5-carbonitrile

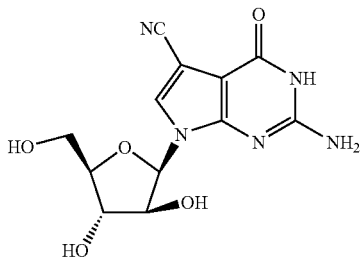

Step A: 2-Amino-7-(β-D-arabinofuranosyl)-4-chloro-7H-pyrrolo[2,3-d]pyrimidine-5-carbonitrile This intermediate was prepared according to *J. Chem. Soc. Perkin Trans.* 1, 2375 (1989).

Step B: 2-Amino-7-(β-D-arabinofuranosyl)-3,4-dihydro-4-oxo-7H-pyrrolo[2,3-d]pyrimidine-5-carbonitrile To a solution of the compound from Step A (163 mg, 0.50 mmol) in DMF (5.0 mL) and dioxane (3.5 mL) was added syn-pyridinealdoxime (336 mg, 2.75 mmol) and then tetramethylguanidine (288 mg, 2.50 mmol). The resulting solution was stirred overnight at rt, evaporated in vacuo and and co-evaporated three times from acetonitrile (20 mL). The oily residue was purified on silica using methanol/dichloromethane (1:4) as eluent. Fractions containing the product were pooled and evaporated in vacuo to give the desired product (72 mg) as a colorless solid.

$^1$H NMR (DMSO-d$_6$): δ 3.60 (m, 2H), 3.73 (m, 1H), 4.01 (m, 2H), 5.06 (m, 1H), 5.48 (m, 2H), 6.12 (m, 1H), 6.52 (bs, 2H), 7.70 (s, 1H), 10.75 (bs, 1H).

EXAMPLE 18

2-Amino-5-methyl-7-(β-D-arabinofuranosyl)-7H-pyrrolo[2,3-d]pyrimidin-4(3H)-one

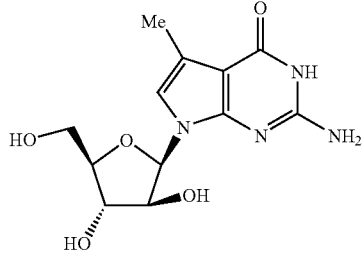

Step A 2-Amino-7-(2,3,5-tri-O-benzyl-β-D-arabinofuranosyl)-4-chloro-5-methyl-7H-pyrrolo[2,3-d]pyrimidine To a solution of 1-O-p-nitrobenzyl-D-arabinofuranose (3.81 g, 6.70 mmol) in DCM was bubbled HBr until TLC (hexane/ethylacetate (2:1)) showed complete reaction (about 30 min). The reaction mixture was filtered and evaporated in vacuo. The oily residue was taken up in acetonitrile (10 mL) and added to a vigorously stirred suspension of 2-amino-4-chloro-5-methyl-7H-pyrrolo[2,3-d]pyrimidine (Liebigs Ann. Chem. (1984), 4,708) (1.11 g, 6.00 mmol) KOH (1.12 g, 20.0 mmol) and tris[2-(2-methoxyethoxy)ethyl]amine (0.216 g, 0.67 mmol) in acetonitrile (80 mL). The resulting suspension was stirred at rt for 30 min, filtered and evaporated in vacuo. The crude product was purified on silica using hexane/ethylacetate (3:1) as the eluent. Fractions containing the product were pooled and evaporated in vacuo to give the desired product (1.13 g) as a colorless foam.

Step B: 2-Amino-7-β-D-arabinofuranosyl-4-chloro-5-methyl-7H-pyrrolo[2,3-d]pyrimidine To a precooled (−78° C.) solution of the compound from Step A (0.99 g, 1.7 mmol) in dichloromethane (30 mL) was added borontrichloride (1M in dichloromethane) (17 mL, 17.0 mmol) over a 10 min. The resulting solution was stirred at −78° C. for 1 h, allowed to warm to −15° C. and stirred for another 3 h. The reaction was quenched by addition of methanol/dichloromethane (1:1) (15 mL), stirred at −15° C. for 30 min, and pH adjusted to 7.0 by addition of NH$_4$OH. The mixture was evaporated in vacuo and the resulting oil purified on silica using methanol/dichloromethane (1:9) as eluent. Fractions containing the product were pooled and evaporated in vacuo to give the desired product (257 mg) as a colorless foam.

Step C: 2-Amino-7-(β-D-arabinofuranosyl)-5-methyl-7H-pyrrolo[2,3-d]pyrimidin-4(3H)-one To the compound from Step B (157 mg, 0.50 mmol) was added NaOH (2M, aqueous) (2 mL). The resulting solution was stirred at reflux for 1 h, cooled and neutralized by addition of HCl (2M, aqueous). The mixture was evaporated in vacuo and the crude product purified on silica using methanol/dichloromethane (2:8) as eluent. Fractions containing the product were pooled and evaporated in vacuo to give the desired product (53 mg) as a colorless powder.

$^1$H NMR (DMSO-d$_6$): δ 2.13 (d, 3H), 3.58 (m, 2H), 3.71 (m, 1H), 4.00 (m, 2H), 5.09 (m, 1H), 6.22 (bs, 2H), 5.50 (m, 2H), 6.12 (m, 1H), 6.64 (s, 1H), 10.75 (bs, 1H).

EXAMPLE 19

2-Amino-7-(3-deoxy-3-fluoro-β-D-ribofuranosyl)-7H-pyrrolo[2,3-d]pyrimidin-4(3H)-one

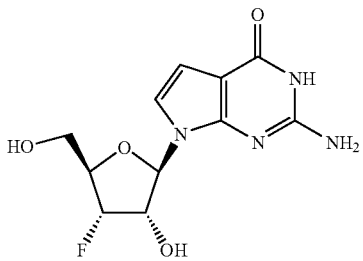

A solution 1-O-acetyl-2-O-benzyl-5-O-(p-toluoyl)-3-deoxy-3-fluoro-D-ribofuranose (410 mg, 1.01 mmol) (prepared by a modified method described for similar sugar derivatives, Helv. Chim. Acta 82: 2052 (1999) and J. Med. Chem.1991, 34, 2195) in anhydrous CH$_2$Cl$_2$ (1.5 mL) was cooled to −15° C. in a dry ice/CH$_3$CN bath. After cooling the reaction mixture for 10 min. under the argon atmosphere, 33% HBr/AcOH (370 μL, 1.5 equiv.) was added slowly over 20 min keeping the bath temperature around −15° C. After the addition was complete, the reaction mixture was stirred at −10° C. for 1 hr. The solvent was removed under reduced pressure and the residue azeotroped with anhydrous toluene (5×10 mL). In a separate flask, 2-amino-4-chloro-7H-pyrrolo[2,3-d]pyrimidine (210 mg, 1.2 mmol) was suspended in anhydrous CH$_3$CN (10 mL) and cooled to −10° C. To this was added 60% NaH dispersion in oil (57 mg) in two portions, and the reaction mixture was stirred for 45 min. during which time the solid dissolved and the bath temperature rose to 0° C. The bath was removed and stirring was continued for about 20 additional min. It was cooled back to −10° C. and the bromo sugar, prepared above, was taken up in anhydrous CH$_3$CN (1.5 mL) and added slowly to the anion of nucleobase . After the addition was complete, the reaction mixture was stirred for an additional 45 min allowing the temperature of the reaction to rise to 0° C. The bath was removed and the reaction allowed to stir at room temperature for 3 hr. Methanol was added carefully to the reaction mixture and the separated solid removed by filtration. The solvent was removed under reduced pressure and the residual oil dissolved in EtOAc (50 mL) and washed with water (3×20 mL). The organic layer was dried over Na$_2$SO$_4$ and concentrated to give an oil. It was purified by column chromatography to furnish fully protected 2-amino-7-(5-O-(p-toluoyl)-2-O-benzyl-3-deoxy-3-fluoro-β-D-ribofuranosyl)-4-chloro-7H-pyrrolo[2,3-d]pyrimidine (190 mg) as an α/β mixture (1:1). After conversion of 4 chloro to 4-oxo by heating the compound with 2N NaOH/dioxane mixture at 105° C. and after the usual workup the residue was debenzylated using 20 mol % w/w of 10% Pd/C and ammonium formate in refluxing methanol to give title compound after purification by HPLC; yield 10%. ESMS: calcd. for C$_{11}$H$_{13}$FN$_4$O$_4$ 284.24, found 283.0 (M+1).

EXAMPLE 20

2-Amino-3,4-dihydro-4-oxo-7-(2-deoxy-β-D-ribofuranosyl)-7H-pyrrolo[2,3-d]pyrimidine-5-carbonitrile

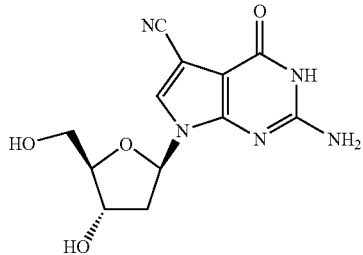

This compound was prepared following the procedures described in *Synthesis* 1327 (1998).

EXAMPLE 21

6-Amino-1-(β-D-ribofuranosyl)-1H-imidazo[4,5-d]pyridin-4(5H)-one

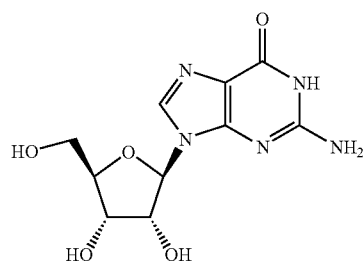

This compound was prepared following the conditions described in *J. Am. Chem. Soc.* 97: 2916 (1975).

EXAMPLE 22

2-Amino-7-(2-O-methyl-β-D-ribofuranosyl)-5H-pyrrolo[3,2-d]pyrimidin-4-(3H)-one

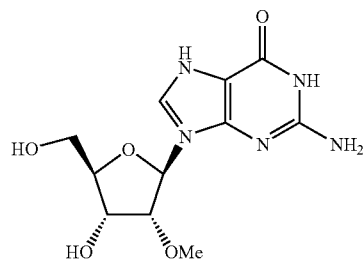

To a suspension of 2-amino-5H-pyrrolo[3,2-d]pyrimidin-4(3H)-one (9-deazaguanine) (0.454 g, 3.0 mmol) (prepared according to *J. Org. Chem.* 1978, 43, 2536) and 2-O-methyl-1,3,5-tri-O-benzoyl-β-D-ribofuranose (1.54 g, 3.2 mmol) in dry nitromethane (23 mL) at 60° C. was added stannic chloride (0.54 mL, 4.5 mmol). The reaction mixture was maintained at this temperature for 0.5 hr., cooled and poured onto ice-cold saturated sodium bicarbonate solution (70 mL). The insoluble material was filtered through florisil and washed with ethyl acetate (3×50 mL). The filtrate was extracted with ethyl acetate (2×50 mL), and organic layer was washed with water (2×50 mL), dried over $Na_2SO_4$ and evaporated to dryness. Chromatography of the resulting foam on silica gel with $CH_2Cl_2$/MeOH(14:1) afforded the benzoylated product (0.419 g, 30% yield). To a suspension of the benzoylated product (0.25 g) in MeOH (2.4 mL) was added t-butylamine (0.52 mL) and stirring at room temperature was continued for 24 hrs. followed by addition of more t-butylamine (0.2 mL). The reaction mixture was stirred at ambient temperature overnight, concentrated in vacuum and the residue was purified by flash chromatography over silica gel using $CH_2Cl_2$/MeOH (85:15) as eluent giving the desired compound as a foam (0.80 g).

$^1$H NMR (200 Mz, DMSO-$d_6$): δ Hz3.28 (s, 3H), 3.40–3.52 (m, 3H), 3.87–3.90 (m, 1H), 4.08–4.09 (m, 1H), 4.67 (d, 1H, J=5.2 Hz), 4.74 (d, 1H, J=7.0 Hz), 5.62 and 5.50 (2 bs, 3H), 7.14 (d, 1H, J=2.6 Hz), 10.43 (s, 1H), 11.38 (s, 1H); Mass spectrum: calcd. for $C_{12}H_{16}N_4O_5$: 296.28; found: 295.11.

EXAMPLE 23

6-Amino-1-(3-deoxy-β-D-ribofuranosyl)-1H-imidazo[4,5-c]pyridine-4(5H)-one (3'-deoxy-3-deaza-guanosine)

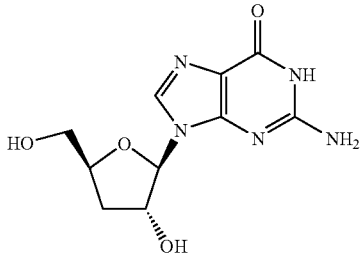

Step A: β-Deoxy-4-O-p-toluoyl-2-O-acetyl-(β-D-ribofuranosyl acetate

A solution of 3-deoxy-4-O-p-toluoyl-1,2-O-isopropylidene-β-D-ribofuranose (*Nucleosides Nucleotides* 1994, 13, 1425 and *Nucleosides Nucleotides* 1992, 11, 787) (5.85 g, 20 mmol) in 64 mL of 80% acetic acid was stirred at 85° C. overnight. The reaction mixture was concentrated and co-evaporated with toluene. The residue was dissolved in 90 mL of pyridine. Acetic anhydride (6 mL) was added at 0° C., and the reaction mixture was stirred at rt for 6 h. After condensation, the residue was dissolved in ethyl acetate and washed with aqueous sodium bicarbonate solution, water and brine. The organic phase was dried and concentrated. Chromatographic purification on a silica gel column using 3:1 and 2:1 hexanes-EtOAc as eluent provided 5.51 g of the title compound as a clear oil.

$^1$H NMR (CDCl$_3$): δ 1.98 (s, 3H), 2.09 (s, 3H), 2.15–2.35 (m, 2H), 2.41 (s, 3H), 4.27–4.42 (m, 1H), 4.46–4.58 (m, 1H), 4.65–4.80 (m, 1H), 5.21–5.28 (m, 1H), 6.20 (s, 1H 7.19–7.31 (m, 2H), 7.90–8.01 (m, 2H).

Step B: Methyl 5-cyanomethyl-1-(3-deoxy4-O-p-toluoyl-2-O-acetyl-β-D-ribofuranosyl)-1H-imidazole-4-carboxylate A mixture of methyl 5(4)-(cyanomethyl)-1H-imidazole-4(5)-carboxylate (*J. Am. Chem. Soc.* 1976, 98, 1492 and *J. Org. Chem.* 1963, 28, 3041) (1.41 g, 8.53 mmol), 1,1,1,3,3,3-hexamethyldisilazane (20.5 mL) and ammonium sulfate (41 mg) was refluxed at 125° C. under Ar atmosphere for 18 h. After evaporation, the residue was dissolved in 10 mL of dichloroethane. A solution of the compound from Step A (2.86 g, 8.5 mmol) in 10 mL of dichloroethane was added followed by addition of SnCl$_4$ (1.44 mL, 3.20 g). The resulted reaction mixture was stirred at rt overnight and diluted with chloroform. The mixture was washed with aqueous sodium bicarbonate water and brine. The organic phase was dried and concentrated. Chromatographic purification of the residue on a silica gel column using 1:1, 1:2, and 1:3 hexanes-EtOAc as eluent provided 2.06 g of the title compound as a white foam.

$^1$H NMR (CDCl$_3$) δ 2.15 (s, 3H), 2.28–2.40 (m, 2H), 2.38 (s, 3H), 3,87 (s, 3H), 4.46 (dd, 2H, J=7.6, 2.0 Hz), 4.50–4.57 (m, 1H), 4.68–4.75 (m, 1H), 4.76–4.83 (m, 1H), 5.41 (d, 1H, J=5.6 Hz), 5.91 (s, 1H), 7.24–7.28 (m, 2H), 7.80 (s, 1H), 7.82–7.90 (m, 2H); $^{13}$C NMR (CDCl$_3$) δ 13.1, 20.7, 21.6, 31.5, 51.8, 63.5, 77.9, 79.2, 89.8, 115.1, 126.2, 129.3, 129.5, 131.7, 135.1, 144.3, 163.1, 166.1, 170.3.

Step C: 6-Amino-1-(3-deoxy-β-D-ribofuranosyl)-1H-imidazo[4,5-c]pyridine-4(5H)-one A solution of the compound from Step B (2.00 g, 4.53 mmol) in methanol (30 mL) was saturated with ammonia at 0° C. Concentrated ammonium hydroxide (30 mL) was added and the sealed metal reactor was heated at 85° C. for 5 h. After cooling to rt, the reaction mixture was transferred directly onto a silica gel column. Elution with 4:1, 3:1 and 2:1 CHCl$_3$-MeOH provided 0.79 g of the title compound as a white solid.

$^1$H NMR (DMSO-d$_6$): δ 2.41–2.46 (m, 1H), 2.52–2.58 (m, 1H), 3.48–3.55 (m, 1H), 3.60–3.70 (m, 1H), 4.27–4.36 (m, 2H), 4.97 (t, 1H, J=5.6 Hz), 5.44 (s, 1H), 5.47 (s, 1H), 5.60 (s, 2H), 5.66, (d, 1H, J=4.4 Hz), 7.90 (s, 1H), 10.33 (s, 1H); $^{13}$C NMR (DMSO d$_6$) δ 34.1, 62.4, 70.4, 74.7, 80.4, 91.6, 123.0, 136.3, 141.9, 147.6, 156.5.

EXAMPLE 24

6-Amino-1-(3-deoxy-3-fluoro-β-D-ribofuranosyl)-1H-imidazo[4,5-c]pyridin-4(3H)-one

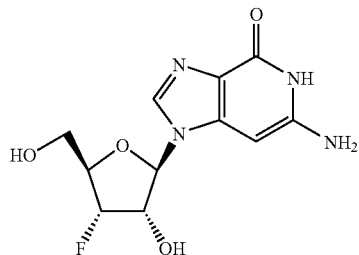

This compound was prepared in a manner similar to the preparation of 2-amino-7-(3-deoxy-3-fluoro-β-D-ribofuranosyl)-7H-pyrrolo[2,3-d]pyrimidin-4(3H)-one (Example 23).

EXAMPLE 25

1-(β-D-Ribofuranosyl)-1H-pyrazolo[3,4-d]pyrimidin-4(3H)-one (Allopurinol riboside)

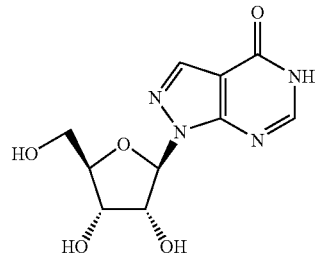

This compound was obtained from commercial sources.

EXAMPLE 26

9-(β-D-Arabinofuranosyl)-9H-purin-6(1H)-one

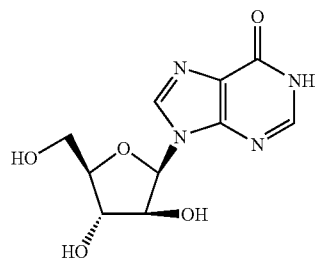

This compound was prepared following the conditions described in J. Med. Chem. 18: 721(1975).

EXAMPLE 27

2-Amino-7-(2-O-methyl-β-D-ribofuranosyl)-7H-pyrrolo[2,3-d]pyrimidin-4(3H)-thione

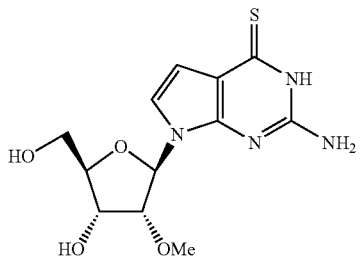

A solution of the compound from Example 11, Step C (1.5 g, 5 mmol), thiourea (0.4 g, 5.2 mmol.) in abs. EtOH was refluxed for 16 hrs. The solution was evaporated and the resulting oil chromatographed on silica gel (EtOAc/MeOH: 9/1) to afford the desired product as a foam.

$^1$H NMR (DMSO-d$_6$): δ 3.30 (s, 3H), 5.00–5.06 (t, 1H), 5.19 (d, 1H), 5.95 (d, 1H), 6.43 (d, 1H), (d, 1H).

EXAMPLE 28

2-Amino-7-(β-D-ribofuranosyl)-7H-pyrrolo[2,3-d]pyrimidine

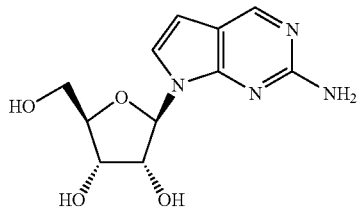

This compound was obtained from commercial sources.

EXAMPLE 29

2-Amino-4-chloro-7-(2-O-methyl-β-D-ribofuranosyl)-7H-pyrrolo[2,3-d]pyrimidin-5-carbonitrile

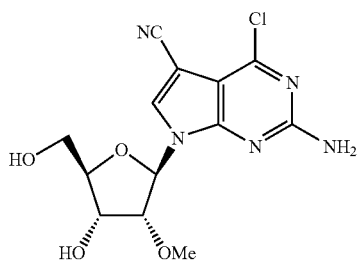

This compound was prepared as described in Example 13, Steps A–C.

EXAMPLE 30

2-Amino-4-chloro-5-ethyl-7-(2-O-methyl-β-D-ribofuranosyl)-7H-pyrrolo[2,3-d]pyrimidine

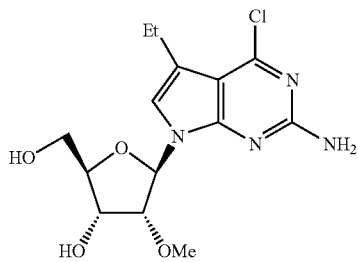

Step A: 2-Amino-4-chloro-5-ethyl-7-[3,5-O-(tetraisopropyldisiloxane-1,3-diyl)-β-D-ribofuranosyl]-7H-pyrrolo[2,3-d]pyrimidine To a solution of 2-amino-4-chloro-5-ethyl-7-(β-D-ribofuranosyl)-7H-pyrrolo[2,3-d]pyrimidine (0.300 g, 0.913 mmol) in pyridine, (8 mL) was added 1,3-dichloro-1,1,3,3-tetraisopropyldisiloxane (0.317 g, 1.003 mmol) dropwise. The solution stirred at rt overnight, evaporated in vacuo to an oil, and evaporated repeatedly from acetonitrile. The crude product was purified on silica using 5% methanol in dichloromethane as eluent. Fractions containing the product were pooled and evaporated in vacuo to give the desired product (254 mg) as a colorless solid.

Step B: 2-Amino-4-chloro-5-ethyl-7-(2-O-methyl-β-D-ribofuranosyl)-7H-pyrrolo[2,3-d]pyrimidine To a pre-cooled solution (0° C.) of the compound from step A (192 mg, 0.337 mmol) in DMF (3 mL) was added methyl iodide (45.4 mg, 0.320 mmol) and then NaH (60% in mineral oil) (8.10 mg, 0.320 mmol). The mixture was stirred at rt for 45 minutes and then poured into a stirred mixture of saturated aqueous ammonium chloride (10 mL) and ethyl acetate (10 mL). The organic phase phase was washed with brine (10 mL) and dried over MgSO$_4$ and evaporated in vacuo. The resulting oily residue was taken up in THF (5 mL) and tetrabutylammonium fluoride (1.1 mmol/g on silica) (0.529 g, 0.582 mmol) was added. The mixture was stirred for 30 minutes, filtered and the filtrate evaporated in vacuo. The crude product was purified on silica using 10% methanol in dichloromethane as eluent. Fractions containing the product were pooled and evaporated in vacuo to give the desired product (66 mg) as a colorless solid.

$^1$H NMR (DMSO-d$_6$): δ 1.15 (t, 3H), 2.65 (q, 2H), 3.20 (s, 3H), 3.51 (m, 2H), 3.84 (m, 1H), 4.04 (m, 1H), 4.21 (m, 1H), 4.99 (m, 2H), 5.15 (m, 2H), 6.07 (m, 2H), 6.62 (s br, 2H), 7.06 (s, 2H).

EXAMPLE 31

2-Amino-4-chloro-5-methyl-7-(2-O-methyl-β-D-ribofuranosyl)-7H-pyrrolo[2,3-d]pyrimidine

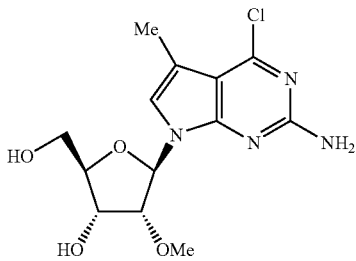

This compound was prepared as described in Example 14, Step A.

$^1$H NMR (CD$_3$OD): δ 2.33 (s, 3H), 3.39 (s, 1H), 3.72, 3.83 (2dd, 2H), 4.03 (m, 1H), 4.17 (t, 1H), 4.39 (dd, 1H), 5.98 (d, 1H, J=5.9 Hz), 6.7 (bs, 2H), 7.01 (s, 1H).

EXAMPLE 32

2-Amino-4-chloro-7-(2-O-methyl-β-D-ribofuranosyl)-7H-pyrrolo[2,3-d]pyrimidine

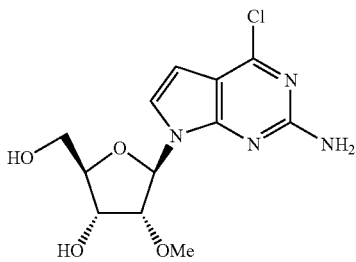

This compound was synthesized as described in Example 11, Steps A–C.

EXAMPLE 33

2-Amino-4-chloro-7-(β-D-ribofuranosyl)-7H-pyrrolo[2,3-d]pyrimidine

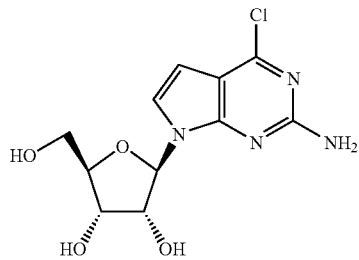

This compound was prepared following the procedures described in *Helv. Chim. Acta* 73: 1879 (1990).

EXAMPLE 34

2-Amino-4-chloro-5-methyl-7-(β-D-ribofuranosyl)-7H-pyrrolo[2,3-d]pyrimidine

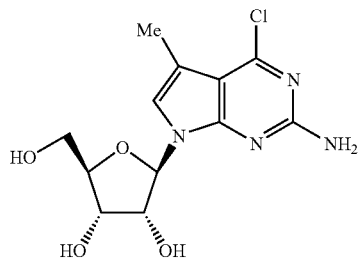

The compound was prepared as described in Example 12, Steps A–B.

$^1$H NMR (DMSO-$d_6$): δ 2.29 (s, 3H), 3.54 (m, 2H), 3.84 (m, 1H), 4.04 (dd, 1H, $J_1$=3.0, $J_2$=4.9 Hz), 4.80–5.50 (bs, 3H), 4.28 (t, 1H), 5.98 (d, 1H, J=6.5 Hz), 6.7 (bs, 2H), 7.13 (s, 1H).

EXAMPLE 35

2-Amino-4-chloro-5-ethyl-7-(β-D-ribofuranosyl)-7H-pyrrolo[2,3-d]pyrimidine

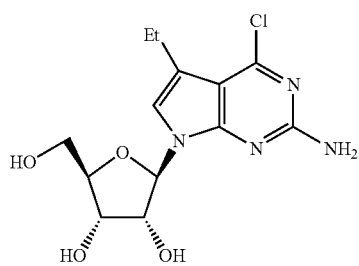

This compound was prepared as described in Example 9, Steps A–B.

$^1$H NMR (DMSO-$d_6$): δ 2.00 (t, 3H), 2.69 (q, 2H), 3.48 (dd, 1 H, $J_1$=4.2 Hz, $J_2$=11.8 Hz), 3.56 (dd, 1H, $J_1$=4.3 Hz, $J_2$=11.8 Hz), 3.80 (m, 1H), 4.02 (dd, 1H, $J_1$=3.1 Hz, $J_2$=5.0 Hz), 4.62 (t, 1H), 5.0 (bs, 2H), 5.2 (bs, 1H), 5.60 (d, 1H, J=6.4 Hz), 6.61 (bs, 2H), 7.09 (s, 1H).

EXAMPLE 36

2-Amino-6-chloro-9-(β-D-ribofuranosyl)-9H-purine

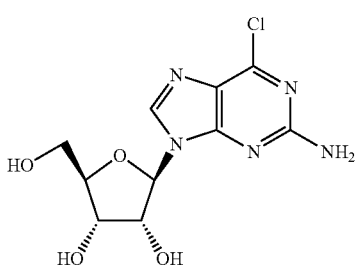

This compound was obtained from commercial sources.

EXAMPLE 37

2-Amino-4-chloro-7-(β-D-ribofuranosyl)-7H-pyrollo[2,3-d]pyrimidine-5-carbonitrile

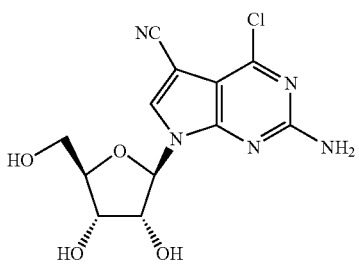

This compound was prepared following the procedures described in *J. Chem. Soc. Perkin Trans.* 1, 2375 (1989).

EXAMPLE 38

2-Amino-4-chloro-7-(2-deoxy-2-fluoro-β-D-arabinofuranosyl)-7H-pyrrolo[2,3-d]pyrimidine

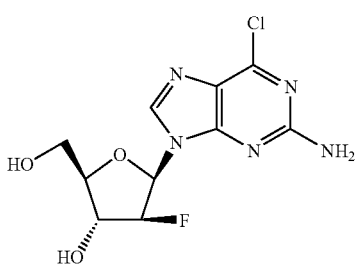

This compound was prepared following the procedures described in *J. Med. Chem.* 38: 3957 (1995).

EXAMPLE 39

2-Amino-4-chloro-5-methyl-7-(β-D-arabinofuranosyl)-7H-pyrrolo[2,3-d]pyrimidine

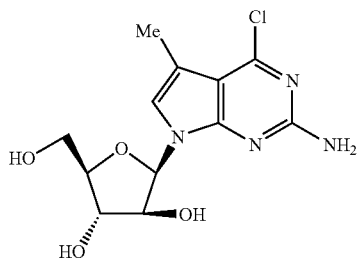

The compound was prepared as described in Example 18, Steps A–B.

$^1$H NMR (DMSO-d$_6$): δ 2.24 (s, 3H), 3.60 (m, 3H), 3.98 (m, 2H), 4.98 (m, 1H), 5.43 (bs, 2H), 6.25 (s, 1H), 6.57 (bs, 2H), 7.01 (s, 1H).

EXAMPLE 40

2'-O-Methylcytidine

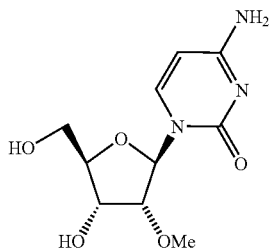

This compound was obtained from commercial sources.

EXAMPLE 41

3'-Deoxy-3'-methylcytidine

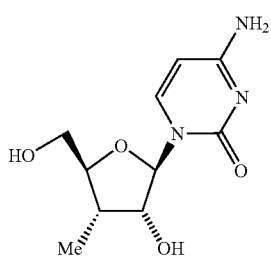

This compound was prepared following the procedures described in U.S. Pat. No. 3,654,262 (1972), which is incorporated by reference herein in its entirety.

EXAMPLE 42

3'-Deoxycytidine

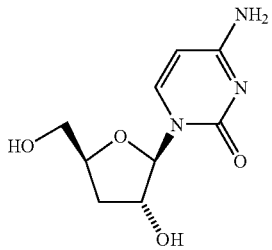

This compound was obtained from commercial sources.

EXAMPLE 43

3'-Deoxy-3'-fluorocytidine

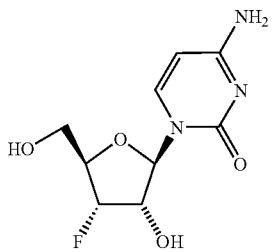

This compound was prepared following the procedures described in *J. Med. Chem.* 34: 2195 (1991).

EXAMPLE 44

1-(β-D-Arabinofuranosyl)-1H-cytosine

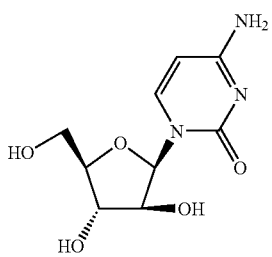

This compound was obtained from commercial sources.

EXAMPLE 45

2'-Amino-2'-deoxycytidine

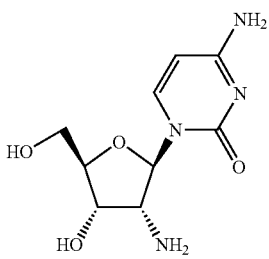

This compound was obtained from commercial sources.

EXAMPLE 46

3'-Deoxy-3'-methyluridine

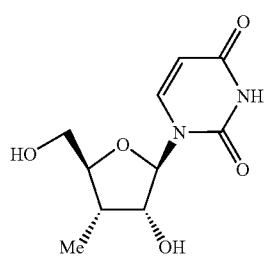

This compound was prepared following procedures described in U.S Pat. No. 3,654,262, which is incorporated by reference herein in its entirety.

EXAMPLE 47

3'-Deoxy-3'-fluorouridine

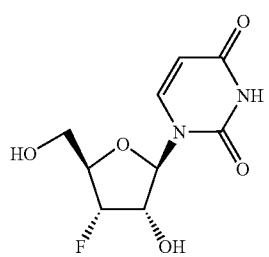

This compound was prepared following procedures described in *J. Med. Chem.* 34: 2195 (1991) and *FEBS Lett.* 250: 139 (1989).

EXAMPLE 48

3'-Deoxy-5-methyluridine

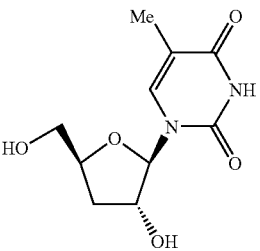

This compound was obtained from commercial sources.

EXAMPLE 49

3'-Deoxy-2'-O-(2-methoxyethyl)-3'-methyl-5-methyluridine

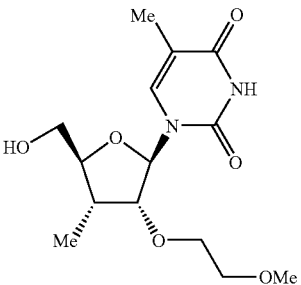

Step A: 5'-O-(tert-butyldiphenylsilyl)-3'-O-(3-tert-butylphenoxythiocarbonyl)-2'-O-(2-methoxyethyl)-5-methyluridine This compound was synthesized by the reaction of the corresponding 5'-protected-2'-substituted-5-methyluridine with 3'-t-butylphenoxy chlorothionoformate following the similar procedure for the preparation of 3'-phenoxythiocarbonyl-2'-deoxy derivative (*Synthesis* 1994, 1163).

Step B: 5'-O-(tert-Butyldiphenylsilyl)-3'-deoxy-2'-O-(2-methoxyethyl)-3'-(2-phenylethenyl)-5-methyluridine To a solution of 5'-O-(tert-butyldiphenylsilyl)-3'-O-(3-tert-butylphenoxythiocarbonyl)-2'-O-(2-methoxyethyl)-5-methyluridine (15.0 g, 20.0 mmol) in 150 mL of benzene was added PhCH=CHSnBu$_3$ (18.7 g, 50 mmol). The resulting solution was degassed three times with argon at rt and 45° C. After AIBN (1.0 g, 6.1 mmol) was added, the resulting solution was refluxed for 2 h. Another portion of AIBN (1.0 g, 6.1 mmol) was added after cooling to about 40° C. and refluxed for 2 h. This procedure was repeated until the starting material disappeared. The solvent was evaporated and the residue was purified by flash chromatography on a silica gel column using 10:1 and 5:1 hexanes-EtOAc as eluent to give 1.74 g of 5'-O-(tert-butyldiphenylsilyl)-3'-deoxy-2'-O-(2-methoxyethyl)-3'-(2-phenylethenyl)5-methyluridine as a white foam.

$^1$H NMR (CDCl$_3$): δ 1.13, (s, 9H), 1.43 (s, 3H), 3.18–3.30 (m, 1H), 3.37 (s, 3H), 3.58–3.62 (m, 2H), 3.79–3.80 (m, 2H), 4.06–4.37 (m, 4H), 4.95 (s, 1H), 6.25–6.40 (m, 1H), 6.62 (d, 1H, J=16 Hz), 7.27–7.71 (m, 16H), 9.21 (s, 1H); $^{13}$C NMR (CDCl$_3$) δ 11.9, 19.6, 27.2, 45.3, 59.0, 62.1, 70.2, 72.0, 84.6, 87.1, 90.2, 110.4, 122.8, 126.4, 127.8, 128.0, 128.3, 128.6, 130.0, 132.7, 133.5, 134.7, 135.3, 135.4, 136.9, 150.3, 154.1; HRMS (FAB) m/z 641.302 (M+H)$^+$ (C$_{37}$H$_{45}$N$_2$O$_6$Si requires 641.304).

Step C: 5'-O-(tert-Butyldiphenylsilyl)-3'-deoxy-3'-(hydroxymethyl -2'-O-(2-methoxyethyl)-5-methyluridine To a solution of 5'-O-(tert-butyldiphenylsilyl)-3'-deoxy-2'-O-(2-methoxyethyl)-3'-(2-phenylethenyl)-5-methyluridine. (5.0 g, 7.8 mmol) and N-methylmorpholine N-oxide (NMO) (1.47 g, 12.5 mmol) in 150 mL of dioxane was added a catalytic amount of osmium tetraoxide (4% aqueous solution, 2.12 mL, 85 mg, 0.33 mmol). The flask was covered by aluminum foil and the reaction mixture was stirred at rt overnight. A solution of NaIO$_4$ (5.35 g, 25 mmol) in 5 mL of water was added to the above stirred reaction mixture. The resulting reaction mixture was stirred for 1 h at 0° C. and 2 h at rt, followed by addition of 10 mL of ethyl acetate. The mixture was filtered through a celite pad and washed with ethyl acetate. The filtrate was washed 3 times with 10% aqueous Na$_2$S$_2$O$_3$ solution until the color of aqueous phase disappeared. The organic phase was further washed with water and brine, dried (Na$_2$SO$_4$) and concentrated. The aldehyde thus obtained was dissolved in 130 mL of ethanol-water (4:1, v/v). Sodium borohydride (NaBH$_4$) (1.58 g, 40 mmol) was added in portions at 0° C. The resulting reaction mixture was stirred at rt for 2 h and then treated with 200 g of ice water. The mixture was extracted with ethyl acetate. The organic phase was washed with water and brine, dried (Na$_2$SO$_4$) and concentrated. The resulted residue was purified by flash chromatography on a silica gel column using 2:1, 1:1 and 1:2 hexanes-EtOAc as eluents to give 1.6 g of 5'-O-(tert-butyldiphenylsilyl)-3'-deoxy-3'-(hydroxymethyl)-2'-O-(2-methoxyethyl)-5-methyluridine as a white foam.

$^1$H NMR (CDCl$_3$): δ 1.09 (s, 9H), 1.50 (s, 3H), 2.25 (bs, 1H), 2.52–2.78 (m, 1H), 3.38 (s, 3H), 3.52–4.25 (m, 10H), 5.86 (s, 1H), 7.38–7.70 (m, 11H), 9.95 (bs, 1H); $^{13}$C NMR (CDCl$_3$): δ 12.1, 19.5, 27.1, 43.1, 58.2, 58.8, 63.1, 69.5, 71.6, 82.3, 86.1, 89.8, 110.5, 128.0, 130.2, 132.5, 133.2, 135.1, 135.3, 136.5, 150.5, 164.4; HRMS (FAB) m/z 569.268 (M+H)$^+$ (C$_{30}$H$_{41}$N$_2$O$_7$Si requires 569.268).

Step D: 5'-O-(tert-Butyldiphenylsilyl -3'-deoxy-3'-(iodomethyl)-2'-O-(2-methoxyethyl)-5-methyluridine To a solution of 5'-O-(tert-butyldiphenylsilyl)-3'-deoxy-3'-(hydroxymethyl)-2'-O-(2-methoxyethyl) - 5-methyluridine (1.34 g, 2.35 mmol) in 25 mL of anhydrous DMP under stirring was added sequentially at 0° C. 2,6-lutidine (0.55 mL, 0.51 g, 4.7 mmol, 2.0 equiv) and methyl triphenoxy-phosphonium iodide (1.28 g, 2.83 mmol). The resulting reaction mixture was stirred at 0° C. for 1 h and at rt for 2 h. The reaction mixture was diluted with 10 mL of ethyl acetate and washed twice with 0.1 N Na$_2$S$_2$O$_3$ aqueous solution to remove iodine. The organic phase was further washed with aqueous NaHCO$_3$ solution, water, and brine. The aqueous phases were back extracted with ethyl acetate. The combined organic phases were dried (Na$_2$SO$_4$) and concentrated. The resulting residue was purified by flash chromatography on a silica gel column using 5:1, 3:1 and then 1:1 hexanes-EtOAc to provide 1.24 g of 5'-O-(tert-butyldiphenylsilyl)-3'-deoxy-3'-(iodomethyl)-2'-O-(2-methoxyethyl)-5-methyluridine as a white foam.

$^1$H NMR (CDCl$_3$): δ 1.13 (s, 9H), 1.62 (s, 3H), 2.64–2.85 (m, 2H), 3.20–3.35 (m, 1H), 3.38 (s, 3H), 3.50–4.25 (m, 8H), 5.91 (s, 1H), 7.32–7.50 (m, 6H), 7.60 (s, 1H), 7.62–7.78 (m, 4H), 10.46 (s, 1H); $^{13}$C NMR (CDCl$_3$): δ 12.4, 19.5, 27.2, 45.0, 58.0, 62.5, 70.3, 71.9, 83.3, 85.6, 88.9, 110.5, 128.1, 128.2, 130.1, 130.3, 132.4, 132.9, 135.0, 135.4, 135.6, 150.7, 164.7; HRMS (FAB) m/z 679.172 (M+H)$^+$ (C$_{30}$H$_{40}$IN$_2$O$_6$Si requires 679.170).

Step E: 3'-Deoxy-3'-tiodomethyl)-2'-O-(2-methoxyethyl)-5-methyluridine

A solution of 5'-O-(tert-butyldiphenylsilyl)-3'-deoxy-3'-(iodomethyl)-2'-O-(2-methoxyethyl)-5-methyluridine (1.12 g, 1.65 mmol) and triethylamine trihydrofluoride (1.1 mL, 1.1 g, 6.7 mmol) in 20 mL of THF was stirred at rt for 24 h. The reaction mixture was diluted with 50 mL of ethyl acetate and washed with water and brine. The organic phase was dried (Na$_2$SO$_4$) and concentrated. The residue was purified by flash chromatography on a silica gel column. Gradient elution with 2:1, 1:2 and then 1:3 hexanes-EtOAc provided 504 mg of the title compound as a white foam.

$^1$H NMR (CD$_3$OD): δ 1.87 (s, 3H), 2.47–2.75 (m, 1H), 3.18–3.37 (m, 2H), 3.40 (s, 3H), 3.59–3.70 (m, 2H), 3.71–3.90 (m, 2H), 3.92–4.17 (m, 4H), 5.87 (s, 1H), 8.17 (s, 1H); $^{13}$C NMR (CD$_3$OD): δ 12.5, 45.2, 59.2, 60.9, 71.0, 72.9, 85.4, 87.3, 89.7, 110.5, 138.0, 152.1, 166.6; HRMS (FAB) m/z 441.053 (M+H)$^+$ (C$_{14}$H$_{22}$IN$_2$O$_6$ requires 441.052).

Step F: 3'-Deoxy-5'-O-(4-methoxytrityl)-3'-(iodomethyl)-2'-O-(2-methoxyethyl)-5-methyluridine A mixture of 3'-deoxy-3'-(iodomethyl)-2'-O-(2-methoxyethyl)-5-methyluridine (472 mg, 1.1 mmol), diisopropylethylamine (0.79 mL, 0.586 g, 4.5 mmol), and p-anisyl chlorodiphenyl methane (4'-methoxytrityl chloride, MMT-Cl) (1.32 g, 4.27 mmol) in 6 mL of ethyl acetate and 4 mL of THF was stirred at rt for 48 h. The reaction mixture was diluted with ethyl acetate and washed with water, followed by brine. The organic phase was dried (Na$_2$SO$_4$) and concentrated. The crude product was purified by flash chromatography on a silica gel column. Gradient elution with 3:1, 2:1, 1:1, and then 1:3 hexanes-EtOAc provided 690 mg of the title compound as a white foam.

$^1$H NMR (CDCl$_3$): δ 1.46 (s, 3H), 2.70–2.89 (m, 2H), 3.19–3.31 (m, 2H), 3.39 (s, 3H), 3.58–3.70 (m, 3H), 3.80 (s, 3H), 3.80–3.94 (m, 1H), 4.05–4.25 (m, 3H), 5.89 (s, 1H), 6.85 (s, 1H), 6.89 (s, 1H), 7.24–7.48 (m, 12H), 7.78 (s, 1H), 9.69 (s, 1H); $^{13}$C NMR (CDCl$_3$): δ 12.3, 45.3, 55.3, 58.9, 61.6, 70.2, 71.9, 82.6, 85.6, 87.1, 89.1, 110.5, 113.4, 127.4, 128.2, 128.4, 130.5, 134.7, 135.3, 143.6, 143.7, 150.5, 158.9, 164.6. HRMS (FAB) m/z 735.155 (M+Na)$^+$ (C$_{34}$H$_{37}$IN$_2$O$_7$Na requires 735.154).

Step G: 3'-Deoxy-5'-O-(4-methoxytrityl)-3'-methyl-2'-O-(2-methoxyethyl)-5-methyluridine A mixture of ammonium phosphinate (410 mg, 5.1 mmol) and 1,1,1,3,3,3-hexamethyldisilazane (1.18 mL, 0.90 g, 5.59 mmol) was heated at 100–110° C. for 2 h under nitrogen atmosphere with condenser. The intermediate BTSP(bis [trimethylsilyl]phosphinate) was cooled to 0° C. and 5 mL of dichloromethane was injected. To this mixture was injected a solution of 3'-deoxy-5'-O-(4-methoxytrityl)-3'-(iodomethyl)-2'-O-(2-methoxyethyl)-5-methyluridine (0.78 g, 1.1 mmol) and diisopropylethylamine (0.39 mL, 287 mg, 2.23 mmol) in 7 mL of dichloromethane. After the reaction mixture was stirred at rt overnight, a mixture of THF-MeOH-NEt$_3$ (3/6/0.3 mL) was added and continued to stir for 1 h. The reaction mixture was filtered through a pad of celite and washed with dichloromethane. The solvent was evaporated and the residue was purified by flash chromatography on a silica gel column using 2:1, 1:1, and then 1:2 hexanes-EtOAc as eluent providing 380 mg of the title compound.

$^1$H NMR (CDCl$_3$): δ 0.97 (d, 3H, J=6.8 Hz), 1.41 (s, 3H), 2.35–2.55 (m, 1H), 3.27 (dd, 1H, J=11.0, 3.0 Hz), 3.37 (s, 3H), 3.54–3.68 (m, 3H), 3.79 (s, 3H), 3.75–3.87 (m, 1H), 3.94 (d, 1H, J=5.0 Hz), 4.03–4.16 (m, 2H), 5.84 (s, 1H), 6.83 (s, 1H), 6.87 (s, 1H), 7.20–7.37 (m, 8H), 7.39–7.50 (m, 4H), 7.86 (s, 1H), 9.50 (s, 1H; $^{13}$C NMR (CDCl$_3$): δ 8.7, 12.1, 35.6, 55.3, 59.0, 61.7, 69.8,72.1, 85.4, 86.4, 86.7, 89.8, 110.0, 113.3, 127.2, 128.0, 128.4, 130.4, 135.0, 135.7, 143.9, 150.5, 158.8, 164.6. HRMS (FAB) m/z 609.256 (M+Na)$^+$ (C$_{34}$H$_{38}$N$_2$O$_7$Na requires 609.257).

Step H: 3'-Deoxy-3'-methyl-2'-O-(2-methoxyethyl)-5-methyluridine

Trifluoroacetic acid (1.5 mL) was added dropwise to a stirred solution of 3'-deoxy-5'-O-(4-methoxytrityl)-3'-methyl-2'-O-(2-methoxyethyl)-5-methyluridine (370 mg, 0.63 mmol) in 50 mL of chloroform at 0° C. The mixture was stirred at rt for 30 min, concentrated, and then dissolved in ethyl acetate. The solution was washed with dilute sodium bicarbonate and brine. The organic phase was dried (Na$_2$SO$_4$) and concentrated. The resulting residue was purified by flash chromatography on a silica gel column. Elution with 1:1, 1:3 and then 0:1 hexanes-EtOAc provided 170 mg of the title compound as a white foam.

$^1$H NMR (CDCl$_3$): δ 1.03 (d, 3H, J=6.8 Hz), 1.83 (s, 3H) 2.20–2.40 (m, 1H), 3.10–3.28 (m, 1H), 3.35 (s, 3H), 3.50–4.15 (m, 10H), 5.81 (s, 1H), 7.89 (s, 1H), 9.77 (s, 1H); $^{13}$C NMR (CDCl$_3$): δ 8.9 12.4, 34.7, 59.0, 60.6, 69.7,72.0, 86.3, 89.8, 109.7, 136.9, 150.4, 164.7. HRMS (FAB) m/z 315.154 (M+H)$^+$ (C$_{14}$H$_{23}$N$_2$O$_6$ requires 315.155).

EXAMPLE 50

2'-Amino-2'-deoxyuridine

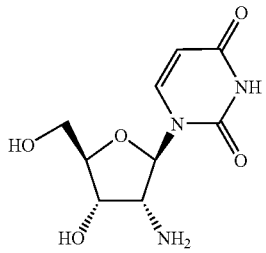

This compound was prepared following the procedures described in *J. Org. Chem*.61: 781 (1996).

EXAMPLE 51

3'-Deoxyuridine

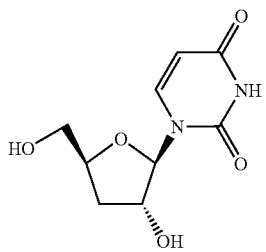

This compound was obtained from commercial sources.

EXAMPLE 52

2'-C-Methyladenosine

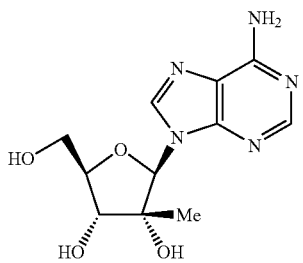

This compound was prepared following the conditions described in *J.Med. Chem*. 41: 1708 (1998).

EXAMPLE 53

3'-Deoxyadenosine (Cordycepin)

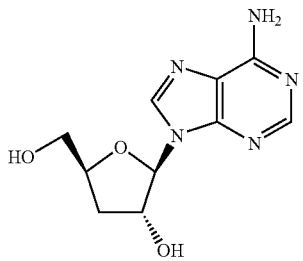

This compound was obtained from commercial sources.

EXAMPLE 54

3'-Amino-3'-deoxyadenosine

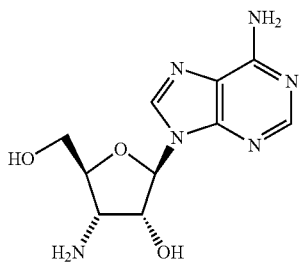

This compound was prepared following the conditions described in *Tetrahedron Lett*. 30: 2329 (1989).

EXAMPLE 55

8-Bromoadenosine

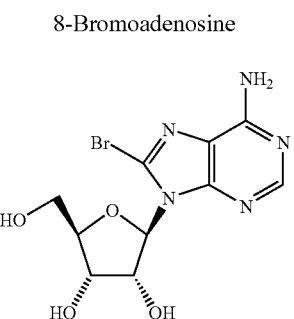

This compound was obtained from commercial sources.

EXAMPLE 56

2'-O-Methyladenosine

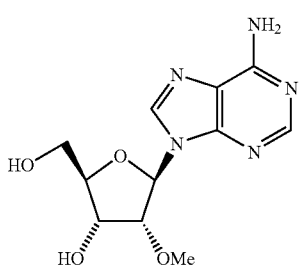

This compound was obtained from commercial sources.

EXAMPLE 57

3'-Deoxy-3'-fluoroadenosine

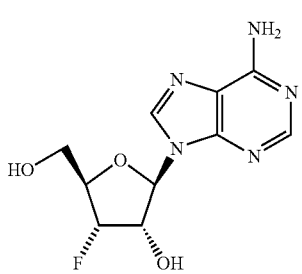

This compound was prepared following the procedures described in *J. Med. Chem.* 34: 2195 (1991).

EXAMPLE 58

6-Methyl-9-(β-D-ribofuranosyl)-9H-purine

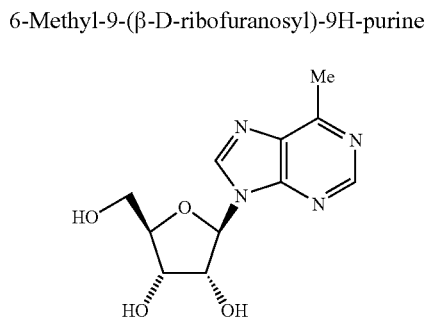

This compound was prepared following the procedures described in *Nucleosides, Nucleotides, Nucleic Acids* 19: 1123 (2000).

EXAMPLE 59

2',3',5'-tri-O-acetyl-8-methylsulfonyladenosine

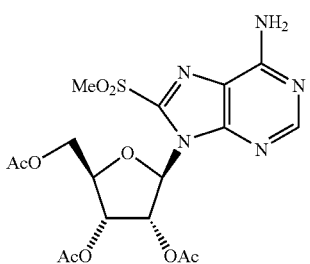

EXAMPLE 60

1-Methyl-9-[2,3,5-tri-O-(p-toluoyl)-β-D-ribofuranosyl]-9H-purine-6(1H)-thione

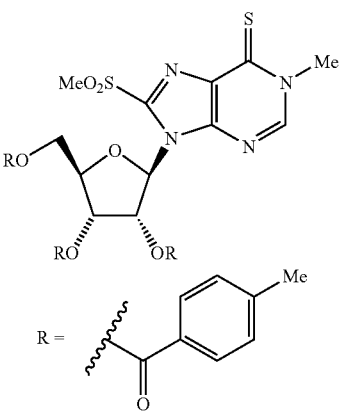

EXAMPLE 61

4-Amino-7-(2-C-methyl-β-D-arabinofuranosyl)-7H-pyrrolo[2,3-d]pyrimidine

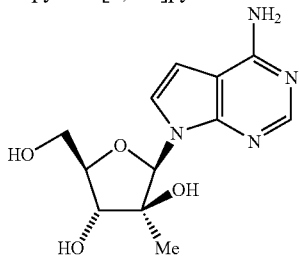

To chromium trioxide (1.57 g, 1.57 mmol) in dichloromethane (DCM) (10 mL) at 0° C. was added acetic anhydride (145 mg, 1.41 mmol) and then pyridine (245 mg, 3.10 mmol). The mixture was stirred for 15 min, then a solution of 7-[3,5-O-[1,1,3,3-tetrakis(1-methylethyl)-1,3-disiloxanediyl]-β-D-ribofuranosyl]-7H-pyrrolo[2,3-d]pyrimidin-4-amine [for preparation, see J. Am. Chem. Soc. 105: 4059 (1983)] (508 mg, 1.00 mmol) in DCM (3 mL) was added. The resulting solution was stirred for 2 h and then poured into ethyl acetate (10 mL), and subsequently filtered through silica gel using ethyl acetate as the eluent. The combined filtrates were evaporated in vacuo, taken up in diethyl ether/TBF (1:1) (20 mL), cooled to −78° C. and methylmagnesium bromide (3M, in TEF) (3.30 mL, 10 mmol) was added dropwise. The mixture was stirred at −78° C. for 10 min, then allowed to come to room temperature (rt) and quenched by addition of saturated aqueous ammonium chloride (10 mL) and extracted with DCM (20 mL). The organic phase was evaporated in vacuo and the crude product purified on silica gel using 5% methanol in dichloromethane as eluent. Fractions containing the product were pooled and evaporated in vacuo. The resulting oil was taken up in THF (5 mL) and tetrabutylammonium fluoride (TBAF) on silica (1.1 mmol/g on silica) (156 mg) was added. The mixture was stirred at rt for 30 min, filtered, and evaporated in vacuo. The crude product was purified on silica gel using 10% methanol in dichloromethane as eluent. Fractions containing the product were pooled and evaporated in vacuo to give the desired compound (49 mg) as a colorless solid.

$^1$H NMR (DMSO-d$_6$): δ 1.08 (s, 3H), 3.67 (m, 2H), 3.74 (m, 1H), 3.83 (m, 1H), 5.19 (m, 1H), 5.23 (m, 1H), 5.48 (m, 1H), 6.08 (1H, s), 6.50 (m, 1H), 6.93 (bs, 2H), 7.33 (m, 1H), 8.02 (s, 1H).

EXAMPLE 62

4-Amino-7-(2-C-methyl-β-D-ribofuranosyl)-7H-pyrrolo[2,3-d]pyrimidine

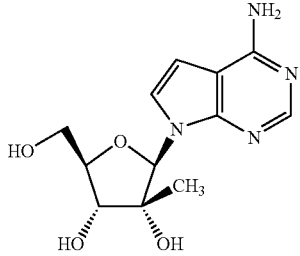

Step A: 3,5-Bis-O-(2,4-dichlorophenylmethyl)-1-O-methyl-α-D-ribofuranose

A mixture of 2-O-acetyl-3,5-bis-O-(2,4-dichlorophenylmethyl)-1-O-methyl-α-D-ribofuranose [for preparation, see: Helv. Chim. Acta 78: 486 (1995)] (52.4 g, 0.10 mol) in methanolic K$_2$CO$_3$ (500 mL, saturated at room temperature) was stirred at room temperature for 45 min. and then concentrated under reduced pressure. The oily residue was suspended in CH$_2$Cl$_2$ (500 mL), washed with water (300 mL+5×200 mL) and brine (200 mL), dried (Na$_2$SO$_4$), filtered, and concentrated to give the title compound (49.0 g) as colorless oil, which was used without further purification in Step B below.

$^1$HMR (DMSO-d$_6$): δ 3.28 (s, 3H, OCH$_3$), 3.53 (d, 2H, J$_{5,4}$=4.5 Hz, H-5a, H-5b), 3.72 (dd, 1H, J$_{3,4}$=3.6 Hz, J$_{3,2}$=6.6 Hz, H-3), 3.99 (ddd, 1H, J$_{2,1}$=4.5 Hz, J$_{2,OH-2}$=9.6 Hz, H-2), 4.07 (m, 1H, H-4), 4.50 (s, 2H, CH$_2$Ph), 4.52, 4.60 (2d, 2H, J$_{gem}$=13.6 Hz, CH$_2$Ph), 4.54 (d, 1H, OH-2), 4.75 (d, 1H, H-1), 7.32–7.45, 7.52–7.57 (2m, 10H, 2Ph).

$^{13}$C NMR (DMSO-d$_6$) δ 55.40, 69.05, 69.74, 71.29, 72.02, 78.41, 81.45, 103.44, 127.83, 127.95, 129.05, 129.28, 131.27, 131.30, 133.22, 133.26, 133.55, 133.67, 135.45, 135.92.

Step B: 3,5-Bis-O-(2,4-dichlorophenylmethyl)-1-O-methyl-α-D-erythro-pentofuranos-2-ulose To an ice-cold suspension of Dess-Martin periodinane (50.0 g, 118 mmol) in anhydrous CH$_2$Cl$_2$ (350 mL) under argon (Ar) was added a solution of the compound from Step A (36.2 g, 75 mmol) in anhydrous CH$_2$Cl$_2$ (200 mL) dropwise over 0.5 h. The reaction mixture was stirred at 0° C. for 0.5 h and then at room temperature for 3 days. The mixture was diluted with anhydrous Et$_2$O (600 mL) and poured into an ice-cold mixture of Na$_2$S$_2$O$_3$.5H$_2$O (180 g) in saturated aqueous NaHCO$_3$ (1400 mL). The layers were separated, and the organic layer was washed with saturated aqueous NaHCO$_3$ (600 mL), water (800 mL) and brine (600 mL), dried (MgSO$_4$), filtered and evaporated to give the title compound (34.2 g) as a colorless oil, which was used without further purification in Step C below.

$^1$H NMR (CDCl$_3$) δ 3.50 (s, 3H, OCH$_3$), 3.79 (dd, 1H, J$_{5a,5b}$=11.3 Hz, J$_{5a,4}$=3.5 Hz, H-5a), 3.94 (dd, 1H, J$_{5b,4}$=2.3 Hz, H-5b), 4.20 (dd, 1H, J$_{3,1}$=1.3 Hz, J$_{3,4}$=8.4 Hz, H-3), 4.37 (ddd, 1H, H-4), 4.58, 4.69 (2d, 2H, J$_{gem}$=13.0 Hz, CH$_2$Ph), 4.87 (d, 1H, H-1), 4.78, 5.03 (2d, 2H, J$_{gem}$=12.5 Hz, CH$_2$Ph), 7.19–7.26, 7.31–7.42 (2m, 10H, 2Ph).

$^{13}$C NMR (DMSO-d$_6$) δ 55.72, 69.41, 69.81, 69.98, 77.49, 78.00, 98.54, 127.99, 128.06, 129.33, 129.38, 131.36, 131.72, 133.61, 133.63, 133.85, 133.97, 134.72, 135.32, 208.21.

Step C: 3,5-Bis-O-(2,4-dichlorophenylmethyl)-2-C-methyl-1-O-methyl-α-D-ribofuranose To a solution of MeMgBr in anhydrous Et$_2$O (0.48 M, 300 mL) at −55° C. was added dropwise a solution of the compound from Step B (17.40 g, 36.2 mmol) in anhydrous Et$_2$O (125 mL). The reaction mixture was allowed to warm to −30° C. and stirred for 7 h at −30° C. to −15° C., then poured into ice-cold water (500 mL) and the mixture vigorously stirred at room temperature for 0.5 h. The mixture was filtered through a Celite pad (10×5 cm) which was thoroughly washed with Et$_2$O. The organic layer was dried (NgSO$_4$), filtered and concentrated. The residue was dissolved in hexanes (~30 mL), applied onto a silica gel column (10×7 cm, prepacked in hexanes) and eluted with hexanes and hexanes/EtOAc (9/1) to give the title compound (16.7 g) as a colorless syrup.

$^1$H NMR (CDCl$_3$): δ 1.36 (d, 3H, J$_{Me,OH}$=0.9 Hz, 2C-Me), 3.33 (q, 1H, OH), 3.41 (d, 1H, J$_{3,4}$=3.3 Hz), 3.46 (s, 3H, OCH$_3$), 3.66 (d, 2H, J$_{5,4}$=3.7 Hz, H-5a, H-5b), 4.18 (apparent q, 1H, H-4), 4.52 (s, 1H, H-1), 4.60 (s, 2H, CH$_2$Ph), 4.63, 4.81 (2d, 2H, J$_{gem}$=13.2 Hz, CH$_2$Ph), 7.19–7.26, 7.34–7.43 (2m, 10H, 2Ph).

$^{13}$C NMR (CDCl$_3$): δ 24.88, 55.45, 69.95, 70.24, 70.88, 77.06, 82.18, 83.01, 107.63, 127.32, 129.36, 130.01, 130.32, 133.68, 133.78, 134.13, 134.18, 134.45, 134.58.

Step D: 4-Chloro-7-[3,5-bis-O-(2,4-dichlorophenylmethyl)-2-C-methyl-β-D-ribofuranosyl]-7H-pyrrolo[2,3-d]pyrimidine To a solution of the compound from Step C (9.42 g, 19 mmol) in anhydrous dichloromethane (285 mL) at 0° C. was added HBr (5.7 M in acetic acid, 20 mL, 114 mmol) dropwise. The resulting solution was stirred at 0° C. for 1 h and then at room temperature for 3 h, evaporated in vacuo and co-evaporated with anhydrous toluene (3×40 mL). The oily residue was dissolved in anhydrous acetonitrile (50 mL) and added to a solution of sodium salt of 4-chloro-1H-pyrrolo[2,3-d]pyrimidine [for preparation, see *J. Chem. Soc.*, 131 (1960)] in acetonitrile [generated in situ from 4-chloro-1H-pyrrolo[2,3-d]pyrimidine (8.76 g, 57 mmol) in anhydrous acetonitrile (1000 mL), and NaH (60% in mineral oil, 2.28 g, 57 mmol), after 4 h of vigorous stirring at room temperature]. The combined mixture was stirred at room temperature for 24 h, and then evaporated to dryness. The residue was suspended in water (250 mL) and extracted with EtOAc (2×500 mL). The combined extracts were washed with brine (300 mL), dried over $Na_2SO_4$, filtered and evaporated. The crude product was purified on a silica gel column (10 cm×10 cm) using ethyl acetate/hexane (1:3 and 1:2) as the eluent. Fractions containing the product were combined and evaporated in vacuo to give the desired product (5.05 g) as a colorless foam.

$^1$H NMR (CDCl$_3$): δ 0.93 (s, 3H, CH$_3$), 3.09 (s, 1H, OH), 3.78 (dd, 1H, J$_{5',5''}$=10.9 Hz, J$_{5',4}$=2.5 Hz, H-5'), 3.99 (dd, 1H, J$_{5'',4}$=2.2 Hz, H-5''), 4.23–4.34 (m, 2H, H-3', H-4'), 4.63, 4.70 (2d, 2H, J$_{gem}$=12.7 Hz, CH$_2$Ph), 4.71, 4.80 (2d, 2H, J$_{gem}$=12.1 Hz, CH$_2$Ph), 6.54 (d, 1H, , J$_{5,6}$=3.8 Hz, H-5), 7.23–7.44 (m, 10H, 2Ph).

$^{13}$C NMR (CDCl$_3$): δ 21.31, 69.10, 70.41, 70.77, 79.56, 80.41, 81.05, 91.11, 100.57, 118.21, 127.04, 127.46, 127.57, 129.73, 129.77, 130.57, 130.99, 133.51, 133.99, 134.33, 134.38, 134.74, 135.21, 151.07, 151.15 152.47.

Step E: 4-Chloro-7-(2-C-methyl-β-D-ribofuranosyl)-7H-pyrrolo[2,3-d]pyrimidine

To a solution of the compound from Step D (5.42 g, 8.8 mmol) in dichloromethane (175 mL) at −78° C. was added boron trichloride (1M in dichloromethane, 88 mL, 88 mmol) dropwise. The mixture was stirred at −78° C. for 2.5 h, then at −30° C. to −20° C. for 3 h. The reaction was quenched by addition of methanol/dichloromethane (1:1) (90 mL) and the resulting mixture stirred at −15° C. for 30 min., then neutralized with aqueous ammonia at 0° C. and stirred at room temperature for 15 min. The solid was filtered and washed with CH$_2$Cl$_2$/MeOH (1/1, 250 mL). The combined filtrate was evaporated, and the residue was purified by flash chromatography over silica gel using CH$_2$Cl$_2$ and CH$_2$Cl$_2$:MeOH (99:1, 98:2, 95:5 and 90:10) gradient as the eluent to furnish desired compound (1.73 g) as a colorless foam, which turned into an amorphous solid after treatment with MeCN.

$^1$H NMR (DMSO-d$_6$) δ 0.64 (s, 3H, CH$_3$), 3.61–3.71 (m, 1H, H-5'), 3.79–3.88 (m, 1H, H-5''), 3.89–4.01 (m, 2H, H-3', H-4'), 5.15–5.23 (m, 3H, 2'-OH, 3'-OH, 5'-OH), 6.24 (s, 1H, H-1'), 6.72 (d, 1H, J$_{5,6}$=3.8 Hz, H-5), 8.13 (d, 1H, H-6), 8.65 (s, 1H, H-2).

$^{13}$C NMR (DMSO-d$_6$) δ 20.20, 59.95, 72.29, 79.37, 83.16, 91.53, 100.17, 117.63, 128.86, 151.13, 151.19, 151.45.

Step F: 4-Amino-7-(2-C-methyl-(β-D-ribofuranosyl)-7H-pyrrolo[2,3-d]pyrimidine

To the compound from Step E (1.54 g, 5.1 mmol) was added methanolic ammonia (saturated at 0° C.; 150 mL). The mixture was heated in a stainless steel autoclave at 85° C. for 14 h, then cooled and evaporated in vacuo. The crude mixture was purified on a silica gel column with CH$_2$Cl$_2$/MeOH (9/1) as eluent to give the title compound as a colorless foam (0.8 g), which separated as an amorphous solid after treatment with MeCN. The amorphous solid was recrystallized from methanol/acetonitrile; m.p. 222° C.

$^1$H NMR (DMSO-d$_6$): δ 0.62 (s, 3H, CH$_3$), 3.57–3.67 (m, 1H, H-5'), 3.75–3.97 (m, 3H, H-5'', H-4', H-3'), 5.00 (s, 1H, 2'-OH), 5.04 (d, 1H, J$_{3'OH,3'}$=6.8 Hz, 3'-OH), 5.06 (t, 1H, J$_{5'OH,5',5''}$=5.1 Hz, 5'-OH), 6.11 (s, 1H, H-1'), 6.54 (d, 1H, J$_{5,6}$=3.6 Hz, H-5), 6.97 (or s, 2H, NH$_2$), 7.44 (d, 1H, H-6), 8.02 (s, 1H, H-2).

$^{13}$C NMR (DMSO-d$_6$): δ 20.26, 60.42, 72.72, 79.30, 82.75, 91.20, 100.13, 103.08, 121.96, 150.37, 152.33, 158.15.

LC-MS: Found: 279.10 (M−H$^+$); calc. for $C_{12}H_{16}N_4O_4$+H$^+$: 279.11.

EXAMPLE 63

4-Amino-7-(3-deoxy-3-methyl-β-D-ribofuranosyl)-7H-pyrrolo[2,3-d]pyrimidin-5-carboxamide

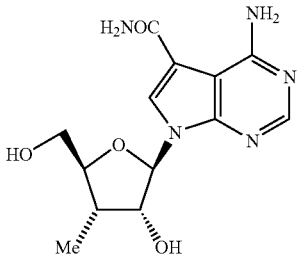

Step A: 4-Amino-6-bromo-7-(2-O-acetyl-5-O-benzoyl-3-deoxy-3-methyl-β-D-ribofuranosyl)-7H-pyrrolo[2,3-d]pyrimidin-5-carbonitrile BSA (0.29 mL, 2.0 mmol) was added into a stirred suspension of 4-amino-6-bromo-5-cyano-1H-pyrrolo[2,3-d]pyrimidine (0.24 g, 1 mmol; prepared according to *Nucleic Acid Chemistry*, Part IV, Townsend, L. B. and Tipson, R. S.; Ed.; Wiley-Interscience: New York, 1991, pp. 16–17 and *Synthetic Commun.* 1998, 28, 3835) in dry acetonitrile (10 mL) at room temperature under argon. After 15 min, 1,2-di-O-acetyl-5-O-benzoyl-3-deoxy-3-methyl-D-ribofuranose (J. Med. Chem. (1976), 19, 1265) (0.36 g, 1.0 mmol) was added along with TMSOTf (0.54 g, 3 mmol). The mixture was stirred at room temperature for 5 min and then at 80° C. for 0.5 h. The solution was cooled, diluted with ethyl acetate (50 mL) and poured into ice-cold saturated aqueous NaHCO$_3$ (15 mL). The layers were separated. The organic layer was washed with brine (15 mL), dried (Na$_2$SO$_4$) and then evaporated. The residue was purified on silica gel column using a solvent system of hexanes/EtOAc: 3/1. Appropriate fractions were collected and evaporated to provide the title compound as colorless foam (0.21 g).

Step B: 4-Amino-7-(2-O-acetyl-5-O-benzoyl-3-deoxy-3-methyl-β-D-ribofuranosyl)-7H-pyrrolo[2,3-d]pyrimidin-5-carbonitrile To a suspension of the title compound from Step A (183 mg, 0.35 mmol) in EtOH (9 mL) were added ammonium formate (0.23 g, 3.6 mmol) and 10% palladium on activated carbon (20 mg) and the mixture was heated at reflux for 1.5 h. The hot reaction mixture was filtered through Celite and washed with hot EtOH. The solvent was removed and the residue treated with MeOH. The pale yellow solid was filtered thus yielding 105 mg of pure title compound. The Step C: 4-Amino-7-(3-deoxy-3-methyl-β-D-ribofuranosyl)-7H-pyrrolo[2,3-d]pyrimidin-5-carboxamide A mixture of the compound from Step B (51 mg, 0.12 mmol), ethanolic ammonia (5 mL, saturated at 0° C.), aqueous ammonia (5 mL, 30%) and aqueous hydrogen peroxide (1 mL, 35%) was stirred room temperature for 8 h. The solution was evaporated and:the residue purified on silica gel column with a solvent system of $CH_2Cl_2$/MeOH: 10/1 to give the title compound as a white solid (28 mg).

$^1$H-MNR (CD$_3$OD): δ 1.12 (d, 3H, J=6.8 Hz), 2.40 (m, 1H), 3.76 (dd, 1H, J$_1$=12.8 Hz, J$_2$=4.0 Hz), 3.94–4.04 (m, 2H), 4.33 (d, 1H, J=5.4 Hz), 6.13 (s, 1H), 8.11 (s, 1H), 8.16 (s, 1H).

EXAMPLE 64

4-Amino-7-(3-deoxy-β-D-ribofuranosyl)-7H-pyrrolo[2,3-d]pyrimidine-5-carboxamide

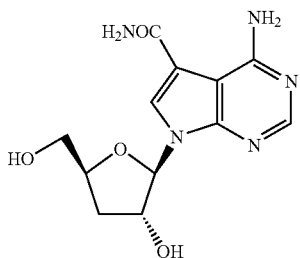

This compound was prepared following the procedures described in *J. Med. Chem.* 26: 25 (1983).

EXAMPLE 65

4-Amino-7-(β-D-ribofuranosyl)-7H-pyrrolo[2,3-d]pyrimidine-5-carboxamide (Sangivamycin)

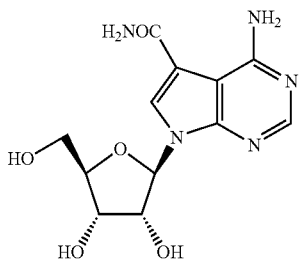

This compound was obtained from commercial sources.

EXAMPLE 66

7-(2-O-methyl-β-D-ribofuranosyl)-7H-pyrrolo[2,3-d]pyrimidine

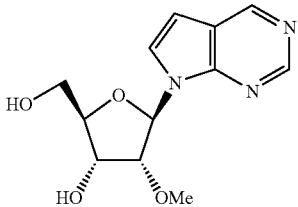

This compound was prepared following the procedures described in *J. Org. Chem.* 39: 1891 (1974).

EXAMPLE 67

4-Amino-7-(3-deoxy-3-fluoro-β-D-ribofuranosyl)-7H-pyrrolo[2,3-d]pyrimidine-5-carboxamide

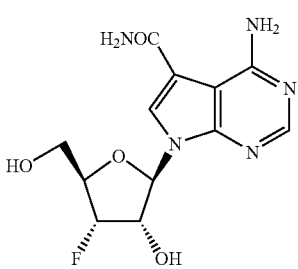

This compound was prepared following the procedures described in *Chem. Pharm. Bull.* 41: 775 (1993).

EXAMPLE 68

4-Amino-7-(3-deoxy-β-D-ribofuranosyl)-7H-pyrrolo[2,3-d]pyrimidine-5-carbonitrile

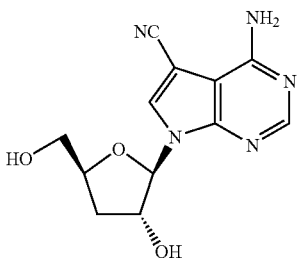

This compound was prepared following the procedures described in *J. Med. Chem.* 30: 481 (1987).

EXAMPLE 69

4-Amino-7-(2-O-methyl-β-D-ribofuranosyl)-7H-pyrrolo[2,3-d]pyrimidine

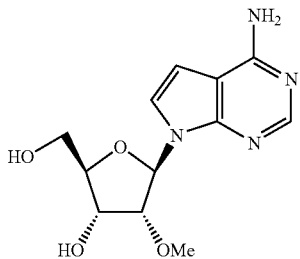

This compound was prepared following the procedures described in *J. Org. Chem.* 39: 1891 (1974).

EXAMPLE 70

3'-Amino-3'-deoxy-2'-O-methyladenosine

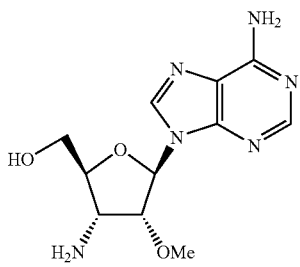

This compound is obtained by the methylation of appropriately protected 3'-amino-3'-deoxyadenosine derivative (Example 54).

EXAMPLE 71

4-Amino-7-(3-deoxy-β-D-ribofuranosyl)-7H-pyrrolo[2,3-d]pyrimidine

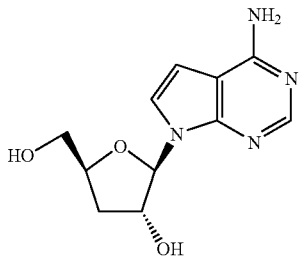

This compound was prepared following the following procedure described in *Can. J. Chem.* 55: 1251 (1977).

EXAMPLE 72

General Process to SATE Prodrug Moiety

S-Acyl-2-Thioethyl (SATE) pronucleotides are discussed in C. R. Wagner, V. V. Iyer, and E. J. McIntee, "Pronucleotides: Toward the In Vivo Delivery of Antiviral and Anticancer Nucleotides," *Med. Res. Rev.*, 20: 1–35 (2000), which is incorporated by reference herein in its entirety. SATE derivatives of nucleosides are also disclosed U.S. Pat. Nos. 5,770,725; 5,849,905; and 6,020,482, the contents of each of which are incorporated by reference herein in their entirety.

Bis(S-acetyl-2-thioethyl)-N,N-diisopropylphosphoramidite:

2-Mercaptoethanol (5 g, 64 mmol) was dissolved in $CH_2Cl_2$ (50 mL). To this solution was added triethylamine (7.67 mL, 57.6 mmol), and the reaction mixture was cooled in an ice bath to 0° C. Acetic anhydride (4.54 mL, 48 mmol) was added dropwise in 10 min, and the reaction mixture was stirred for 1 h at 0° C. The reaction mixture was then allowed to come to room temperature over a period of 2 h. The reaction mixture was diluted with $CH_2Cl_2$ (50 mL), washed with water (75 mL), 5% aqueous $NaHCO_3$ (75 mL) and brine (75 mL). The organic phase was dried over anhydrous $Na_2SO_4$ and concentrated in vacuo to give an oil. The oil was then dissolved in anhydrous THF (40 mL) and anhydrous triethylamine (7.76 mL) was, added. To this mixture was added activated molecular sieves (4Å) and was kept at room temperature for 10 min. The reaction mixture was cooled in an ice bath to 0° C. and diisopropylphosphoramidous dichloride (6.47 g, 32.03 mmol) was added. The reaction mixture was stirred at 0° C. for 2 h under inert atmosphere. Hexane (40 mL) was added to the reaction mixture and the precipitate formed was filtered. The filtrate was concentrated to one fourth of the volume, purified by loaded silica gel column chromatography and eluted with hexane containing 3% triethylamine and incremental amount of ethyl acetate (0 to 7%) to give the title compound as an oil (2.36 g).

$^1$H NMR ($CDCl_3$): δ 1.17 (s, 6H), 1.21 (s, 6H), 2.36 (s, 6H), 3.14 (t, J=6.44 Hz), 3.51–3.84 (m, 6H); $^{13}$C NMR ($CDCl_3$): δ 24.47, 24.61, 30.48, 42.85, 43.1, 61.88, 62.23, 195.26; $^{13}$P NMR ($CDCl_3$): δ 146.96.

EXAMPLE 73

2'-O-Methylguanosine-5'-[bis-(S-acetyl-2-thioethyl)phosphate]

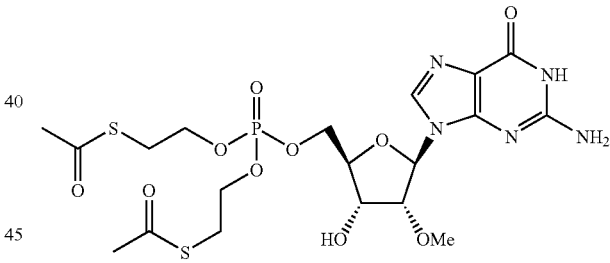

Step A: $N^{2-}$(4-monomethoxytrityl)-2'-O-methylguanosine-5'-[bis-(S-acetyl-2-thioethyl)phosphate]

$N^{2-}$(4-monomethoxytrityl)-2'-O-methylguanosine (0.74 g, 1.31 mmol) was mixed with 1H-tetrazole (0.061 g, 0.87 mmol) and dried over $P_2O_5$ in vacuo overnight. To this mixture was added anhydrous acetonitrile (8 mL). To the turbid solution, bis(S-acetyl-2-thioethyl)N,N-diisopropylphosphoramidite (0.3 g, 0.87 mmol) was added slowly and the reaction mixture was stirred at ambient temperature under inert atmosphere for 2 h. Solvent was removed in vacuo. The residue was cooled to −40° C. and a solution of 3-chloroperbenzoic acid (0.2 g) in $CH_2Cl_2$ (7 mL) was added. The solution was allowed to warm up to room temperature over 1 h. Sodium hydrogensulfite (10% aqueous solution, 2 mL) was added to reduce the excess of 3-chloroperbenzoic acid. The organic phase separated, diluted with $CH_2Cl_2$ (20 mL), washed with saturated aqueous $Na_2CO_3$ (10 mL), water (10 mL), dried over $Na_2SO_4$ and evaporated to dryness. The residue was purified by silica gel column chromatography and eluted with $CH_2Cl_2$ containing incremental amount of MeOH (5 to 10%) as eluent to yield the title compound (0.36 g) as a foam.

$^1$H NMR (MSO-d$_6$): δ 2.35 (s, 6H), 2.97 (s, 3H), 3.11 (t, 4H, J=6.0 Hz), 3.5 (m, 1H), 3.74 (s, 3H), 3.72–3.83 (m, 2H), 3.97–4.11 (m, 6H), 5.1 (d, 1H, J=6.4 Hz), 5.29 (d, 1H, J=3.1 Hz), 6.89 (d, 2H, J=8.8 Hz), 7.15–7.37 (m, 12H), 7.68 (s, 1H), 7.73 (s, 1H), 10.72 (s, 1H); $^{13}$C NMR (CDCl$_3$): δ 30.36, 55.38, 57.99, 66.08, 66.19, 67.22, 69.15, 70.49, 81.18, 81.57, 86.64, 113.04, 117.99, 126.66, 127.71, 128.67, 130.04, 136.09, 136.56, 144.51, 144.82, 149.52, 151.29, 158.15, 194.56; $^{13}$P NMR (CDCl$_3$): δ −2.04; MS (API-ES) 852.10 [M−H]$^+$.

Step B: 2'-O-methylguanosine-5'-[bis-(S-acetyl-2-thioethyl) phosphate]

N$^2$-(4-monomethoxytrityl)-2'-O-methylguanosine-5'-[bis-(S-acetyl-2-thioethyl)phosphate] (0.2 g, 0.23 mmol) was dissolved in acetic acid: MeOH:H$_2$O, 3:6:1 and heated at 55° C. for 24 h. Solvent was removed and the residue was purified by HPLC on reverse phase column (Hamilton PRP-1, 250×22 mm, A=Acetonitrile, B=H$_2$O 20 to 100 B in 65 min, flow 10 mL min$^{-1}$). Fractions containing the product were pooled together and evaporated to give the title compound (40% yield).

$^{13}$P NMR (CDCl$_3$): δ −0.72; MS (API-ES) m/z 582.1 [M+H]$^+$.

EXAMPLE 74

2'-O-Methylguanosine-5'-[bis-(S-pivaloyl-2-thioethyl)phosphate]

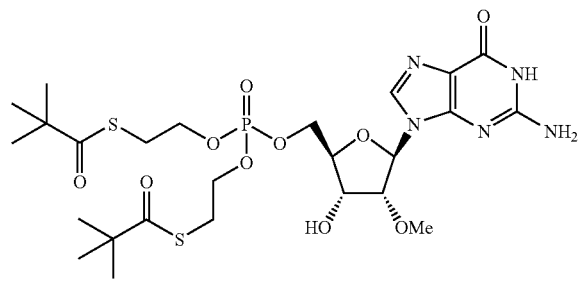

Step A: Bis(S-pivaloyl-2-thioethyl)-N,N-diisopropylphosphoramidite

S-pivaloyl-2-thioethanol (6.3 g, 39.6 mmol) was dissolved in anhydrous THF (100 mL). To this solution was added activated molecular sieves (4 Å) and kept at room temperature for 30 min. Anhydrous triethylamine (7.9 mL, 59.4 mmol) was added and the reaction mixture was cooled in an ice bath to 0° C. To this mixture diisopropylphosphoramidous dichloride (4 g, 19.8 mmol) was added dropwise. The mixture was stirred the reaction mixture at 0° C. for 2 h under inert gas atmosphere. Hexane (100 mL) was added to the reaction mixture, and the precipitate formed was filtered. The filtrate was concentrated to one fourth of the volume. This was purified by flash silica gel column chromatography using hexane containing 2% triethylamine and incremental amount of ethyl acetate (0 to 3%) as eluent to give the title compound as an oil (5.23 g).

$^1$H NMR (CDCl$_3$): δ 1.13–1.31 (m, 30H), 1.21 (s, 6H), 3.09 (t, J=6.6 Hz, 4H), 3.51–3.84 (m, 6H); $^{13}$C NMR (CDCl$_3$): δ 24.47, 24.61, 27.32, 30.00, 42.85,43.1, 46.32, 61.98, 62.33, 206.1; $^{13}$P NMR (CDCl$_3$): δ 148.51.

Step B: 2'-O-methylguanosine-5'-[bis-(S-pivaloyl-2-thioethyl)phosphate]

N$^2$-(4-monomethoxytrityl)-2'-O-methylguanosine (0.6 g, 1.05 mmol) was mixed with 1H-tetrazole (0.05 g, 0.7 mmol) and dried over P$_2$O$_5$ in vacuo overnight. To this mixture anhydrous acetonitrile (13.8 mL) was added. The reaction mixture was cooled to 0° C. in an ice bath and bis(S-pivaloyl-2-thioethyl)N,N-diisopropylphosphoramidite (0.32 g, 0.7 mmol) was added slowly. The reaction mixture was stirred at 0° C. for 5 minutes. The ice bath was removed and the reaction mixture was allowed to stir at room temperature under an inert atmosphere for 2 h. Solvent was removed in vacuo. The residue was cooled to 40° C. and a solution of 3-chloroperbenzoic acid (0.24 g, 1.4 mmol, 57–80%) in CH$_2$Cl$_2$ (10 mL) was added. The solution was allowed to warm up to −10° C. over 1 h. Sodium hydrogensulfite (10% aqueous solution, 10 mL) was added to reduce the excess of 3-chloroperbenzoic acid. The organic phase separated, diluted with CH$_2$Cl$_2$ (50 mL), washed with saturated aqueous Na$_2$CO$_3$ (40 mL), water (40 mL), dried over Na$_2$SO$_4$ and evaporated to dryness. The residue was chromatographed on a flash silica gel column using a CH$_2$Cl$_2$ containing incremental amount of MeOH (0 to 5%) as eluent. Fractions containing the product were pooled together and evaporated. The residue was dissolved in a solution of acetic acid/water/methanol (10 mL, 3:1:6) and heated at 55° C. for 24 h. Evaporated the solution in vacuum to get an oil. The oil was dissolved in 20% MeOH in water and purified by HPLC on C-18 column (Luna C-18, 250×2.12 mm, A=water, B=acetonitrile, 20 to 10% B in 65 min., flow 10 mL min$^{-1}$, λ 260 nm) to yield the title compound (0.082 g).

$^1$H NMR (DMSO-d$_6$): δ 1.18 (s, 18H), 3.08 (m, 4H), 3.33 (s, 3H) 3.94–4.10 (m, 6H), 4.14–4.21 (m, 2H), 4.29 (m, 1H), 5.42 (d, 1H, J=5.4 Hz), 5.81 (d, 1H, J=5.8 Hz), 6.49 (bs, 2H), 7.86 (s, 1H), 10.66 (bs, 1H); $^{13}$P NMR (DMSO-d$_6$): δ −0.71; MS (API-ES) m/z 664.2 [M−H]$^-$.

EXAMPLE 75

8-Bromo-2'-O-methylguanosine-5'-[bis-(S-pivaloyl-2-thioethyl)phosphate]

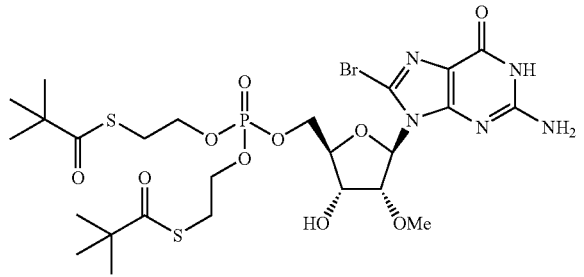

This compound was synthesized according to the procedure used for the synthesis of Example 74 starting with 8-bromo-N$^2$-(4-monomethoxytrityl)-2'-O-methylguanosine (0.46 g, 0.63 mmol). Other reagents used were 1H-tetrazole (0.034 g, 0.49 mmol), bis(S-pivaloyl-2-thioethyl)N,N-diisopropylphosphoramidite (0.22 g, 0.49 mmol), acetonitrile (8.3 ml), 3-chloroperbenzoic acid (0.17 g, 0.98 mmol, 57–80%) in CH$_2$Cl$_2$ (4 mL). The title compound was isolated in 13% yield (0.061 g).

$^1$H NMR (DMSO-d$_6$): δ 1.14 and 1.16 (m, 18H), 3.06 (m, 4H), 3.32 (s, 3H) 3.96–4.06 (m, 5H), 4.18–4.3 (m, 2H), 4.46 (d, 1H, J=2.4 Hz), 4.66 (t, 1H, J=2.6 Hz), 5.37 (d, 1H, J=2.6 Hz), 5.78 (d, 1H, J=2.8 Hz), 6.62 (bs, 2H), 10.99 (bs, 1H); $^{13}$P NMR (DMSO-d$_6$) δ −0.79; MS (API-ES) m/z 742.13 and 744.13 [M−H]$^-$.

EXAMPLE 76

2-Amino-3,4-dihydro-7-(2-O-methyl-β-D-ribofuranosyl)-4-oxo-7H-pyrrolo[2,3-d]pyrimidine-5'-[bis-(S-pivaloyl-2-thioethyl)phosphate]

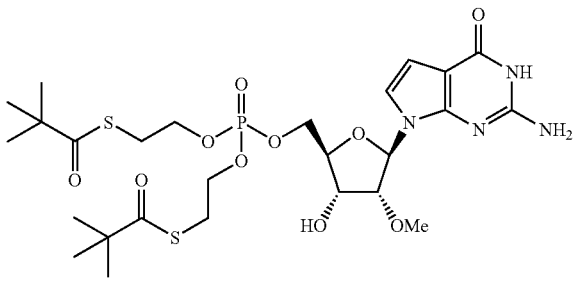

This compound was synthesized according to the procedure used for the synthesis of Example 74 starting with 7-deaza-N²-(4-monomethoxytrityl)-2'-O-methylguanosine (0.47 g, 0.82 mmol). Other reagents used were 1H-tetrazole (0.044 g, 0.63 mmol), bis(S-pivaloyl-2-thioethyl)N,N-diisopropylphosphoramidite (0.29 g, 0.63 mmol), acetonitrile (11 mL), 3-chloroperbenzoic acid (0.21 g, 1.26 mmol, 57–80%) in CH$_2$Cl$_2$ (5.2 mL). The title compound was isolated in 29% yield (0.158 g).

$^1$H NMR (DMSO-d$_6$): δ 1.14 (s, 18H), 3.06 (m, 4H), 3.31 (s, 3H) 3.96–4.26 (m, 9H), 5.35 (d, 1H, J=2.6 Hz), 5.78 (d, 1H, J=5.2 Hz), 5.99 (d, 1H, J=6.6 Hz), 6.27 (m, 3H), 6.86 (d, 1H, J=3.6 Hz), 10.39 (s, 1H); $^{13}$P NMR (DMSO-d$_6$): δ −0.72; MS (API-ES) m/z 663.20 [M−H]$^-$; HRMS Calcd for C$_{26}$H$_{42}$N$_4$O$_{10}$PS$_2$ 665.2074 found 665.2071.

EXAMPLE 77

3'-Deoxyguanosine-5'-[bis-(S-pivaloyl-2-thioethyl)phosphate]

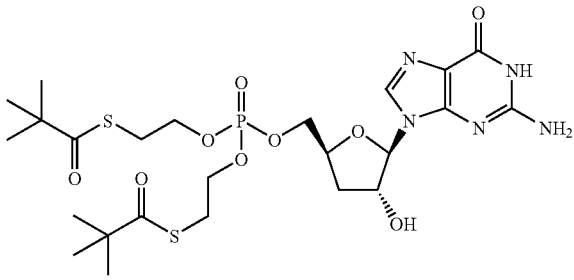

N²-(4-Monomethoxytrityl)-3'-deoxyguanosine (0.20 g, 0.35 mmol) was mixed with 1H-tetrazole (0.019 g, 0.27 mmol) and dried over P$_2$O$_5$ in vacuo overnight. To this mixture anhydrous acetonitrile (4.7 mL) was added to give a turbid solution. The reaction mixture was cooled to 0° C. in an ice bath and bis(S-pivaloyl-2-thioethyl)N,N-diisopropylphosphoramidite (0.12 g, 0.27 mmol) was added slowly. The reaction mixture was stirred at 0° C. for 5 minutes. The ice bath was removed and the reaction mixture was allowed to come to room temperature. The reaction mixture was stirred at room temperature under an inert gas atmosphere for 2 h. Solvent was removed in vacuo. The residue was cooled to 40° C. and a solution of 3-chloroperbenzoic acid (0.12 g, 0.7 mmol, 57–80%) in CH$_2$Cl$_2$ (2.2 mL) was added. The solution was allowed to warm up to −10° C. over 1 h. Sodium hydrogensulfite (10% aqueous solution, 2 mL) was added to reduce the excess of 3-chloroperbenzoic acid. The organic phase was separated, diluted with CH$_2$Cl$_2$ (30 mL), washed with saturated aqueous Na$_2$CO$_3$ (20 mL), water (20 mL), dried over Na$_2$SO$_4$ and evaporated to dryness. The residue was chromatographed on a flash silica gel column using CH$_2$Cl$_2$ containing incremental amount of MeOH (0 to 5%) as eluent. Fractions containing the product were pooled and evaporated. The residue was dissolved in a solution of acetic acid/water/methanol (5 mL, 3:1:6) and heated at 55° C. for 24 h. Evaporated the solution in vacuum to get an oil. The oil was dissolved in 20% MeOH in water and purified by HPLC on C-18 column (Luna C-18, 250×2.12 mm, A=water, B=acetonitrile, 20 to 10% B in 65 min., flow 10 mL min$^{-1}$, λ 260 nm) to yield the title compound (0.027 g).

$^1$H NMR (DMSO-d$_6$): δ 1.15 (s, 18H), 1.92–2.01 (m, 1H), 2.17–2.28 (m, 1H), 3.04 (t, 4H, J=6.2 Hz), 3.91–4.23 (m, 6 H), 4.37–4.55 (m, 2H), 5.67 (m, 2H), 6.45 (bs, 2H), 7.75 (s, 1H), 10.61 (s, 1H); $^{13}$P NMR (DMSO-d$_6$): δ −0.75; MS (API-ES) m/z 634.2 [M−H]$^-$.

EXAMPLE 78

2-Amino-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate]

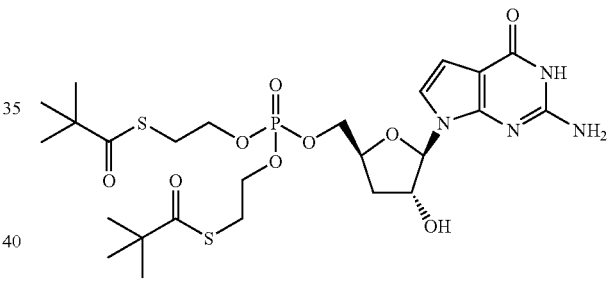

2-(4-Monomethoxytrityl)amino-7-(3-deoxy-β-D-ribofuranosyl)-7H-pyrrolo[2,3-d]pyrimidin-4(3H)-one (0.30 g, 0.52 mmol) was mixed with 1H-tetrazole (0.028 g, 0.40 mmol) and dried over P$_2$O$_5$ in vacuo overnight. To this mixture anhydrous acetonitrile (7 mL) was added, and the solution was cooled to 0° C. in an ice bath. Bis(S-pivaloyl-2-thioethyl)-N,N-diisopropylphosphoramidite (0.18 g, 0.40 mmol) was added slowly. The reaction mixture was allowed to come to at room temperature and stirred at room temperature under an inert atmosphere for 2 h. The solvent was removed in vacuo. The residue was cooled to 40° C., and a solution of 3-chloroperbenzoic acid (0.14 g, 0.8 mmol, 57–80%) in CH$_2$Cl$_2$ (5 mL) was added. The solution was allowed to warm up to −10° C. over 2 h. Sodium hydrogensulfite (10% aqueous solution, 5 mL) was added to reduce the excess of 3-chloroperbenzoic acid. The organic phase was separated, diluted with CH$_2$Cl$_2$ (50 mL), washed with saturated aqueous Na$_2$CO$_3$ (40 mL), water (40 mL), dried over Na$_2$SO$_4$ and evaporated to dryness. The residue was chromatographed on a flash silica gel column using CH$_2$Cl$_2$ containing incremental amount of MeOH (0 to 5%) as eluent. Fractions containing the product were pooled and evaporated. The residue was dissolved in a solution of acetic acid/water/methanol (10 mL, 3:1:6) and heated at 55° C. for 24 h. The solution was evaporated to give an oil. The oil was dissolved in 20% MeOH in water and purified by HPLC on C-18 column (Luna C-18,250×2.12 mm, A=water, B=acetonitrile 20 to 10% B in 65 mL, flow 10 mL/min, λ 260 nm) to give the title compound (0.053 g).

$^1$H NMR (DMSO-$d_6$): δ 1.16 (s, 18H), 1.91–2.01 (m, 1H), 2.17–2.25 (m, 1H), 3.05 (t, 4H, J=6.2 Hz), 3.92–4.2 (m, 6H), 4.35 (bs, 2H), 5.56 (d, 1H, J=4.2 Hz), 5.86 (d, 1H, J=2.4 Hz), 6.24 (m, 3H), 6.77 (d, 1H, J=3.6 Hz), 10.36 (s, 1H); $^{13}$P NMR DMSO-$d_6$): δ −0.89; HRMS (MALDI) Calcd for $C_{25}H_{39}N_4O_9PS_2$.635.1969 found 635.1964.

EXAMPLE 79

2-Amino-5-bromo-7-(3-deoxy-β-D-ribofuranosyl)-3,4-dihydro-4-oxo-7H-pyrrolo[2,3-d]pyrimidine-5'-[bis-(S-pivaloyl-2-thioethyl)phosphate]

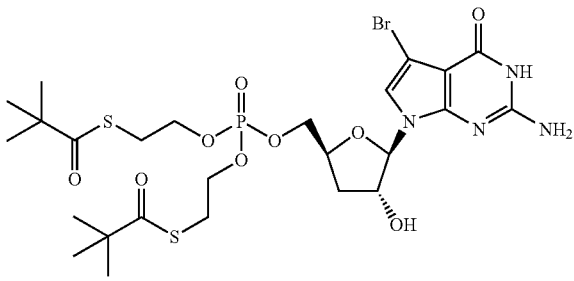

2-(4-Monomethoxytrityl)amino-5-bromo-7-(3-deoxy-β-D-ribofuranosyl)-7H-pyrrolo[2,3-d]pyrimidin-4(3H)-one (0.066 g, 0.17 mmol) was mixed with imidazole triflate (0.017 g, 0.17 mmol) and dried over $P_2O_5$ in vacuo overnight. To this mixture anhydrous acetonitrile (7 mL) and bis(S-pivaloyl-2-thioethyl)N,N-diisopropyl- phosphoramidite (0.97 g, 0.24 mmol) were added slowly. The reaction mixture was stirred under an inert atmosphere for 18 h. Solvent was removed in vacuo. The residue was cooled to −40° C. and a solution of 3-chloroperbenzoic acid (0.059 g, 0.34 mmol, 57–80%) in $CH_2Cl_2$ (2 mL) was added. The solution was allowed to warm up to −10° C. over 2 h. Sodium hydrogensulfite (10% aqueous solution, 5 mL) was added to reduce the excess of 3-chloroperbenzoic acid. The organic phase was separated, diluted with $CH_2Cl_2$ (30 mL), washed with saturated aqueous $Na_2CO_3$ (20 mL), water (20 mL), dried over $Na_2SO_4$ and evaporated to dryness. The residue was chromatographed on flash silica gel column using $CH_2Cl_2$ containing incremental amount of MeOH (0 to 5%) as eluent. Fractions containing the product were pooled and evaporated. The residue was dissolved in a solution of acetic acid/water/methanol (3 mL, 3:1:6) and heated at 55° C. for 24 h. The solution was evaporated to give an oil. The oil was dissolved in 20% MeOH in water and purified by HPLC on C-18 column (Luna C-18,250× 2.12 mm, A=water, B=acetonitrile 20 to 10% B in 65 mL, flow 10 mL min$^{-1}$, λ 260 nm) to afford the title compound (0.036 g).

$^1$H NMR (DMSO-$d_6$): δ 1.17 (s, 18H), 1.87–2.03 (m, 1H), 2.17–2.26 (m, 1H), 3.05 (t, 4H, J=6.4 Hz), 3.92–4.2 (m, 6H), 4.37 (bs, 2H), 5.70 (d, 1H, J=4.4 Hz), 5.85 (d, 1H, J=2.6 Hz), 6.36 (bs, 2H), 6.93 (s, 1H), 10.51 (s, 1H); $^{13}$P NMR (DMSO-$d_6$): δ −0.89; MS (AP-ES) m/z 711.11 and 713.09 [M−H]$^-$; HRMS (MALDI) Calcd for $C_{25}H_{38}BrN_4O_9PS_2$.713.1074 and 715.1074 found 713.1081 and 715.102.

EXAMPLE 80

2'-O-Methylcytidine-5'-[bis-(S-pivaloyl-2-thioethyl) phosphate]

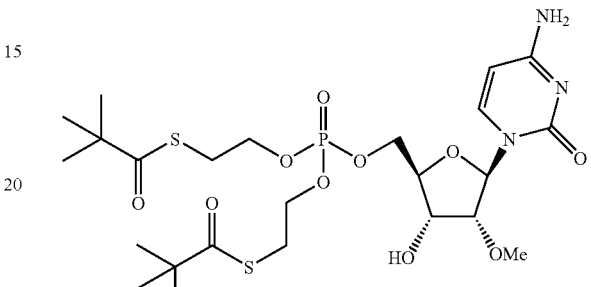

$N^4$-(4,4'-Dimethoxytrityl)-2'-O-methylcytidine (0.49 g, 0.86 mmol) was mixed with 1H-tetrazole (0.06 g, 0.86 mmol) and dried over $P_2O_5$ in vacuo overnight. To this mixture anhydrous acetonitrile (6 mL) and bis-(S-pivaloyl-2-thioethyl)-N,N-diisopropylphosphoramidite (0.39 g, 0.86 mmol) were added at 0° C. The reaction mixture was allowed to come to room temperature and stirred under an inert atmosphere for 18 h. Solvent was removed in vacuo. The residue was cooled to −40° C. and a solution of 3-chloroperbenzoic acid (0.3 g, 1.72 mmol, 57–80%) in $CH_2Cl_2$ (5.5 mL) was added. The solution was allowed to warm up to −10° C. over 2 h. Sodium hydrogensulfite (10% aqueous solution, 5 mL) was added to reduce the excess of 3-chloroperbenzoic acid. The organic phase was separated, diluted with $CH_2Cl_2$ (30 mL), washed with saturated aqueous $Na_2CO_3$ (20 mL), water (20 mL), dried over $Na_2SO_4$ and evaporated to dryness. The residue was chromatographed on a flash silica gel column using $CH_2Cl_2$ containing incremental amount of MeOH (0 to 10%) as eluent. Fractions containing the product were pooled and evaporated. The residue was dissolved in a solution of acetic acid/water/methanol (10 mL, 3:1:6) and heated at 55° C. for 24 h. The solution was evaporated to give an oil. The oil was dissolved in 20% MeOH in water and purified by HPLC on C-18 column (Luna C18,250×2.12 mm, A=water, B=acetonitrile 20 to 10% B in 65 mL, flow 10 mL min$^{-1}$, λ 260 nm) to yield the title compound (0.076 g).

$^1$H NMR (DMSO-$d_6$): δ 1.18 (s, 18H), 3.12 (t, 4H, J=6.4 Hz), 3.39 (s, 3H), 3.69 (t, 1H, J=4.2 Hz), 3.93–4.3 (m, 8H), 5.29 (d, 1H, J=6.2 Hz), 5.72 (d, 1H, J=7.4 Hz), 5.86 (d, 1H, J=4 Hz), 7.21 (bs, 2H), 7.58 (d, 1H, J=7.4 Hz); $^{13}$P NMR (CD$_3$CN): δ −0.64; MS (AP-ES) m/z 625.69 [M+H]$^+$; HRMS (MALDI) Calcd for $C_{24}H_{40}N_3O_{10}PS_2Na$ 648.1785 found 648.1804.

EXAMPLE 81

5-Bromo-2'-O-methylcytidine-5'-[bis-(S-pivaloyl-2-thioethyl)phosphate]

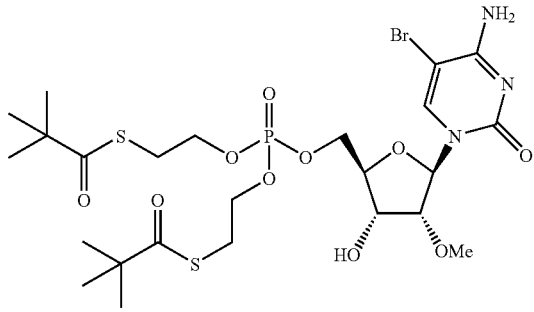

Step A: 5-Bromo-3'-O-(t-butyldimethyl)silyl-2'-O-methylcytidine

2'-O-Methylcytidine (1.5 g, 5.83 mmol) was mixed with imidazole (3.97 g, 58.32 mmol) and dried in vacuo. This mixture was dissolved in anhydrous DMF (4 mL) and t-butyldimethylsilyl chloride (4.41 g, 29.25 mmol) was added and the reaction mixture was stirred for 18 h at room temperature under an inert atmosphere. Reaction mixture was diluted with water (100 mL) and extracted with ethyl acetate (2×60 mL). The organic phase was dried over anhydrous $Na_2SO_4$ and evaporated. The residue was purified by silica gel column chromatography and eluted with ethyl acetate/hexane, 6:4. Fractions containing the product were pooled and evaporated. The product obtained (2.76 g) was dissolved in acetonitrile (19.43 mL), LiBr (0.623 g, 7.18 mmol) and stirred to get a clear solution. To this ammonium ceric (IV) nitrate (6.24 g, 11.37 mmol) was added and the reaction mixture was allowed to stir at room temperature for 3 h. Solvent was removed in vacuum. The residue obtained was taken in ethyl acetate (100 mL) and washed with water (80 mL). The organic phase was separated, dried over anhydrous $Na_2SO_4$ and evaporated. Residue purified by silca gel column chromatography and eluted with 5% MeOH in $CH_2Cl_2$. The product obtained (2.66 g) was dissolved in 80% acetic acid in water and heated at 50° C. for 6 h. The solvent was removed and the residue purified on a silica gel column and eluted with 5% MeOH in $CH_2Cl_2$ to give the title compound (0.85 g).

$^1$H NMR (DMSO-$d_6$): δ 0.78 (s, 6H), 0.85 (s, 9H), 3.31 (s, 3H), 3.44–3.6 (m, 2H), 3.69–3.9 (m, 2H), 4.24 (m, 1H), 5.29 (t, 1H, J=4.4 Hz), 5.76 (d, 1H, J=3.2 Hz), 7.06 (bs, 1H), 7.88 (bs, 1H), 8.39 (s, 1H).

Step B: 5-Bromo-2'-O-methylcytidine-5'-[bis-(S-pivaloyl-2-thioethyl)phosphate]

5-Bromo-3'-O-(t-butyldimethyl)silyl-2'-O-methylcytidine (0.093 g, 0.21 mmol) was mixed with 1H-tetrazole (0.03 g, 0.42 mmol) and dried over $P_2O_5$ in vacuo overnight. To this mixture anhydrous acetonitrile (2 mL). Bis-(S-pivaloyl-2-thioethyl)-N,N-diisopropylphosphoramidite (0.2 g, 0.42 mmol) was added at 0° C. The reaction mixture was allowed to come to room temperature and stirred under an inert atmosphere for 4 h. Solvent was removed in vacuo. The residue was cooled to −40° C. and a solution of 3-chloroperbenzoic acid (0.072 g, 0.42 mmol, 57–80%) in $CH_2Cl_2$ (2 mL) was added. The solution was allowed to warm up to −10° C. over 2 h. Sodium hydrogensulfite (10% aqueous solution, 2 mL) was added to reduce the excess of 3-chloroperbenzoic acid. The organic phase separated, diluted with $CH_2Cl_2$ (30 mL), washed with saturated aqueous $Na_2CO_3$ (20 mL), water (20 mL), dried over $Na_2SO_4$ and evaporated to dryness. The residue was dissolved in THF (2.1 mL) and triethylamine trihydrofluoride (0.17 g, 1.1 mmol). The reaction mixture was stirred at room temperature for 18 h. The solution was evaporated to give an oil. The oil was dissolved in ethyl acetate (30 mL) and washed with water (20 mL), 5% aqueous $NaHCO_3$ and brine (20 mL). The organic phase was dried over anhydrous $Na_2SO_4$ and evaporated. The residue was dissolved in 20% MeOH in water and purified by HPLC on C-18 column (Luna C18, 250×2.12 mm, A=water, B=acetonitrile 20 to 10% B in 65 mL, flow 10 mL min$^{-1}$, λ260 nm) to give the title compound (0.054 g).

$^1$H NMR (DMSO-$d_6$): δ 1.17 (s, 18H), 3.11 (t, 4H, J=6.2 Hz), 3.39 (s, 3H), 3.75 (t, 1H, J=4.8 Hz), 3.934.3 (m, 8H), 5.23 (d, 1H, J=6.4 Hz), 5.8 (d, 1H, J=3.8 Hz), 7.07 (bs, 1H), 7.89 (s, 1H) 7.94 (bs, 1H); $^{13}$P NMR (CD$_3$CN): δ −0.34; MS (AP-ES) m/z 702.00 and 704.00 [M−H]$^-$; HRMS (MALDI) Calcd for $C_{24}H_{39}BrN_3O_{10}PS_2Na$ 726.0890 and 728.0890 found 726.0893 and 728.086.

EXAMPLE 82

3'-Deoxycytidine-5'-[bis-(S-pivaloyl-2-thioethyl)phosphate]

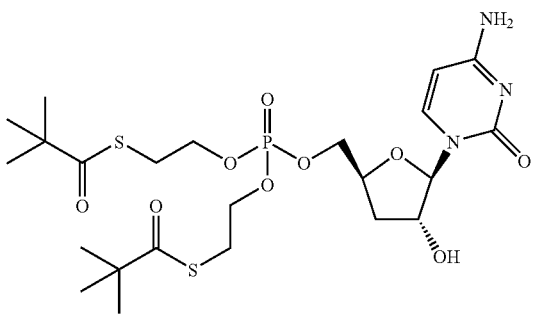

Step A: N$^4$-(4,4'-dimethoxytrityl)-3'-deoxycytidine

3'-Deoxycytidine (0.8 g, 3.54 mmol) was mixed with imidazole (2.41 g, 35.4 mmol) and dried over $P_2O_5$ in vacuum overnight at 40° C. The mixture was dissolved in anhydrous DMF and t-butyldimethylsilyl chloride (2.68 g, 17.78 mmol) was added and the reaction mixture was stirred under an argon atmosphere for 18 h at room temperature. The reaction mixture was diluted with water (100 mL) and extracted with ethyl acetate (2×75 mL). The organic phase was separated, dried over anhydrous $Na_2SO_4$ and evaporated. The residue was purified by silica gel column chromatography and eluted with ethyl acetate/hexane (6:4) to yield 2',5'-bis(t-butyldimethylsilyl)-3'-deoxycytidine (1.27 g). This was then mixed with DMAP (0.34 g, 2.79 mmol) and dried in vacuum. This mixture was dissolved in anhydrous pyridine (8 mL) and 4,4'-dimethoxytrityl chloride (1.89 g, 5.58 mmol) was added. The reaction mixture was stirred at room temperature under an argon atmosphere for 18 h. Solvent was removed in vacuo. The residue obtained was taken in ethyl acetate (100 mL) and washed with 5% $NaHCO_3$ in water (75 mL) and brine (75 ml). The organic phase was dried over anhydrous $Na_2SO_4$ and evaporated. The residue obtained was dissolved in THF (28 mL). To this triethylamine trihydrofluoride (2.26 mL, 13.74 mmol) and triethylamine (0.95 mL, 6.87 mmol) were added and stirred at room temperature for 18 h. Solvent was removed and the residue dissolved in ethyl acetate (50 mL), washed with water (50 mL) and 5% $NaHCO_3$ in water (50 mL). The organic phase was dried over anhydrous $Na_2SO_4$ and evaporated. The residue obtained was purified by silica gel column chromatography and eluted with 5% MeOH in $CH_2Cl_2$ to yield the title compound (0.66 g).

$^1$H NMR (DMSO-$d_6$): δ 1.66 (m, 1H), 1.85 (m, 1H1), 3.47 (m, 1H), 3.63 (m, 1H), 3.71 (s, 6H), 4.00 (bs, 1H), 4.19 (m, 1H), 4.96 (t, 1H, J 5.2 Hz), 5.39 (bs, 1H), 5.53 (s, 1H), 6.17 (bs, 1H), 6.83 (d, 4H, J=8.8 Hz), 7.04–7.22 (m, 9H), 7.77 (d, 1H, J=7.6 Hz), 8.27 (bs, 1H); MS (AP-ES) m/z 528.1 [M–H]$^{31}$.

Step B: 3'-Deoxycytidine-5'-[bis-(S-pivaloyl-2-thioethyl) phosphate]

This compound was synthesized following the similar synthetic procedure used for the synthesis of Example 80 starting with $N^4$-(4,4'-dimethoxytrityl)-3'-deoxycytidine (0.3 g, 0.57 mmol). Other reagents used for the synthesis were 1H-tetrazole (0.04 g, 0.57 mmol), acetonitrile (4 mL), bis-(S-pivaloyl-2-thioethyl)-N,N-diisopropylphosphoramidite (0.52 g, 1.14 mmol) and 3-chloroperbenzoic acid (0.2g, 1.14 mmol, 57–80%) in $CH_2Cl_2$ (3.6 mL). The product was isolated in 22% yield (0.073 g) after HPLC purification.

$^1$H NMR (200 MHz, DMSO-$d_6$): δ 1.17 (s, 18H), 1.84 (m, 2H), 3.11 (t, 4H, J=6.4 Hz), 3.93–4.31 (m, 8H), 4.39 (m, 1H), 5.55 (d, 1H, J=4.2 Hz), 5.67(dd, 2H, J=7.4 and 1.8 Hz), 7.1 (bs, 2H), 7.56 (d, 1H, J=7.4 Hz); $^{13}$P NMR (CD$_3$CN): δ −0.71; MS (AP-ES) m/z 596.1 [M+H]$^+$; HRMS (MALDI) Calcd for $C_{23}H_{38}N_3O_9PS_2Na$ 618.1679 found 618.1600.

EXAMPLE 83

2'-O-Methylcytidine-5'-[bis-(isoprovyloxycarbonyloxymethyl)]phosphate

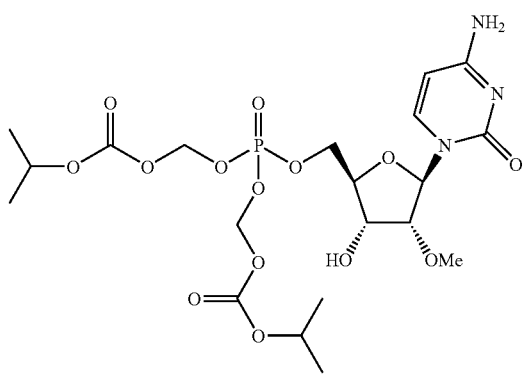

Phosphonomethoxy nucleoside analogs are discussed in C. R. Wagner, V. V. Iyer, and E. J. McIntee, "Pronucleotides: Toward the In Vivo Delivery of Antiviral and Anticancer Nucleotides," Med. Res. Rev., 20: 1–35 (2000), which is incorporated by reference herein in its entirety. They are also disclosed U.S. Pat. Nos. 5,922,695; 5,977,089; 6,043,230; and 6,069,249, the contents of each of which are incorporated by reference herein in their entirety.

Step A: iso-Propyl chloromethyl carbonate

This was prepared according to Antiviral Chemistry & Chemotherapy 8: 557 (1997).

Step B: 2'-O-Methylcytidine-5'-phosphate

This intermediate was prepared as described in Tetrahedron Lett. 50: 5065 (1967).

Step C: 2'-O-Methylcytidine-5'-[bis (isopropyloxycarbonyloxymethyl)]phosphate

2'-O-Methylcytidine-5'-phosphate (0.4 g, 1.19 mmol) was dried over $P_2O_5$ in vacuum overnight at 40° C. It was then suspended in anhydrous DMF (4 mL). To this mixture was added diisopropylethylamine (0.86 mL, 4.92 mmol) and iso-propyl chloromethyl carbonate (1.56 g, 7.34 mmol). The mixture was heated at 50° C. for 1 h. The reaction mixture was then allowed to come to room temperature. The reaction mixture was stirred at room temperature for 48 h and then filtered. The filtrate was diluted with water (100 mL) and extracted with $CH_2Cl_2$ (3×50 mL). The organic phase was dried over anhydrous $Na_2SO_4$ and evaporated. The residue was dissolved in 20% MeOH in water and purified by HPLC on C-18 column (Luna C18,250×2.12 mm, A=water, B=acetonitrile 20 to 10% B in 65 ML, flow 10 mL min$^{-1}$, λ 260 nm) to give the title compound (2.5 mg). $^{13}$P NMR (CD$_3$CN): δ −3.09; MS (AP-ES) m/z 570.1 [M+H]$^+$.

EXAMPLE 84

2'-O-Methylcytidine-5'-[(2-decyloxy-3-dodecylthio-1-propyl)phosphate]

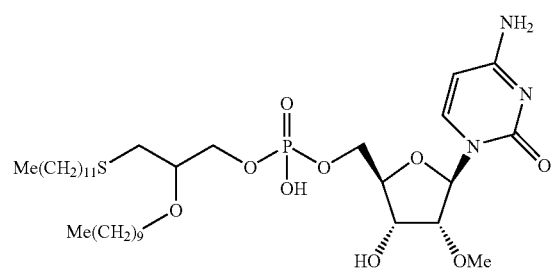

The procedure is described for similar nucleoside analogs in German Patent 408366 (1992) and J. Acquired Immune Defic. Syndr.2000, 23, 227. The reaction of the appropriately protected 2'-O-methylcytidine with (2-decyloxy-3-dodecylthio-1-propyl)phosphate [prepared by the reaction of 2-decyloxy-3-dodecylthio-1-propanol with POCl$_3$ in ether in presence of triethylamine] under refluxing conditions in a toluene-ether mixture furnishes the desired compound.

EXAMPLE 85

2'-O-Methylcytidine-5'-[rac-(3-octadecylthio-2-palmitoyloxy-1-propyl)phosphate]

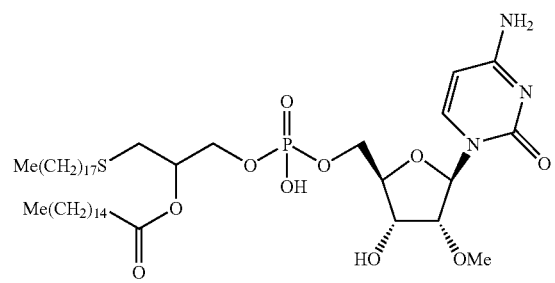

This compound is synthesized by the reaction of 2'-O-methylcytidine-5'-monophosphoromorpholidate with rac-1-S-octadecyl-2-O-palmitoyl-1-thioglycerol in pyridine following the similar procedure described for AZT and ddC in J. Med. Chem. 39: 1771 (1996).

EXAMPLE 86

Nucleoside 5'-Triphosphates

The nucleoside 5'-triphosphates of the present invention were prepared according to the general procedures described in Chem. Rev.100: 2047 (2000).

EXAMPLE 87

Purification and Purity Analysis of Nucleoside 5'-Triphosphates

Triphosphates were purified by anion exchange (AX) chromatography using a 30×100 mm Mono Q column (Pharmacia) with a buffer system of 50 mM Tris, pH 8. Elution gradients were typically from 40 mM NaCl to 0.8 M NaCl in two column volumes at 6.5 mL/min. Appropriate fractions from anion exchange chromatography were collected and desalted by reverse-phase (RP) chromatography using a Luna C18 250×21 mm column (Phenomenex) with a flow rate of 10 ml/min. Elution gradients were generally from 1% to 95% methanol in 14 min at a constant concentration of 5 mM triethylammonium acetate (TEAA).

Mass spectra of the purified triphosphates were determined using on-line HPLC mass spectrometry on a Hewlett-Packard (Palo Alto, Calif.) MSD 1100. A Phenomenex Luna (C18(2)), 150×2 mm, plus 30×2 mm guard column, 3-µm particle size was used for RP HPLC. A 0 to 50% linear gradient (15 min) of acetonitrile in 20 mM TEAA (triethylammonium acetate) pH 7 was performed in series with mass spectral detection in the negative ionization mode. Nitrogen gas and a pneumatic nebulizer were used to generate the electrospray. The mass range of 150–900 was sampled. Molecular masses were determined using the HP Chemstation analysis package.

The purity of the purified triphosphates was determined by analytical RP and AX HPLC. RP HPLC with a Phenomenex Luna or Jupiter column (250×4.6 mm), 5-µm particle size was typically run with a 2–70% acetonitrile gradient in 15 min in 100 mM TEAA, pH 7. AX HPLC was performed on a 1.6×5 mm Mono Q column (Pharmacia). Triphosphates were eluted with a gradient of 0 to 0.4 M NaCl at constant concentration of 50 mM Tris, pH 8. Purity of the triphosphates was generally >80%.

EXAMPLE 88

Nucleoside 5'-Monophosphates

The nucleoside 5'-monophosphates of the present invention were prepared according to the general procedure described in *Tetrahedron Lett.* 50: 5065 (1967).

EXAMPLE 89

2-Amino-9-(β-D-arabinofuranosyl)-9H-purin-6(1H)-one

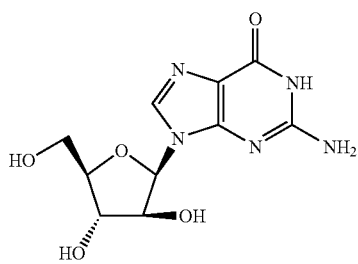

This compound was obtained from commercial sources.

EXAMPLE 90

3'-Deoxy-3'-methylguanosine

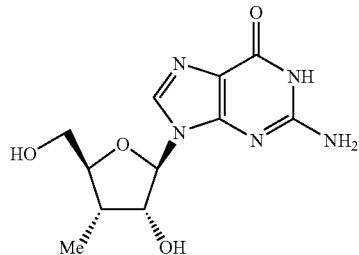

This compound was prepared following procedures described in U.S. Pat. No. 3,654,262 (1972).

EXAMPLE 91

2'-O-[4-(Imidazolyl-1)butyl]guanosine

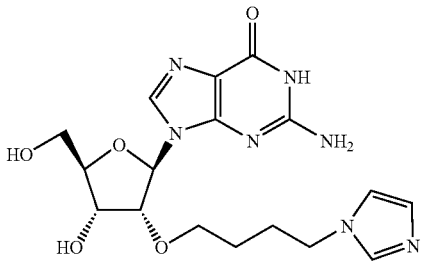

Step A: 2'-O-[4-(Imidazolyl-1)butyl]-2-aminoadenosine

A solution 2-aminoadenosine (7.36 g, 26 mmol) in dry DMF (260 mL) was treated portionwise with 60% NaH (3.92 g, 1000 mmol). After 1 hr., a solution of bromobutylimidazole (9.4 g, 286 mmol) in DMF (20ml) was added. After 16 hrs., the solution was conc. in vacuo, partitioned between $H_2O$/EtOAc and separated. The aqueous layer was evaporated, and the residue was chromatographed on silica gel ($CHCl_3$/MeOH) to afford the title nucleoside as a white solid; yield 4.2 g.

$^1$H NMR (DMSO-$d_6$): δ 1.39 (t, 2H), 1.67 (t, 2H), 3.3–3.7 (m, 4H), 3.93 (m, 3H), 4.29 (m, 2H), 4.40 (d, 1H), 5.50 (5, 1H), 5.72 (d, 1H), 5.82 (bs, 2H), 6.72 (bs, 2H), 6.86 (s, 1H), 7.08 (s, 1H), 7.57 (s, 1H). 7.91 (s, 1H).

Step B: 2'-O-[4-(Imidazolyl-1)butyl]guanosine

A mixture of the intermediate from Step A (3.2 g, 8 mmol) in $H_2O$ (200 mL), DMSO (10 mL), trisodium phosphate (10 g), and adenosine deaminase (0.3 g) was stirred at room temperature and pH 7. The solution was filtered and and then evaporated. The resulting solid was crystallized from EtOAc/MeOH to afford the title compound as a white solid; yield 2.6 g.

$^1$H NMR (DMSO-$d_6$): δ 1.39 (t, 2H), 1.67 (t, 2H), 3.3–3.7 (m, 4H), 3.93 (m, 3H), 4.29 (m, 2H), 5.10 (t, 1H), 5.20 (d, 1H), 5.79 (d, 1H), 6.50 (bs, 2H), 6.86 (s, 1H), 7.08 (s, 1H), 7.57 (s, 1H) 7.9 (s, 1H).

EXAMPLE 92

2'-Deoxy-2'-fluorogulanosine

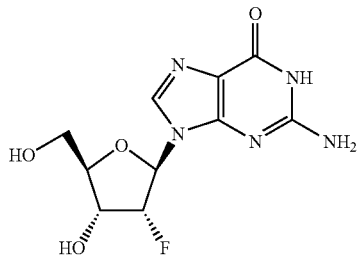

This compound was prepared following the conditions described in Chem. Pharm. Bull. 29: 1034 (1981).

EXAMPLE 93

2'-Deoxyguanosine

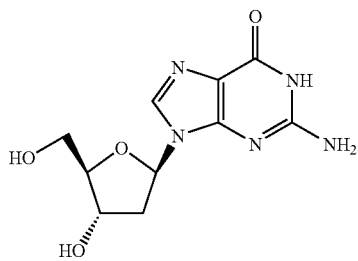

This compound was obtained from commercial sources.

EXAMPLE 94

2-Amino-7-(2-deoxy-2-fluoro-β-D-ribofuranosyl)-7H-pyrrolo[2,3-d]pyrimidin-4(3H)-one

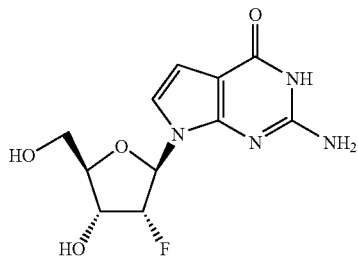

Step A: 2-Amino-4-chloro-7-(2,3,5-tri-O-benzyl-β-D-arabinofuranosyl)-7H-pyrrolo[2,3-d]-pyrimidine To a suspension of 2-amino-4-chloro-1H-pyrrolo[2,3-d]pyrimidine [Liebigs Ann. Chem. 1: 137 (1983)] (3.03 g, 18 mmol) in anhydrous MeCN (240 mL), powdered KOH (85%; 4.2 g, 60 mmol) and tris[2-(2-methoxyethoxy)-ethyl]amine (0.66 mL, 2.1 mmol) were added and the mixture was stirred at room temperature for 10 min. Then a solution of 2,3,5-tri-O-benzyl-D-arabinofuranosyl bromide [prepared from corresponding 1-O-p-nitrobenzoate (11.43 g, 20.1 mmol) according to Seela et al., J. Org. Chem. (1982), 47, 226] in MeCN (10 mL) was added and stirring continued for another 40 min. Solid was filtered off, washed with MeCN (2×25 mL) and combined filtrate evaporated. The residue was purified on a silica gel column with a solvent system of hexanes/EtOAc: 7/1, 6/1 and 5/1. Two main zones were separated. From the more rapidly migrating zone was isolated the α anomer (0.74 g) and from the slower migrating zone the desired β anomer (4.01 g).

Step B: 2-Amino-7-(β-D-arabinofuranosyl)-4-chloro-7H-pyrrolo[2,3-d]pyrimidine

To a solution of the compound from Step A (4.0 g, 7 mmol) in $CH_2Cl_2$ (150 ml) at −78° C. was added a solution of 1.0 M $BCl_3$ in $CH_2Cl_2$ (70 mL, 70 mmol) during 45 min. The mixture was stirred at −78° C. for 3 h and at −20° C. for 2.5 h. MeOH—$CH_2Cl_2$ (70 mL, 1:1) was added to the mixture, which was then stirred at −20° C. for 0.5 h and neutralized with conc. aqueous $NH_3$ at 0° C. The mixture was stirred at room temperature for 10 min. and then filtered. The solid was washed with MeOH—$CH_2Cl_2$ (70 mL, 1:1) and the combined filtrate evaporated. The residue was purified on a silica gel column with a solvent system of $CH_2Cl_2$/MeOH: 20/1 to give the desired nucleoside (1.18 g) as a white solid.

Step C: 2-Amino-7-[3,5-O-(1,3,3-tetraisopropyldisiloxane-1,3-diyl)-β-D-arabinofuranosyl]-4-chloro-7H-pyrrolo[2,3-d]pyrimidine The compound from Step B (0.87 g, 2.9 mmol) and imidazole (0.43 g, 5.8 mmol were dissolved in DMF (3.5 mL). 1,3-Dichloro-1,1,3,3-tetraisopropyldisiloxane (1.0 mL) was added to the solution. The reaction mixture was stirred at room temperature for 1 h and then evaporated. The residue was partitioned between $CH_2Cl_2$ (150 mL) and water (30 mL). The layers were separated. The organic layer was dried ($Na_2SO_4$) and evaporated. The residue was purified on a silica gel column with a solvent system of hexanes/EtOAc: 7/1 and 5/1 to give the title compound (1.04 g).

Step D: 2-Amino-7-[2-O-acetyl-3,5-O-(1,1,3,3-tetraisopropyldisiloxane-1,3-diyl)-β-D-arabinofuranosyl]-4-chloro-7H-pyrrolo[2,3-d]pyrimidine A mixture of the compound from Step C (0.98 g, 1.8 mmol) in MeCN (12 mL), $Et_3N$ (0.31 mL) $Ac_2O$ (0.21 mL) and DMAP (5 mg, 0.25 eq.) was stirred at room temperature for 5 h and then evaporated. The oily-residue was dissolved in EtOAc (200 mL), washed with water (2×20 mL), dried ($Na_2SO_4$) and evaporated to yield pure title compound (1.12 g).

Step E: 2-Amino-7-[2-O-acetyl-β-D-arabinofuranosyl]-4-chloro-7H-pyrrolo[2,3-d]pyrimidine To an ice-cold solution of the compound from Step D (0.95 g, 1.63 mmol) in THF (10 mL) and AcOH (0.19 mL) was added dropwise 1.0 M tetrabutylammonium fluoride solution in THF (3.4 mL) and stirred at 0° C. for 15 min. The solution was concentrated and the oily residue applied onto a silica gel column packed in $CH_2Cl_2$ and eluted with $CH_2Cl_2$/MeOH: 50/1, 25/1 and 20/1. Appropriate fractions were pooled and evaporated to give the title nucleoside (0.56 g) as a white solid.

Step F: 2-Amino-7-[2-O-acetyl-3,5-di-O-(tetrahydro-2-pyranyl)-β-D-arabinofuranosyl]-4-chloro-7H-pyrrolo[2,3-d]pyrimidine To a solution of the compound from Step E (0.5 g, 1.46 mmol) in $CH_2Cl_2$ (10 mL) and 3,4-dihydro-2-H-pyrane (0.67 mL) was added dropwise TMSI (30 μL, 0.2 mmol). The reaction mixture was stirred at room temperature for 1 h and then evaporated. The oily residue was purified on a silica gel column packed in a solvent system of hexanes/EtOAc/$Et_3N$: 75/25/1 and eluted with a solvent system of hexanes/EtOAc: 3/1. The fractions containing the product were collected and evaporated to give the desired compound (0.60 g).

Step G: 2-Amino-7-[3,5-di-O-(tetrahydro-2-pyranyl)-β-D-arabinofuranosyl]-4-chloro-7H-pyrrolo[2,3-d]pyrimidine A mixture of the compound from Step F (0.27 g, 0.53 mmol) and methanolic ammonia (saturated at 0° C.; 10 mL) was kept overnight at 0° C. Evaporation of the solvent yielded the desired compound (0.25 g).

Step H: 2-Amino-7-[2-deoxy-2-fluoro-3,5-di-O-(tetrahydro-2-pyranyl)-β-D-ribofuranosyl]-4-chloro-7H-pyrrolo[2,3-d]pyrimidine To a solution of the compound from Step G (0.24 g, 0.51 mmol) in CH$_2$Cl$_2$ (5 mL) and pyridine (0.8 mL) at −60° C. was added diethylaminosulfur trifluoride (DAST; 0.27 mL) dropwise under Ar. The solution was stirred at −60° C. for 0.5 h, at 0° C. overnight and at room temperature for 3 h. The mixture was diluted with CH$_2$Cl$_2$ (25 mL) and poured into saturated aqueous NaHCO$_3$ (15 mL). The organic layer was washed with water (10 mL), dried (Na$_2$SO$_4$) and evaporated. The residue was purified on a silica gel column with a solvent system of hexanes/EtOAc: 5/1 to give the title compound (45 mg) as a pale yellow foam.

Step I: 2-Amino-7-(2-deoxy-2-fluoro-β-D-ribofuranosyl)-4-chloro-7H-pyrrolo[2,3-d]-primidine A solution of the compound from Step H (40 mg. 0.08 mmol) in EtOH (2 mL) was stirred with pyridinium p-toluenesulfonate (40 mg, 0.16 mmol) at 60° C. for 3 h. The mixture was then evaporated and the residue purified on a silica gel column with a solvent system of hexanes/EtOAc: 1/1 and 1/2 to give the desired compound (24 mg).

Step J: 2-Amino-7-(2-deoxy-2-fluoro-β-D-ribofuranosyl)-7H-pyrrolo[2,3-d]pyrimidin-4(3H)-one A mixture of the compound from Step I (4 mg, 0.08 mmol) in 2N aqueous NaOH (1.2 mL) was stirred at reflux temperature for 1.5 h. The solution was cooled in an ice-bath, neutralized with 2 N aqueous HCl and evaporated to dryness. The residue was suspended in MeOH, mixed with silica gel and evaporated. The solid residue was placed onto a silica gel column (packed in a solvent system of CH$_2$Cl$_2$/MeOH: 10/1) which was eluted with a solvent system of CH$_2$Cl$_2$/MeOH: 10/1. The fractions containing the product were collected and evaporated to dryness to yield the title compound (20 mg) as a white solid.

$^1$H NMR (CD$_3$OD): δ 3.73, 3.88 (2dd, 2H, J=12.4, 3.8, 2.6 Hz), 4.01 (m, 1H), 4.47 (ddd, 1H J=16.5, 6.6 Hz), 5.14 (ddd, 1H, J=5.3, 4.7 Hz), 6.19 (dd, 1H, J=17.8, 3.0 Hz), 6.39 (d, 1H, J=3.6 Hz), 6.95 (d, 1H).

$^{19}$F NMR (CD$_3$OD): δ −206.53 (dt).

EXAMPLE 95

2-Amino-7-(β-D-ribofuranosyl)-7H-pyrrolo[2,3-d]pyrimidin-4(3H)-one

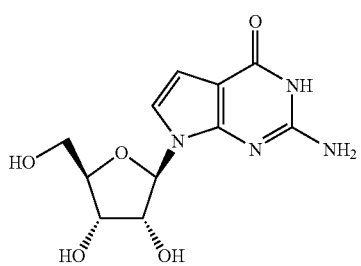

This compound was prepared following the procedures described in *J. Chem. Soc. Perkin Trans.* 1, 2375 (1989).

EXAMPLE 96

2-Amino-7-(2-deoxy-β-D-ribofuranosyl)-7H-pyrrolo[2,3-d]pyrimidin-4(3H)-one

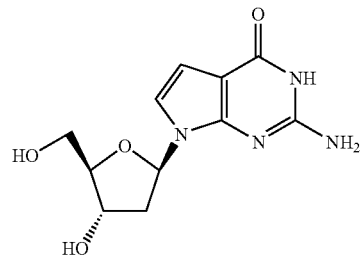

This compound was prepared following the procedures in *Tetrahedron Lett.* 28: 5107 (1987).

EXAMPLE 97

6-Amino-1-(2-O-methyl-β-D-ribofuranosyl)-1H-imidazo[4,5-c]pyridin-4(5H)-one

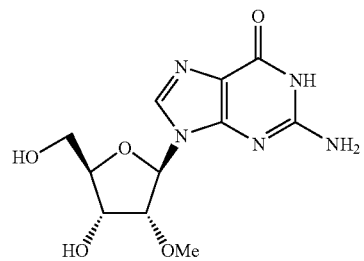

This compound was prepared in a manner similar to the preparation of 2-amino-7-(3-deoxy-3-fluoro-β-D-ribofuranosyl)-7H-pyrrolo[2,3-d]pyridin-4(3H)-one (Example 23).

EXAMPLE 98

6-Amino-1-(2-deoxy-β-D-ribofuranosyl)-1H-imidazo[4,5-c]pyridin-4(5H)-one

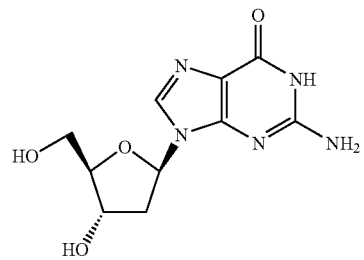

This compound was prepared following the procedures described in *J. Med. Chem.* 26: 286 (1983).

EXAMPLE 99

6-Amino-1-(3-deoxy-3-methyl-β-D-ribofuranosyl)-1H-imidazo[4,5-c]pyridin-4(5H)-one

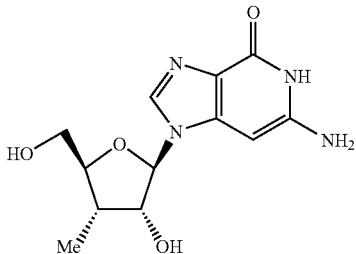

This compound was prepared in a manner similar to the preparation of 2-amino-7-(3-deoxy-3-fluoro-β-D-ribofuranosyl)-7H-pyrrolo[2,3-d]pyrimidin-4(3H)-one (Example 23).

EXAMPLE 100

6-Amino-1-(2-deoxy-2-fluoro-β-D-ribofuranosyl)-1H-imidazo[4,5-c]pyridin-4(5H)-one

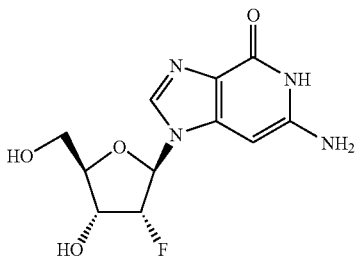

This compound was prepared in a manner similar to the preparation of 2-amino-7-(3-deoxy-3-fluoro-β-D-ribofuranosyl)-7H-pyrrolo[2,3-d]pyrimidin-4(3H)-one (Example 23).

EXAMPLE 101

6-Amino-1-(β-D-arabinofuranosyl)-1H-imidazo[4,5-c]pyridin-4(5H)-one

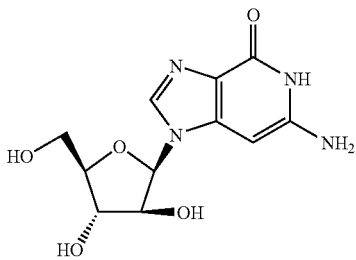

A preparation of this compound is given in Eur. Pat. Appln. 43722 A1 (1982).

EXAMPLE 102

2'-O-[2-(N,N-diethylaminooxy)ethyl]-5-methyluridine

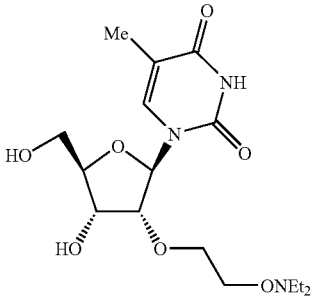

Step A: 5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g) were added with manual stirring. The reactor was sealed and heated in an oil bath until an internal temperature of 160° C. was reached and then maintained for 16 h (pressure <100 psig). The reaction vessel was cooled to ambient and opened. The reaction mixture was concentrated under reduced pressure (10 to 1 mm Hg) in a warm water bath (40–100° C.) with the more extreme conditions used to remove the ethylene glycol. The residue was purified by column chromatography (2 kg silica gel, ethyl acetate:hexanes gradient 1:1 to 4:1). The appropriate fractions were combined, stripped and dried to product as white crisp foam (84 g), contaminated starting material (17.4 g) and pure reusable starting material (20 g). TLC and NMR were consistent with 99% pure product.

$^1$H NMR (DMSO-$d_6$): δ 1.05 (s, 9H), 1.45 (s, 3H), 3.5–4.1 (m, 8H), 4.25 (m, 1H), 4.80 (t, 1H), 5.18 (d, 2H), 5.95 (d, 1H), 7.35–7.75 (m, 11H), 11.42 (s, 1H).

Step B: 2'-O-[2-(2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL) was added to get a clear solution. Diethyl azodicarboxylate (6.98 mL, 44.36 mmol) was added dropwise to the reaction mixture. The rate of addition was maintained such that resulting deep red coloration is just discharged before adding the next drop. After the addition was complete, the reaction was stirred for 4 h. By that time TLC showed the completion of the reaction (ethyl acetate/hexane, 60:40). The solvent was evaporated under vacuum. Residue obtained was placed on a flash silica gel column and eluted with ethyl acetate-hexane (60:40) to give the title compound as a white foam (21.8.g).

$^1$H NMR (DMSO-$d_6$): δ 11.32 (s, 1H), 7.82 (m, 4H), 7.6–7.65 (m, 5H), 7.34–7.46 (m, 6H), 5.90 (d, 1H, J=6Hz), 5.18 (d, J=5.6 Hz), 4.31 (bs, 2H), 4.25 (m, 1H), 4.09 (t, 1H, J=5.6 Hz), 3.81–3.94 (m, 5H), 1.44 (s, 3H), 1.1 (s, 9H); $^{13}$C NMR (CDCl$_3$): δ 11.8, 19.40, 26.99, 62.62, 68.36, 68.56, 77.64, 83.04, 84.14, 87.50, 110.93, 123.59, 127.86, 129.89, 132.45, 134.59, 134.89, 135.17, 150.50, 163.63, 163.97; MS [FAB] m/z 684 [M–H]⁻.

Step C: 5'-O-tert-Butyldiphenylsilyl-2'-O-[2-(acetaldoximinooxy)ethyl]-5-methyluridine 2'-O-[2-(2-Phthalimidoxy)ethyl]-5'-t-butyldiphenylsilyl-5-methyluridine (10 g, 14.6 mmol) was dissolved in $CH_2Cl_2$ (146 mL) and cooled to –10° C. in an isopropanol-dry ice bath. To this methylhydrazine (1.03 mL, 14.6 mmol) was added dropwise. Reaction mixture was stirred at –10° C. to 0° C. for 1 h. A white precipitate formed and was filtered and washed thoroughly with $CH_2Cl_2$ (ice cold). The filtrate was evaporated to dryness. Residue was dissolved in methanol (210 mL) and acetaldehyde (0.89 mL, 16 mmol) was added and stirred at room temperature for 12 h. Solvent was removed in vacuo and residue was purified by silica gel column chromatography using and ethyl acetate/hexane (6:4) as solvent system to yield the title compound (4.64 g).

¹H NMR (DMSO-$d_6$): δ 1.02 (s, 9H), 1.44 (s, 3H), 1.69 (dd, 3H, J=5.6 Hz), 3.66 (m, 1H), 3.76 (m, 2H), 3.94 (m, 2H), 4.05 (s, 2H), 4.15 (m, 1H), 4.22 (m, 1H), 5.18 (d, 1H, J=6.0 Hz), 5.9 (dd, 1H, J=4.4 Hz), 7.36 (m, 1H), 7.40 (m, 7H), 7.63 (m, 5H), 11.38 (s, 1H); ¹³C NMR (CDCl₃): δ 11.84, 15.05, 19.38, 26.97, 63.02, 68.62, 70.26, 71.98, 72.14, 82.72, 84.34, 87.02, 111.07, 127.89, 130.02, 134.98, 135.13, 135.42, 147.85, 150.51, 164.12; HRMS (FAB) Calcd for $C_{30}H_{39}N_3O_7 SiNa^\oplus$ 604.2455, found 604.2471.

Step D: 5'-O-tert-Butyldiphenylsilyl-2'-O-[2-(N N-diethylaminooxy)ethyl]-5-methyluridine 5'-O-tert-Butyldiphenylsilyl-2'-O-[2-(acetaldoximinooxy)ethyl]-5-methyluridine (4.5 g, 7.74 mmol) was dissolved in 1M pyridinium p-toluenesulfonate (PPTS) in MeOH (77.4 mL). It was then cooled to 10° C. in an ice bath. To this mixture $NaBH_3CN$ (0.97 g, 15.5 mmol) was added and the mixture was stirred at 10° C. for 10 minutes. Reaction mixture was allowed to come to room temperature and stirred for 4 h. Solvent was removed in vacuo to give an oil. Diluted the oil with ethyl acetate (100 mL), washed with water (75 mL), 5% $NaHCO_3$ (75 mL) and brine (75 mL). The organic phase was dried over anhydrous $Na_2SO_4$ and evaporated. Residue obtained was dissolved in 1M PPTS in MeOH (77.4 mL), acetaldehyde (0.48 mL, 8.52 mmol) was added and stirred at ambient temperature for 10 minutes. Then reaction mixture was cooled to 10° C. in an ice bath and $NaBH_3CN$ (0.97 g, 15.50 mmol) was added and stirred at 10° C. for 10 minutes. Reaction mixture was allowed to come to room temperature and stirred for 4 h. Solvent was removed in vacuo to get an oil. The oil was dissolved in ethyl acetate (100 mL), washed with water (75 mL), 5% $NaHCO_3$ (75 mL) and brine (75 mL). The organic phase was dried over anhydrous $Na_2SO_4$ and evaporated to dryness. The residue obtained was purified by silica gel column chromatography and eluted with $CH_2Cl_2$/MeOH /$NEt_3$, 94:5:1 to give title compound (3.55 g) as a white foam.

¹H NMR (DMSO-$d_6$): δ 0.95 (t, 6H, J=7.2 Hz), 1.03 (s, 9H), 1.43 (s, 3H), 2.58 (q, 4H, J=7.2 Hz), 3.59 (m, 1H), 3.73 (m, 3H), 3.81 (m, 1H), 3.88 (m, 1H), 3.96 (m, 2H), 4.23 (m, 1H), 5.21 (d, 1H, J=5.6 Hz), 5.95 (d, 1H, J=6.4 Hz), 7.43 (m, 7H), 7.76 (m, 4H), 11.39 (s, 1H); ¹³C NMR (CDCl₃): δ 11.84, 19.35, 26.97, 52.27, 63.27, 68.81, 70.27, 72.27, 82.64, 84.47, 86.77, 111.04, 127.87, 130.01, 135.11, 135.41, 141.32, 150.48, 164.04; HRMS (FAB), Calcd for $C_{32}H_{45}N_3O_7SiCs^\oplus$, 744.2081, found 744.2067.

Step E: 2'-O-[2-(N,N-diethylaminooxy)ethyl]-5-methyluridine

A mixture of triethylamine trihydrogenfluoride (4.39 mL, 26.81 mmol) and triethylamine (1.87 mL, 13.41 mmol) in THF (53.6 mL) was added to 5'-O-tert-butyldiphenylsilyl-2'-O-[2-(N,N-diethylaminooxy)ethyl]-5-methyluridine (3.28 g, 5.36 mmol). The reaction mixture was stirred at room temperature for 18 h. Solvent was removed in vacuo. The residue was placed on a silica gel column and eluted with $CH_2Cl_2$/MeOH/$NEt_3$, 89: 10: 1, to yield the title compound (1.49 g).

¹H NMR (DMSO-$d_6$): δ 0.97 (t, 6H, J=7.2 Hz), 1.75 (s, 3H), 2.58 (q, 4H, J=7.2 Hz), 3.55 (m, 4H), 3.66 (m, 2H), 3.83 (bs, 1H), 3.95 (t, 1H, J=5.6 Hz), 4.11 (q, 1H, J=4.8 Hz and 5.6 Hz), 5.05 (d, 1H, J=5.6 Hz), 5.87 (d, 1H, J=6.0 Hz), 7.75 (s, 1H), 11.31 (s, 1H); ¹³C NMR (CDCl₃): δ 11.75, 12.27, 52.24, 61.31, 68.86, 70.19, 72.25, 81.49, 85.10, 90.29, 110.60, 137.79, 150.57, 164.37; HRMS (FAB) Calcd for $C_{16}H_{28}N_3O_7^\oplus$ 374.1927, found 374.1919.

EXAMPLE 103

1-(2-C-Methyl-β-D-arabinofuranosyl)uracil

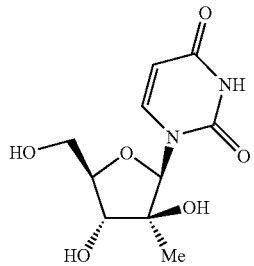

This compound was prepared following the procedures described in Chem. Pharm. Bull. 35: 2605 (1987).

EXAMPLE 104

5-Methyl-3'-deoxycytidine

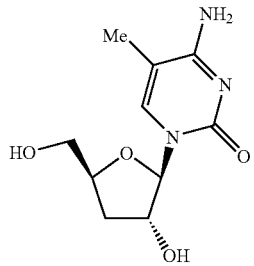

This compound was prepared following the procedures described in Chem. Pharm. Bull. 30: 2223 (1982).

EXAMPLE 105

2-Amino-2'-O-methyladenosine

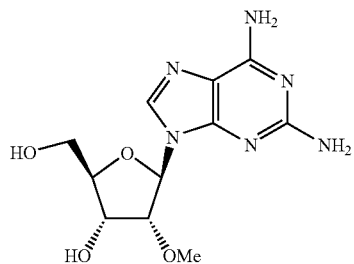

This compound was obtained from commercial sources.

EXAMPLE 106

2'-Deoxy-2'-fluoroadenosine

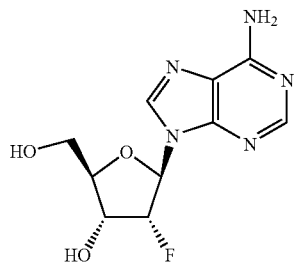

This compound was obtained from commercial sources.

EXAMPLE 107

3'-Deoxy-3'-fluoroadenosine

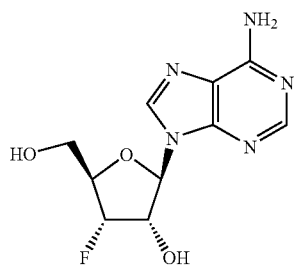

This compound was prepared following the procedures described in *Nucleosides Nucleotides* 10: 719 (1991).

EXAMPLE 108

3'-Deoxy-3'-methyladenosine

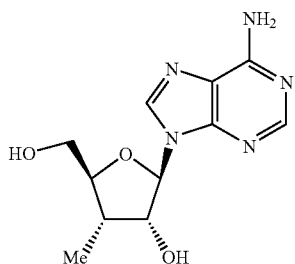

This compound was prepared following the procedures described in *J. Med. Chem.* 19: 1265 (1976).

EXAMPLE 109

2-Amino-7-(2-deoxy-β-D-ribofuranosyl)-7H-pyrrolo[2,3-d]pyrimidine

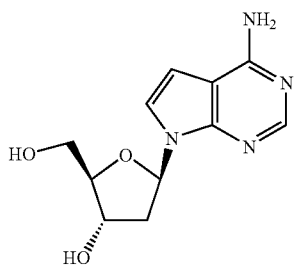

This compound was prepared following the procedures described in *J. Am. Chem. Soc.* 106: 6379 (1984).

EXAMPLE 110

4-Amino-7-(β-D-arabinofuranosyl)-7H-pyrrolo[2,3-d]pyrimidine

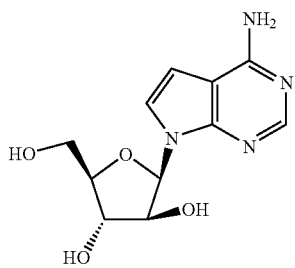

This compound is described in U.S. Pat. No. 4,439,604, which is incorporated by reference herein in its entirety.

EXAMPLE 111

4-Amino-1-(3-deoxy-3-fluoro-β-D-ribofuranosyl)-1H-imidazo[4,5-c]pyridine

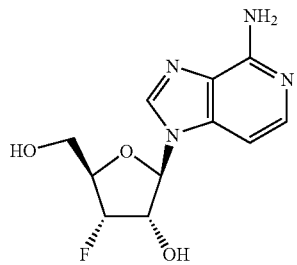

This compound can be prepared readily by the similar method described for the preparation of Example 24 except the nucleobase is 3-deazaadenine.

EXAMPLE 112

4-Amino-7-(β-D-ribofuranosyl)-7H-pyrrolo[2,3-d]pyrimidine (tubercidin)

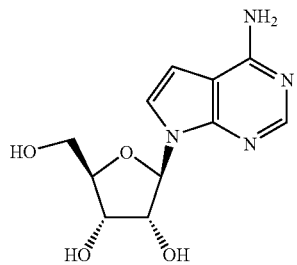

This compound was obtained from commercial sources.

EXAMPLE 113

4-Amino-1-(3-deoxy-β-D-ribofuranosyl)-1H-imidazo[4,5-c]pyridine

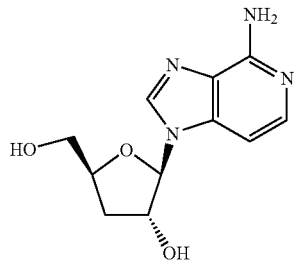

This compound is described in *Acta Crystallogr., Sect. C: Cryst. Struct. Commun.* C43: 1790 (1987).

EXAMPLE 114

4-Amino-1-(3-deoxy-3-methyl-β-D-ribofuranosyl)-1H-imidazo[4,5-c]pyridine

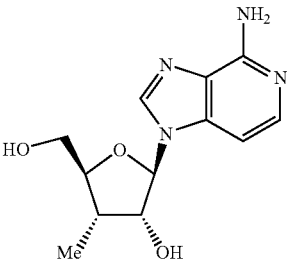

The procedure described earlier for Example 23 is used to synthesize this example by reacting the appropriately substituted 3-C-methyl-sugar intermediate with a protected 3-deazaadenine derivative.

EXAMPLE 115

4-Amino-1-β-D-ribofuranosyl-1H-imidazo[4,5-c]pyridine

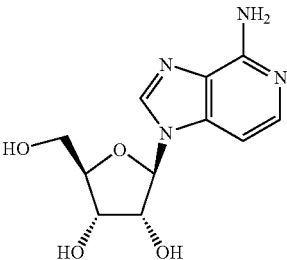

This compound was obtained from commercial sources.

EXAMPLE 116

9-(2-C-Methyl-β-D-arabinofuranosyl)adenine

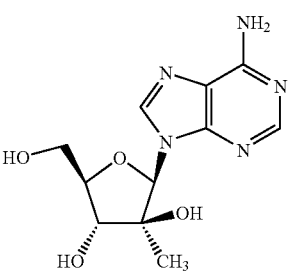

This compound is prepared from 4-amino-9-(3,5-bis-O-tert-butyldimethylsilyl-β-D-erythro-pentofuran-2-ulosyl)purine (*J. Med. Chem.* 1992, 35, 2283) by reaction with MeMgBr and deprotection as described in Example 61.

EXAMPLE 117

4-Amino-7-(2-C-ethyl-β-D-ribofuranosyl)-7H-pyrrolo[2,3-d]pyrimidine

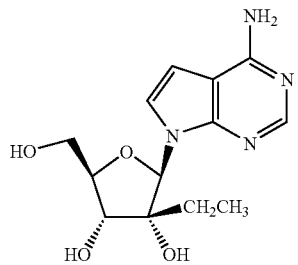

Step A: 3,5-Bis-O-(2,4-dichlorophenylmethyl)-2-C-ethyl-1-O-methyl-α-D-ribofuranose To diethyl ether (300 mL) at −78° C. was slowly added EtMgBr (3.0 M, 16.6 mL) and then dropwise the compound from Step B of Example 62 (4.80 g, 10.0 mmol) in anhydrous Et$_2$O (100 mL). The reaction mixture was stirred at −78° C. for 15 min, allowed to warm to −15° C. and stirred for another 2 h, and then poured into a stirred mixture of water (300 mL) and Et$_2$O (600 mL). The organic phase was separated, dried (MgSO4), and evaporated in vacuo. The crude product was purified on silica gel using ethyl acetate/hexane (1:2) as eluent. Fractions containing the product were pooled and evaporated in vacuo to give the desired product (3.87 g) as a colorless oil.

Step B: 4-Chloro-7-[3,5-bis-O-(2,4-dichlorophenylmethyl)-2-C-ethyl-β-D-ribofuranosyl]-7H-pyrrolo[2,3-d]pyrimidine To a solution of the compound from Step A (1.02 mg, 2.0 mmol) in dichloromethane (40 mL) was added HBr (5.7 M in acetic acid) (1.75 mL, 10.0 mmol) dropwise at 0° C. The resulting solution was stirred at rt for 2 h, evaporated in vacuo and co-evaporated twice from toluene (10 mL). The oily residue was dissolved in acetonitrile (10 mL) and added to a vigorously stirred mixture of 4-chloro-1H-pyrrolo[2,3-d]pyrimidine (307 mg, 2.0 mmol), potassium hydroxide (337 mg, 6.0 mmol) and tris[2-(2-methoxyethoxy)ethyl]amine (130 mg, 0.4 mmol) in acetonitrile (10 mL). The resulting mixture was stirred at room temperature overnight, and then poured into a stirred mixture of saturated ammonium chloride (100 mL) and ethyl acetate (100 mL). The organic layer was separated, washed with brine (100 mL), dried over MgSO$_4$, filtered and evaporated in vacuo. The crude product was purified on silica gel using ethyl acetate/hexane (1:2) as eluent to give the desired product (307 mg) as a colorless foam.

Step C: 4-Chloro-7-(2-C-ethyl-β-D-ribofuranosyl)-7H-pyrrolo[2,3-d]pyrimidine

To a solution of the compound from Step B (307 mg, 0.45 mmol) in dichloromethane (8 mL) was added boron trichloride (1M in dichloromethane) (4.50 mL, 4.50 mmol) at −78° C. The mixture was stirred at −78° C. for 1 h, then at −10° C. for 3 h. The reaction was quenched by addition of methanol/dichloromethane (1:1) (10 mL), stirred at −15° C. for 30 min, and neutralized by addition of aqueous ammonium hydroxide. The mixture was evaporated in vacuo and the resulting oil purified on silica gel using methanol/dichloromethane (1:9) as eluent. Fractions containing the product were pooled and evaporated in vacuo to give the desired product (112 mg) as a colorless foam.

Step D: 4-Amino-7-(2-C-ethyl-β-D-ribofuranosyl)-7H-pyrrolo[2,3-d]pyrimidine

To the compound from Step C (50 mg, 0.16 mmol) was added saturated ammonia in methanol (4 mL). The mixture was stirred at 75° C. for 72 h in a closed container, cooled and evaporated in vacuo. The crude mixture was purified on silica gel using methanol/dichloromethane (1:9) as eluent. Fractions containing the product were pooled and evaporated in vacuo to give the desired product (29 mg) as a colorless powder.

$^1$H NMR (200 MHz, DMSO-d$_6$): δ 0.52 (t, 3H), 1.02 (m, 2H), 4.01–3.24 (m, 6H), 5.06 (m, 1H), 6.01 (s, 1H), 6.51 (d, 1H), 6.95 (s br, 2H), 6.70 (d, 1H), 7.99 (s, 1H).

LC-MS: Found: 295.2 (M+H$^+$); calc. for $C_{13}H_{18}N_4O_4$+ H$^+$: 295.14.

EXAMPLE 118

2-Amino-7-(2-C-methyl-β-D-ribofuranosyl)-7H-pyrrolo[2,3-d]pyrimidin-4(3H)-one

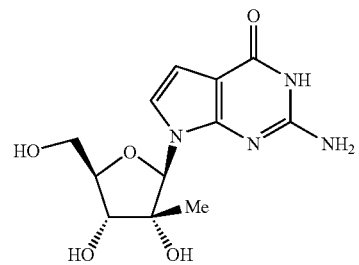

Step A: 2-Amino-4-chloro-7-[3,5-bis-O-(2,4-dichlorophenylmethyl)-2-C-methyl-β-D-ribofuranosyl]-7H-pyrrolo[2,3-d]pyrimidine To an ice-cold solution of product from Step C of Example 62 (1.27 g, 2.57 mmol) in CH$_2$Cl$_2$ (30 mL) was added HBr (5.7 M in acetic acid; 3 mL) dropwise. The reaction mixture was stirred at room temperature for 2 h, concentrated in vacuo and co-evaporated with toluene (2×15 mL). The resulting oil was dissolved in MeCN (15 mL) and added dropwise into a well-stirred mixture of 2-amino-4-chloro-7H-pyrrolo[2,3-d]pyrimidine [for preparation see *Heterocycles* 35: 825 (1993)] (433 mg, 2.57 mmol), KOH (85%, powdered) (0.51 g, 7.7 mmol), tris-[2-(2-methoxyethoxy)ethyl]amine (165 μL, 0.51 mmol) in acetonitrile (30 mL). The resulting mixture was stirred at rt for 1 h, filtered and evaporated. The residue was purified on a silica gel column using hexanes/EtOAc, 5/1, 3/1 and 2/1 as eluent to give the title compound as a colorless foam (0.65 g).

Step B: 2-Amino chloro-7-(2-C-methyl-β-D-ribofuranosyl)-7H-pyrrolo[2,3-d]pyrimidine To a solution of the product from Step A (630 mg, 1.0 mmol) in CH$_2$Cl$_2$ (20 mL) at −78° C. was added boron trichloride (1M in CH$_2$Cl$_2$) (10 mL, 10 mmol). The mixture was stirred at −78° C. for 2 h, then at −20° C. for 2.5 h. The reaction was quenched with CH$_2$Cl$_2$/MeOH (1:1) (10 mL), stirred at −20° C. for 0.5 h, and neutralized at 0° C. with aqueous ammonia. The solid was filtered, washed with CH$_2$Cl$_2$/MeOH (1:1) and the combined filtrate evaporated in vacuo. The residue was purified on a silica gel column with CH$_2$Cl$_2$/MeOH, 50/1 and 20/1 as eluent to give the title compound as a colorless foam (250 mg).

Step C: 2-Amino-7-(2-C-methyl-β-D-ribofiuranosyl)-7H-pyrrolo[2,3-d]pyrimidin-4(3H)-one A mixture of product from Step B (90 mg, 0.3 mmol) in aqueous NaOH (2N, 9 mL) was heated at reflux temperature for 5 h, then neutralized at 0° C. with 2 N aqueous HCl and evaporated to dryness. Purification on a silica gel column with CH$_2$Cl$_2$/MeOH, 5/1 as eluent afforded the title compound as a white solid (70 mg).

$^1$H NMR (200 MHz, CD$_3$OD): δ 0.86 (s, 3H), 3.79 (m 1H), 3.90–4.05 (m, 3H), 6.06 (s, 1H), 6.42 (d, J=3.7 Hz, 1H), 7.05 (d, J=3.7 Hz, 1H).

EXAMPLE 119

2-Amino-4-cyclopropylamino-7-(2-C-methyl-β-D-ribofiuranosyl)-7H-pyrrolo[2,3-d]pyrimidine

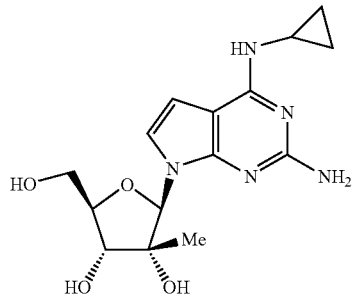

A solution of 2-amino-4-chloro-7-(2-C-methyl-β-D-ribofuranosyl)-7H-pyrrolo[2,3-d]pyrimidine (Example 118, Step B) (21 mg, 0.07 mmol) in cyclopropylamine (0.5 mL) was heated at 70° C. for two days, then evaporated to an oily residue and purified on a silica gel column with CH$_2$Cl$_2$/MeOH, 20/1, as eluent to give the title compound as a white solid (17 mg).

$^1$H NMR (200 MHz, CD$_3$CN): δ 0.61 (m, 2H), 0.81 (m, 2H), 0.85 (s, 3H), 2.83 (m, 1H), 3.74–3.86 (m, 1H), 3.93–4.03 (m, 2H), 4.11 (d, J=8.9 Hz, 1H), 6.02 (s, 1H), 6.49 (d, J=3.7 Hz, 1H), 7.00 (d, J=3.7 Hz, 1H).

EXAMPLE 120

3',5'-Bis-[O-(1-oxooctyl)]-2'-O-methylcytidine

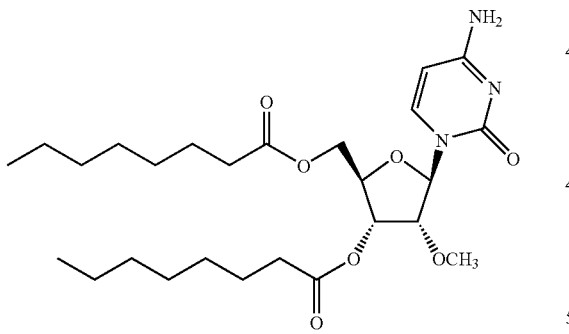

1,3-Dicyclohexylcarbodiimide (21.48 g, 104 mmol) was dissolved in anhydrous dichloromethane (100 mL). To the solution was added octanoic acid (5.49 mL, 34.5 mmol, made anhydrous by keeping over molecular sieves, 4 Å overnight at room temperature), and the resulting reaction mixture was stirred under argon atmosphere for 6 h. The white precipitate which formed was filtered, and the filtrate was concentrated under reduced pressure. The residue obtained was dissolved in anhydrous pyridine and added to N$^4$-(4,4'-dimethoxytrityl)-2'-O-methylcytidine (0.43 g, 0.77). DMAP (0.09 g, 0.77 mmol) was added and the resulting mixture was stirred at room temperature under argon atmosphere for 12 h. The solvent was removed under reduced pressure and the residue obtained was dissolved in ethyl acetate (100 mL). The organic phase was washed with aqueous sodium bicarbonate (5%, 50 mL), dried over anhydrous Na$_2$SO$_4$ and concentrated under reduced pressure. The residue was purified by flash silica gel column chromatography and eluted with 5% MeOH in dichloromethane. The product obtained was dissolved in a mixture of acetic acid: MeOH:H2O (20 mL, 3:6:1). The resulting mixture was heated at 50° C. for 24 h. The solvent was removed under reduced pressure. The residue obtained was purified by flash silica gel column chromatography and eluted with dichloromethane containing 0 to 5% of MeOH to give the title compound (0.22.g).

$^1$H NMR (200 MHz, DMSO-d$_6$) δ 0.83 (m, 6H), 1.23 (br s, 16H), 1.51 (m, 4H), 2.33 (m, 4H), 3.26 (s, 3H), 4.06 (t, J=5.2 Hz, 1H), 4.21 (m, 3H), 5.11 (t, J=5.2 Hz, 1H), 5.75 (d, J3=7.4 Hz, 1H), 5.84 (d, J3=4.8 Hz, 1H), 7.26 (br s, 2H), 7.61 (d, J=7.4 Hz, 1H). MS (ES): m/z 510.3 [M+H]$^+$; HRMS (FAB) Calcd for C$_{26}$H$_{44}$N$_3$O$_7$: 510.3179; found 510.3170.

EXAMPLE 121

4-Amino-1-(β-D-ribofuranosyl)-1H-pyrazolo[3,4-d]pyrimidine

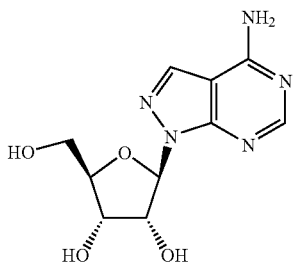

This compound was prepared following procedures described in *Nucleic Acids Res.*, 11: 871–872 (1983).

EXAMPLE 122

2' C-Methyl-cytidine

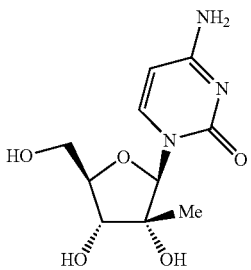

This compound was prepared following procedures described in L. Beigelman et al., *Carbohyd. Res.* 166: 219–232 (1987) or X-Q Tang, et al., *J. Org. Chem.* 64: 747–754 (1999).

EXAMPLE 123

4-Amino-7-(2-C-methyl-β-D-ribofuranosyl)-7H-pyrrolo[2,3-d]pyrimidine-5-carbonitrile

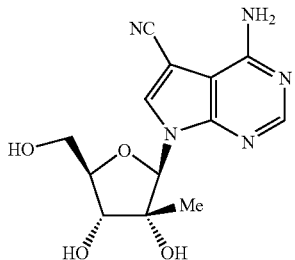

This compound was prepared following procedures described by Y. Murai et al. in *Heterocycles* 33: 391–404 (1992).

EXAMPLE 124

4-Amino-7-(2-C-methyl-β-D-ribofuranosyl)-7H-pyrrolo[2,3-d]pyridine-5-carboxamide

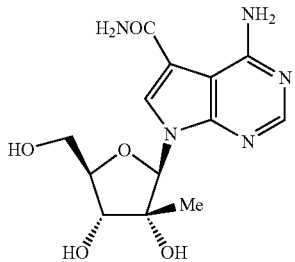

This compound was prepared following procedures described by Y. Murai et al. in *Heterocycles* 33: 391–404 (1992).

EXAMPLE 125

8-Aminoadenosine

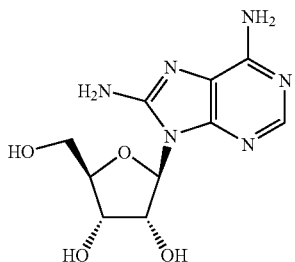

This compound was prepared following the procedure described in M. Ikehara and S. Yamada, *Chem. Pharm. Bull.*, 19: 104 (1971).

EXAMPLE 126

Mass Spectral Characterization of Nucleoside 5'-Triphosphates

Mass spectra of nucleoside 5'-triphosphates were determined as described in Example 87. Listed in the following table are the calculated and experimental masses for the nucleoside 5'-triphosphates prepared according to the procedures of Example 86. The example numbers correspond to the parent nucleoside of the nucleoside 5'-triphosphate.

| Example | Calculated | Found |
| --- | --- | --- |
| 1 | 507.0 | 506.9 |
| 2 | 525.0 | 524.9 |
| 5 | 537.0 | 537.0 |
| 6 | 539.0 | 539.0 |
| 7 | 565.0 | 565.0 |
| 8 | 547.0 | 546.9 |
| 9 | 550.0 | 550.0 |
| 10 | 506.0 | 505.9 |
| 11 | 536.0 | 535.9 |
| 12 | 536.0 | 536.0 |
| 13 | 561.0 | 560.9 |
| 14 | 550.0 | 550.0 |
| 15 | 524.0 | 524.0 |
| 16 | 522.0 | 521.9 |
| 17 | 547.0 | 546.9 |
| 18 | 536.0 | 536.0 |
| 20 | 531.0 | 530.9 |
| 21 | 522.0 | 522.0 |
| 22 | 536.0 | 536.0 |
| 23 | 506.0 | 506.1 |
| 24 | 524.0 | 524.0 |
| 25 | 508.0 | 508.0 |
| 26 | 508.0 | 508.0 |
| 27 | 552.0 | 552.0 |
| 28 | 506.0 | 506.0 |
| 29 | 579.0 | 578.9 |
| 30 | 582.0 | 582.0 |
| 31 | 568.0 | 567.9 |
| 32 | 554.0 | 553.9 |
| 33 | 540.0 | 539.9 |
| 34 | 554.0 | 553.9 |
| 35 | 568.0 | 567.9 |
| 36 | 541.0 | 541.0 |
| 37 | 565.0 | 564.9 |
| 38 | 542.0 | 541.9 |
| 39 | 554.0 | 553.9 |
| 41 | 481.0 | 481.0 |
| 42 | 467.0 | 467.0 |
| 43 | 485.0 | 484.8 |
| 46 | 482.0 | 482.0 |
| 47 | 486.0 | 485.8 |
| 48 | 482.0 | 482.0 |
| 49 | 554.0 | 554.0 |
| 51 | 468.0 | 468.1 |
| 52 | 521.0 | 521.0 |
| 53 | 491.0 | 491.2 |
| 55 | 584.9 | 585.1 |
| 56 | 521.0 | 521.2 |
| 58 | 506.0 | 506.0 |
| 61 | 520.0 | 519.9 |
| 62 | 520.0 | 520.0 |
| 63 | 547.0 | 547.0 |
| 64 | 533.0 | 533.0 |
| 65 | 549.0 | 549.0 |
| 67 | 551.0 | 551.0 |
| 68 | 515.0 | 514.9 |
| 69 | 520.0 | 520.1 |
| 71 | 490.0 | 489.9 |
| 89 | 523.0 | 522.9 |
| 90 | 521.0 | 520.9 |
| 91 | 645.1 | 645.0 |
| 94 | 524.0 | 523.9 |
| 95 | 522.0 | 521.8 |
| 98 | 536.0 | 535.9 |
| 99 | 520.0 | 520.0 |
| 102 | 613.1 | 613.0 |
| 103 | 498.0 | 497.9 |
| 104 | 481.0 | 481.0 |
| 105 | 536.0 | 536.2 |
| 106 | 509.0 | 508.9 |
| 108 | 505.0 | 505.0 |
| 112 | 506.0 | 506.1 |

-continued

| Example | Calculated | Found |
|---------|-----------|-------|
| 113 | 490.0 | 490.0 |
| 117 | 534.0 | 534.0 |
| 118 | 536.0 | 536.0 |

EXAMPLE 127

[4-Amino-7-(2-C-methyl-β-D-ribofuranosyl)-7H-pyrrolo[2,3-d]-pyrimidine]-5'-monophosphate

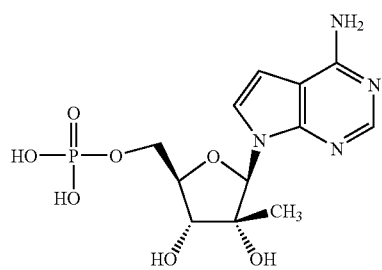

To the compound from Step F of Example 62 (14 mg, 0.05 mmol) (dried by coevaporation with pyridine and several times with toluene) was added trimethyl phosphate (0.5 mL). The mixture was stirred- overnight in a sealed container. It was then cooled to 0° C. and phosphorous oxychloride (0.0070 mL, 0.075 mmol) was added via a syringe. The mixture was stirred for 3 h at 0° C., then the reaction was quenched by addition of tetraethylammonium bicarbonate (TEAB) (1M) (0.5 mL) and water (5 mL). The reaction mixture was purified and analyzed according to the procedure described in Example 87.

Electron spray mass spectrum (ES-MS): Found: 359.2 $(M-H^+)$, calc. for $C_{12}H_{17}N_4O_7P-H^+$: 359.1.

EXAMPLE 128

[4-Amino-7-(2-C-methyl-β-D-ribofuranosyl)-7H-pyrrolo[2,3-d]-pyrimidine]-5'-diphosphate

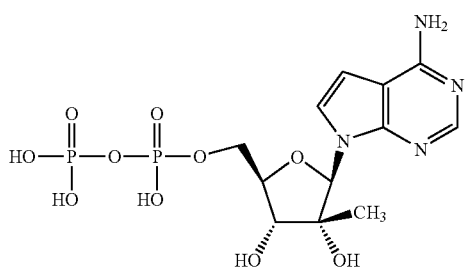

To the compound from Step F of Example 62 (56 mg, 0.20 mmol) (dried by coevaporation with pyridine and several times with toluene) was added trimethyl phosphate (stored over sieves) (1.0 mL). The mixture was stirred overnight in a sealed container. It was then cooled to 0° C. and phosphorous oxychloride (0.023 mL, 0.25 mmol) was added via a syringe. The mixture was stirred for 2 h at 0° C., then tributylamine (0.238 mL, 1.00 mmol) and tributylammonium phosphate (generated from phosphoric acid and tributylamine in pyridine, followed by repeated azeotropic evaporation with pyridine and acetonitrile) (1.0 mmol in 3.30 mL acetonitrile) was added. The mixture was stirred for an additional 30 min at 0° C., the sealed vial was then opened and the reaction quenched by addition of TEAB (1M) (1.0 mL) and water (5 mL). The reaction mixture was purified and analyzed according to the procedure described in Example 87.

ES-MS: Found: 439.0 $(M-H^+)$, calc. for $C_{12}H_{18}N_4O_{10}P_2-H^+$: 439.04.

EXAMPLE 129

[4-Amino-7-(2-C-methyl-β-D-ribofuranosyl)-7H-pyrrolo[2,3-d]-pyrimidine]-5'-triphosphate

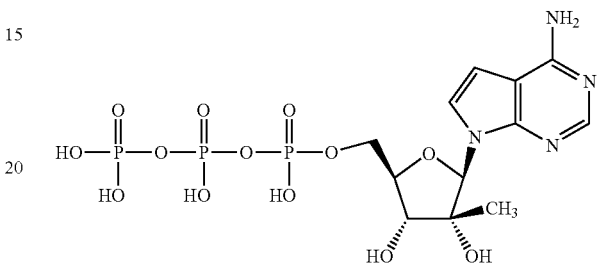

To the compound from Step F of Example 62 (20 mg, 0.07 mmol) (dried by coevaporation with pyridine and several times with toluene) was added trimethyl phosphate (stored over sieves) (0.4 mL). The mixture was stirred overnight in a sealed container. It was then cooled to 0° C. and phosphorous oxychloride (0.0070 mL, 0.075 mmol) was added via syringe. The mixture was stirred for 3 h at 0° C., then tributylamine (0.083 mL, 0.35 mmol), tributylammonium pyrophosphate (0.35 mmol, 127 mg) and acetonitrile (stored over sieves) (0.25 mL) were added. The mixture was stirred for an additional 30 min at 0° C., the sealed vial was then opened and the reaction quenched by addition of TEAB (1M) (0.5 mL) and water (5 mL). The reaction mixture was purified and analyzed according to the procedure described in Example 87.

ES-MS: Found: 519.0 $(M-H^+)$, calc. for $C_{12}H_{19}N_4O_{13}P_3-H^+$: 519.01.

EXAMPLE 130

7-(2-C-methyl-β-D-ribofuranosyl)-7H-pyrrolo[2,3-d]pyrimidin-4(3H)-one

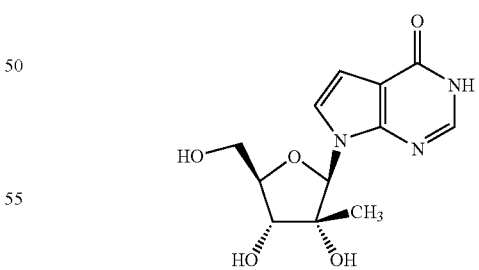

To the compound from Step E of Example 62 (59 mg, 0.18 mmol) was added aqueous sodium hydroxide (1M). The mixture was heated to reflux for 1 hr, cooled, neutralized with aqueous HCl (2M) and evaporated in vacuo. The residue was purified on silica gel using dichloromethane/methanol (4:1) as eluent. Fractions containing the product were pooled and evaporated in vacuo to give the desired product (53 mg) as a colorless oil.

¹H NMR (CD₃CN): δ 0.70 (s, 3H), 3.34–4.15 (overlapping m, 7H), 6.16 (s, 1H), 6.57 (d, 3.6 Hz, 1H), 7.37 (d, 3.6 Hz, 1H), 8.83 (s, 1H).

EXAMPLE 131

4-Amino-5-chloro-7-(2-C-methyl-β-D-ribofuranosyl)-7H-pyrrolo[2,3-d]pyrimidine

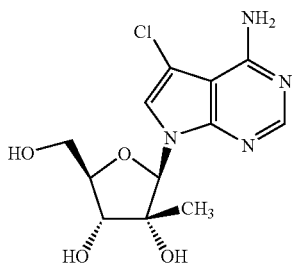

To a pre-cooled solution (0° C.) of the compound from Step F of Example 62 (140 mg, 0.50 mmol) in DMF (2.5 mL) was added N-chlorosuccinimide (0.075 g, 0.55 mmol) in DMF (0.5 mL) dropwise. The solution was stirred at rt for 1 h and the reaction quenched by addition of methanol (4 mL) and evaporated in vacuo. The crude product was purified on silica gel using methanol/dichloromethane (1:9) as eluent. Fractions containing the product were pooled and evaporated in vacuo to give the desired product (55 mg) as a colorless solid.

¹H NMR (CD₃CN): δ 0.80 (s, 3H), 3.65–4.14 (overlapping m, 7H), 5.97 (s br, 2H), 6.17 (s, 1H), 7.51 (s, 1H), 8.16 (s, 1H).

ES-MS: Found: 315.0 (M+H⁺), calc.for $C_{12}H_{15}ClN_4O_4$+ H⁺: 315.09.

EXAMPLE 132

4-Amino-5-bromo-7-(2-C-methyl-β-D-ribofuranosyl)-7H-pyrrolo[2,3-d]pyrimidine

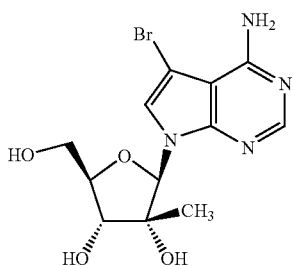

To a pre-cooled solution (0° C.) of the compound from Step F of Example 62 (28 mg, 0.10 mmol) in DMF (0.5 mL) was added N-bromosuccinimide (0.018 g, 0.10 mmol) in DMF (0.5 mL) dropwise. The solution was stirred at 0° C. for 20 min, then at rt for 10 min. The reaction was quenched by addition of methanol (4 mL) and evaporated in vacuo. The crude product was purified on silica gel using methanol/dichloromethane (1:9) as eluent. Fractions containing the product were pooled and evaporated in vacuo to give the desired product (13.0 mg) as a colorless solid.

¹H NMR (CD₃CN): δ 0.69 (s, 3H), 3.46–4.00 (overlapping m, 7H), 5.83 (s br, 2H), 6.06 (s, 1H), 7.45 (s, 1H), 8.05 (s, 1H).

ES-MS: Found: 359.1 (M+H⁺), calc. for $C_{12}H_{15}BrN_4O_4$+ H⁺: 359.04.

EXAMPLE 133

2-Amino-7-(2-C-methyl-β-D-ribofuranosyl)-7H-pyrrolo[2,3-d]pyrimidine

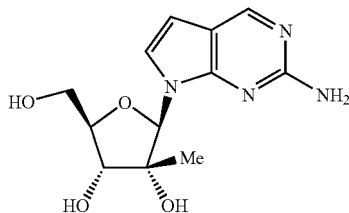

A mixture of 2-amino-4-chloro-7-(2-C-methyl-β-D-ribofuranosyl)-7H-pyrrolo[2,3-d]pyrimidine (Example 118, Step B) (20 mg, 0.07 mmol) in EtOH (1.0 mL), pyridine (0.1 mL) and 10% Pd/C (6 mg) under H₂ (atmospheric pressure) was stirred overnight at room temperature. The mixture was filtered through a Celite pad which was thoroughly washed with EtOH. The combined filtrate was evaporated and purified on a silica gel column with CH₂Cl₂/MeOH, 20/1 and 10/1, as eluent to give the title compound as a white solid (16 mg).

¹H NMR (200 MHz, CD₃OD): δ 0.86 (s, 3H, 2'C-Me), 3.82 (dd, $J_{5'4'}$=3.6 Hz, $J_{5',5''}$=12.7 Hz, 1H, H-5'), 3.94–4.03 (m, 2H, H-5', H4'), 4.10 (d, $J_{3'4'}$=8.8 Hz, 1H, H-3'), 6.02 (s, 1H, H-1'), 6.41 (d, $J_{5,6}$=3.8 Hz, 1H, H-5), 7.39 (d, 1H, H-6), 8.43 (s, 1H, H-4). ES MS: 281.4 (MH⁺).

EXAMPLE 134

2-Amino-5-methyl-7-(2-C,2-O-dimethyl-β-D-ribofuranosyl)-7H-pyrrolo[2,3-d]pyrimidin-4(3H)-one

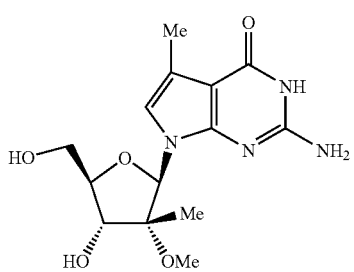

Step A: 2-Amino-4-chloro-7-[3,5-bis-O-(2,4-dichlorophenylmethyl)-2-C-methyl-β-D-ribofuranosy]-5-methyl-7H-pyrrolo[2,3-d]pyrimidine To an ice-cold solution of the product from Step C of Example 62 (1.57 g, 3.16 mmol) in CH₂Cl₂ (50 mL) was added HBr (5.7 M in acetic acid; 3.3 mL) dropwise. The reaction mixture was stirred at 0° C. for 1 h and then at room temperature for 2 h, concentrated in vacuo and co-evaporated with toluene (2×20 mL). The resulting oil was dissolved in MeCN (20 mL) and added dropwise to a solution of the sodium salt of 2-amino-4-chloro-5-methyl-1H-pyrrolo[2,3-d]pyrimidine in acetonitrile [generated in situ from 2-amino-4-chloro-5-methyl-1H-pyrrolo[2,3-d] pyrimidine [for preparation, see Liebigs Ann. Chem. 1984: 708–721] (1.13 g, 6.2 mmol) in anhydrous acetonitrile (150 mL), and NaH (60% in mineral oil, 248 mg, 6.2 mmol), after 2 h of vigorous stirring at rt]. The combined mixture was stirred at rt for 24 h and then evaporated to dryness. The residue was suspended in water (100 mL) and extracted with EtOAc (300+150 mL). The combined extracts were washed with brine (100 mL), dried over Na$_2$SO$_4$, filtered and evaporated. The crude product was purified on a silica gel column (5×7 cm) using ethyl acetate/hexane (0 to 30% EtOAc in 5% step gradient) as the eluent. Fractions containing the product were combined and evaporated in vacuo to give the desired product (0.96 g) as a colorless foam.

Step B: 2-Amino-4-chloro-7-[3,5-bis-O-(2,4-dichlorophenylmethyl)-2-C,2-O-dimethyl-β-D-ribofuranosyl]-5-methyl-7H-pyrrolo[2,3-d]pyrimidine To an ice-cold mixture of the product from Step A (475 mg, 0.7 mmol) in THF (7 mL) was added NaH (60% in mineral oil, 29 mg) and stirred at 0° C. for 0.5 h. Then MeI (48 µL) was added and reaction mixture stirred at rt for 24 h. The reaction was quenched with MeOH and the mixture evaporated. The crude product was purified on a silica gel column (5×3.5 cm) using hexane/ethyl acetate (9/1, 7/1, 5/1 and 3/1) as eluent. Fractions containing the product were combined and evaporated to give the desired compound (200 mg) as a colorless foam.

Step C: 2-Amino-7-[3,5-bis-O-(2,4-dichlorophenylmethyl)-2-C,2-O-dimethyl-β-D-ribofuranosyl]-5-methyl-7H-pyrrolo[2,3-d]pyrimidine-4(3H)-one A mixture of the product from Step B (200 mg, 0.3 mmol) in 1,4-dioxane (15 mL) and aqueous NaOH (2N, 15 mL) in a pressure bottle was heated overnight at 135° C. The mixture was then cooled to 0° C., neutralized with 2N aqueous HCl and evaporated to dryness. The crude product was suspended in MeOH, filtered, and the solid thoroughly washed with MeOH. The combined filtrate was concentrated, and the residue purified on a silica gel column (5×5 cm) using CH$_2$Cl$_2$/MeOH (40/1, 30/1 and 20/1) as eluent to give the desired compound (150 mg) as a colorless foam.

Step D: 2-Amino-5-methyl-7-(2-C,2-O-dimethyl-β-D-ribofuranosyl)-7H-pyrrolo[2,3-d]pyrimidin-4(3H)-one A mixture of the product from Step C (64 mg, 0.1 mmol) in MeOH (5 mL) and Et$_3$N (0.2 mL) and 10% Pd/C (24 mg) was hydrogenated on a Parr hydrogenator at 50 psi at r.t. for 1.5 days, then filtered through a Celite pad which was thoroughly washed with MeOH. The combined filtrate was evaporated and the residue purified on a silica gel column (3×4 cm) with CH$_2$Cl$_2$/MeOH (30/1, 20/1) as eluent to yield 2-amino-5-methyl-7-(5-O-benzyl-2-C,2-O-dimethyl-β-D-ribofuranosyl)-7H-pyrrolo[2,3-d]pyrimidin-4(3H)-one. The compound (37 mg) was further hydrogenated in EtOH (2 mL) with 10% Pd/C and under atmospheric pressure of hydrogen. After stirring 2 days at r.t., the reaction mixture was filtered through Celite, the filtrate evaporated and the crude product purified on a silica gel column (1×7 cm) with CH$_2$Cl$_2$/MeOH (30/1, 20/1 and 10/1) as eluent to yield the title compound (12 mg) after freeze-drying.

$^1$H NMR (200 MHz, CD$_3$OD): δ 0.81 (s, 3H, 2'C-Me), 2.16 (d, $J_{H-6,C5-Me}$=1.3 Hz, 3H, C5-Me), 3.41 (s, 3H, 2'-OMe), 3.67 (dd, $J_{5',4'}$=3.4 Hz, $J_{5',5''}$=12.6 Hz, 1H, H-5'), 3.81–3.91 (m, 3H, H-5", H-4', H-3'), 6.10 (s, 1H, H-1'), 6.66 (d, 1H, H-6).

ES MS: 323.3 (M−H)$^+$.

EXAMPLE 135

4-Amino-5-methyl-7-(2-C-methyl-β-D-ribofuranosyl)-7H-pyrrolo[2,3-d]pyrimidine

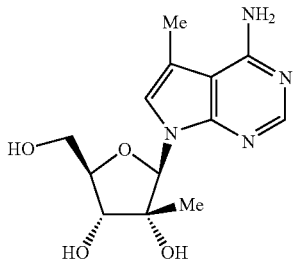

Step A: 4-Chloro-7-[3,5-bis-O-(2,4-dichlorophenylmethyl)-2-C-methyl-β-D-ribofuranosyl]-5-methyl-7H-pyrrolo[2,3-d]pyrimidine To an ice-cold solution of the product from Step C of Example 62 (1.06 g, 2.1 mmol) in CH$_2$Cl$_2$ (30 mL) was added HBr (5.7 M in acetic acid; 2.2 mL) dropwise. The reaction mixture was stirred at 0° C. for 1 h and then at room temperature for 2 h, concentrated in vacuo and co-evaporated with toluene (2×15 mL). The resulting oil was dissolved in MeCN (10 mL) and added dropwise into a solution of the sodium salt of 4-chloro-5-methyl-1H-pyrrolo[2,3-d]pyrimidine in acetonitrile [generated in situ from 4-chloro-5-methyl-1H-pyrrolo[2,3-d]pyrimidine [for preparation, see J. Med. Chem. 33: 1984 (1990)] (0.62 g, 3.7 mmol) in anhydrous acetonitrile (70 mL), and NaH (60% in mineral oil, 148 mg, 3.7 mmol), after 2 h of vigorous stirring at rt]. The combined mixture was stirred at rt for 24 h and then evaporated to dryness. The residue was suspended in water (100 mL) and extracted with EtOAc (250+100 mL). The combined extracts were washed with brine (50 mL), dried over Na$_2$SO$_4$, filtered and evaporated. The crude product was purified on a silica gel column (5×5 cm) using hexane/ethyl acetate (9/1, 5/1, 3/1) gradient as the eluent. Fractions containing the product were combined and evaporated in vacuo to give the desired product (0.87 g) as a colorless foam.

Step B: 4-Chloro-5-methyl-7-(2-C-methyl-β-D-ribofuranosyl)-7H-pyrrolo[2,3-d]pyrimidine To a solution of the compound from Step A (0.87 g, 0.9 mmol) in dichloromethane (30 mL) at −78° C. was added boron trichloride (1M in dichloromethane, 9.0 mL, 9.0 mmol) dropwise. The mixture was stirred at −78° C. for 2.5 h, then at −30° C. to −20° C. for 3 h. The reaction was quenched by addition of methanol/dichloromethane (1:1) (9 mL) and the resulting mixture stirred at −15° C. for 30 min., then neutralized with aqueous ammonia at 0° C. and stirred at rt for 15 min. The solid was filtered and washed with CH$_2$Cl$_2$/MeOH (1/1, 50 mL). The combined filtrate was evaporated, and the residue was purified on a silica gel column (5×5 cm) using CH$_2$Cl$_2$ and CH$_2$Cl$_2$/MeOH (40/1 and 30/1) gradient as the eluent to furnish the desired compound (0.22 g) as a colorless foam.

Step C: 4-Amino-5-methyl-7-(2-C-methyl-β-D-ribofuranosyl)-7H-pyrrolo[2,3-d]pyrimidine To the compound from Step B (0.2 g, 0.64 mmol) was added methanolic ammonia (saturated at 0° C.; 40 mL). The mixture was heated in a stainless steel autoclave at 100° C. for 14 h, then cooled and evaporated in vacuo. The crude mixture was purified on a silica gel column (5×5 cm) with CH$_2$Cl$_2$/MeOH (50/1, 30/1, 20/1) gradient as eluent to give the title compound as a white solid (0.12 g).

$^1$H NMR (DMSO-d$_6$): δ 0.60 (s, 3H, 2'C-Me), 2.26 (s, 3H, 5C-Me), 3.52–3.61 (m, 1H, H-5'), 3.70–3.88 (m, 3H, H-5", H4', H-3'), 5.00 (s, 1H, 2'-OH), 4.91–4.99 (m, 3H, 2'-OH, 3'-OH, 5'-OH), 6.04 (s, 1H, H-1'), 6.48 (br s, 2H, NH2), 7.12 (s, 1H, H-6), 7.94 (s, 1H, H-2). ES MS: 295.2 (MH$^+$).

EXAMPLE 136

4-Amino-7-(2-C-methyl-β-D-ribofuranosyl)-7H-pyrrolo[2,3-d]pyrimidine-5-carboxylic Acid

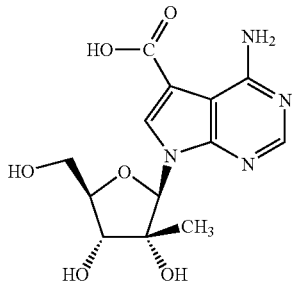

The compound of Example 123 (0.035 g, 0.11 mmol) was dissolved in a mixture of aqueous ammonia (4 mL, 30 wt %) and saturated methanolic ammonia (2 mL), and a solution of H$_2$O$_2$ in water (2 mL, 35 wt %) was added. The reaction mixture was stirred at room temperature for 18 h. Solvent was removed under reduced pressure, and the residue obtained was purified by HPLC on a reverse phase column (Altech Altima C-18, 10×299 mm, A=water, B=acetonitrile, 10 to 60% B in 50 min, flow 2 mL/min) to yield the title compound (0.015 g, 41%) as a white solid.

$^1$H NMR (CD$_3$OD): δ 0.85 (s, 3H, Me), 3.61 (m, 1H), 3.82 (m, 1H) 3.99–4.86 (m, 2H), 6.26 (s, 1H), 8.10 (s, 2H) 8.22(s, 1H); $^{13}$C NMR (CD$_3$OD): 20.13, 61.37, 73.79, 80.42, 84.01, 93.00, 102.66, 112.07, 130.07, 151.40, 152.74, 159.12, 169.30. HRMS (FAB) Calcd for C$_{13}$H$_{17}$N$_4$O$_6$+ 325.1148, found 325.1143.

EXAMPLE 137

4-Amino-7-(2-C-vinyl-β-D-ribofuranosyl)-7H-pyrrolo[2,3-d]pyrimidine

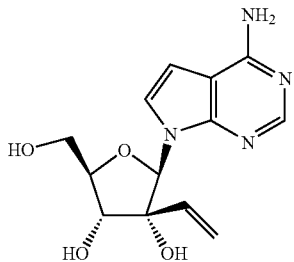

Step A: 3,5-Bis-O-(2,4-dichlorophenylmethyl)-2-C-vinyl-1-O-methyl-α-D-ribofuranose Cerium chloride heptahydrate (50 g, 134.2 mmol) was finely crushed in a pre-heated mortar and transferred to a round-bottom flask equipped with a mechanical stirrer. The flask was heated under high vacuum overnight at 160° C. The vacuum was released under argon and the flask was cooled to room temperature. Anhydrous THF (300 mL) was cannulated into the flask. The resulting suspension was stirred for 4 h and then cooled to −78° C. Vinylmagnesium bromide (1M in THF, 120 mL, 120 mmol) was added and stirring continued at −78° C. for 2 h. To this suspension was added a solution of 3,5-bis-O-(2,4-dichlorophenylmethyl)-1-O-methyl-α-D-erythro-pentofuranose-2-ulose (14 g, 30 mmol) [from Example 2, Step B] in anhydrous THF (100 mL), dropwise with constant stirring. The reaction was stirred at −78° C. for 4 h. The reaction was quenched with saturated ammonium chloride solution and allowed to come to room temperature. The mixture was filtered through a celite pad and the residue washed with Et$_2$O (2×500 mL). The organic layer was separated and the aqueous layer extracted with Et$_2$O (2×200 mL). The combined organic layers were dried over anhydrous Na$_2$SO$_4$ and concentrated to a viscous yellow oil. The oil was purified by flash chromatography (SiO$_2$, 10% EtOAc in hexanes). The title compound (6.7 g, 13.2 mmol) was obtained as a pale yellow oil.

Step B: 4-Chloro-7-[3,5-bis-O-(2,4-dichlorophenylmethyl)-2-C-vinyl-β-D-ribofuranosyl]-7H-pyrrolo[2,3-d]pyrimidine To a solution of the compound from Step A (6.4 g, 12.6 mmol) in anhydrous dichloromethane (150 mL) at −20° C. was added HBr (30% solution in AcOH, 20 mL, 75.6 mmol) dropwise. The resulting solution was stirred between −10° C. and 0° C. for 4 h, evaporated in vacuo and co-evaporated with anhydrous toluene (3×40 mL). The oily residue was dissolved in anhydrous acetonitrile (100 mL) and added to a solution of the sodium salt of 4-chloro-1H-pyrrolo[2,3-d]pyrimidine (5.8 g, 37.8 mmol) in acetonitrile (generated in situ as described in Example 62) at −20° C. The resulting mixture was allowed to come to room temperature and stirred at room temperature for 24 h. The mixture was then evaporated to dryness, taken up in water and extracted with EtOAc (2×300 mL). The combined extracts were dried over Na$_2$SO$_4$, filtered and evaporated. The crude mixture was purified by flash chromatography (SiO$_2$, 10% EtOAc in hexanes) and the title compound (1.75 g) isolated as a white foam.

Step, C: 4-Amino-7-[3,5-bis-O-(2,4-dichlorophenylmethyl)-2-C-vinyl-β-D-ribofuranosyl]-7H-pyrrolo[2,3-d]pyrimidine The compound from Step B (80, mg) was dissolved in the minimum amount of 1,4-dioxane and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step D: 4-Amino-7-(2-C-vinyl-β-D-ribofuranosyl)-7H-pyrrolo[2,3-d]pyridine

To a solution of the compound from Step C (60 mg) in dichloromethane at −78° C. was added boron trichloride (1M in dichloromethane) dropwise. The mixture was stirred at −78° C. for 2.5 h, then at −30° C. to −20° C. for 3 h. The reaction was quenched by addition of methanol/dichloromethane (1:1) and the resulting mixture stirred at −15° C. for 0.5 h, then neutralized with aqueous ammonia at 0° C. and stirred at room temperature for 15 min. The solid was filtered and washed with methanol/dichloromethane (1:1). The combined filtrate was evaporated and the residue purified by flash chromatography (SiO$_2$, 10% methanol in EtOAc containing 0.1% triethylamine). The fractions containing the product were evaporated to give the title compound as a white solid (10 mg).

$^1$H NMR (DMSO-d6): δ 3.6 (m, 1H, H-5'), 3.8 (m, 1H, H-5"), 3.9 (m d, 1-H, H4'), 4.3 (t, 1H, H-3'), 4.8–5.3(m, 6H, CH=CH$_2$, 2'-OH, 3'-OH, 5'-OH) 6.12 (s, 1H, H-1'), 6.59 (d, 1H, H-5), 7.1 (br s, 1H, NH2), 7.43 (d, 1H, H-6), 8.01 (s, 1H, H-2).

ES-MS: Found: 291.1 (M−H⁻); calc. for $C_{13}H_{16}N_4O_4$−H⁻: 291.2.

EXAMPLE 138

4-Amino-7-(2-C-hydroxymethyl-β-D-ribofuranosyl)-7H-pyrrolo[2,3-d]pyrimidine

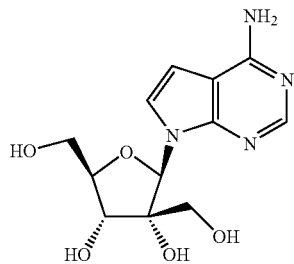

Step A: 4-Chloro-7-[3,5-bis-O-(2,4-dichlorophenylmethyl)-2-C-hydroxymethyl-β-D-ribofuranosyl]-7H-pyrrolo[2,3-d]pyrimidine To a solution of the compound from Example 137, Step B (300 mg, 0.48 mmol) in 1,4-dioxane (5 mL) were added N-methylmorpholine-N-oxide (300 mg, 2.56 mmol) and osmium tetroxide (4% solution in water, 0.3 mL). The mixture was stirred in the dark for 14 h. The precipitate was removed by filtration through a celite plug, diluted with water (3×), and extracted with EtOAc. The EtOAc layer was dried over $Na_2SO_4$ and concentrated in vacuo. The oily residue was taken up in dichloromethane (5 mL) and stirred over $NaIO_4$ on silica gel (3 g, 10% $NaIO_4$) for 12 h. The silica gel was removed by filtration and the residue was evaporated and taken up in absolute ethanol (5 mL). The solution was cooled in an ice bath and sodium borohydride (300 mg, 8 mmol) was added in small portions. The resulting mixture was stirred at room temperature for 4 h and then diluted with EtOAc. The organic layer was washed with water (2×20 mL), brine (20 mL) and dried over $Na_2SO_4$. The solvent was evaporated and the residue purified by flash chromatography ($SiO_2$, 2:1 hexanes/EtOAc) to give the title compound (160 mg, 0.25 mmol) as white flakes.

Step B: 4-Amino-7-[3,5-bis-O-(2,4-dichlorophenylmethyl)-2-C-hydroxymethyl-β-D-ribofuranosyl]-7H-pyrrolo[2,3-d]pyrimidine The compound from Step A (150 mg, 0.23 mmol) was dissolved in the minimum amount of 1,4-dioxane (10 mL) and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step C: 4-Amino-7-(2-C-hydroxymethyl-β-D-ribofuranosyl)-7H-pyrrolo[2,3-d]pyrimidine The compound from Step B (120 mg, 0.2 mmol) was dissolved in 1:1 methanol/dichloromethane, 10% Pd-C was added, and the suspension stirred under an $H_2$ atmosphere for 12 h. The catalyst was removed by filtration through a celite pad and washed with copious amounts of methanol. The combined filtrate was evaporated in vacuo and the residue was purified by flash chromatography ($SiO_2$, 10% methanol in EtOAc containing 0.1% triethylamine) to give the title compound (50 mg) as a white powder.

$^1$H NMR ($CD_3OD$): δ 3.12 (d, 1H, $CH_2$'), 3.33 (d, 1H, $CH_2$"), 3.82 (m, 1H, H-5'), 3.99–4.1(m, 2H, H-4', H-5"), 4.3 (d, 1H, H-3'), 6.2 (s, 1H, H-1'), 6.58 (d, 1H, H-5), 7.45 (d, 1H, H-6), 8.05 (s, 1H, H-2).

LC-MS: Found: 297.2 (M+H⁺); calc. for $C_{12}H_{16}N_4O_5$+H⁺: 297.3.

EXAMPLE 139

4-Amino-7-(2-C-fluoromethyl-β-D-ribofuranosyl)-7H-pyrrolo[2,3-d]pyrimidine

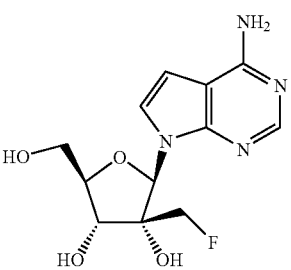

Step A: 4-Chloro-7-[3,5-bis-O-(2,4-dichlorophenylmethyl)-2-C-fluoromethyl-β-D-ribofuranosyl]-7H-pyrrolo[2,3-d]pyrimidine To a solution of the compound from Example 138, Step A (63 mg, 0.1 mmol) in anhydrous dichloromethane (5 mL) under argon, were added 4-dimethylaminopyridine (DMAP) (2 mg, 0.015 mmol) and triethylamine (62 μL, 0.45 mmol). The solution was cooled in an ice bath and p-toluenesulfonyl chloride (30 mg, 0.15 mmol) was added. The reaction was stirred at room temperature overnight, washed with $NaHCO_3$ (2×10 mL), water (10 mL), brine (10 mL), dried over $Na_2SO_4$ and concentrated to a pink solid in vacuo. The solid was dissolved in anhydrous THF (5 mL) and cooled in an icebath. Tetrabutylammonium fluoride (1M solution in THF, 1 mL, 1 mmol) was added and the mixture stirred at room temperature for 4 h. The solvent was removed in vacuo, the residue taken up in dichloromethane, and washed with $NaHCO_3$ (2×10 mL), water (10 mL) and brine (10 mL). The dichloromethane layer was dried over anhydrous $Na_2SO_4$, concentrated in vacuo, and purified by flash chromatography ($SiO_2$, 2:1 hexanes/EtOAc) to afford the title compound (20 mg) as a white solid.

Step B: 4-Amino-7-[3.5-bis-O-(2,4-dichlorophenylmethyl)-2-C-fluoromethyl-β-D-ribofuranosyl]-7H-pyrrolo[2,3-d]pyrimidine The compound from Step A (18 mg, 0.03 mmol) was dissolved in the minimum amount of 1,4-dioxane and placed in a stainless steel bomb. The bomb was cooled to −78° C. and liquid ammonia was added. The bomb was sealed and heated at 90° C. for 24 h. The ammonia was allowed to evaporate and the residue concentrated to a white solid which was used in the next step without further purification.

Step C: 4-Amino-7-(2-C-fluoromethyl-β-D-ribofuranosyl)-7H-pyrrolo[2,3-d]pyrimidine The compound from Step B (16 mg) was dissolved in 1:1 methanol/dichloromethane, 10% Pd—C was added, and the suspension stirred under an $H_2$ atmosphere for 12 h. The catalyst was removed by filtration through a celite pad and washed with copious amounts of methanol. The combined filtrate was evaporated in vacuo and the residue was purified by flash chromatography ($SiO_2$, 10% methanol in EtOAc containing 0.1% triethylamine) to give the title compound (8 mg) as a white powder.

$^1$H NMR (DMSO-$d_6$): δ 3.6–3.7 (m, 1H, 1H-5'), 3.8–4.3 (m, 5H, H-5", H-4', H-3', $CH_2$) 5.12 (t, 1H, 5'-OH), 5.35 (d, 1H, 3'-OH), 5.48 (s, 1H, 2'-OH), 6.21 (s, 1H, H-1'), 6.52 (d, 1H, H-5), 6.98 (br s, 2H, NH2), 7.44 (d, 1 H, H-6), 8.02 (s, 1H, H-2). $^{19}$F NMR (DMSO-$d_6$): δ −230.2 (t).

ES-MS: Found: 299.1 (M+H$^+$), calc.for $C_{12}H_{15}FN_4O_4$+H$^+$: 299.27.

EXAMPLES 140 AND 141

4-Amino-7-(3-deoxy-2-C-methyl-β-D-ribofuranosyl)-7H-pyrrolo[2,3-d]pyrimidine and 4-amino-7-(3-deoxy-2-C-methyl-β-D-arabinofuranosyl)-7H-pyrrolo[2,3-d]-pyrimidine

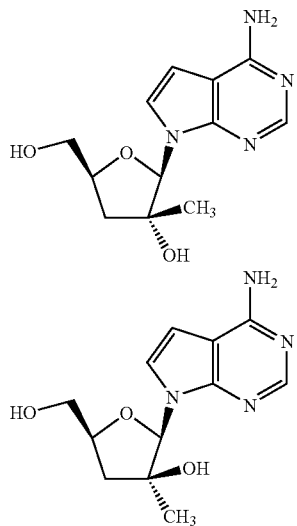

Step A: 7-[2,5-Bis-O-(tert-butyldimethylsilyl)-β-D-ribofuranosyl]-7H-pyrrolo[2,3-d]pyrimidine and 7-[3,5-Bis-O-(tert-butyldimethylsilyl)-β-D-ribofuranosyl]-7H-pyrrolo[2,3-d]pyrimidine To a stirred solution of tubercidin (5.0 g, 18.7 mmol) in a mixture of pyridine (7.5 mL) and DMF(18.5mL) was added silver nitrate (6.36 g, 38.8 mmol). This mixture was stirred at room temperature for 2 h. It was cooled in an ice bath and THF (37.4 mL) and tert-butyldimethylsilyl chloride (5.6 g, 37 mmol) was added and the mixture was stirred at room temperature for 2 h. The mixture was then filtered through a pad of celite and washed with THF. The filtrate and washings were diluted with ether containing a small amount of chloroform. The organic layer was washed successively with sodium bicarbonate and water (3×50 mL), dried over anhydrous sodium sulfate and concentrated. The pyridine was removed by coevaporation with toluene and the residue was purified by flash chromatography on silica gel using 5–7% MeOH in CH$_2$Cl$_2$ as the eluent; yield 3.0 g.

Step B: 7-[2,5-Bis-O-(tert-butyldimethylsilyl)-β-D-ribofuranosyl)]-4-[di-(4-methoxyphenyl)phenylmethyl]amino-7H-pyrrolo[2.3-d]pyrimidine and 7-[3,5-bis-O-(tert-butyldimethylsilyl)-β-D-ribofuranosyl]-4-[di-(4-methoxyphenyl)phenylmethyl]amino-7H-pyrrolo[2,3-d]pyrimidine To a solution of mixture of the compounds from Step A (3.0 g, 6.0 mmol) in anhydrous pyridine (30 mL) was added 4,4'-dimethoxytrityl chloride (2.8 g, 8.2 mmol) and the reaction mixture was stirred at room temperature overnight. The mixture was then triturated with aqueous pyridine and extracted with ether. The organic layer was washed with water, dried over anhydrous sodium sulfate and concentrated to a yellow foam (5.6 g). The residue was purified by flash chromatography over silica gel using 20–25% EtOAc in hexanes as the eluent. The appropriate fractions were collected and concentrated to furnish 2',5'-O-bis-O-(tert-butyldimethylsilyl)- and 3',5'-bis-O-(tert-butyldimethylsilyl) protected nucleosides as colorless foams (2.2 g and 1.0 g, respectively).

Step C: 7-[2,5-Bis-O-(tert-butyldimethylsilyl)-3-O-tosyl-β-D-ribofuranosyl)]-4-[di-(4methoxyphenyl)phenylmethyl]amino-7H-pyrrolo[2,3-d]pyrimidine To an ice-cooled solution of 2',5'-bis-O-(tert-butyldimethylsilyl)-protected nucleoside from Step B (2.0 g, 2.5 mmol) in pyridine (22 mL) was added p-toluenesulfonyl chloride (1.9 g, 9.8 mmol). The reaction mixture was stirred at room temperature for four days. It was then triturated with aqueous pyridine (50%, 10 mL) and extracted with ether (3×50 mL) containing a small amount of CH$_2$Cl$_2$ (10 mL). The organic layer was washed with sodium bicarbonate and water (3×30 mL). The organic layer was dried over anhydrous Na$_2$SO$_4$ and concentrated. Pyridine was removed by co-evaporation with toluene (3×25 mL). The residual oil was filtered through a pad of silica gel using hexane:ethyl acetate (70:30) as eluent; yield 1.4 g.

Step D: 4-[di-(4-methoxyphenyl)phenylmethyl]amino-7-[3-O-tosyl-β-D-ribofuranosyl-7H-pyrrolo[2,3-d]pyrimidine A solution of the compound from Step C (1.0 g, 1.1 mmol) and THF (10 mL) was stirred with tetrabutylammonium fluoride (1M solution in THF, 2.5 mL) for 0.5 h. The mixture was cooled and diluted with ether (50 mL). The solution was washed with water (3×50 mL), dried over anhydrous Na$_2$SO$_4$, and concentrated to an oil. The residue was purified by passing through a pad of silica gel using hexane: ethyl acetate (1:1) as eluent; yield 780 mg.

Step E: 4-Amino-7-(3-deoxy-2-C-methyl-β-D-ribofuranosyl)-7H-pyrrolo[2,3-d]-pyrimidine and 4-amino-7-(3-deoxy-2-C-methyl-β-D-arabinofuranosyl)-7H-pyrrolo-[2,3-d]pyrimidine A solution of CH$_3$MgI (3.0 M solution in ether, 3.0 mL) in anhydrous toluene (3.75 mL) was cooled in an ice bath. To this was added a solution of the compound from Step D (500 mg, 0.8 mmol) in anhydrous toluene (3.7 mL). The resulting mixture was stirred at room temperature for 3.5 h. It was cooled and treated with aqueous NH$_4$Cl solution and extracted with ether (50 mL containing 10 mL of CH$_2$Cl$_2$). The organic layer was separated and washed with brine (2×30 mL) and water (2×25 mL), dried over anhydrous Na$_2$SO$_4$ and concentrated to an oil which was purified by flash chromatography on silica gel using 4% MeOH in CH$_2$Cl$_2$ to furnish the 2-C-α-methyl compound (149 mg) and the 2-C-β-methyl compound (34 mg). These derivatives were separately treated with 80% acetic acid and the reaction mixture stirred at room temperature for 2.5 h. The acetic acid was removed by repeated co-evaporation with ethanol and toluene. The residue was partitioned between chloroform and water. The aqueous layer was washed with chloroform and concentrated. The evaporated residue was purified on silica gel using 5–10% MeOH in CH$_2$Cl$_2$ as the eluent to furnish the desired compounds as white solids.

4-Amino-7-(3-deoxy-2-C-methyl-β-D-ribofuranosyl)-7H-pyrrolo[2,3-d]pyrimidine (9.0 mg)

$^1$H NMR (DMSO-d$_6$): δ 0.74 (s, 3H, CH$_3$), 1.77 (dd, 1H, H-3'), 2.08 (t, 1H, H-3"), 3.59 (m, 1H, H-5'), 3.73 (m, 1H, H-5"), 4.15 (m, 1H, H-4'), 5.02 (t, 1H, OH-5'), 5.33 (s, 1H, OH-2'), 6.00 (s, 1H, H-1'), 6.54 (d, 1H, H-7), 6.95 (br s, 2H, NH$_2$), 7.47 (d, 1H, H-8), 8.00 (s, 1H, H-2); ES-MS: 263.1 [M−H].

4-Amino-7-(3-deoxy-2-C-methyl-β-D-arabinofuranosyl)-7H-pyrrolo[2,3-d]pyrimidine (15 mg):

$^1$H NMR (DMSO-d$_6$): δ 1.23 (s, 3H, CH$_3$), 2.08 (ddd, 2H, H-3 and 3"), 3.57 (m, 2H, H-5' and 5"), 4.06 (m, 1H, H4), 5.10 (s, 1H, OH-2'), 5.24 (t, 1H, OH-5'), 6.01 (s, 1H, H-1'), 6.49 (d, 1H, H-7), 6.89 (br s, 2H, NH$_2$), 7.35 (d, 1H, H-8), 8.01 (s,1H,H-2).

ES-MS: 265.2[M+H].

EXAMPLE 142

4-Amino-7-(2,4-C-dimethyl-β-D-ribofiuranosyl)-7H-pyrrolo[2,3-d]pyrimidine

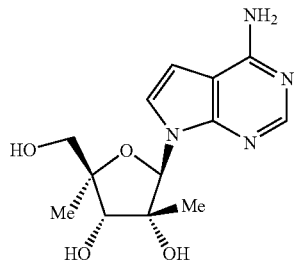

Step A: 5-Deoxy-1,2-O-isopropylidene-D-xylofuranose 1,2-O-Isopropylidene-D-xylofuranose (38.4 g, 0.2 mol), 4-dimethylaminopyridine (5 g), triethylamine (55.7 mL, 0.4 mol) were dissolved in dichloromethane (300 mL). p-Toluenesulfonyl chloride (38.13 g, 0.2 mol) was added and the reaction mixture was stirred at room temperature for 2 h. The reaction mixture was then poured into saturated aqueous sodium bicarbonate (500 mL) and the two layers were separated. The organic layer was washed with aqueous citric acid solution (20%, 200 mL), dried (Na$_2$SO$_4$) and evaporated to give a solid (70.0 g). The solid was dissolved in dry THF (300 mL) and LiAlH$_4$ (16.0 g, 0.42 mol) was added in portions over 30 min. The mixture was stirred at room temperature for 15 h. Ethyl acetate (100 mL) was added dropwise over 30 min and the mixture was filtered through a silica gel bed. The filtrate was concentrated and the resulting oil was chromatographed on silica gel (EtOAc/hexane 1/4) to afford the product as a solid (32.5 g).

Step B: 3,5-Bis-O-(2,4-dichlorophenylmethyl)-1-O-methyl-4-methyl-α-D-ribofuranose Chromium oxide (50 g, 0.5 mol), acetic anhydride (50 mL, 0.53 mol) and pyridine (100 mL, 1.24 mol) were added to dichloromethane (1 L) in an ice water bath and the mixture was stirred for 15 min. 5-Deoxy-1,2-O-isopropylidene-D-xylofuranose (32 g, 0.18 mol) in dichloromethane (200 mL) was added, and the mixture was stirred at the same temperature for 30 min. The reaction solution was diluted with ethyl acetate (1 L) and filtered through a silica gel bed. The filtrate was concentrated to give a yellow oil. The oil was dissolved in 1,4-dioxane (1 L) and formaldehyde (37%, 200 mL). The solution was cooled to 0° C. and solid KOH (50 g) was added. The mixture was stirred at room temperature overnight and was then extracted with ethyl acetate (6×200 mL). After concentration, the residue was chromatographed on silica gel (EtOAc) to afford the product as an oil (1.5 g). The oil was dissolved in 1-methyl-2-pyrrolidinone (20 mL) and 2,4-dichlorophenylmethyl chloride (4 g, 20.5 mmol) and NaH (60%, 0.8 g) were added. The mixture was stirred overnight and diluted with toluene (100 mL). The mixture was then washed with saturated aqueous sodium bicarbonate (3×50 mL), dried (Na$_2$SO$_4$) and evaporated. The residue was dissolved in methanol (50 mL) and HCl in dioxane (4 M, 2 mL) was added. The solution was stirred overnight and evaporated. The residue was chromatographed on silica gel (EtOAc/hexane:1/4) to afford the desired product as an oil (2.01 g).

Step C: 3,5-Bis-O-(2,4-dichlorophenylmethyl)-2,4-di-C-methyl-1-O-methyl-α-D-ribofuranose The product (2.0 g, 4.0 mmol) from Step B and Dess-Martin periodinane (2.0 g) in dichloromethane (30 mL) were stirred overnight at room temperature and was then concentrated under reduced pressure. The residue was triturated with ether ether (50 mL) and filtered. The filtrate was washed with a solution of Na$_2$S$_2$O$_3$.5H$_2$O(2.5 g) in saturated aqueous sodium bicarbonate solution (50 mL), dried (MgSO$_4$), filtered and evaporated. The residue was dissolved in anhydrous Et$_2$O (20 mL) and was added dropwise to a solution of MeMgBr in Et$_2$O (3 M, 10 mL) at −78° C. The reaction mixture was allowed to warm to −30° C. and stirred at −30° C. to −15° C. for 5 h, then poured into saturated aqueous ammonium chloride (50 mL). The two layers were separated and the organic layer was dried (MgSO$_4$), filtered and concentrated. The residue was chromatographed on silica gel (EtOAc/hexane: 1/9) to afford the title compound as a syrup (1.40 g).

Step D: 4-Chloro-7-[3,5-bis-O-(2,4-dichlorophenylmethyl)-2,4-di-C-methyl-β-D-ribofuranosyl]-7H-pyrrolo[2,3-d]pyrimidine To the compound from Step C (0.70 g, 1.3 mmol) was added HBr (5.7 M in acetic acid, 2 mL). The resulting solution was stirred at room temperature for 1 h, evaporated in vacuo and co-evaporated with anhydrous toluene (3×10 mL). 4-Chloro-1H-pyrrolo[2,3-d]pyrimidine (0.5 g, 3.3 mmol) and powdered KOH (85%, 150 mg, 2.3 mmol) were stirred in 1-methyl-2-pyrrolidinone (5 mL) for 30 min and the mixture was co-evaporated with toluene (10 mL). The resulting solution was poured into the above bromo sugar residue and the mixture was stirred overnight. The mixture was diluted with toluene (50 mL), washed with water (3×50 mL) and concentrated under reduced pressure. The residue was chromatographed on silica gel eluting with (EtOAc/Hexane 15/85) to afford a solid (270 mg).

Step E: 4-Amino-7-(2,4-di-C-methyl-β-D-ribofuranosyl)-7H-pyrrolo[2,3-d]pyrimidine The compound from Step D (270 mg) was dissolved in dioxane (2 mL) and liquid ammonia (20 g) was added in a stainless steel autoclave. The mixture was heated at 100° C. for 15 h, then cooled and evaporated. The residue was chromatographed on silica gel (EtOAc) to afford a solid (200 mg). The solid (150 mg) and Pd/C (10% 150 mg) in methanol (20 mL) were shaken under H$_2$ (30 psi) for 3 h, filtered and evaporated. The residue was chromatographed on silica gel (MeOH/CH$_2$Cl$_2$: 1/9) to afford the desired product as a solid (35 mg).

$^1$H NMR (DMSO-d$_6$): δ 0.65 (s, 3H), 1.18 (s, 3H), 3.43 (m, 2H), 4.06 (d, 1H, J 6.3 Hz), 4.87 (s, 1H), 5.26 (br, 1H), 5.08 (d, 1H, J 6.3 Hz), 5.25 (t, 1H, J 3.0 Hz), 6.17 (s, 1H), 6.54 (d, 1H, J 3.5 Hz), 6.97 (s, br, 2H), 7.54 (d, 1H, J 3.4 Hz), 8.02 (s, 1H).

$^{13}$C NMR (DMSO-d$_6$): δ 18.19, 21.32, 65.38, 73.00, 79.33, 84.80, 90.66, 99.09, 102.41, 121.90, 149.58, 151.48, 157.38.

LC-MS: Found: 295.1 (M+H$^+$); calculated for C$_{13}$H$_{18}$N$_4$O$_4$+H$^+$: 295.1

EXAMPLE 143

4-Amino-7-(3-deoxy-3-fluoro-2-C-methyl-β-D-ribofuranosyl)-7H-pyrrolo[2,3-d]pyrimidine

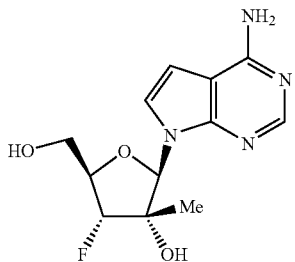

Step A: 3-Deoxy-3-fluoro-1-O-methyl-5-O-toluoyl-α-D-ribofuranose 1,2-O-Isopropylidene-D-xylofuranose (9.0 g, 50 mmol) and p-toluoyl chloride (7.0 mL, 50 mmol) in pyridine (50 mL) were stirred for 30 min. Water (10 mL) was added and the mixture was concentrated under reduced pressure. The residue was dissolved in toluene (500 mL) and the solution was washed with water (200 mL) and saturated aqueous sodium bicarbonate (200 mL). The two layers were separated and the organic layer was evaporated. The residue was dissolved in methanol (100 mL) and HCl in dioxane (4 M, 10 mL) was added. The mixture was stirred at room temperature overnight and was then evaporated under reduced pressure. The resulting oil was chromatographed on silica gel (EtOAc/hexane: 1/1) to afford an oil (10.1 g). The oil was dissolved in dichloromethane (100 mL) and diethylaminosulfur trifluoride (DAST) (5.7 mL) was added. The mixture was stirred overnight and was then poured into saturated aqueous sodium bicarbonate solution (100 mL). The mixture was extracted with toluene (2×50 mL) and the combined organic layers were concentrated. The residue was chromatographed on silica gel (EtOAc/hexane: 15/85) to afford the title compound as an oil (1.50 g).

Step B: 3-Deoxy-3-fluoro-2-C-methyl-1-O-methyl-5-O-toluoyl-α-D-ribofuranose

The product from Step A (1.0 g, 3.5 mmol) and Dess-Martin periodinane (2.5 g) in dichloromethane (20 mL) were stirred overnight at room temperature and was then concentrated under reduced pressure. The residue was triturated with diethyl ether (50 mL) and filtered. The filtrate was washed with a solution of $Na_2S_2O_3 \cdot 5H_2O$ (12.5 g) in saturated aqueous sodium bicarbonate (100 mL), dried ($MgSO_4$), filtered and evaporated. The residue was dissolved in anhydrous THF (50 mL). $TiCl_4$ (3 mL) and methyl magnesium bromide in ethyl ether (3 M, 10 mL) were added at −78° C. and the mixture was stirred at −50 to −30° C. for 2 h. The mixture was poured into saturated aqueous sodium bicarbonate solution (100 mL) and filtered through Celite. The filtrate was extracted with toluene (100 mL) and evaporated. The residue was chromatographed on silica gel (EtOAc/hexane: 15/85) to afford the title compound as an oil (150 mg).

Step C: 4-Amino-7-(3-deoxy-3-fluoro-2-C-methyl-β-D-ribofuranosyl)-7H-pyrrolo[2,3-d]pyriridine The product from Step B (150 mg, 0.5 mmol) was dissolved in HBr (30%) in acetic acid (2 mL). After one hour, the mixture was evaporated under reduced pressure and co-evaporated with toluene (10 mL). 4-Chloro-1H-pyrrolo[2,3-d]pyrimidine (0.5 g, 3.3 mmol) and powdered KOH (85%, 150 mg, 2.3 mmol) were stirred in DMF (3 mL) for 30 min and the mixture was co-evaporated with toluene (2 mL). The resulting solution was poured into the above bromo sugar and the mixture was stirred overnight. The mixture was diluted with toluene (50 mL), washed with water (3×50 mL) and concentrated under reduced pressure. The residue was chromatographed on silica gel (EtOAc/hexane 15/85) to afford an oil (60 mg). The oil was dissolved in dioxane (2 mL) and liquid ammonia (20 g) was added in a stainless steel autoclave. The mixture was heated at 85° C. for 18 h, then cooled and evaporated. The residue was chromatographed on silica gel (methanol/dichloromethane: 1/9) to afford the title compound as a solid (29 mg).

$^1$H NMR (DMSO-$d_6$): δ 0.81 (s, 3H), 3.75 (m, 2H), 4.16 (m, 1H), 5.09 (dd, 1H, J 53.2, 7.8 Hz), 5.26 (br, 1H), 5.77 (s, 1H), 6.15 (d, 1H, J 2.9 Hz), 6.59 (d, 1H, J 3.4 Hz), 7.02 (s br, 2H), 7.39 (d, 1H, J 3.4 Hz), 8.06 (s, 1H).

$^{13}$C NMR (DMSO-$d_6$): 19.40, 59.56, 77.24, 79.29, 90.15, 91.92, 99.88, 102.39, 121.17, 149.80, 151.77, 157.47.

$^{19}$F NMR (DMSO-$d_6$): δ 14.66 (m).

ES-MS: Found: 283.1 (M+H$^+$); calculated for $C_{12}H_{15}FN_4O_3$+H$^+$: 283.1.

EXAMPLE 144

8-Amino-2'-C-methyladenosine

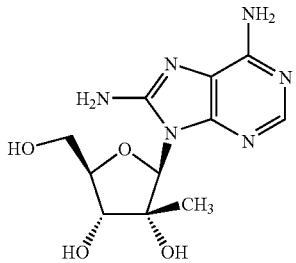

Step A: 8-Bromo-2'-C-methyladenosine

To a solution of 2'-C-methyladenosine [for preparation, see *J. Med. Chem.* 41: 1708 (1998)] (138 mg, 0.5 mmol) in DMF (4 mL) was added N-bromosuccinimide (231 mg, 1.35 mmol). The solution was stirred protected from light at rt for 2 d and then evaporated in vacuo. The crude product was purified on a silica gel column (3×9 cm) using dichloromethane/methanol (25/1, 20/1 and 15/1) as eluent. Fractions containing the product were pooled and evaporated in vacuo to give the desired product (38 mg) as a white solid.

Step B: 8-Amino-2'-C-methyladenosine

A solution of the compound from Step A (38 mg, 0.11 mmol) in liquid ammonia (10 mL) was heated in a stainless steel autoclave at 105° C. for 1 d, then cooled and evaporated. The residue was purified by HPLC [C-18 Phenomenex Luna (10μ; 250×21.2 mm) RP-column; solvents: (A) water, (13) acetonitrile; Linear gradient: 2–35% B in 76 min.] to yield the title compound (12 mg) as a white fluffy material after freeze-drying.

$^1$H NMR (DMSO-$d_6$): δ 0.70 (s, 3H, Me), 3.55–3.75 (m, 3H, H-5', H-5", H-4'), 4.03 (m, 1H, H-3'), 4.81 (s, 1H, 2'-OH), 5.10 (d, 1H, 3'-OH), 5.45 (t, 1H, 5'-OH), 5.86 (s, 1H, H-1'), 6.30, 6.39 (2s, 6H, 2 NH$_2$), 7.78 (s, 1H, H-2).

ES-MS: Found: 295.0 (M−H$^+$).

EXAMPLE 145

4-Amino-7-(2-C,2-O-dimethyl-β-D-ribofuranosyl)-7H-pyrrolo[2,3-d]pyrimidine

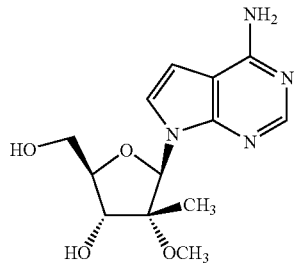

Step A: 4-chloro-7-[3,5-bis-O-(2,4-dichlorophenylmethyl)-2-C,2-O-dimethyl-β-D-ribofuranosyl]-7H-pyrrolo[2,3-d]pyrimidine To a pre-cooled (0° C.) solution of the compound from Example 62, Step D (618 mg, 1.0 mmol) in THF (8 mL) was added methyl iodide (709 mg, 5.0 mmol) and NaH (60% in mineral oil) (44 mg, 1.1 mmol). The resulting mixture was stirred overnight at rt and then poured into a stirred mixture of saturated aqueous ammonium chloride (50 mL) and dichloromethane (50 mL). The organic layer was washed with water (50 mL), dried (MgSO$_4$) and evaporated in vacuo. The resulting crude product was purified on silica gel using ethyl acetate/hexane as the eluent. Fractions containing the product were pooled and evaporated in vacuo to give the desired product (735 mg) as a colorless foam.

Step B: 4-amino-7-[3,5-bis-O-(2,4-dichlorophenylmethyl)-2-C,2-O-dimethyl-β-D-ribofuranosyl]-7H-pyrrolo[2,3-d]pyrimidine To the compound from Step A (735 mg, 1.16 mmol) was added methanolic ammonia (saturated at 0° C.) (20 mL). The mixture was heated in a stainless steel autoclave at 80° C. overnight, then cooled and the content evaporated in vacuo. The crude mixture was purified on silica gel using ethyl acetate/hexane as the eluent. Fractions containing the product were pooled and evaporated in vacuo to give the desired product (504 mg) as colorless foam.

Step C: 4-amino-7-(2-C,2-O-dimethyl-β-D-ribofiuranosyl)-7H-pyrrolo[2,3-d]pyrimidine A mixture of the product from Step C (64 mg, 0.1 mmol), MeOH (5 mL), Et$_3$N (0.2 mL) and 10% Pd/C (61 mg) was hydrogenated on a Parr hydrogenator at 50 psi at room temperature overnight. The mixture was filtered throught celite, evaporated in vacuo and filtered through a pad of silica gel using 2% methanol in dichloromethane as eluent. The desired product was collected and evaporated in vacuo. The compound was redissolved in methanol (10 mL) and 10% Pd/C (61 mg) was added. The mixture was hydrogenated on a Parr hydrogenator at 55 psi at room temperature for two weeks. The mixture was filtered through celite, evaporated in vacuo and purified on silica gel using 10% methanol in dichloromethane as eluent. Fractions containing the product were pooled and evaporated in vacuo to give the desired product (110 mg) as a colorless foam.

$^1$H NMR (DMSO-d$_6$): δ 0.68 (s, 3H,), 3.40 (s, 3H), 3.52–3.99 (overlapping m, 4H), 4.92 (d, 1H), 5.07 (t, 1H), 6.26 (s, 1H), 6.55 (d, 1H), 7.00s br, 2H), 7.46 (d, 1H), 8.05 (s, 1H).

LC-MS: Found: 293.1 (M–H$^+$); calc. for C$_{12}$H$_{16}$N$_4$O$_4$–H$^+$: 293.12.

EXAMPLE 146

4-Methylamino-7-(2-C-methyl-β-D-ribofuranosyl)-7H-pyrrolo[2,3-d]pyrimidine

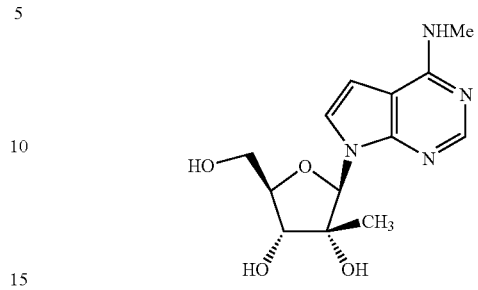

The compound from Step E of Example 62 (200 mg, 0.67 mmol) was added to methylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (144 mg).

$^1$H NMR (DMSO-d$_6$): δ 0.63 (s, 3H, CH$_3$), 3.32 (s, 3H, N CH$_3$), 3.58–3.67 (m, 1H, H-5'), 3.79–3.39 (m, 3H, H-5", H4', H-3'), 5.03 (s, 1H, 2'-OH), 5.04–5.11 (1H,3'-OH, 1H, 5'-OH), 6.14 (s, 1H, H-1'), 6.58 (d, 1H, J$_{5,6}$=3.6 Hz, H-5), 7.46 (d, 1H, H-6), 7.70 (br s, 1H, NH), 8.14 (s, 1H, H-2).

LC-MS: Found: 295.1 (M–H$^+$); calc. for C$_{13}$H$_{18}$N$_4$O$_4$+H$^+$: 294.3.

EXAMPLE 147

4-Dimethylamino-7-(2-C-methyl-β-D-ribofuranosyl)-7H-pyrrolo[2,3-d]pyrimidine

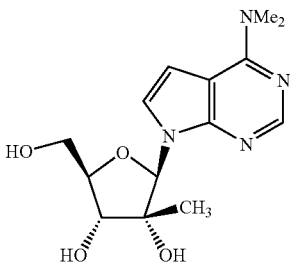

The compound from Step E of Example 62 (200 mg, 0.67 mmol) was added to dimethylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (164 mg).

$^1$H NMR (DMSO-d$_6$): δ 0.64 (s, 3H, CH$_3$), 3.29 (s, 3H, N CH$_3$), 3.32 (s, 3H, N CH$_3$), 3.60–3.66 (m, 1H, H-5'), 3.77–3.97 (m, 3H, H-5", H-4', H-3'), 5.04 (s, 1H, 2'-OH), 5.06–5.11 (1H, 3'-OH, 1H, 5'-OH), 6.21 (s, 1H, H-1'), 6.69 (d, 1H, J$_{5,6}$=3.6 Hz, H-5), 7.55 (d, 1H, H-6), 8.13 (s, 1H, H-2).

LC-MS: Found: 309.3 (M–H$^+$); calc. for C$_{14}$H$_{20}$N$_4$O$_4$+H$^+$: 308.33.

EXAMPLE 148

4-Cyclopropylamino-7-(2-C-methyl-β-D-ribofuranosyl)-7H-pyrrolo[2,3-d]pyrimidine

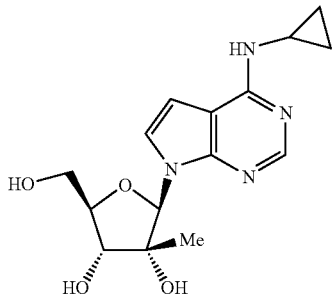

The compound from Step E of Example 62 (200 mg, 0.67 mmol) was added to cyclopropylamine (5 mL condensed in a small stainless steel autoclave) and warmed at 85° C. for 48 h, then cooled and evaporated in vacuo. The crude mixture was purified on a silica gel with ethanol as the eluent to give the title compound which separated as an amorphous solid after treatment with MeCN. The amorphous solid was dissolved in water and lyophilized to give a colorless powder (148 mg).

$^1$H NMR (DMSO-d$_6$): δ 0.51–0.58 (m, 2H), 0.64 (s, 3H, CH$_3$), 0.74–0.076 (m, 2H), 3.62–3.67 (m, 1H, H-5'), 3.79–3.82 (m, 3H, H-5"), 3.92–3.96 (m, H-4', H-3'), 5.03 (s, 1H, 2'-OH), 5.05–5.10 (1H, 3'-OH, 1H, 5'-OH), 6.15 (s, 1H, H-1'), 7.48 (d, 1H, J$_{5,6}$=3.6 Hz, H-5), 7.59 (d, 1H, H-6), 8.13 (s, 1H, H-2).

LC-MS: Found: 321.1 (M–H$^+$); calc. for C$_{15}$H$_{20}$N$_4$O$_4$+H$^+$: 320.3.

EXAMPLE 149

4-Amino-7-(3-C-methyl-β-D-xylofuranosyl)-7H-pyrrolo[2,3-d]pyrimidine

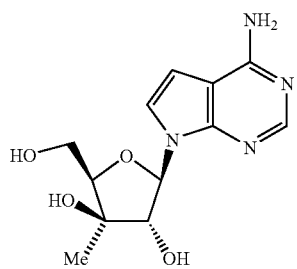

Step A: 7-[2,5-Bis-O-(tert-butyldimethylsilyl)-β-D-ribofuranosyl)]-4-[(4-methoxyphenyl)diphenylmethyl]amino-7H-pyrrolo[2,3-d]pyrimidine and 7-[3,5-bis-O-(tert-butyldimethylsilyl)-β-D-ribofuranosyl]-4-[(4-methoxyphenyl)diphenylmethyl]amino-7H-pyrrolo[2,3-d]pyrimidine To a solution of mixture of the compounds from Step A of Examples 140 and 141 (0.32 g, 0.65 mmol) in anhydrous pyridine (6 mL) was added monomethoxytrityl chloride (0.30 g, 0.98 mmol) and the reaction mixture was stirred at room temperature overnight. The mixture was then concentrated and the residue was partitioned between CH$_2$Cl$_2$ (70 mL) and water (20 mL). The organic layer was washed with water and brine, dried (Na$_2$SO$_4$) and concentrated. The residue was purified on silica gel column using 5–13% EtOAc in hexanes as the eluent. The appropriate fractions were collected and concentrated to furnish 2',5'-bis-O-(tert-butyldimethylsilyl)- and 3',5'-bis-O-(tert-butyldimethylsilyl) protected nucleosides as colorless foams (343 mg and 84 mg, respectively).

Step B: 7-[2,5-Bis-O-(tert-butyldimethylsilyl)-β-D-erythro-pentofuranos-3-ulosyl]-4-[(4-methoxyphenyl)diphenylmethyl]amino-7H-pyrrolo[2,3-d]pyrimidine To a well-stirred suspension of chromium trioxide (91 mg, 0.91 mmol) in CH$_2$Cl$_2$ (4 mL) at 0° C. were added pyridine (147 μL, 1.82 mmol) and then acetic anhydride (86 μL, 0.91 mmol). The mixture was stirred at room temperature for 0.5 h. Then the 2',5'-bis-O-(tert-butyldimethylsilyl) protected nucleoside from step A (343 mg 0.45 mmol) in CH$_2$Cl$_2$ (2.5 mL) was added and the mixture stirred at room temperature 2 h. The mixture was then poured into ice-cold EtOAc (10 mL) and filtered through a short silica gel column using EtOAc as the eluent. The filtrate was evaporated and the residue purified on a silica gel column with hexanes and hexanes/EtOAc (7/1) as the eluent to give the title compound (180 mg).

Step C: 7-[2,5-Bis-O-(tert-butyldimethylsilyl)-3-C-methyl-β-D-ribofuranosyl)-4-[(4-methoxyphenyl)diphenylmethyl]amino-7H-pyrrolo[2,3-d]pyrimidine and 7-[2,5-Bis-O-(tert-butyldimethylsilyl)-3-C-methyl-β-D-xylofuranosyl)-4-[(4-methoxyphenyl)diphenylmethyl]amino-7H-pyrrolo[2,3-d]pyrimidine To a mixture of MeMgBr (3.0 M solution in ether; 0.17 mL, 0.5 mmol) in anhydrous hexanes (1.5 mL) at room temperature was added dropwise a solution of the compound from Step B (78 mg, 0.1 mmol) in anhydrous hexanes (0.5 mL). After 2 h stirring at room temperature, the reaction mixture was poured into ice-cold water (10 mL) and diluted with EtOAc (20 mL), then filtered through Celite which was then thoroughly washed with EtOAc. The layers were separated and the organic layer was washed with brine, dried (Na$_2$SO$_4$) and concentrated. The residue was purified on a silica gel column using 8 to 25% EtOAc in hexanes as eluent to give the 3-C-methyl xylo- (60 mg) and the 3-C-methyl ribo-isomer (20 mg).

Step D: 4-Amino-7-(3-C-methyl-β-D-xylofuranosyl)-7H-pyrrolo[2,3-d]pyrimidine

To an ice-cold solution of 3-C-methyl-xylo isomer from Step C (60 mg, 0.08 mmol) in THF (2 mL) was added TBAF (1 M in THF; 0.32 ml, 0.32 mmol). The reaction mixture was stirred at room temperature for 5 h, then diluted with CH$_2$Cl$_2$ (50 mL), washed with water (3×15 mL), dried, and evaporated. The residue was dissolved in dioxane (0.3 mL) and 80% acetic acid (3 mL) was added. The reaction mixture was stirred at room temperature for 1 d and then evaporated. The residue was co-evaporated with dioxane, taken up in water (50 mL) and washed with CH$_2$Cl$_2$ (2×10 mL). The aqueous layer was concentrated and then freeze-dried. The residue was purified on silica gel column with CH$_2$Cl$_2$/MeOH (20/1 and 10/1) as the eluent to give the title compound as a white fluffy compound after freeze drying (10 mg).

$^1$H NMR (CD$_3$CN): δ 1.28 (s, 3H, CH$_3$), 3.56 (br s, 1H, OH), 3.78 (m, 3H, H-4', H-5', H-5"), 4.10 (br s, 1H, OH), 4.44 (d, 1H, J$_{2',1'}$=3.9 Hz, H-2'), 5.58 (d, 1H, H-1'), 5.85 (br s, 2H, NH$_2$), 6.15 (br s, 1H, OH), 6.48 (d, 1H, J$_{5,6}$=3.7 Hz, H-5), 7.23 (d, 1H, H-6), 8.11 (s, 1H, H-2). ES-MS: 281 [MH]$^+$.

EXAMPLE 150

4-Amino-7-(3-C-methyl-β-D-ribofuranosyl)-7H-pyrrolo[2,3-d]pyrimidine

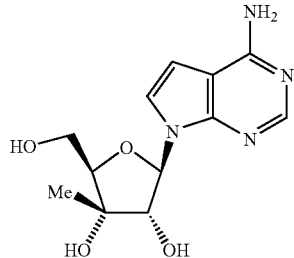

The ribo-isomer (20 mg) from Step C of Example 149 was deprotected using the procedure described in Step D of Example 32 to yield the title compound (4 mg).

$^1$H NMR (CD$_3$CN): δ 1.43 (s, 3H, CH$_3$), 3.28 (br s, 1H, OH), 3.58 (m, 2H, H-5', H-5"), 3.99 (m, 1H, H-4'), 4.10 (br s, 1H, OH), 4.62 (d, 1H, J$_{2',1'}$=8.1 Hz, H-2'), 5.69 (d, 1H, H-1'), 5.88 (br s, 3H, OH, NH$_2$), 6.45 (br s, 1H, OH), 6.51 (d, 1H, J$_{5,6}$=3.7 Hz, H-5), 7.19 (d, 1H, H-6), 8.12 (s, 1H, H-2). ES-MS: 281 [MH]$^+$.

EXAMPLE 151

2,4-Diamino-7-(2-C-methyl-β-D-ribofuranosyl)-7H-pyrrolo[2,3-d]pyrimidine

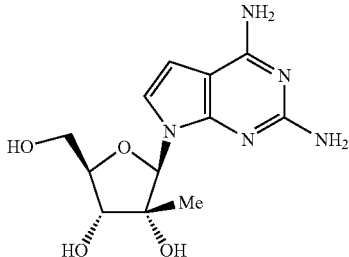

A mixture of the product from Step B of Example 118 (24 mg) in aqueous ammonia (30%, 10 mL) was heated in a stainless steel autoclave at 100° C. overnight, then cooled and evaporated. The residue was purified on a silica gel column with CH$_2$Cl$_2$/MeOH (10/1 and 5/1) as the eluent to afford the title compound (15 mg).

$^1$H NMR (DMSO-d$_6$): δ 0.68 (s, 3H, CH$_3$), 3.48–3.58 (m 1H, H-5'), 3.68–3.73 (m, 2H, H-5", H-4'), 3.84 (m, 1H, H-3'), 4.72 (s, 1H, 2'-OH), 4.97–5.03 (m, 2H, 3'-OH, 5'-OH), 5.45 (br s, 2H, NH$_2$), 6.00 (s, 1H, H-1'), 6.28 (d, 1H, J=3.7 Hz, H-5), 6.44 (br s, 2H, NH$_2$) 6.92 (d, 1H J=3.7 Hz, H-6).

ES MS: 294.1 (M–H$^+$).

EXAMPLE 152

4-Amino-2-fluoro-7-(2-C-methyl-β-D-ribofuranosyl)-7H-pyrrolo[2,3-d]pyrimidine

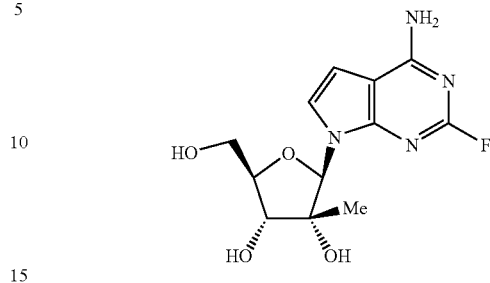

To a solution of HF/pyridine (70%, 2 mL) diluted with pyridine (1 mL) at –30° C. is added the compound of Example 151 (60 mg, 0.2 mmol) in 0.5 mL pyridine followed by tert-butyl nitrite (36 µL, 0.3 mmol). Stirring is continued for 5 min –25° C. Then the solution is poured into ice-water (5 mL), neutralized with 2 N aqueous NaOH, and evaporated to dryness. The residue is purified on a silica gel column with CH$_2$Cl$_2$/MeOH (20/1 and 10/1) as the eluent to afford the title compound.

EXAMPLE 153

4-Amino-5-fluoro-7-(2-C-methyl-β-D-ribofuranosyl)-7H-pyrrolo[2,3-d]pyrimidine

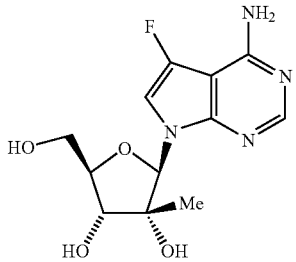

Step A: 4-Acetylamino-7-(2,3,5-tri-O-acetyl-2-C-methyl-β-D-ribofuranosyl)-7H-pyrrolo[2,3-d]pyrimidine To a solution of the compound from step F of Example 62 (280 mg, 1.00 mmol) in pyridine is added acetic anhydride (613 mg, 6.0 mmol). The resulting solution is stirred overnight at ambient temperature evaporated in vacuo and the resulting crude mixture is purified on silica gel using ethyl acetate/hexane as the eluent. Fractions containing the desired product are pooled and evaporated in vacuo to give the desired product.

Step B: 4-Acetylamino-5-bromo-7-(2,3,5-tri-O-acetyl-2-C-methyl-β-D-ribofuranosyl)-7H-pyrrolo[2,3-d]pyrimidine To a pre-cooled (0° C.) solution of the compound from Step A (460 mg, 1.00 mmol) in DMF is added N-bromosuccinimide (178 mg, 1.0 mmol) in DMF. The resulting solution is stirred at 0° C. for 30 min then at room temperature for another 30 min. The reaction is quenched by addition of methanol and evaporated in vacuo. The resulting crude mixture is purified on silica gel using ethyl acetate/hexane as the eluent. Fractions containing the desired product are pooled and evaporated in vacuo to give the desired product.

Step C: 4-Amino-5-fluoro-7-(2-C-methyl-β-D-ribofuranosyl)-7H-pyrrolo[2,3-d]pyrimidine To a pre-cooled (–78° C.) solution of the compound from Step B (529 mg, 1.00 mmol) in THF is added butyl lithium (2M in hexanes) (0.5 mL, 1.00 mmol). The resulting solution is stirred at −78° C. for 30 min and then quenched with N-fluorobenzensulfonimide (315 mg, 1.00 mmol) in THF. The resulting solution is very slowly allowed to come to ambient temperature and then poured into a stirred mixture of saturated aqueous ammonium chloride and dichloromethane. The organic phase is evaporated in vacuo and treated with ammonium hydroxide at 55° C. in a closed container overnight. The resulting crude mixture is purified on silica gel using dichloromethane/methanol as the eluent. Fractions containing the desired product are pooled and evaporated in vacuo to give the desired product.

EXAMPLE 154

4-Amino-1-(2-C-methyl-β-D-ribofuranosyl)-1H-pyrazolo[3,4-d]pyrimidine

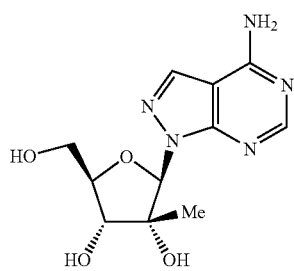

Step A: 4-Amino-1-[3,5-bis-O-(2,4-dichlorophenylmethyl)-2-C-methyl-β-D-ribofuranosyl]-1H-pyrazolo[3,4-d]pyrimidine To the compound from Step C of Example 62 (1.00 g, 2.02 mmol) in dichloromethane (20 mL) was bubbled HBr gas for 5 min until it was saturated. The resulting solution was stirred at room temperature for 10 min, evaporated in vacuo and coevaporated with anhydrous toluene (10 mL). 4-Amino-1H-pyrazolo[3,4-d]pyrimidine (Aldrich, 0.43 g, 3.18 mmol) and NaH (60%, 150 mg, 3.8 mmol) were stirred in 1-methyl-2-pyrrolidinone (10 mL) for 30 min. The resulting solution was poured into the above bromo sugar residue and the mixture was stirred overnight. The mixture was diluted with toluene (50 mL), washed with brine (10%, 3×50 mL) and concentrated under reduced pressure. The residue was chromatographed on silica gel (EtOAc as eluent) to afford a solid (400 mg).

Step B: 4-Amino-1-(2-C-methyl-β-D-ribofuranosyl)-1H-pyrazolo[3,4-d]pyrimidine

To a solution of the compound from Step A (0.20 g, 0.33 mmol) in dichloromethane (10 mL) at −78° C. was added boron trichloride (1M in dichloromethane) (3 mL, 3 mmol) dropwise. The mixture was stirred at −78° C. for 0.5 h, then at −45° C. to −30° C. for 2 h. The reaction was quenched by addition of sodium acetate (1.0 g) and methanol (10 mL). The solution was evaporated and the residue was purified by flash chromatography over silica gel using $CH_2Cl_2$ and $CH_2Cl_2$/MeOH (95:5–90:10) gradient as the eluent to furnish the desired compound (60 mg) as a solid, which was recrystallized from methanol and acetonitrile to give the title compound as an off-white solid (40 mg).

$^1$H NMR (DMSO-$d_6$): δ 0.75 (s, 3H), 3.59 (m, 1H), 3.69 (m, 1H), 3.91 (m, 1H), 4.12 (m, 1H), 4.69 (t, 1H, J 5.1 Hz), 5.15 (m, 2H), 6.13 (s, 1H), 7.68 (s, br, 1H), 7.96 (s, br, 1H), 8.18 (s, 1H), 8.21 (s, 1H).

$^{13}$C NMR (DMSO-$d_6$): 19.32, 62.78, 74.11, 78.60, 83.65, 90.72, 99.79, 133.50, 153.89, 156.21, 158.05.

LC-MS: Found: 282.1 (M+H$^+$); calculated for $C_{11}H_{15}N_5O_4$+H$^+$. 282.1.

BIOLOGICAL ASSAYS

The assays employed to measure the inhibition of HCV NS5B polymerase and HCV replication are described below.

The effectiveness of the compounds of the present invention as inhibitors of HCV NS5B RNA-dependent RNA polymerase (RdRp) was measured in the following assay.

A. Assay for Inhibition of HCV NS5B Polymerase:

This assay was used to measure the ability of the nucleoside derivatives of the present invention to inhibit the enzymatic activity of the RNA-dependent RNA polymerase (NS5B) of the hepatitis C virus (HCV) on a heteromeric RNA template.

Procedure:

Assay Buffer Conditions: (50 μL -total/reaction)

20 mM Tris, pH 7.5

50 μM EDTA 5 mM DTT 2 mM $MgCl_2$ 80 mM KCl 0.4 U/μL RNAsin (Promega, stock is 40 units/μL)

0.75 μg t500 (a 500-nt RNA made using T7 runoff transcription with a sequence from the NS2/3 region of the hepatitis C genome)

1.6 μg purified hepatitis C NS5B (form with 21 amino acids C-terminally truncated)

1 μM A,C,U,GTP (Nucleoside triphosphate mix)

[alpha-$^{32}$P]-GTP or [alpha-$^{33}$P]-GTP

The compounds were tested at various concentrations up to 100 μM final concentration.

An appropriate volume of reaction buffer was made including enzyme and template t500. Nucleoside derivatives of the present invention were pipetted into the wells of a 96-well plate. A mixture of nucleoside triphosphates (NTP's), including the radiolabeled GTP, was made and pipetted into the wells of a 96-well plate. The reaction was initiated by addition of the enzyme-template reaction solution and allowed to proceed at room temperature for 1–2 h.

The reaction was quenched by addition of 20 μL 0.5M EDTA, pH 8.0. Blank reactions in which the quench solution was added to the NTPs prior to the addition of the reaction buffer were included.

50 μL of the quenched reaction were spotted onto DE81 filter disks (Whatman) and allowed to dry for 30 min. The filters were washed with 0.3 M ammonium formate, pH 8 (150 mL/wash until the cpm in 1 mL wash is less than 100, usually 6 washes). The filters were counted in 5-mL scintillation fluid in a scintillation counter.

The percentage of inhibition was calculated according to the following equation: % Inhibition=[1−(cpm in test reaction−cpm in blank)/(cpm in control reaction−cpm in blank)]×100.

Representative compounds tested in the HCV NS5B polymerase assay exhibited $IC_{50}$'s less than 100 micromolar.

B. Assay for Inhibition of HCV RNA Replication:

The compounds of the present invention were also evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Sub-genomic Hepatitis C Virus RNAs in a Hepatoma Cell Line," *Science* 285:110 (1999).

Protocol:

The assay was an in situ Ribonuclease protection, Scintillation Proximity based-plate assay (SPA). 10,000–40,000 cells were plated in 100–200 μL of media containing 0.8 mg/mL G418 in 96-well cytostar plates (Amersham). Compounds were added to cells at various concentrations up to 100 μM in 1% DMSO at time 0 to 18 h and then cultured for 24–96 h. Cells were fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells were washed, treated with RNAse, washed, heated to 65° C. and counted in a Top-Count. Inhibition of replication was read as a decrease in counts per minute (cpm).

Human HuH-7 hepatoma cells, which were selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds tested in the replication assay exhibited $EC_{50}$'s less than 100 micromolar.

The nucleoside derivatives of the present invention were also evaluated for cellular toxicity and anti-viral specificity in the counterscreens described below.

C. Counterscreens:

The ability of the nucleoside derivatives of the present invention to inhibit human DNA polymerases was measured in the following assays.

a. Inhibition of Human DNA Polymerases Alpha and Beta:

Reaction Conditions:

50 μL reaction volume

Reaction Buffer Components:

20 mM Tris-HCl, pH 7.5

200 μg/mL bovine serum albumin 100 mM KCl 2 mM β-mercaptoethanol 10 mM $MgCl_2$ 1.6 μM dA, dG, dC, dTTP α-$^{33}$P-dATP Enzyme and Template:

0.05 mg/mL gapped fish sperm DNA template 0.01 U/μL DNA polymerase α or β

Preparation of Gapped Fish Sperm DNA Template:

Add 5 μL 1M $MgCl_2$ to 500 μL activated fish sperm DNA (USB 70076);

Warm to 37° C. and add 30 μL of 65 U/μL of exonuclease III (GibcoBRL 18013-011);

Incubate 5 min at 37° C.;

Terminate reaction by heating to 65° C. for 10 min;

Load 50–100 μL aliquots onto Bio-spin 6 chromatography columns (Bio-Rad 732-6002) equilibrated with 20 mM Tris-HCl, pH 7.5;

Elute by centrifugation at 1,000×g for 4 min;

Pool eluate and measure absorbance at 260 nm to determine concentration.

The DNA template was diluted into an appropriate volume of 20 mM Tris-HCl, pH 7.5 and the enzyme was diluted into an appropriate volume of 20 mM Tris-HCl, containing 2 mM 1B-mercaptoethanol, and 100 mM KCl. Template and enzyme were pipetted into microcentrifuge tubes or a 96 well plate. Blank reactions excluding enzyme and control reactions excluding test compound were also prepared using enzyme dilution buffer and test compound solvent, respectively. The reaction was initiated with reaction buffer with components as listed above. The reaction was incubated for 1 hour at 37° C. The reaction was quenched by the addition of 20 μL 0.5M EDTA. 50 μL of the quenched reaction was spotted onto Whatman DE81 filter disks and air dried. The filter disks were repeatedly washed with 150 mL 0.3M ammonium formate, pH 8 until 1 mL of wash is <100 cpm. The disks were washed twice with 150 mL absolute ethanol and once with 150 mL anhydrous ether, dried and counted in 5 mL scintillation fluid.

The percentage of inhibition was calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma was measured in reactions that included 0.5 μg/μL enzyme; 10 μM dATP, dGTP, dCTP, and TTP; 2 μCi/reaction [α-$^{33}$P]-dATP, and 0.4 μg/μL activated fish sperm DNA (purchased from US Biochemical) in a buffer containing 20 mM Tris pH8, 2 mM β-mercaptoethanol, 50 mM KCl, 10 mM MgCl2, and 0.1 μg/μL BSA. Reactions were allowed to proceed for 1 h at 37° C. and were quenched by addition of 0.5 M EDTA to a final concentration of 142 mM. Product formation was quantified by anion exchange filter binding and scintillation counting. Compounds were tested at up to 50 μM.

The percentage of inhibition was calculated according to the following equation: % inhibition=[1−(cpm in test reaction−cpm in blank)/(cpm in control reaction−cpm in blank)]×100.

The ability of the nucleoside derivatives of the present invention to inhibit HIV infectivity and HIV spread was measured in the following assays.

c. HIV Infectivity Assay

Assays were performed with a variant of HeLa Magi cells expressing both CXCR4 and CCR5 selected for low background β-galactosidase (β-gal) expression. Cells were infected for 48 h, and β-gal production from the integrated HIV-1 LTR promoter was quantified with a chemiluminescent substrate (Galactolight Plus, Tropix, Bedford, Mass.). Inhibitors were titrated (in duplicate) in twofold serial dilutions starting at 100 μM; percent inhibition at each concentration was calculated in relation to the control infection.

d. Inhibition of HIV Spread

The ability of the compounds of the present invention to inhibit the spread of the human immunedeficiency virus (HIV) was measured by the method described in U.S. Pat. No. 5,413,999 (May 9, 1995), and J. P. Vacca, et al., *Proc. Natl. Acad. Sci.*, 91: 4096–4100 (1994), which are incorporated by reference herein in their entirety.

The nucleoside derivatives of the present invention were also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures were prepared in appropriate media at concentrations of approximately $1.5 \times 10^5$ cells/mL for suspension cultures in 3 day incubations and $5.0 \times 10^4$ cells/mL for adherent cultures in 3 day incubations. 99 μL of cell culture was transferred to wells of a 96-well tissue culture treated plate, and 1 μL of 100-times final concentration of the test compound in DMSO was added. The plates were incubated at 37° C. and 5% $CO_2$ for a specified period of time. After the incubation period, 20 µL of CellTiter 96 Aqueous One Solution Cell Proliferation Assay reagent (MTS) (Promega) was added to each well and the plates were incubated at 37° C. and 5% $CO_2$ for an additional period of time up to 3 h. The plates were agitated to mix well and absorbance at 490 nm was read using a plate reader. A standard curve of suspension culture cells was prepared with known cell numbers just prior to the addition of MTS reagent. Metabolically active cells reduce MTS to formazan. Formazan absorbs at 490 nm. The absorbance at 490 nm in the presence of compound was compared to absorbance in cells without any compound added. *Reference*: Cory, A. H. et al., "Use of an aqueous soluble tetrazolium/formazan assay for cell growth assays in culture," *Cancer Commun.* 3: 207 (1991).

The following assays were employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797–801 (1971).

Viruses:

Rhinovirus type 2 (RV-2), strain HGP, was used with KB cells and media (0.1% $NaHCO_3$, no antibiotics) as stated in the Sidwell and Huffman reference. The virus, obtained from the ATCC, was from a throat swab of an adult male with a mild acute febrile upper respiratory illness.

Rhinovirus type 9 (RV-9), strain 211, and rhinovirus type 14 (RV-14), strain Tow, were also obtained from the American Type Culture Collection (ATCC) in Rockville, Md. RV-9 was from human throat washings and RV-14 was from a throat swab of a young adult with upper respiratory illness. Both of these viruses were used with HeLa Ohio-1 cells (Dr. Fred Hayden, Univ. of VA) which were human cervical epitheloid carcinoma cells. MEM (Eagle's minimum essential medium) with 5% Fetal Bovine serum (FBS) and 0.1% $NaHCO_3$ was used as the growth medium.

Antiviral test medium for all three virus types was MEM with 5% FBS, 0.1% NaHCO3, 50 µg gentamicin/mL, and 10 mM $MgCl_2$.

2000 µg/mL was the highest concentration used to assay the compounds of the present invention. Virus was added to the assay plate approximately 5 min after the test compound. Proper controls were also run. Assay plates were incubated with humidified air and 5% $Co_2$ at 37° C. Cytotoxicity was monitored in the control cells microscopically for morphologic changes. Regression analysis of the virus CPE data and the toxicity control data gave the ED50 (50% effective dose) and CC50 (50% cytotoxic concentration). The selectivity index (SI) was calculated by the formula: SI=CC50÷ED50.

b. Determination of In Vitro Antiviral Activity of Compounds Against Dengue, Banzi, and Yellow Fever (CPE Inhibition Assay)

Assay details are provided in the Sidwell and Huffman reference above.

Viruses:

Dengue virus type 2, New Guinea strain, was obtained from the Center for Disease Control. Two lines of African green monkey kidney cells were used to culture the virus (Vero) and to perform antiviral testing (MA-104). Both Yellow fever virus, 17D strain, prepared from infected mouse brain, and Banzi virus, H336 strain, isolated from the serum of a febrile boy in South Africa, were obtained from ATCC. Vero cells were used with both of these viruses and for assay.

Cells and Media:

MA-104 cells (BioWhittaker, Inc., Walkersville, Md.) and Vero cells (ATCC) were used in Medium 199 with 5% FBS and 0.1% $NaHCO_3$ and without antibiotics.

Assay medium for dengue, yellow fever, and Banzi viruses was MEM, 2% FBS, 0.18% NaHCO3 and 50 µg gentamicin/mL.

Antiviral testing of the compounds of the present invention was performed according to the Sidwell and Huffman reference and similar to the above rhinovirus antiviral testing. Adequate cytopathic effect (CPE) readings were achieved after 5–6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, was obtained from the Center for Disease Control. Vero cells were grown and used as described above. Test medium was MEM, 1% PBS, 0.1% NaHCO3 and 50 µg gentamicin/mL.

Antiviral testing of the compounds of the present invention was performed following the methods of Sidwell and Huffman which are similar to those used to assay for rhinovirus activity. Adequate cytopathic effect (CPE) readings were achieved after 5–6 days.

d. Determination of In Vitro Antiviral Activity of Compounds Against Rhino, Yellow Fever, Dengue, Banzi, and West Nile Viruses (Neutral Red Uptake Assay)

After performing the CPE inhibition assays above, an additional cytopathic detection method was used which is described in "Microtiter Assay for Interferon: Microspectrophotometric Quantitation of Cytopathic Effect," *Appl. Environ. Microbiol.* 31: 35–38 (1976). A Model EL309 microplate reader (Bio-Tek Instruments Inc.) was used to read the assay plate. ED50's and CD50's were calculated as above.

Example of a Pharmaceutical-Formulation

As a specific embodiment of an oral composition of a compound of the present invention, 50 mg of Example 61 or Example 62 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A method of treating hepatitis C virus (HCV) infection comprising administering to a mammal in need of such treatment a therapeutically effective amount of a compound of structural formula III, or a pharmaceutically acceptable salt or acyl derivatives thereof,

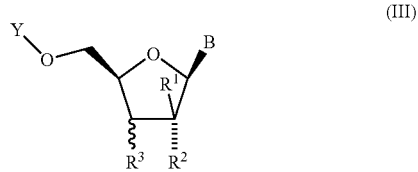

wherein B is

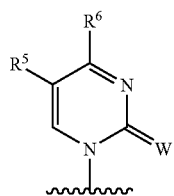

W is O or S;

Y is H, $C_1$-10 alkylcarbonyl, $P_3O_9H_4$, $P_2O_6H_3$, or $P(O)R^9R^{10}$;

$R^1$ is $CF_3$, or $C_{1-4}$ alkyl and one of $R^2$ and $R^3$ is OH or $C_{1-4}$ alkoxy and the other of $R^2$ and $R^3$ is fluoro;

$R^6$ is H, OH, SH, $NH_2$, $C_{1-4}$ alkylamino, di($C_{1-4}$ alkyl) amino, $C_{3-6}$ cycloalkylamino, halogen, $C_{1-4}$ alkyl, $C_{1-4}$ alkoxy, or $CF_3$;

$R^5$ is H, $C_{1-6}$ alkyl, $C_{2-6}$ alkenyl, $C_{2-6}$ alkynyl, $C_{1-4}$ alkylamino, $CF_3$, or halogen; and $R^9$ and $R^{10}$ are each independently hydroxy, $OCH_2CH_2SC(=O)$t-butyl, or $OCH_2O(C=O)$iPr.

2. The method of claim 1 wherein a compound of structural formula III, or a pharmaceutically acceptable salt or acyl derivatives thereof is in combination with a therapeutic amount of another agent active against HCV infection selected from the group consisting of ribavirin; levovirin; thymosin apha-1; an inhibitor of NS3 serine protease; an inhibitor of inosine monophosphate dehydrogenase; and interferon-α or pegylated interferon-α.

* * * * *

UNITED STATES PATENT AND TRADEMARK OFFICE
CERTIFICATE OF CORRECTION

PATENT NO. : 7,105,499 B2
APPLICATION NO. : 10/250873
DATED : September 12, 2006
INVENTOR(S) : Steven S. Carroll et al.

Page 1 of 1

It is certified that error appears in the above-identified patent and that said Letters Patent is hereby corrected as shown below:

Claim 1, Column 138, Line 2, cancel "$C_1$-10 alkylcarbonyl" and substitute therefor -- $C_{1-10}$ alkylcarbonyl --

Claim 2, Column 138, Line 23, cancel "apha-1" and substitute therefor -- alpha-1 --

Signed and Sealed this

Second Day of January, 2007

JON W. DUDAS
*Director of the United States Patent and Trademark Office*